United States Patent

Ashton et al.

[11] Patent Number: 5,281,614
[45] Date of Patent: Jan. 25, 1994

[54] SUBSTITUTED 1,2,4-TRIAZOLES BEARING ACIDIC FUNCTIONAL GROUPS AS ANGIOTENSIN II ANTAGONISTS

[75] Inventors: Wallace T. Ashton, Clark; Prasun K. Chakravarty, Edison; Linda L. Chang, Wayne; William J. Greenlee, Teaneck; Dooseop Kim, Scotch Plains; Nathan B. Mantlo; Arthur A. Patchett, both of Westfield, all of N.J.

[73] Assignee: Merck & Co., Inc., Rahway, N.J.

[21] Appl. No.: 970,360

[22] Filed: Nov. 2, 1992

Related U.S. Application Data

[63] Continuation-in-part of Ser. No. 875,038, May 1, 1992, abandoned, which is a continuation-in-part of Ser. No. 698,505, May 10, 1991, abandoned.

[51] Int. Cl.⁵ .................. A61K 31/41; A61K 31/505; A61K 31/535; C07D 249/10; C07D 249/12; C07D 249/14
[52] U.S. Cl. .................. 514/359; 514/222.5; 514/227.8; 514/231.5; 514/235.5; 514/236.2; 514/236.5; 514/236.8; 514/237.8; 514/238.2; 514/238.8; 514/255; 514/256; 514/340; 514/343; 514/361; 514/362; 514/364; 514/365; 514/383; 514/384; 544/2; 544/60; 544/111; 544/122; 544/124; 544/132; 544/133; 544/243; 544/333; 544/337; 544/360; 544/366; 544/367; 546/276; 546/277; 546/280; 548/125; 548/129; 548/133; 548/135; 548/196; 548/202; 548/204; 548/263.2; 548/263.4; 548/264.2; 548/264.4; 548/266; 548/269

[58] Field of Search ............. 514/222.5, 227.8, 231.5, 514/235.5, 235.8, 236.2, 236.5, 236.8, 237.8, 238.2, 238.8, 255, 256, 340, 343, 365, 383, 384, 359, 361, 362, 364; 544/2, 60, 122, 124, 132, 133, 243, 333, 337, 360, 366, 367, 111; 546/276, 277, 280; 548/196, 202, 204, 263.4, 264.2, 264.4, 266, 269, 125, 129, 133, 135

[56] References Cited

FOREIGN PATENT DOCUMENTS

| | | |
|---|---|---|
| 323841 | 7/1989 | European Pat. Off. . |
| 400974 | 12/1990 | European Pat. Off. . |
| 409332 | 1/1991 | European Pat. Off. . |
| 412594 | 2/1991 | European Pat. Off. . |
| 475898 | 3/1992 | European Pat. Off. . |
| WO92/20662 | 11/1992 | World Int. Prop. O. . |

*Primary Examiner*—Cecilia Tsang
*Assistant Examiner*—Y. N. Gupta
*Attorney, Agent, or Firm*—Valerie J. Camara; Mark R. Daniel; Joseph F. DiPrima

[57] ABSTRACT

Novel substituted triazolinone, triazolinethione, and triazolinimine compounds of the formula I are useful as angiotensin II antagonists.

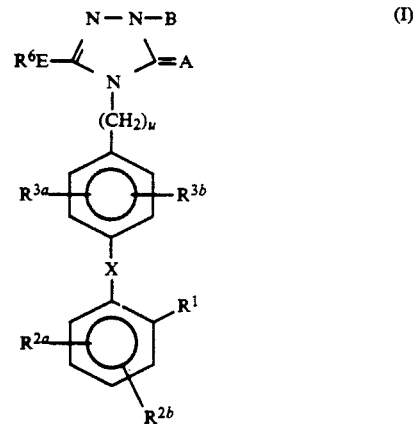

11 Claims, No Drawings

SUBSTITUTED 1,2,4-TRIAZOLES BEARING ACIDIC FUNCTIONAL GROUPS AS ANGIOTENSIN II ANTAGONISTS

RELATED APPLICATION

The present patent application is a continuation-in-part of copending application Ser. No. 07/875,038 filed May 1, 1992 now abandoned, which is a continuation-in-part application of application Ser. No. 07/698,505, filed May 10, 1991, now abandoned.

SUMMARY OF THE INVENTION

This invention relates to novel compounds of structural formula I which are angiotensin II antagonists useful in the treatment of hypertension, congestive heart failure, and elevated intraocular pressure.

It also relates to processes for preparing the novel compounds; pharmaceutical formulations comprising one or more of the compounds as active ingredient; and, a method of treatment of hypertension, congestive heart failure, and elevated intraocular pressure.

The compounds of this invention also have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (A II) is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 392,317; 399,731; 403,158; 403,159; 407,342; 411,507; 412,848; and 415,886; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. European Patent Applications 028,834 and 253,310 and the above three articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridine-6-carboxylic acid and analogs thereof as antihypertensive agents, specifically $Ca^{2+}$ channel blockers.

More recently, non-peptide substituted triazolinone compounds have been described as A II antagonists; see European Patent application 0 412 594 and PCT application WO 91/18888.

DETAILED DESCRIPTION OF THE INVENTION

This invention relates to novel substituted triazole compounds and derivatives thereof which are useful as angiotensin II antagonists, primarily as antihypertensives. The compounds of this invention have the general formula (I):

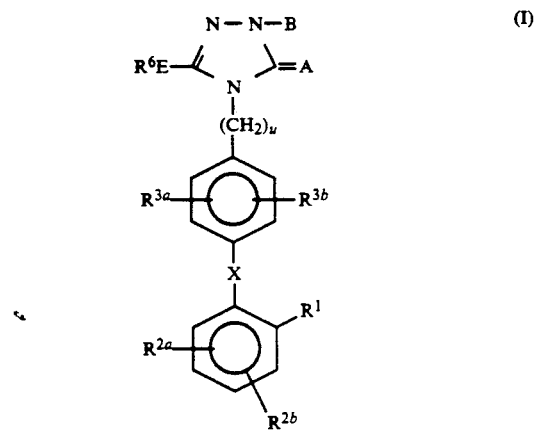

or a pharmaceutically acceptable salt thereof, wherein:
$R^1$ is (a) $-SO_2N(R^{23})-OR^{23}$, (b) $-SO_2NHSO_2R^{22}$, (c) $-SO_2NH-\overset{O}{\underset{\|}{P}}(R^{24})_2$, (d) $-CONH-\overset{O}{\underset{\|}{P}}(R^{24})_2$, (e) $-SO_2NHCN$, (f) $-SO_2NHCO_2R^{22}$, (g) $-SO_2NHSO_2-N\underset{\diagdown\_\diagup}{\diagup^{\displaystyle\frown}\diagdown}Z$, (h) $-NHSO_2NHSO_2R^{22}$, -continued (i) —NHSO$_2$NHP(O)(R$^{24}$)$_2$,

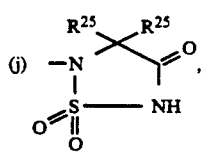
(j)

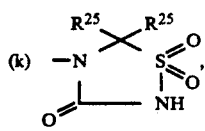
(k)

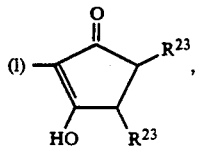
(l)

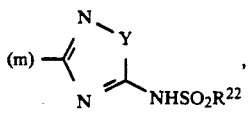
(m)

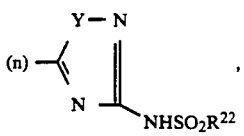
(n)

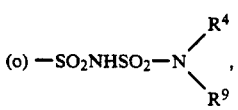
(o) —SO$_2$NHSO$_2$—N(R$^4$)(R$^9$)

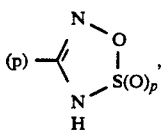
(p)

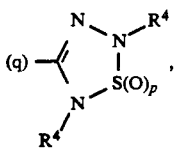
(q)

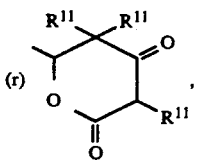
(r)

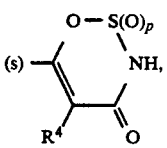
(s)

-continued

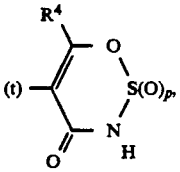
(t)

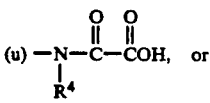
(u) —N(R$^4$)—C(O)—COH, or (v) —NHSO$_2$R$^{22}$;

wherein
Y is O or S and
Z is O, S(O)$_p$ or NR$^{11}$;
R$^{2a}$ and R$^{2b}$ are each independently:
(a) hydrogen,
(b) halogen (Cl, Br, I, F),
(c) —NO$_2$,
(d) NH$_2$,
(e) C$_1$-C$_4$-alkylamino,
(f) —SO$_2$NHR$^9$,
(g) CF$_3$,
(h) C$_1$-C$_6$-alkyl substituted with:
  (1) H,
  (2) F,
  (3) aryl,
  (4) thiophenyl,
  (5) furyl,
  (6) pyridyl,
  (7) imidazolyl,
  (8) pyrimidinyl,
  (9) C$_1$-C$_6$-alkoxy,
  (10) —O(CH$_2$)$_m$—O—C$_1$-C$_4$-alkyl, wherein m is 2 to 4, or
  (11) C$_3$-C$_7$-cycloalkyl, or
when R$^{2a}$ and R$^{2b}$ are on adjacent carbons, they can be bonded together to form a phenyl ring;
R$^{3a}$ is
(a) H,
(b) halo (Cl, Br, I, F),
(c) C$_1$-C$_6$-alkyl,
(d) C$_1$-C$_6$-alkoxy, or
(e) C$_1$-C$_6$-alkoxy-C$_1$-C$_4$-alkyl;
R$^{3b}$ is
(a) H,
(b) halo (Cl, Br, I, F),
(c) NO$_2$,
(d) C$_1$-C$_6$-alkyl,
(e) C$_1$-C$_5$-alkylcarbonyloxy,
(f) C$_3$-C$_6$-cycloalkyl,
(g) C$_1$-C$_6$-alkoxy,
(h) —NHSO$_2$R$^4$,
(i) hydroxy-C$_1$-C$_4$-alkyl,
(j) aryl-C$_1$-C$_4$-alkyl,
(k) C$_1$-C$_4$-alkylthio,
(l) C$_1$-C$_4$-alkylsulfinyl,
(m) C$_1$-C$_4$-alkylsulfonyl,
(n) NH$_2$,
(o) C$_1$-C$_4$-alkylamino,
(p) di(C$_1$-C$_4$-alkyl)amino,
(q) CF$_3$,
(r) —SO$_2$—NHR$^9$,
(s) aryl, (t) furyl, or when $R^{3a}$ and $R^{3b}$ are on adjacent carbons, they can be bonded together to form a phenyl ring;

wherein aryl is phenyl, biphenyl or naphthyl unsubstituted or substituted with one, two or three substituents selected from the group consisting of halo (Cl, Br, I, F), $C_1$-$C_4$-alkyl, $C_1$-$C_4$-alkoxy, $NO_2$, $CF_3$, $C_1$-$C_4$-alkyl-$S(O)_p$—, $CF_3SO_2$—, —OH, —$NR^9R^{10}$, —$SO_2NR^9R^{10}$, $C_3$-$C_7$-cycloalkyl, —$CO_2H$, —$CO_2$-$C_1$-$C_4$-alkyl, —$CONR^{21}R^{22}$, —CN, $C_3$-$C_{10}$-alkenyl, —$NHCOR^9$, —$OCF_3$, phenyl-$C_1$-$C_2$-alkyl, phenyl-$S(O)_p$ and phenyl-$C_1$-$C_2$-alkyl-$S(O)_p$;

$R^4$ is H, straight chain or branched $C_1$-$C_6$ alkyl, —$CH_2$-aryl or aryl;

$R^5$ is H or —$CH(R^4)$—O—CO—$R^{4a}$; wherein $R^{4a}$ is $C_1$-$C_6$-alkyl, aryl or —$CH_2$-aryl;

E is a single bond, —$NR^{13}(CH_2)_s$—, —$S(O)_x(CH_2)_s$— where x is 0 to 2 and s is 0 to 5, —CH(OH)—, —$O(CH_2)_s$—, or —CO—;

$R^6$ is (a) phenyl unsubstituted or substituted with 1 or 2 substituents selected from the group consisting of Cl, Br, I or F, —O—$C_1$-$C_4$-alkyl, $C_1$-$C_4$-alkyl, —$NO_2$, —$CF_3$, —$SO_2NR^9R^{10}$, —S—$C_1$-$C_4$-alkyl, —OH, —$NH_2$, $C_3$-$C_7$-cycloalkyl and $C_3$-$C_{10}$-alkenyl, (b) straight chain or branched $C_1$-$C_6$-alkyl, $C_2$-$C_6$-alkenyl or $C_2$-$C_6$-alkynyl each of which is unsubstituted or substituted with one or more substituents selected from the group consisting of aryl as defined above, $C_3$-$C_7$-cycloalkyl, halo (Cl, Br, I, F), —OH, —O—$C_1$-$C_4$-alkyl, —$NH_2$, —NH(-$C_1$-$C_4$-alkyl), —$N(C_1$-$C_4$-alkyl)$_2$, —NH—$SO_2R^4$, —$COOR^4$, —$SO_2NHR^9$, —S—$C_1$-$C_4$-alkyl, (c) heteroaryl, wherein heteroaryl is an unsubstituted, monosubstituted or disubstituted five- or six-membered aromatic ring which contains 1 to 2 heteroatoms selected from the group consisting of O, N and S and wherein the substituents are members selected from the group consisting of —OH, —SH, —$C_1$-$C_4$-alkyl, —$C_1$-$C_4$-alkoxy, —$CF_3$, Cl, Br, F, I, —$NO_2$, —$CO_2H$, —$CO_2$-$C_1$-$C_4$-alkyl, —$NH_2$, —$NH(C_1$-$C_4$-alkyl) and —$N(C_1$-$C_4$-alkyl)$_2$, (d) mono-, di-, tri- or polyfluoro-$C_1$-$C_5$-alkyl, (e) $C_3$-$C_7$-cycloalkyl optionally substituted with one or more substituents selected from the group consisting of $C_1$-$C_4$-alkyl, O—$C_1$-$C_4$-alkyl, S—$C_1$-$C_4$-alkyl, OH, perfluoro-$C_1$-$C_4$-alkyl, or halo (Cl, Br, F, I), or (f) $C_3$-$C_7$-cycloalkyl-$C_1$-$C_3$-alkyl wherein the cycloalkyl is substituted as in (e) above;

A is O, S or $NR^{21}$;

B is (a) H provided A is not $NR^{21}$;

(b) $C_1$-$C_{10}$-alkyl;

(c) substituted $C_1$-$C_{10}$-alkyl in which one or more substituent(s) is selected from (1) halogen (I, Br, Cl, F), (2) hydroxy, (3) $C_1$-$C_{10}$-alkoxy, (4) $C_1$-$C_5$-alkoxycarbonyl, (5) $C_1$-$C_4$-alkylcarbonyloxy, (6) $C_3$-$C_8$-cycloalkyl, (7) phenyl, biphenyl or naphthyl, (8) substituted phenyl, biphenyl or naphthyl in which the substituents are $V_1$, $V_2$, $V_3$, $V_4$ and $V_5$, (9) $C_1$-$C_{10}$-alkyl-$S(O)_p$,

(10) $C_3$-$C_8$-cycloalkyl-$S(O)_p$,

(11) phenyl-$S(O)_p$,

(12) substituted phenyl-$S(O)_p$ in which the substituents are $V_1$-$V_5$,

(13) oxo,

(14) carboxy,

(15) $NR^9R^9$,

(16) $C_1$-$C_5$-alkylaminocarbonyl,

(17) di($C_1$-$C_5$-alkyl)aminocarbonyl,

(18) cyano,

(19) —$OCONR^{21}R^{22}$,

(20) —$NR^{21}COR^{22}$,

(21) —$NR^{21}CO_2R^{22}$,

(22) —$NR^{21}CONR^{21}R^{22}$,

(23) —$NR^{21}CON(CH_2CH_2)_2L$,

(24) —$OCON(CH_2CH_2)_2L$, wherein L is a single bond, $CH_2$, O, $S(O)_p$ or $NR^9$, (d) $C_2$-$C_{10}$-alkenyl, (e) $C_2$-$C_{10}$-alkynyl, (f) $C_3$-$C_8$-cycloalkyl, (g) substituted $C_3$-$C_8$-cycloalkyl or substituted $C_3$-$C_8$-cycloalkyl-$C_1$-$C_4$-alkyl having one or more substituents selected from the group:

(1) halo (Cl, Br, F, I), (2) hydroxy, (3) $C_1$-$C_6$-alkyl, (4) $C_1$-$C_6$-alkoxy, (5) $C_1$-$C_4$-alkylcarbonyloxy, (6) $C_1$-$C_5$-alkoxycarbonyl, (7) carboxy, (8) oxo, (9) $C_1$-$C_5$-alkylaminocarbonyl,

(10) di($C_1$-$C_5$-alkyl)aminocarbonyl,

(11) $C_1$-$C_4$-alkylcarbonyl,

(12) aryl,

(13) substituted phenyl or naphthyl in which the substituents are $V_1$, $V_2$, $V_3$, $V_4$ and $V_5$,

(14) —$NR^{21}COR^{22}$,

(15) —$NR^{21}CO_2R^{22}$,

(16) —$OCONR^{21}R^{22}$, and

(17) —CN, (h) phenyl, biphenyl or naphthyl, (i) substituted phenyl, biphenyl or naphthyl in which the substituents are $V_1$, $V_2$, $V_3$, $V_4$ and $V_5$, (j) phenyl—$(CH_2)_r$—$(Q)_c$—$(CH_2)_r$—, (k) substituted phenyl—$(CH_2)_r$—$(Q)_c$—$(CH_2)_r$— in which the phenyl group is substituted with $V_1$, $V_2$, $V_3$, $V_4$ and $V_5$, or (l) heterocycle—$(CH_2)_r$—$(Q)_c$—$(CH_2)_r$—, wherein the heterocycle is 5- or 6-membered containing one or two heteroatoms such as pyridine, furan, pyrrole, imidazole or thiazole and unsubstituted or substituted with $V_1$ and $V_2$;

$R^9$ is H, $C_1$-$C_5$-alkyl, aryl or —$CH_2$-aryl;

$R^{10}$ is H, $C_1$-$C_4$-alkyl, or $R^9$ and $R^{10}$ together can be —$(CH_2)_m$— where m is 3-6;

$R^{11}$ is H, $C_1$-$C_6$-alkyl, $C_2$-$C_4$-alkenyl, $C_1$-$C_4$-alkoxy-$C_1$-$C_4$-alkyl, or —$CH_2$—$C_6H_4R^{20}$;

$R^{12}$ is —CN, —$NO_2$ or —$CO_2R^4$;

$R^{13}$ is H, $C_2$-$C_4$-alkanoyl, $C_1$-$C_6$-alkyl, allyl, $C_3$-$C_6$-cycloalkyl, phenyl or benzyl;

$R^{14}$ is H, $C_1$-$C_8$-alkyl, $C_1$-$C_8$-perfluoroalkyl, $C_3$-$C_6$-cycloalkyl, phenyl or benzyl;

$R^{15}$ is H, $C_1$-$C_6$-alkyl, hydroxy;

$R^{16}$ is H, $C_1$-$C_6$-alkyl, $C_3$-$C_6$-cycloalkyl, phenyl or benzyl;

$R^{17}$ is —$NR^9R^{10}$, —$OR^{10}$, —$NHCONH_2$, —$NHCSNH_2$, —$NHSO_2CF_3$,

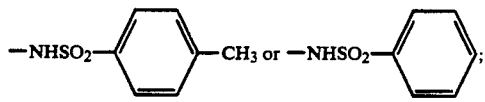 or 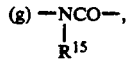;

$R^{18}$ and $R^{19}$ are independently $C_1$-$C_4$-alkyl or taken together are —$(CH_2)_q$— where q is 2 or 3;

$R^{20}$ is H, —$NO_2$, —$NH_2$, —OH or —$OCH_3$;

$R^{21}$ is
(a) H,
(b) phenyl unsubstituted or substituted with 1 or 2 substituents selected from the group consisting of Cl, Br, I or F, —O—$C_1$-$C_4$-alkyl, $C_1$-$C_4$-alkyl, —$NO_2$, —$CF_3$, —$SO_2NR^9R^{10}$, —S—$C_1$-$C_4$-alkyl, —OH, —$NH_2$, —$COOR^4$, $C_3$-$C_7$-cycloalkyl and $C_3$-$C_{10}$-alkenyl,
(c) straight chain or branched $C_1$-$C_6$-alkyl, $C_2$-$C_6$-alkenyl or $C_2$-$C_6$-alkynyl each of which is unsubstituted or substituted with one or more substituents selected from the group consisting of aryl as defined above, $C_3$-$C_7$-cycloalkyl, halo (Cl, Br, I, F), —OH, —O—$C_1$-$C_4$-alkyl, —$NH_2$, —$NH(C_1$-$C_4$-alkyl), —$N(C_1$-$C_4$-alkyl)$_2$, —NH—$SO_2R^4$, —$COOR^4$, —$SO_2NHR^9$, —S—$C_1$-$C_4$-alkyl,
(d) heteroaryl as defined hereinabove, or
(e) $C_3$-$C_7$-cycloalkyl unsubstituted or substituted with one or more substituents selected from the group consisting of $C_1$-$C_4$-alkyl, —O—$C_1$-$C_4$-alkyl, —S—$C_1$-$C_4$-alkyl, —OH, —$COOR^4$, perfluoro-$C_1$-$C_4$-alkyl or halo (Cl, Br, F, I);

$R^{22}$ is $R^{21}$, excluding H;

$R^{23}$ is
(a) H,
(b) aryl as defined above, or
(c) $C_1$-$C_6$-alkyl unsubstituted or substituted with aryl, F, Cl, Br, —OH, —$NH_2$, —$NH(C_1$-$C_4$-alkyl), —$N(C_1$-$C_4$-alkyl)$_2$, or $CF_3$;

$R^{24}$ is
(a) aryl as defined above,
(b) $C_1$-$C_6$-alkyl unsubstituted or substituted with aryl, F, Cl, Br, —OH, —$NH_2$, —$NH(C_1$-$C_4$-alkyl), —$N(C_1$-$C_4$-alkyl)$_2$, $CF_3$, —$COOR^4$, or CN,
(c) —$OCH(R^4)$—O—CO—$R^{4a}$, or
(d) —OH, —O—$C_1$-$C_6$-alkyl wherein alkyl is as defined in (b);

$R^{25}$ is
(a) H,
(b) $C_1$-$C_6$-alkyl unsubstituted or substituted with aryl, F, Cl, Br, —OH, —$NH_2$, —$NH(C_1$-$C_4$-alkyl), —$N(C_1$-$C_4$-alkyl)$_2$, $CF_3$, —$COOR^4$, or CN, or
(c) F, Cl, Br;

X is
(a) a single bond,
(b) —CO—,
(c) —O—,
(d) —S—,
(e) 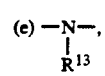
(f) 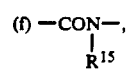

(g) 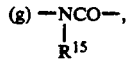
(h) —$OCH_2$—,
(i) —$CH_2O$—
(j) —$SCH_2$—,
(k) —$CH_2S$—,
(l) —$NHC(R^9)(R^{10})$—,
(m) —$NR^9SO_2$—,
(n) —$SO_2NR^9$—,
(o) —$C(R^9)(R^{10})NH$—,
(p) —CH=CH—,
(q) —CF=CF—,
(r) —CH=CF—,
(s) —CF=CH—,
(t) —$CH_2CH_2$—,
(u) —$CF_2CF_2$—, (v) 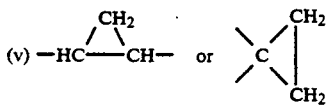

(w) 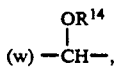

(x) 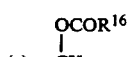

(y) 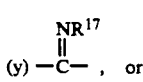, or (z) 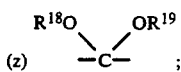;

Q is —C(O)—, —S—, —O— or —$NR^4$;
c is 0 or 1;
p, r and t are 0 to 2;
$V_1$, $V_2$, $V_3$, $V_4$ and $V_5$ are each independently selected from:
(a) H,
(b) $C_1$-$C_5$-alkoxy,
(c) $C_1$-$C_5$-alkyl,
(d) hydroxy,
(e) $C_1$-$C_5$-alkyl-$S(O)_p$,
(f) —CN,
(g) —$NO_2$,
(h) —$NR^9R^{10}$,
(i) $C_1$-$C_5$-alkyl-$CONR^{21}R^{22}$,
(j) —$CONR^{21}R^{22}$,
(k) —$CO_2R^9$,
(l) —$(CH_2)_rCOR^{22}$,
(m) $CF_3$,
(n) halogen (I, Br, Cl, F),
(o) hydroxy-$C_1$-$C_4$-alkyl-,
(p) carboxy-$C_1$-$C_4$-alkyl-,
(q) -1H-tetrazol-5-yl,
(r) —NH—$SO_2CF_3$,
(s) aryl,
(t) $C_1$-$C_5$-alkyl-$CO_2R^9$,
(u) aryloxy,
(v) aryl-$C_1$-$C_3$-alkoxy,
(w) aryl-$C_1$-$C_3$-alkyl,
(x) carboxyphenyl,

9

(y) heteroaryl,
(z) 2-oxazolin-2-yl optionally bearing one or more $C_1$-$C_4$-alkyl substituents,
(aa) —$(CH_2)_t$OOCOR$^{22}$,
(bb) —$(CH_2)_t$OCONR$^{21}$R$^{22}$,
(cc) —$(CH_2)_t$NR$^{21}$COR$^{22}$,
(dd) —$(CH_2)_t$NR$^{21}$CO$_2$R$^{22}$,
(ee) —$(CH_2)_t$NR$^{21}$CONR$^{21}$R$^{22}$,
(ff) —$(CH_2)_t$NR$^{21}$CON(CH$_2$CH$_2$)$_2$L,
(gg) —$(CH_2)_t$OCON(CH$_2$CH$_2$)$_2$L,
(hh) —N(CH$_2$CH$_2$)$_2$L,
(ii) —$C_1$-$C_5$-alkyl-CON(CH$_2$CH$_2$)$_2$L,
(jj) —CON(CH$_2$CH$_2$)$_2$L, wherein L is a single bond, O, CH$_2$, S(O)$_p$ or NR$^9$, and
u is 1 or 2; and
Z is O, NR$^{13}$ or S.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall means the normal butyl substituent, n-butyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

One embodiment of the compounds of Formula (I) are those compounds wherein:
R$^1$ is:

(a)  —SO$_2$N(R$^{23}$)—OR$^{23}$, (b)  —SO$_2$NHSO$_2$R$^{22}$, (c) 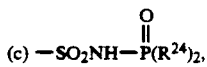 —SO$_2$NH—P(R$^{24}$)$_2$ (=O), (d) 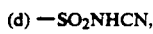 —SO$_2$NHCN, (e)  —SO$_2$NHCO$_2$R$^{22}$, (f) 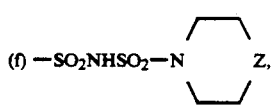 —SO$_2$NHSO$_2$—N   Z, (g)  —SO$_2$NHSO$_2$—N(R$^4$)(R$^9$), (h)  —NHSO$_2$NHSO$_2$R$^{22}$, (i)  —NHSO$_2$NHP(R$^{24}$)$_2$ (=O), (j) 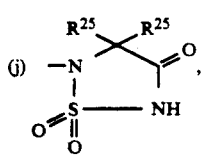,

10

-continued (k) 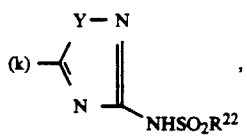, (l) 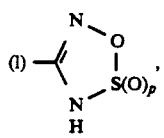, (m) 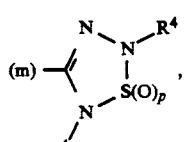, (n) 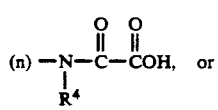 —N(R$^4$)—C(=O)—COH, or (o)  —NHSO$_2$R$^{22}$;

R$^{2a}$ and R$^{2b}$ are independently: H, F, Cl, CF$_3$ or $C_1$-$C_4$-alkyl;
R$^{3a}$ is H or F;
R$^{3b}$ is H, F, Cl, CF$_3$, $C_1$-$C_4$-alkyl, $C_5$-$C_6$-cycloalkyl, —COOCH$_3$, —COOC$_2$H$_5$, —SO$_2$—CH$_3$, NH$_2$, —N($C_1$-$C_4$-alkyl)$_2$ or —NH—SO$_2$CH$_3$;
E is a single bond, —O— or —S—;
R$^6$ is
(a) $C_1$-$C_6$-alkyl optionally substituted with a substituent selected from the group consisting of Cl, F, CF$_3$, —OH, —O—CH$_3$, —OC$_2$H$_5$, —S—CH$_3$, —S—C$_2$H$_5$, phenyl, $C_1$-$C_2$-alkylcyclopropyl or cyclopropyl,
(b) $C_2$-$C_6$-alkenyl or $C_2$-$C_6$-alkynyl,
(c) aryl as defined above,
(d) a heteroaryl selected from the group consisting of 2-pyridyl, 4-pyridyl, 2-pyrimidyl, 4-pyrimidyl, imidazolyl, thiazolyl, thienyl, or furyl,
(e) perfluoro-$C_1$-$C_4$-alkyl which is a member selected from the group consisting of CF$_3$—, CF$_3$CF$_2$—, CF$_3$CF$_2$CF$_2$—, or CF$_3$CF$_2$CF$_2$CF$_2$—, or
(f) $C_3$-$C_7$-cycloalkyl optionally substituted with a substituent selected from the group consisting of methyl, ethyl, CF$_3$ or CF$_3$CF$_2$;
A is O, S or NR$^{21}$;
B is
(a) H provided A is not NR$^{21}$,
(b) $C_1$-$C_{10}$-alkyl,
(c) substituted $C_1$-$C_{10}$-alkyl in which one or two substituents are selected from:
(1) hydroxy,
(2) $C_1$-$C_5$-alkoxy,
(3) $C_1$-$C_5$-alkoxycarbonyl,
(4) $C_1$-$C_4$-alkylcarbonyloxy,
(5) $C_3$-$C_8$-cycloalkyl,
(6) phenyl,
(7) substituted phenyl in which the substituents are V$_1$, V$_2$, V$_3$, V$_4$ and V$_5$,
(8) $C_1$-$C_5$-alkyl-S(O)$_p$,
(9) phenyl-S(O)$_p$,
(10) substituted phenyl-S(O)$_p$ in which the substituent is V,

(11) oxo,
(12) carboxy,
(13) $C_1$-$C_5$-alkylaminocarbonyl,
(d) $C_2$-$C_{10}$-alkenyl,
(e) $C_2$-$C_{10}$-alkynyl,
(f) $C_3$-$C_8$-cycloalkyl,
(g) substituted $C_3$-$C_8$-cycloalkyl or substituted $C_3$-$C_8$-cycloalkyl-$C_1$-$C_4$-alkyl in which one or more substituent(s) is selected from:
 (1) hydroxy,
 (2) $C_1$-$C_5$-alkoxy,
 (3) $C_1$-$C_5$-alkoxycarbonyl,
 (4) $C_1$-$C_4$-alkylcarbonyloxy,
 (5) $C_1$-$C_6$-alkyl,
 (6) phenyl,
 (7) substituted phenyl in which the substituents are $V_1$, $V_2$, $V_3$, $V_4$, and $V_5$,
 (8) oxo,
 (9) carboxy,
 (10) $C_1$-$C_5$-alkylaminocarbonyl,
(h) mono-, di-, tri-, or polyfluoro-$C_1$-$C_{10}$-alkyl,
(i) phenyl, biphenyl or naphthyl,
(j) substituted phenyl, biphenyl or naphthyl in which the substituents are $V_1$, $V_2$, $V_3$, $V_4$ and $V_5$,
(k) phenyl-$(CH_2)_r$—$(Q)_c$—$(CH_2)_r$—,
(l) substituted phenyl-$(CH_2)_r$—$(Q)_c$—$(CH_2)_r$—, or
(m) heterocycle-$(CH_2)_r$—$(Q)_c$—$(CH_2)_r$—, wherein the heterocycle is 5- or 6-membered containing one or two heteroatoms such as pyridine, furan, pyrrole, imidazole or thiazole and unsubstituted or substituted with $V_1$ and $V_2$;

$V_1$, $V_2$, $V_3$, $V_4$ and $V_5$ are independently selected from:
 (a) hydrogen,
 (b) $C_1$-$C_5$-alkoxy,
 (c) $C_1$-$C_5$-alkyl,
 (d) hydroxy,
 (e) $NR^9R^{10}$,
 (f) $CO_2R^9$,
 (g) trifluoromethyl,
 (h) halogen,
 (i) hydroxy-$C_1$-$C_4$-alkyl,
 (j) -1H-tetrazol-5-yl,
 (k) —NH—$SO_2CF_3$,
 (l) CN,
 (m) $NO_2$,
 (n) $C_1$-$C_5$-alkyl-$CO_2R^9$,
 (o) aryl,
 (p) aryl-$C_1$-$C_3$-alkyl,
 (q) heteroaryl,
 (r) $C_1$-$C_5$-alkyl-$CONR^{21}R^{22}$,
 (s) —$CONR^{21}R^{22}$,
 (t) 2-oxazolin-2-yl optionally bearing one or more $C_1$-$C_4$-alkyl substituents,
 (u) $C_1$-$C_5$-alkyl-$S(O)_p$,
 (v) $(CH_2)_t OCOR^{22}$,
 (w) $(CH_2)_t NR^{21}COR^{22}$,
 (x) $(CH_2)_t NR^{21}CONR^{21}R^{22}$,
 (y) —$(CH_2)_t OCONR^{21}R^{22}$,
 (z) —$(CH_2)_t NR^{21}CO_2R^{22}$,
 (aa) —$(CH_2)_t NR^{21}CON(CH_2CH_2)_2L$,
 (bb) —$(CH_2)_t OCON(CH_2CH_2)_2L$,
 (cc) —$N(CH_2CH_2)_2L$,
 (dd) —$C_1$-$C_5$-alkyl-$CON(CH_2CH_2)_2L$,
 (ee) —$CON(CH_2CH_2)_2L$,
 (ff) aryl-$C_1$-$C_3$-alkoxy, or
 (gg) —$(CH_2)_t COR^{22}$;
u is 1; and
X is:
 (a) a single bond,
 (b) —C(O)—, or
 (c) —$NR^{15}C(O)$—.

In one class of this embodiment are those compounds of formula (I) wherein:
$R^1$ is (a) —$SO_2N(R^{23})$—$OR^{23}$, (b) —$SO_2NHSO_2R^{22}$, (c) —$SO_2NH$—$\overset{\overset{O}{\|}}{P}(R^{24})_2$, (d) —$SO_2NHCN$, (e) —$SO_2NHCO_2R^{22}$, (f) —$SO_2NHSO_2$—$N\underset{\diagdown}{\diagup}Z$, (g) —$SO_2NHSO_2$—$N\overset{R^4}{\underset{R^9}{\diagdown}}$, (h) —$NHSO_2NHSO_2R^{22}$, (i) —$NHSO_2NH\overset{\overset{O}{\|}}{P}(R^{24})_2$, (j)

(k)

(l)

(m)

(n) —$\underset{R^4}{N}$—$\overset{\overset{O}{\|}}{C}$—$\overset{\overset{O}{\|}}{C}OH$, or (o) —$NHSO_2R^{22}$;

E is a single bond or —S—; and
$R^6$ is
 (a) $C_1$-$C_6$ alkyl unsubstituted or substituted with —F, —$CF_3$, cyclopropyl, or $C_1$-$C_2$-alkyl-cyclopropyl, or (b) cyclopropyl, unsubstituted or substituted with —CH₃, —C₂H₅, —CF₃ or —CF₂CF₃.

Illustrating this class is the subclass consisting of those compounds of formula (I) wherein:

A is O, S or NR²¹;

B is (a) H provided A is not NR²¹,
(b) $C_1$–$C_{10}$-alkyl,
(c) $C_3$–$C_8$-cycloalkyl,
(d) $C_3$–$C_8$-cycloalkyl-$C_1$–$C_4$-alkyl,
(e) substituted $C_1$–$C_{10}$-alkyl, $C_3$–$C_8$-cycloalkyl, or $C_3$–$C_8$-cycloalkyl-$C_1$–$C_4$-alkyl each of which can have one or two substituents selected from the group:
 (1) hydroxy,
 (2) $C_1$–$C_5$-alkoxy,
 (3) $C_1$–$C_5$-alkoxycarbonyl,
 (4) phenyl, naphthyl or biphenyl,
 (5) substituted phenyl, naphthyl or biphenyl wherein the substitutents are $V_1$, $V_2$, $V_3$, $V_4$ and $V_5$,
 (6) carboxy,
 (7) $C_1$–$C_5$-alkylaminocarbonyl,
 (8) oxo,
 (9) —NR²¹COR²²,
 (10) —NR²¹CO₂R²²,
 (11) —OCONR²¹R²², or
 (12) —CN,
(f) mono-, di-, tri-, or polyfluoro$C_1$–$C_{10}$-alkyl,
(g) phenyl, biphenyl or naphthyl,
(h) substituted phenyl in which the substituents are $V_1$, $V_2$, $V_3$, $V_4$ and $V_5$,
(i) phenyl—(CH₂)ᵣ—(Q)ᶜ—(CH₂)ᵣ-,
(j) substituted phenyl—(CH₂)ᵣ—(Q)ᶜ—(CH₂)ᵣ-in which the substituents are $V_1$, $V_2$, $V_3$, $V_4$ and $V_5$, or
(k) a heterocyclic moiety selected from:

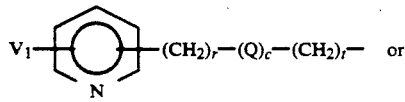

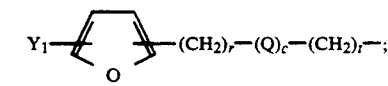

$V_1$, $V_2$, $V_3$, $V_4$ and $V_5$ are selected from:
(a) hydrogen,
(b) $C_1$–$C_5$-alkyl,
(c) $C_1$–$C_5$-alkoxy,
(d) CO₂R⁹,
(e) halogen,
(f) hydroxy-$C_1$–$C_4$-alkyl-,
(g) $C_1$–$C_5$-alkyl-CO₂R⁹,
(h) $C_1$–$C_5$-alkyl-CONR²¹R²²,
(i) CONR²¹R²²,
(j) CN,
(k) NO₂,
(l) CF₃,
(m) aryl,
(n) heteroaryl,
(o) 2-oxazolin-2-yl optionally bearing one or more $C_1$–$C_4$-alkyl substituents,
(p) $C_1$–$C_5$-alkyl-S(O)ₚ,
(q) (CH₂)ᵣOCOR²²,
(r) (CH₂)ᵣNR²¹COR²²,
(s) (CH₂)ᵣNR²¹CO₂R²²,
(t) (CH₂)ᵣNR²¹CONR²¹R²²,
(u) —(CH₂)ᵣOCONR²¹R²²,
(v) —(CH₂)ᵣNR²¹CON(CH₂CH₂)₂L,
(w) —(CH₂)ᵣOCON(CH₂CH₂)₂L,
(x) —N(CH₂CH₂)₂L,
(y) —$C_1$–$C_5$-alkyl-CON(CH₂CH₂)₂L,
(z) —CON(CH₂CH₂)₂L,
(aa) hydroxy,
(bb) NR⁹R¹⁰,
(cc) aryl-$C_1$–$C_3$-alkyl,
(dd) aryl-$C_1$–$C_3$-alkoxy, or
(ee) —(CH₂)ᵣCOR²²; and X is —NR¹⁵C(O)— or a carbon—carbon single bond.

Exemplifying this subclass are the following compounds of the Formula II shown in Table A:

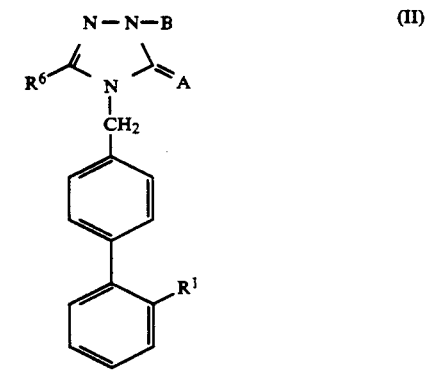

TABLE A

| Compound No. | R¹ | R⁶ | A | B |
|---|---|---|---|---|
| A1 | —SO₂NHOH | Bu | O | iPr |
| A2 | —SO₂NHSO₂Ph | Bu | O | iPr |
| A3 | —SO₂NHSO₂Me | Bu | S | 2-Cl-Ph |
| A4 | —SO₂NHSO₂—C(CH₃)₃ | Bu | O | 2-CF₃-Ph |
| A5 | (cyclic structure with N, O, N—S(O)₂, H) | Bu | O | 2-CF₃-Ph |
| A6 | (cyclic structure with N, N—Ph, N—S=O, H) | Bu | O | 2-CF₃-Ph |
| A7 | —NH—C(O)—CO₂H | Bu | S | iPr |
| A8 | —SO₂NHSO₂—C(CH₃)₃ | Bu | S | 2-F-Ph |
| A9 | —SO₂NHP(O)(O—CH₂Ph)₂ | Bu | O | 2-F-Ph |

TABLE A-continued

| Compound No. | R¹ | R⁶ | A | B |
|---|---|---|---|---|
| A10 | [structure: N-acyl sulfamide ring with N-H] | Bu | O | 2-CF₃-Ph |
| A11 | [structure: N-oxide heterocycle with —NHSO₂Ph] | Bu | O | 2-CF₃-Ph |
| A12 | [structure: N-O-S(=O)₂-NH heterocycle] | Bu | O | Ph |
| A13 | —NHSO₂-(2-thienyl) | Bu | O | i-Pr |
| A14 | —NHSO₂-(2,4-difluorophenyl) | Bu | O | 2-CF₃-Ph |
| A15 | —SO₂NHPO(OEt)₂ | Bu | O | 2-CF₃-Ph |
| A16 | —SO₂NHSO₂-Ph | Bu | O | 2-CF₃-Ph |
| A17 | —SO₂NHSO₂i-Pr | Bu | O | 2-CF₃-Ph |
| A18 | —SO₂NHSO₂CF₃ | Bu | O | 2-CF₃-Ph |
| A19 | —SO₂NHSO₂NMe | Bu | O | 2-CF₃-Ph |

Further illustrating this class is a second subclass consisting of those compounds of formula (I) wherein:

R¹ is —SO₂NHCO₂R²²;
R⁶ is $C_1$–$C_6$-alkyl;
R²¹ is H, substituted or unsubstituted aryl, substituted or unsubstituted $C_1$–$C_6$-alkyl, or heteroaryl;
R²² is
  (a) substituted or unsubstituted aryl,
  (b) substituted or unsubstituted $C_1$–$C_6$-alkyl, or
  (c) heteroaryl;
A is O;
B is substituted phenyl in which the substituents are $V_1$, $V_2$, $V_3$, $V_4$ and $V_5$;
$V_1$, $V_2$, $V_3$, $V_4$ and $V_5$ are selected from:
  (a) hydrogen,
  (b) $C_1$–$C_5$-alkyl,
  (c) $C_1$–$C_5$-alkoxy,
  (d) $C_1$–$C_5$-alkyl-S(O)$_p$,
  (e) halogen,
  (f) CONR⁹R¹⁰,
  (g) CN,
  (h) NO₂,
  (i) CF₃,
  (j) aryl,
  (k) heteroaryl,
  (l) NR²¹COR²²,
  (m) NR²¹CO₂R²²,
  (n) NR²¹CONR²¹R²²,
  (o) NR²¹CON(CH₂CH₂)₂L,
  (p) —CON(CH₂CH₂)₂L,
  (q) NR⁹R¹⁰, or
  (r) —(CH₂)$_r$COR²²;
X is a carbon—carbon single bond;
E is a single bond; and
u is 1.

Exemplifying this second subclass are the following compounds of the Formula III shown in Table B:

TABLE B (III)

[structure of Formula III: biphenyl-methyl substituted triazolinone with R¹, R², R³ on biphenyl and Rˣ, Rʸ, Rᶻ on N-phenyl]

| R¹ | R² | R³ | Rˣ | Rʸ | Rᶻ |
|---|---|---|---|---|---|
| —SO₂NHCO₂Et | H | H | CF₃ | H | H |
| —SO₂NHCO₂i-Pr | H | H | CF₃ | H | H |
| —SO₂NHCO₂n-Pr | H | H | CF₃ | H | H |
| —SO₂NHCO₂i-Bu | H | H | CF₃ | H | H |
| —SO₂NHCO₂n-Bu | H | H | CF₃ | H | H |
| —SO₂NHCO₂t-Bu | H | H | CF₃ | H | H |

TABLE B-continued

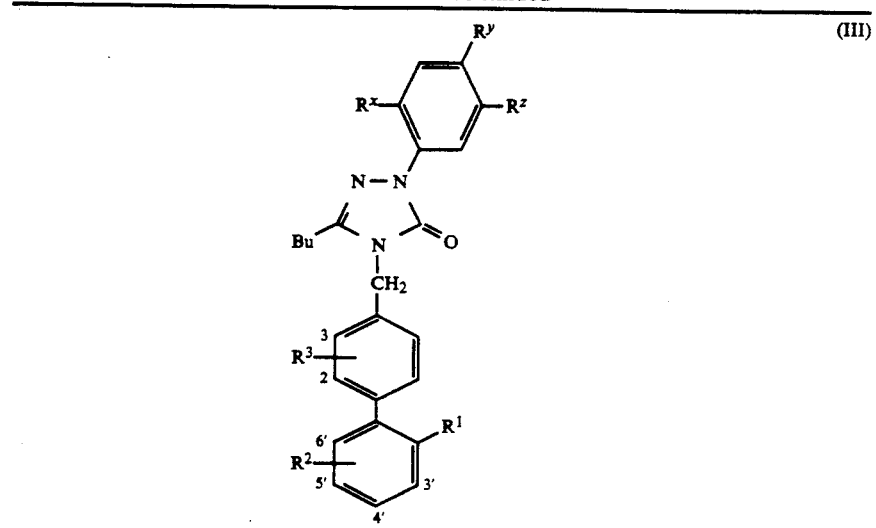

(III)

| R¹ | R² | R³ | Rˣ | Rʸ | R<sup>z</sup> |
|---|---|---|---|---|---|
| —SO₂NHCO₂t-Bu | H | H | Cl | H | H |
| —SO₂NHCO₂t-Bu | H | H | Br | H | H |
| —SO₂NHCO₂t-Bu | 5'-n-Pr | H | CF₃ | H | H |
| —SO₂NHCO₂t-Bu | 5'-n-Pr | 3-F | CF₃ | H | H |
| —SO₂NHCO₂t-Bu | H | 3-F | CF₃ | H | H |
| —SO₂NHCO₂t-Bu | H | H | CF₃ | NO₂ | H |
| —SO₂NHCO₂t-Bu | H | H | CF₃ | NH₂ | H |
| —SO₂NHCO₂t-Bu | H | H | CF₃ | NHCOCH₂CH₃ | H |
| —SO₂NHCO₂t-Bu | H | H | Cl | H | NO₂ |
| —SO₂NHCO₂t-Bu | H | H | Cl | H | NH₂ |
| —SO₂NHCO₂t-Bu | H | H | Cl | H | NH(CH₂)₃CH₃ |
| —SO₂NHCO₂t-Bu | H | H | Cl | H | NHCH₂-phenyl |
| —SO₂NHCO₂t-Bu | H | H | Cl | H | NHCOCH₃ |
| —SO₂NHCO₂t-Bu | H | H | Cl | H | NHCOCH₂CH₃ |
| —SO₂NHCO₂t-Bu | H | H | Cl | H | NHCO(CH₂)₂CH₃ |
| —SO₂NHCO₂t-Bu | H | H | Cl | H | NHCO(CH₂)₃CH₃ |
| —SO₂NHCO₂t-Bu | H | H | Cl | H | NHCOCH(CH₃)₂ |
| —SO₂NHCO₂t-Bu | H | H | Cl | H | NHCOCH₂CH(CH₃)₂ |
| —SO₂NHCO₂t-Bu | H | H | Cl | H | NHCO-cyclopropyl |
| —SO₂NHCO₂t-Bu | H | H | Cl | H | NHCO-phenyl |
| —SO₂NHCO₂t-Bu | H | H | Cl | H | NHCOCH₂-phenyl |
| —SO₂NHCO₂t-Bu | H | H | Cl | H | NHCO(CH₂)₂-phenyl |
| —SO₂NHCO₂t-Bu | H | 3-F | Cl | H | NHCO-(4-pyridyl) |
| —SO₂NHCO₂t-Bu | H | 3-F | Cl | H | NHCO-(3-pyridyl) |
| —SO₂NHCO₂t-Bu | H | H | Cl | H | NHCOO(CH₂)₂CH₃ |
| —SO₂NHCO₂t-Bu | H | H | Cl | H | NHCONH(CH₂)₂CH₃ |
| —SO₂NHCO₂t-Bu | H | 3-F | Cl | H | NHCO-(4-morpholinyl) |
| —SO₂NHCO₂t-Bu | H | 3-F | Cl | H | NHCOCH₂OCH₂CH₃ |
| —SO₂NHCO₂t-Bu | H | 3-F | Cl | H | NHCOCH₂SCH₂CH₃ |
| —SO₂NHCO₂t-Bu | H | 3-F | Cl | H | CONHCH₂CH₃ |
| —SO₂NHCO₂t-Bu | H | H | Cl | H | CONH(CH₂)₂CH₃ |
| —SO₂NHCO₂t-Bu | H | H | Cl | H | CONH(CH₂)₃CH₃ |
| —SO₂NHCO₂t-Bu | H | H | Cl | H | CON(CH₃)(CH₂)₃CH₃ |
| —SO₂NHCO₂t-Bu | H | 3-F | Cl | H | COCH₂CH₃ |
| —SO₂NHCO₂t-Bu | H | H | Cl | H | CO(CH₂)₂CH₃ |
| —SO₂NHCO₂t-Bu | H | H | Cl | H | CO(CH₂)₃CH₃ |
| —SO₂NHCO₂t-Bu | H | 3-F | Cl | H | CO(CH₂)₄CH₃ |
| —SO₂NHCO₂t-Bu | H | 3-F | Cl | H | SO(CH₂)₃CH₃ |
| —SO₂NHCO₂t-Bu | H | 3-F | Cl | H | NHCOCH₃ |
| —SO₂NHCO₂t-Bu | 5'-n-Pr | 3-F | Cl | H | NHCOCH₃ |
| —SO₂NHCO₂t-Bu | H | 3-F | Cl | H | NHCOCH₂CH₃ |
| —SO₂NHCO₂t-Bu | H | 3-F | Cl | H | NHCO(CH₂)₂CH₃ |
| —SO₂NHCO₂t-Bu | H | 3-F | Cl | H | NHCO(CH₂)₃CH₃ |
| —SO₂NHCO₂t-Bu | H | 3-F | Cl | H | NHCO-phenyl |
| —SO₂NHCO₂t-Bu | H | 3-F | Cl | H | CONH(CH₂)₂CH₃ |
| —SO₂NHCO₂t-Bu | H | 3-F | Cl | H | CONH(CH₂)₃CH₃ |
| —SO₂NHCO₂t-Bu | H | 3-F | Cl | H | CO(CH₂)₂CH₃ |
| —SO₂NHCO₂t-Bu | H | 3-F | Cl | H | CO(CH₂)₃CH₃ |
| —SO₂NHCO₂t-Bu | 5'-Et | 3-F | Cl | H | NHCOCH₂CH₃ |
| —SO₂NHCO₂t-Bu | 5'-F | 3-F | Cl | H | NHCOCH₂CH₃ |
| —SO₂NHCO₂t-Bu | 3',6'-diF | H | Cl | H | NHCOCH₂CH₃ |
| —SO₂NHCO₂t-Bu | H | 2-F | Cl | H | NHCOCH₂CH₃ |
| —SO₂NHCO₂t-Bu | H | H | CF₃ | H | NHCOCH₂CH₃ |
| —SO₂NHCO₂t-Bu | H | H | CF₃ | H | NHCO(CH₂)₂CH₃ |
| —SO₂NHCO₂t-Bu | H | H | CF₃ | H | NHCO(CH₂)₃CH₃ |
| —SO₂NHCO₂t-Bu | H | H | CF₃ | H | NHCO-phenyl |

TABLE B-continued

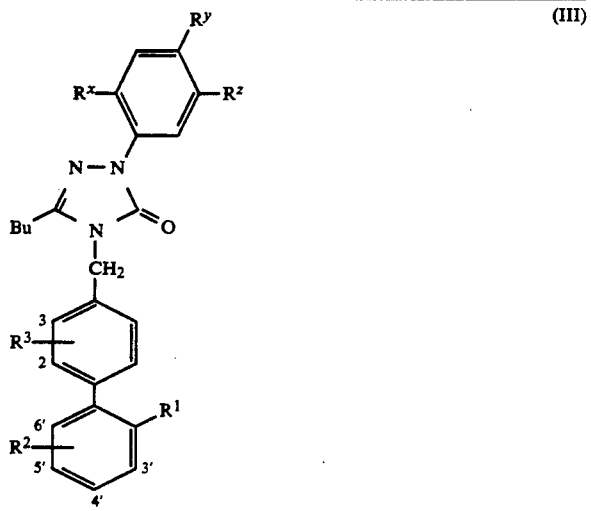

(III)

| R¹ | R² | R³ | R$^x$ | R$^y$ | R$^z$ |
|---|---|---|---|---|---|
| —SO$_2$NHCO$_2$t-Bu | H | H | CF$_3$ | H | CONH(CH$_2$)$_2$CH$_3$ |
| —SO$_2$NHCO$_2$t-Bu | H | H | CF$_3$ | H | CONH(CH$_2$)$_3$CH$_3$ |
| —SO$_2$NHCO$_2$t-Bu | H | H | CF$_3$ | H | CO(CH$_2$)$_2$CH$_3$ |
| —SO$_2$NHCO$_2$t-Bu | H | H | CF$_3$ | H | CO(CH$_2$)$_3$CH$_3$ |
| —SO$_2$NHCO$_2$t-Bu | H | 3-F | CF$_3$ | H | NHCOCH$_2$CH$_3$ |
| —SO$_2$NHCO$_2$t-Bu | H | 3-F | CF$_3$ | H | NHCO(CH$_2$)$_2$CH$_3$ |
| —SO$_2$NHCO$_2$t-Bu | H | 3-F | CF$_3$ | H | NHCO(CH$_2$)$_3$CH$_3$ |
| —SO$_2$NHCO$_2$t-Bu | H | 3-F | CF$_3$ | H | NHCO-phenyl |
| —SO$_2$NHCO$_2$t-Bu | H | 3-F | CF$_3$ | H | CONH(CH$_2$)$_2$CH$_3$ |
| —SO$_2$NHCO$_2$t-Bu | H | 3-F | CF$_3$ | H | CONH(CH$_2$)$_3$CH$_3$ |
| —SO$_2$NHCO$_2$t-Bu | H | 3-F | CF$_3$ | H | CO(CH$_2$)$_2$CH$_3$ |
| —SO$_2$NHCO$_2$t-Bu | H | 3-F | CF$_3$ | H | CO(CH$_2$)$_3$CH$_3$ |
| —SO$_2$NHCO$_2$t-Bu | H | H | Br | H | NHCOCH$_2$CH$_3$ |
| —SO$_2$NHCO$_2$t-Bu | H | H | Br | H | NHCO(CH$_2$)$_2$CH$_3$ |
| —SO$_2$NHCO$_2$t-Bu | H | H | Br | H | NHCO(CH$_2$)$_3$CH$_3$ |
| —SO$_2$NHCO$_2$t-Bu | H | H | Br | H | NHCO-phenyl |
| —SO$_2$NHCO$_2$t-Bu | H | H | Br | H | CONH(CH$_2$)$_2$CH$_3$ |
| —SO$_2$NHCO$_2$t-Bu | H | H | Br | H | CONH(CH$_2$)$_3$CH$_3$ |
| —SO$_2$NHCO$_2$t-Bu | H | H | Br | H | CO(CH$_2$)$_2$CH$_3$ |
| —SO$_2$NHCO$_2$t-Bu | H | H | Br | H | CO(CH$_2$)$_3$CH$_3$ |
| —SO$_2$NHCO$_2$t-Bu | H | 3-F | Br | H | NHCOCH$_2$CH$_3$ |
| —SO$_2$NHCO$_2$t-Bu | H | 3-F | Br | H | NHCO(CH$_2$)$_2$CH$_3$ |
| —SO$_2$NHCO$_2$t-Bu | H | 3-F | Br | H | NHCO(CH$_2$)$_3$CH$_3$ |
| —SO$_2$NHCO$_2$t-Bu | H | 3-F | Br | H | NHCO-phenyl |
| —SO$_2$NHCO$_2$t-Bu | H | 3-F | Br | H | CONH(CH$_{22}$CH$_3$ |
| —SO$_2$NHCO$_2$t-Bu | H | 3-F | Br | H | CONH(CH$_{23}$CH$_3$ |
| —SO$_2$NHCO$_2$t-Bu | H | 3-F | Br | H | CO(CH$_2$)$_2$CH$_3$ |
| —SO$_2$NHCO$_2$t-Bu | H | 3-F | Br | H | CO(CH$_2$)$_3$CH$_3$ |
| —SO$_2$NHCO$_2$t-Bu | H | H | H | H | NHCO(CH$_2$)$_3$CH$_3$ |
| —SO$_2$NHCO$_2$t-Bu | H | H | H | H | CONH(CH$_2$)$_3$CH$_3$ |
| —SO$_2$NHCO$_2$t-Bu | H | 3-F | H | H | NHCO(CH$_2$)$_3$CH$_3$ |
| —SO$_2$NHCO$_2$t-Bu | H | 3-F | H | H | CONH(CH$_2$)$_3$CH$_3$ |
| —SO$_2$NHCO$_2$t-Bu | 5'-n-Pr | 3-F | H | H | NHCOCH$_2$CH$_3$ |
| —SO$_2$NHCO$_2$t-Bu | 5'-n-Pr | 3-F | H | H | CONHCH$_2$CH$_3$ |
| —SO$_2$NHCO$_2$n-Bu | H | 3-F | Cl | H | NHCOCH$_2$CH$_3$ |
| —SO$_2$NHCO$_2$i-Bu | H | 3-F | Cl | H | NHCOCH$_2$CH$_3$ |
| —SO$_2$NHCO$_2$n-Pr | H | 3-F | Cl | H | NHCOCH$_2$CH$_3$ |
| —SO$_2$NHCO$_2$Et | H | 3-F | Cl | H | NHCOCH$_2$CH$_3$ |
| —SO$_2$NHCO$_2$Et | 5'-n-Pr | 3-F | Cl | H | NHCOCH$_3$ |
| —SO$_2$NHCO$_2$Et | 5'-n-Pr | 3-F | Cl | H | NHCOCH$_2$CH$_3$ |
| —SO$_2$NHCO$_2$t-Bu | H | 3-F | H | H | COCH$_2$-phenyl |
| —SO$_2$NHCO$_2$t-Bu | H | 3-F | H | H | CO-phenyl |
| —SO$_2$NHCO$_2$t-Bu | H | 3-F | H | H | NHCO(CH$_2$)$_4$CH$_3$ |
| —SO$_2$NHCO$_2$t-Bu | H | 3-F | H | H | NHCO(CH$_2$)$_5$CH$_3$ |
| —SO$_2$NHCO$_2$t-Bu | H | 3-F | H | H | CONH-phenyl |
| —SO$_2$NHCO$_2$t-Bu | 5'-Et | 3-F | H | H | NHCO(CH$_2$)$_3$CH$_3$ |
| —SO$_2$NHCO$_2$t-Bu | 5'-F | 3-F | CF$_3$ | H | NHCOCH$_2$CH$_3$ |
| —SO$_2$NHCO$_2$t-Bu | 3',6'-diF | H | CF$_3$ | H | NHCOCH$_2$CH$_3$ |
| —SO$_2$NHCO$_2$t-Bu | H | 2-F | CF$_3$ | H | NHCOCH$_2$CH$_3$ |
| —SO$_2$NHCO$_2$t-Bu | H | 3-F | CF$_3$ | H | NHCOCH$_2$(CH$_2$)$_4$CH$_3$ |
| —SO$_2$NHCO$_2$t-Bu | H | 3-F | CF$_3$ | H | NHCOCH$_2$OCH$_2$CH$_3$ |
| —SO$_2$NHCO$_2$t-Bu | H | 3-F | CF$_3$ | H | NHCOCH$_2$SCH$_2$CH$_3$ |
| —SO$_2$NHCO$_2$t-Bu | H | 3-F | CF$_3$ | H | NHCOCH$_2$SCH$_3$ |
| —SO$_2$NHCO$_2$t-Bu | H | 3-F | CF$_3$ | H | NHCOCH$_2$OCH$_3$ |
| —SO$_2$NHCO$_2$t-Bu | H | 3-F | CF$_3$ | H | NHCO(CH$_2$)$_2$OCH$_2$CH$_3$ |
| —SO$_2$NHCO$_2$t-Bu | H | 3-F | CF$_3$ | H | NHCO(CH$_2$)$_2$SCH$_2$CH$_3$ |

TABLE B-continued

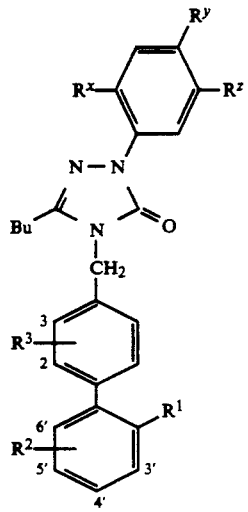

(III)

| $R^1$ | $R^2$ | $R^3$ | $R^x$ | $R^y$ | $R^z$ |
|---|---|---|---|---|---|
| —SO$_2$NHCO$_2$t-Bu | H | 3-F | CF$_3$ | H | NHCO(CH$_2$)$_2$OCH$_3$ |
| —SO$_2$NHCO$_2$t-Bu | H | 3-F | CF$_3$ | H | NHCO(CH$_2$)$_2$SCH$_3$ |
| —SO$_2$NHCO$_2$t-Bu | H | 3-F | Br | H | NHCOCH$_2$OCH$_2$CH$_3$ |
| —SO$_2$NHCO$_2$t-Bu | H | 3-F | Br | H | NHCOCH$_2$SCH$_2$CH$_3$ |
| —SO$_2$NHCO$_2$t-Bu | H | 3-F | Br | H | NHCOCH$_2$SCH$_3$ |
| —SO$_2$NHCO$_2$t-Bu | H | 3-F | Br | H | NHCOCH$_2$OCH$_3$ |
| —SO$_2$NHCO$_2$t-Bu | H | 3-F | Br | H | NHCO(CH$_2$)$_2$OCH$_2$CH$_3$ |
| —SO$_2$NHCO$_2$t-Bu | H | 3-F | Br | H | NHCO(CH$_2$)$_2$SCH$_2$CH$_3$ |
| —SO$_2$NHCO$_2$t-Bu | H | 3-F | Br | H | NHCO(CH$_2$)$_2$OCH$_3$ |
| —SO$_2$NHCO$_2$t-Bu | H | 3-F | Br | H | NHCO(CH$_2$)$_2$SCH$_3$ |
| —SO$_2$NHCO$_2$t-Bu | H | 3-F | Cl | H | NHCOCH$_2$SCH$_3$ |
| —SO$_2$NHCO$_2$t-Bu | H | 3-F | Cl | H | NHCOCH$_2$OCH$_3$ |
| —SO$_2$NHCO$_2$t-Bu | H | 3-F | Cl | H | NHCO(CH$_2$)$_2$OCH$_2$CH$_3$ |
| —SO$_2$NHCO$_2$t-Bu | H | 3-F | Cl | H | NHCO(CH$_2$)$_2$SCH$_2$CH$_3$ |
| —SO$_2$NHCO$_2$t-Bu | H | 3-F | Cl | H | NHCO(CH$_2$)$_2$OCH$_3$ |
| —SO$_2$NHCO$_2$t-Bu | H | 3-F | Cl | H | NHCO(CH$_2$)$_2$SCH$_3$ |
| —SO$_2$NHCO$_2$t-Bu | H | 3-F | CF$_3$ | H | CONH(CH$_2$)$_4$CH$_3$ |
| —SO$_2$NHCO$_2$t-Bu | H | 3-F | CF$_3$ | H | CONH(CH$_2$)$_5$CH$_3$ |
| —SO$_2$NHCO$_2$t-Bu | H | 3-F | CF$_3$ | H | CONHCH$_2$CH$_3$ |
| —SO$_2$NHCO$_2$t-Bu | H | 3-F | CF$_3$ | H | CONH-phenyl |
| —SO$_2$NHCO$_2$t-Bu | H | 3-F | CF$_3$ | H | CO(CH$_2$)$_4$CH$_3$ |
| —SO$_2$NHCO$_2$t-Bu | H | 3-F | CF$_3$ | H | CO-phenyl |
| —SO$_2$NHCO$_2$t-Bu | H | 3-F | CF$_3$ | H | COCH$_2$-phenyl |
| —SO$_2$NHCO$_2$t-Bu | H | 3-F | Br | H | CONH(CH$_2$)$_4$CH$_3$ |
| —SO$_2$NHCO$_2$t-Bu | H | 3-F | Br | H | CONHCH$_2$CH$_3$ |
| —SO$_2$NHCO$_2$t-Bu | H | 3-F | Br | H | NHCO(CH$_2$)$_4$CH$_3$ |
| —SO$_2$NHCO$_2$t-Bu | H | 3-F | Br | H | CO(CH$_2$)$_4$CH$_3$ |
| —SO$_2$NHCO$_2$t-Bu | H | 3-F | Br | H | CO-phenyl |
| —SO$_2$NHCO$_2$t-Bu | H | 3-F | Br | H | COCH$_2$-phenyl |
| —SO$_2$NHCO$_2$t-Bu | H | 3-F | Cl | H | CONH(CH$_2$)$_2$OCH$_3$ |
| —SO$_2$NHCO$_2$t-Bu | H | 3-F | Cl | H | CONH(CH$_2$)$_2$SCH$_3$ |
| —SO$_2$NHCO$_2$t-Bu | H | 3-F | Cl | H | CONH(CH$_2$)$_2$OCH$_2$CH$_3$ |
| —SO$_2$NHCO$_2$t-Bu | H | 3-F | Cl | H | CONH(CH$_2$)$_2$SCH$_2$CH$_3$ |
| —SO$_2$NHCO$_2$t-Bu | H | 3-F | Br | H | CONH(CH$_2$)$_2$OCH$_3$ |
| —SO$_2$NHCO$_2$t-Bu | H | 3-F | Br | H | CONH(CH$_2$)$_2$SCH$_3$ |
| —SO$_2$NHCO$_2$t-Bu | H | 3-F | Br | H | CONH(CH$_2$)$_2$OCH$_2$CH$_3$ |
| —SO$_2$NHCO$_2$t-Bu | H | 3-F | Br | H | CONH(CH$_2$)$_2$SCH$_2$CH$_3$ |
| —SO$_2$NHCO$_2$t-Bu | H | 3-F | CF$_3$ | H | CONH(CH$_2$)$_2$OCH$_3$ |
| —SO$_2$NHCO$_2$t-Bu | H | 3-F | CF$_3$ | H | CONH(CH$_2$)$_2$SCH$_3$ |
| —SO$_2$NHCO$_2$t-Bu | H | 3-F | CF$_3$ | H | CONH(CH$_2$)$_2$OCH$_2$CH$_3$ |
| —SO$_2$NHCO$_2$t-Bu | H | 3-F | CF$_3$ | H | CONH(CH$_2$)$_2$SCH$_2$CH$_3$ |
| —SO$_2$NHCO$_2$t-Bu | H | 3-F | CF$_3$ | H | NHCO-(4-pyridyl) |
| —SO$_2$NHCO$_2$t-Bu | H | 3-F | CF$_3$ | H | NHCO-(3-pyridyl) |
| —SO$_2$NHCO$_2$t-Bu | H | 3-F | Br | H | NHCO-(4-pyridyl) |
| —SO$_2$NHCO$_2$t-Bu | H | 3-F | Br | H | NHCO-(3-pyridyl) |
| —SO$_2$NHCO$_2$n-Pr | H | 3-F | CF$_3$ | H | NHCOCH$_2$CH$_3$ |
| —SO$_2$NHCO$_2$t-Bu | 5'-n-Pr | 3-F | Cl | H | NHCO-(cyclopropyl) |
| —SO$_2$NHCO$_2$Et | 5'-n-Pr | 3-F | Cl | H | NHCO-(cyclopropyl) |
| —SO$_2$NHCO$_2$Et | H | 3-F | Cl | H | NHCOCH$_3$ |
| —SO$_2$NHCO$_2$Et | H | 3-F | Cl | H | NHCO-(cyclopropyl) |
| —SO$_2$NHCO$_2$Et | H | 3-F | Cl | H | NHCO(CH$_2$)$_2$CH$_3$ |
| —SO$_2$NHCO$_2$Et | H | 3-F | Cl | H | NHCO(CH$_2$)$_3$CH$_3$ |
| —SO$_2$NHCO$_2$Et | H | 3-F | Cl | H | NHCO(CH$_2$)$_4$CH$_3$ |
| —SO$_2$NHCO$_2$Et | H | 3-F | Cl | H | NHCO-phenyl |
| —SO$_2$NHCO$_2$Et | H | 3-F | Cl | H | COCHCH$_2$CH$_3$ |
| —SO$_2$NHCO$_2$Et | H | 3-F | Cl | H | CONH(CH$_2$)$_2$CH$_3$ |

TABLE B-continued

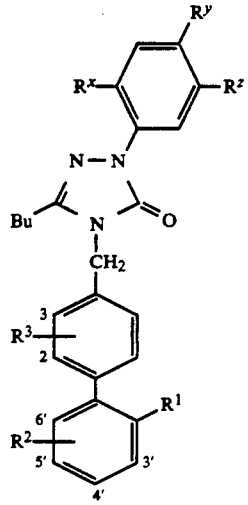
(III)

| R¹ | R² | R³ | Rˣ | Rʸ | Rᶻ |
|---|---|---|---|---|---|
| —SO₂NHCO₂Et | H | 3-F | Cl | H | CONH(CH₂)₃CH₃ |
| —SO₂NHCO₂Et | H | 3-F | Cl | H | CONH(CH₂)₂OCH₂CH₃ |
| —SO₂NHCO₂Et | H | 3-F | Cl | H | CONH(CH₂)₂SCH₂CH₃ |
| —SO₂NHCO₂Et | H | 3-F | Cl | H | CONH(CH₂)₂OCH₃ |
| —SO₂NHCO₂Et | H | 3-F | Cl | H | CONH(CH₂)₂SCH₃ |
| —SO₂NHCO₂Et | H | 3-F | Cl | H | CO(CH₂)₂CH₃ |
| —SO₂NHCO₂Et | H | 3-F | Cl | H | CO(CH₂)₃CH₃ |
| —SO₂NHCO₂Et | H | 3-F | Cl | H | CO-phenyl |
| —SO₂NHCO₂Et | H | 3-F | Cl | H | COCH₂-phenyl |
| —SO₂NHCO₂Et | H | 3-F | Cl | H | NHCOCH₂OCH₂CH₃ |
| —SO₂NHCO₂Et | H | 3-F | Cl | H | NHCOCH₂SCH₂CH₃ |
| —SO₂NHCO₂Et | H | 3-F | Cl | H | NHCOCH₂SCH₃ |
| —SO₂NHCO₂Et | H | 3-F | Cl | H | NHCOCH₂OCH₃ |
| —SO₂NHCO₂Et | H | 3-F | Cl | H | NHCO(CH₂)₂OCH₂CH₃ |
| —SO₂NHCO₂Et | H | 3-F | Cl | H | NHCO(CH₂)₂SCH₂CH₃ |
| —SO₂NHCO₂Et | H | 3-F | Cl | H | NHCO(CH₂)₂OCH₃ |
| —SO₂NHCO₂Et | H | 3-F | Cl | H | NHCO(CH₂)₂SCH₃ |
| —SO₂NHCO₂Et | H | 3-F | Cl | H | NHCO-(4-pyridyl) |
| —SO₂NHCO₂Et | H | 3-F | Cl | H | NHCO-(3-pyridyl) |
| —SO₂NHCO₂Et | H | 3-F | Cl | H | SO(CH₂)₃CH₃ |
| —SO₂NHCO₂Et | H | 3-F | CF₃ | H | NHCOCH₃ |
| —SO₂NHCO₂Et | H | 3-F | CF₃ | H | NHCO-cyclopropyl |
| —SO₂NHCO₂Et | H | 3-F | CF₃ | H | NHCOCH₂CH₃ |
| —SO₂NHCO₂Et | H | 3-F | CF₃ | H | NHCO(CH₂)₂CH₃ |
| —SO₂NHCO₂Et | H | 3-F | CF₃ | H | NHCO(CH₂)₃CH₃ |
| —SO₂NHCO₂Et | H | 3-F | CF₃ | H | NHCO(CH₂)₄CH₃ |
| —SO₂NHCO₂Et | H | 3-F | CF₃ | H | NHCO-phenyl |
| —SO₂NHCO₂Et | H | 3-F | CF₃ | H | CONHCH₂CH₃ |
| —SO₂NHCO₂Et | H | 3-F | CF₃ | H | CONH(CH₂)₂CH₃ |
| —SO₂NHCO₂Et | H | 3-F | CF₃ | H | CONH(CH₂)₃CH₃ |
| —SO₂NHCO₂Et | H | 3-F | CF₃ | H | CONH(CH₂)₂OCH₂CH₃ |
| —SO₂NHCO₂Et | H | 3-F | CF₃ | H | CONH(CH₂)₂SCH₂CH₃ |
| —SO₂NHCO₂Et | H | 3-F | CF₃ | H | CONH(CH₂)₂OCH₃ |
| —SO₂NHCO₂Et | H | 3-F | CF₃ | H | CONH(CH₂)₂SCH₃ |
| —SO₂NHCO₂Et | H | 3-F | CF₃ | H | CO(CH₂)₂CH₃ |
| —SO₂NHCO₂Et | H | 3-F | CF₃ | H | CO(CH₂)₃CH₃ |
| —SO₂NHCO₂Et | H | 3-F | CF₃ | H | CO-phenyl |
| —SO₂NHCO₂Et | H | 3-F | CF₃ | H | COCH₂-phenyl |
| —SO₂NHCO₂Et | H | 3-F | CF₃ | H | NHCOCH₂OCH₂CH₃ |
| —SO₂NHCO₂Et | H | 3-F | CF₃ | H | NHCOCH₂SCH₂CH₃ |
| —SO₂NHCO₂Et | H | 3-F | CF₃ | H | NHCOCH₂SCH₃ |
| —SO₂NHCO₂Et | H | 3-F | CF₃ | H | NHCOCH₂OCH₃ |
| —SO₂NHCO₂Et | H | 3-F | CF₃ | H | NHCO(CH₂)₂OCH₂CH₃ |
| —SO₂NHCO₂Et | H | 3-F | CF₃ | H | NHCO(CH₂)₂SCH₂CH₃ |
| —SO₂NHCO₂Et | H | 3-F | CF₃ | H | NHCO(CH₂)₂OCH₃ |
| —SO₂NHCO₂Et | H | 3-F | CF₃ | H | NHCO(CH₂)₂SCH₃ |
| —SO₂NHCO₂Et | H | 3-F | CF₃ | H | NHCO-(4-pyridyl) |
| —SO₂NHCO₂Et | H | 3-F | CF₃ | H | NHCO-(3-pyridyl) |
| —SO₂NHCO₂Et | H | 3-F | CF₃ | H | SO(CH₂)₃CH₃ |
| —SO₂NHCO₂Et | H | 3-F | Br | H | NHCOCH₃ |
| —SO₂NHCO₂Et | H | 3-F | Br | H | NHCO-cyclopropyl |
| —SO₂NHCO₂Et | H | 3-F | Br | H | NHCOCH₂CH₃ |
| —SO₂NHCO₂Et | H | 3-F | Br | H | NHCO(CH₂)₂CH₃ |
| —SO₂NHCO₂Et | H | 3-F | Br | H | NHCO(CH₂)₃CH₃ |
| —SO₂NHCO₂Et | H | 3-F | Br | H | NHCO(CH₂)₄CH₃ |
| —SO₂NHCO₂Et | H | 3-F | Br | H | NHCO-phenyl |

TABLE B-continued

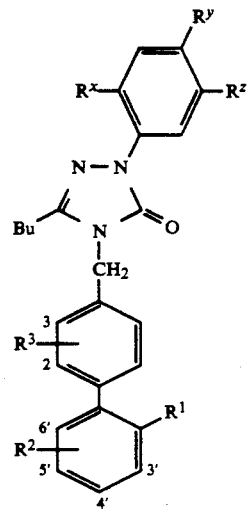
(III)

| R¹ | R² | R³ | Rˣ | Rʸ | Rᶻ |
|---|---|---|---|---|---|
| —SO₂NHCO₂Et | H | 3-F | Br | H | CONHCH₂CH₃ |
| —SO₂NHCO₂Et | H | 3-F | Br | H | CONH(CH₂)₂CH₃ |
| —SO₂NHCO₂Et | H | 3-F | Br | H | CONH(CH₂)₃CH₃ |
| —SO₂NHCO₂Et | H | 3-F | Br | H | CONH(CH₂)₂OCH₂CH₃ |
| —SO₂NHCO₂Et | H | 3-F | Br | H | CONH(CH₂)₂SCH₂CH₃ |
| —SO₂NHCO₂Et | H | 3-F | Br | H | CONH(CH₂)₂OCH₃ |
| —SO₂NHCO₂Et | H | 3-F | Br | H | CONH(CH₂)₂SCH₃ |
| —SO₂NHCO₂Et | H | 3-F | Br | H | CO(CH₂)₂CH₃ |
| —SO₂NHCO₂Et | H | 3-F | Br | H | CO(CH₂)₃CH₃ |
| —SO₂NHCO₂Et | H | 3-F | Br | H | CO-phenyl |
| —SO₂NHCO₂Et | H | 3-F | Br | H | COCH₂-phenyl |
| —SO₂NHCO₂Et | H | 3-F | Br | H | NHCOCH₂OCH₂CH₃ |
| —SO₂NHCO₂Et | H | 3-F | Br | H | NHCOCH₂SCH₂CH₃ |
| —SO₂NHCO₂Et | H | 3-F | Br | H | NHCOCH₂SCH₃ |
| —SO₂NHCO₂Et | H | 3-F | Br | H | NHCOCH₂OCH₃ |
| —SO₂NHCO₂Et | H | 3-F | Br | H | NHCO(CH₂)₂OCH₂CH₃ |
| —SO₂NHCO₂Et | H | 3-F | Br | H | NHCO(CH₂)₂SCH₂CH₃ |
| —SO₂NHCO₂Et | H | 3-F | Br | H | NHCO(CH₂)₂OCH₃ |
| —SO₂NHCO₂Et | H | 3-F | Br | H | NHCO(CH₂)₂SCH₃ |
| —SO₂NHCO₂Et | H | 3-F | Br | H | NHCO-(4-pyridyl) |
| —SO₂NHCO₂Et | H | 3-F | Br | H | NHCO-(4-pyridyl) |
| —SO₂NHCO₂Et | H | 3-F | Br | H | SO(CH₂)₃CH₃. |

A list of compounds of the invention are:

4-[[2'-[N-(t-Butoxycarbonyl)sulfamoyl]biphenyl-4-yl]methyl]-5-n-butyl-2,4-dihydro-2-[2-(trifluoromethyl)phenyl]-3H-1,2,4-triazol-3-one, 4-[[2'-[N-(t-Butoxycarbonyl)sulfamoyl]biphenyl-4-yl]methyl]-5-n-butyl-2-[2-chloro-5-(valerylamino)phenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[5-(N-n-butylcarbamoyl)-2-chlorophenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-(trifluoromethyl)phenyl]-2,4-dihydro-3H-1,2,4-triazol-3-one, 4-[[2'[N-(t-Butoxycarbonyl)sulfamoyl]biphenyl-4-yl]methyl]-5-n-butyl-2-[2-(trifluoromethyl)-5-(propionylamino)phenyl]-2,4-dihydro-3H-1,2,4-triazol-3-one, 2-[2-Bromo-5-(propionylamino)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[5-(Benzoylamino)-2-bromophenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-(propionylamino)-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[2-(trifluoromethyl)-5-(valerylamino)phenyl]-3H-1,2,4-triazol-3-one, 2-[5-(Benzoylamino)-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-chloro-5-(propionylamino)phenyl]-2,4-dihydro-3H-1,2,4-triazol-3-one, 4-[[2'-[N-(t-Butoxycarbonyl)sulfamoyl]biphenyl-4-yl]methyl]-5-n-butyl-2-[2-chloro-5-(propionylamino)phenyl]-2,4-dihydro-3H-1,2,4-triazol-3-one, 2-[5-(Acetylamino)-2-chlorophenyl]-4-[[2'-[N-(t-butoxycarbonyl)sulfamoyl]-3-fluoro-5'-n-propylbiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-chloro-5-(2-ethoxyacetylamino)phenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-chloro-5-[(ethylthioacetyl)amino]phenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[5-(N-n-butylcarbamoyl)-2-(trifluoromethyl)phenyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-(N-n-propylcarbamoyl)-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-(N-ethylcarbamoyl)-2-(trifluoromethyl)phenyl]-3H-1,2,4-triazol-3-one, 4-[[2'-[N-t-Butoxycarbonyl)sulfamoyl]-3-fluorobiphenyl-4-yl]methyl]-5-n-butyl-2,4-dihydro-2-[5-(N-phenylcarbamoyl)-2-(trifluoromethyl)phenyl]-3H-1,2,4-triazol-3-one, 2-[2-Bromo-5-(N-n-butylcarbamoyl)phenyl]-4-[[2'-N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-(N-n-propylcarbamoyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-(N-ethylcarbamoyl)phenyl]-4-[[2'-[N-(t-butoxycarbonyl)sulfamoyl]-3-fluorobiphenyl-4-]methyl]-5-n-butyl-2,4-dihydro-3H-1,2,4-triazol-3-one, 2-[2-Bromo-5-(N-phenylcarbamoyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(ethylthioacetyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(methylthioacetyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[[3-(methylthio)propionyl]amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl-5-n-butyl-2,4-dihydro-2-[5-[(ethoxyacetyl)amino]-2-(trifluoromethyl)phenyl]3H-1,2,4-triazol-3-one, 4-[[2'-[N-t-Butoxycarbonyl)sulfamoyl]-3-fluorobiphenyl-4-yl]methyl]-5-n-butyl-2,4-dihydro-2-[5-[(methoxyacetyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(3-methoxypropionyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(3-ethoxypropionyl)amino]-2-(trifluoromethyl)phenyl]-3H-1,2,4-triazol-3-one, 2-[2-Bromo-5-[(ethylthioacetyl)amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(methylthioacetyl)amino]phenyl]-4-[[2'-[N-t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[[3-(methylthio)propionyl]amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(ethoxyacetyl)amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(methoxyacetyl)amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(3-methoxypropionyl)amino]phenyl]-4-[[2'-[N-(t-butoxycarbonyl)sulfamoyl]-3-fluorobiphenyl-4-yl]methyl]methyl]5-n-butyl-2,4-dihydro-3H-1,2,4-triazol-3-one, 2-[2-Bromo-5-[(3-ethoxypropionyl)amino]phenyl-4-[[2'-[N-t-butoxycarbonyl)sulfamoyl]-3-fluorobiphenyl-4-]-methyl-5-n-butyl-2,4-dihydro-3H-1,2,4-triazol-3-one, 2-[5-(Acetylamino)-2-chlorophenyl]-5-n-butyl-2,4-dihydro-4-[[2'-[N-(ethoxycarbonyl)sulfamoyl]-3-fluoro-5'-n-propylbiphenyl-4-yl]methyl]-3H-1,2,4-triazol-3-one, 2-[5-(Acetylamino)-2-chlorophenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[2-chloro-5-[(cyclopropanecarbonyl)amino]phenyl]-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[2-chloro-5-(propionylamino)phenyl]-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[5-(N-n-butylcarbamoyl)-2-chlorophenyl]-2,4-dihydro-4-[[2'-[N-(ethoxycarbonyl)sulfamoyl]-3-fluorobiphenyl-4-yl]methyl]-3H-1,2,4-triazol-3-one, 2-[5-(Acetylamino)-2-(trifluoromethyl)phenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[5-[(cyclopropanecarbonyl)amino]-2-(trifluoromethyl)phenyl]-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2,4-dihydro-4-[[2'-[N-(ethoxycarbonyl)sulfamoyl]-3-fluorobiphenyl-4-yl]methyl]-2-[5-(propionylamino)-2-(trifluoromethyl)phenyl]-3H-1,2,4-triazol-3-one, 5-n-Butyl-2-[5-(N-n-butylcarbamoyl)-2-(trifluoromethyl)phenyl]-2,4-dihydro-4-[[2'-[N-(ethoxycarbonyl)sulfamoyl]-3-fluorobiphenyl-4-yl]methyl]-3H-1,2,4-triazol-3-one, 2-[2-Bromo-5-(propionylamino)phenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 2-[2-Bromo-5-(N-n-butylcarbamoyl)phenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 2-[5-(Acetylamino)-2-chlorophenyl]-4-[[2'-[N-(t-butoxycarbonyl)sulfamoyl]-3-fluorobiphenyl-4-yl]methyl]-2,4-dihydro-5-n-propyl-3H-1,2,4-triazol-3-one, 4-[[2'-[N-(t-Butoxycarbonyl)sulfamoyl]-3-fluorobiphenyl-4-yl]methyl]-2-[2-chloro-5-[(cyclopropanecarbonyl)amino]phenyl]-2,4-dihydro-5-n-propyl-3H-1,2,4-triazol-3-one, 4-[[2'-[N-(t-Butoxycarbonyl)sulfamoyl]-3-fluorobiphenyl-4-yl]methyl]-2-[2-chloro-5-(propionylamino)phenyl]-2,4-dihydro-5-n-propyl-3H-1,2,4-triazol-3-one, 2-[5-(N-n-Butylcarbamoyl)-2-chlorophenyl]-4-[[2'-[N-(t-butoxycarbonyl)sulfamoyl]-3-fluorobiphenyl-4-yl]methyl]-2,4-dihydro-5-n-propyl-3H-1,2,4-triazol-3-one, 2-[5-(Acetylamino)-2-(trifluoromethyl)phenyl]-4-[[2'-[N-(t-butoxycarbonyl)sulfamoyl]-3-fluorobiphenyl-4-yl]methyl]-2,4-dihydro-5-n-propyl-3H-1,2,4-triazol-3-one, 4-[[2'-[N-(t-Butoxycarbonyl)sulfamoyl]-3-fluorobiphenyl-4-yl]methyl]-2,4-dihydro-2-[5-[(cyclopropanecarbonyl)amino]-2-(trifluoromethyl)phenyl]-5-n-propyl-3H-1,2,4-triazol-3-one, 4-[[2'-[N-(t-Butoxycarbonyl)sulfamoyl]-3-fluorobiphenyl-4-yl]methyl]-2,4-dihydro-2-[5-(propionylamino)-2-(trifluoromethyl)phenyl]-5-n-propyl-3H-1,2,4-triazol-3-one, 4-[[2'-[N-(t-Butoxycarbonyl)sulfamoyl]-3-fluorobiphenyl-4-yl]methyl]-2-[5-(N-n-butylcarbamoyl)-2-(trifluoromethyl)phenyl]-2,4-dihydro-5-n-propyl-3H-1,2,4-triazol-3-one, 2-[5-(Acetylamino)-2-chlorophenyl]-2,4-dihydro-4-[[2'-[N-(ethoxycarbonyl)sulfamoyl]-3-fluorobiphenyl-4-yl]methyl]-5-n-propyl-3H-1,2,4-triazol-3-one, 2-[2-Chloro-5-[(cyclopropanecarbonyl)amino]phenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[2-Chloro-5-(propionylamino)phenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[5-(N-n-Butylcarbamoyl)-2-chlorophenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[5-(Acetylamino)-2-(trifluoromethyl)phenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[5-[(Cyclopropanecarbonyl)amino]-2-(trifluoromethyl)phenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2,4-Dihydro-4-[[2'-[N-(ethoxycarbonyl)sulfamoyl]-3-fluorobiphenyl-4-yl]methyl]-2-[5-(propionylamino)-2-(trifluoromethyl)phenyl]-5-n-propyl-3H-1,2,4-triazol-3-one, or 2-[5-(N-n-Butylcarbamoyl)-2-(trifluoromethyl)phenyl]-2,4-dihydro-4-[[2'-[N-(ethoxycarbonyl)sulfamoyl]-3-fluorobiphenyl-4-yl]methyl]-5-n-propyl-3H-1,2,4-triazol-3-one.

Abbreviations used in the schemes and examples are listed in Table 1.

TABLE 1

| Reagents | |
|---|---|
| NaOEt | sodium ethoxide |
| Et₃N | triethylamine |

TABLE 1-continued

| | |
|---|---|
| MeI | methyl iodide |
| RX (or R'X) | an alkylating agent, such as an alkyl or benzyl halide or p-toluenesulfonate |
| Ph₃P | triphenylphosphine |
| MeNH₂ | methylamine |
| t-BuLi | tert-butyllithium |
| NBS | N-bromosuccinimide |
| BzO₂ | benzoyl peroxide |
| TrCl | trityl chloride (triphenylmethyl chloride) |
| ImH | imidazole |
| AIBN | 2,2'-azobis(isobutyronitrile) |
| DBU | 1,8-diazabicyclo[5.4.0]undec-7-ene |
| BOP reagent | benzotriazol-1-yloxy-tris(dimethylamino)phosphonium hexafluorophosphate |
| DMAP | 4-(dimethylamino)pyridine |
| TFA | trifluoroacetic acid |
| Solvents | |
| EtOH | ethanol |
| DMF | dimethylformamide |
| AcOH | acetic acid |
| DMSO | dimethylsufoxide |
| THF | tetrahydrofuran |
| EtOAc | ethyl acetate |
| hex | hexane |
| MeOH | methanol |
| Others | |
| Ar (or Ar') | aryl |
| Et | ethyl |
| Me | methyl |
| Het | heteroaryl |
| i-Pn | isopentyl: —(CH₂)₂CH(CH₃)₂ |
| t-Bu | tert-butyl |
| Bu | n-butyl |
| Pr | n-propyl |
| Bn | benzyl: —CH₂—phenyl |
| Im | imidazol-1-yl |
| FAB | fast atom bombardment |
| EI | electron impact |
| MS | mass spectrum |

DISCUSSION OF CHEMISTRY AND REACTION SCHEMES

The compounds of Formula I can be prepared by a variety of methods typified by those described below. General synthetic methods for 2,4,5-trisubstituted-2,4-dihydro-3H-1,2,4-triazol-3-ones and -triazole-3-thiones are discussed in books or review articles such as:

(1) C. Temple and J. A. Montgomery, "Triazoles: 1,2,4" (Vol. 37 of *The Chemistry of Heterocyclic Compounds*, A. Weissberger and E. C. Taylor, eds.), Wiley-Interscience, New York, 1981, pp. 365-442.

(2) J. B. Polya, *Comprehensive Heterocyclic Chemistry. The Structure, Reactions, Synthesis and Uses of Heterocyclic Compounds*, A. R. Katritzky and C. W. Rees, eds., Vol. 5, Pergamon Press, Oxford, 1984, pp. 733-790.

(3) J. H. Boyer, *Heterocyclic Compounds*, R. C. Elderfield, ed., Vol. 7, John Wiley & Sons, New York, 1961, pp. 384-461.

In general, the compounds of Formula I are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine (or isocyanate or isothiocyanate) or from a benzyl halide (or methanesulfonate, p-toluenesulfonate, etc.).

Although the Reaction Schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionality present in the molecule.

The Reaction Schemes below have been generalized for simplicity. It is to be understood that the "ArCH$_2$" substituent present at N$^4$ of the triazole derivatives or in their precursors is any substituted arylmethyl moiety consistent with the definition of the N$^4$ substituent in Formula I or which may be transformed to such a grouping either before or after the assembly of the triazole ring system. Such transformations may involve protection and/or deprotection, formation of the "X" linkage between the two aromatic rings as shown in Formula I, or other modifications. It is also to be understood that in most of the Reaction Schemes, the "ArCH$_2$" (Ar=aryl) substituent may be replaced by the homologous "Ar(CH$_2$)$_2$" group as consistent with the definition of Formula I.

It is further to be understood that in the generalized schemes below, unless specified otherwise, the R, R' and R'' groups represent functionalized or unfunctionalized alkyl, aryl, heteroaryl, aralkyl, and the like, while Ar' represents a functionalized or unfunctionalized aryl or heteroaryl group. The moiety, R'X, represents an alkylating agent in which R' is typically a functionalized or unfunctionalized alkyl or aralkyl group, while X is a leaving group such as chloro, bromo, iodo, methanesulfonate, or p-toluenesulfonate. In structures showing an "X" group double-bonded to a carbon atom (as in 22 and products derived therefrom), X is O or S.

SCHEME 1

$$\text{R}^6\overset{\overset{\text{O}}{\|}}{\text{C}}\text{NHNH}_2 \;+\; \text{ArCH}_2\text{NCO} \longrightarrow$$
1          2

$$\text{R}^6\overset{\overset{\text{O}}{\|}}{\text{C}}\text{NHNH}\overset{\overset{\text{O}}{\|}}{\text{C}}\text{NHCH}_2\text{Ar} \xrightarrow[\Delta]{\text{NaOH or NaOEt}}$$
3

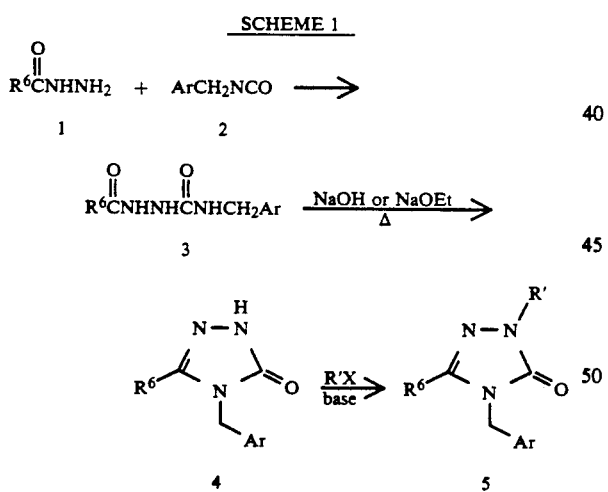

4                5

One of the most widely used routes to 2,4,5-trisubstituted-2,4-dihydro-3H-1,2,4-triazol-3-ones ("triazolinones") is shown in Scheme 1 in its adaptation for the synthesis of compounds of Formula I. Reaction of a carboxylic acid hydrazide 1 (readily obtained from the corresponding ester) with the appropriate arylmethyl isocyanate 2 gives the 1-acyl-4-(arylmethyl)semicarbazide 3. The isocyanate 2 itself is obtainable by well-known methods from various sources, including the (arylmethyl)amine (by phosgene treatment), the arylmethyl halide (by treatment with cyanate anion), and the arylacetic acid or derivative (via Curtius rearrangement of the acyl azide). Upon heating in the presence of hydroxide or alkoxide, cyclization of 3 to the triazolinone 4 occurs. Finally, in the presence of a base (e.g., sodium hydride, sodium ethoxide, sodium hydroxide, or potassium carbonate), 4 is converted to the trisubstituted triazolinone 5 on treatment with a suitable alkylating agent R'X, where R' is alkyl, aralkyl, etc., and X is bromo, iodo, chloro, methanesulfonate, p-toluenesulfonate, and the like. Such reaction pathways have been described by D. L. Temple, Jr., and W. G. Lobeck, Jr., U.S. Pat. No. 4,487,773 (1984), R. E. Gammans, D. W. Smith, and J. P. Yevich, U.S. Pat. No. 4,613,600 (1986), and (in part) H. Gehlen and W. Schade, *Liebigs Ann. Chem.*, 675, 180 (1964), G. Palazzo, U.S. Pat. No. 3,857,845 (1974), and K. H. Hauptmann and K. Zeile, British Patent 971,606 (1964). A modified approach to an intermediate of type 3 and its subsequent cyclization to a triazolinone analogous to 4 have been reported by H. Hrebabecky and J. Beranek, *Collect. Czech. Chem. Commun.*, 50, 779 (1985).

SCHEME 2

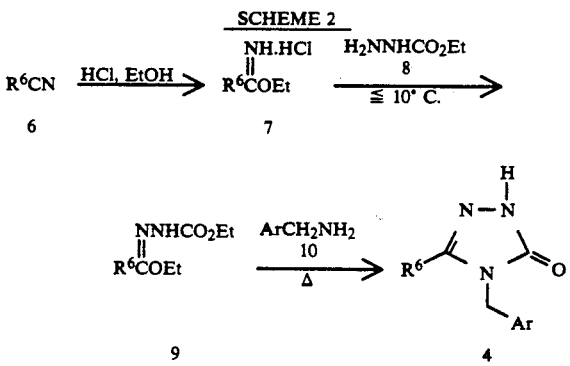

A highly useful alternative route to 4 is shown in Scheme 2. This approach has been described by M. Pesson, S. Dupin, and M. Antoine, *Compt. Rend.*, 253, 285 (1961) and R. Un and A. Ikizler, *Chim. Acta Turc.*, 3, 113 (1975). Addition of ethyl carbazate (8) to the imidate 7 (which is readily prepared from the corresponding nitrile 6) yields an adduct 9, which can be converted to the triazolinone 4 on heating with the (arylmethyl)amine 10 (typically at temperatures from 70°–150° C.). As in Scheme 1, 4 can be alkylated to give the trisubstituted triazolinone 5.

SCHEME 3

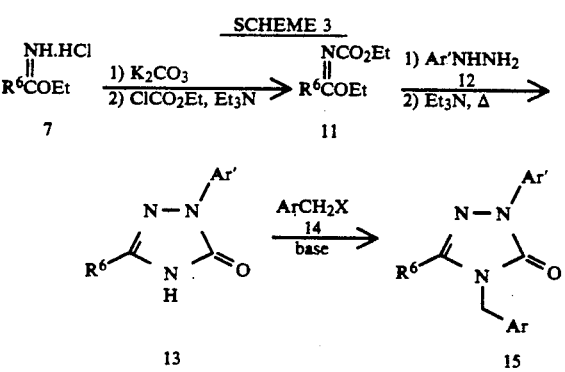

The procedures of Schemes 1 and 2 are not suitable for the introduction of most aryl or heteroaryl substituents at N$^2$. In contrast, the procedures of Schemes 3 to 6 are especially well suited for the synthesis of compounds of Formula I having aryl or heteroaryl substituents at N², since the triazolinone ring is constructed with the N²-substituent in place, whereas the N⁴-substituent is introduced subsequently by alkylation. Scheme 3 presents a route patterned after that reported by K. Yabutani, K. Taninaka, M. Kajioka, K. Takagi, H. Matsui, K. Sutoh, and M. Yamamoto, European Patent Application 220,952 (1987). The N-carbethoxy imidate 11 (obtained by reaction of 7 with ethyl chloroformate) is treated with an arylhydrazine 12 (or analog), typically at about 40°–50° C. Without isolation of the intermediate, further heating at elevated temperature (usually in the range of 90°–150° C.) in the presence of a tertiary amine such as triethylamine effects cyclization to the triazolinone 13. In the presence of a suitable base (e.g., sodium hydride, sodium alkoxide, sodium hydroxide) treatment of 13 with the appropriate ArCH₂X, where X=bromo, iodo, chloro, methanesulfonate, p-toluenesulfonate, and the like, yields the N⁴-alkylated product 15. A variant of the method using a thioimidate has been described by M. Kajioka, H. Kurono, K. Okawa, and M. Harada, U.S. Pat. No. 4,318,731 (1982).

SCHEME 4

$$R^6\overset{O}{\underset{\|}{C}}Cl + H_2NCO_2Et \xrightarrow{\Delta}$$
16   17

$$R^6\overset{O}{\underset{\|}{C}}NHCO_2Et \xrightarrow[P_2O_5, \Delta]{Ar'NHNH_2 \atop 12} $$
18

13 (triazolinone structure with Ar', N-N, R⁶, N-H, =O)

An alternative route to the N²-substituted triazolinone intermediate 13 is shown in Scheme 4. This chemistry has been described by T. N. Ghosh and M. V. Betrabet, *J. Indian Chem. Soc.*, 7, 899 (1930), S. Bellioni, *Ann. Chim. (Rome)*, 52, 187 (1962), G. Palazzo and G. Picconi, *Boll. Chim. Farm.*, 105, 217 (1966), and British Patent 1,021,070 (1966). An acid chloride 16 is heated with urethane (17) (typically at 80°–100° C.), to give the acylurethane 18. Reaction of 18 with an arylhydrazine 12 and phosphorus pentoxide (usually in toluene or xylene at reflux) gives 13, which can then be further alkylated on N⁴ as in Scheme 3. A (thioacyl)urethane modification of this pathway has been reported by D. L. Temple, Jr., and W. G. Lobeck, Jr., U.S. Pat. No. 4,487,773 (1984).

SCHEME 5

$$R^6\overset{O}{\underset{\|}{C}}Cl \xrightarrow{H_2N\overset{O}{\underset{\|}{C}}NH_2, \Delta}$$
16

$$R^6\overset{O}{\underset{\|}{C}}NH\overset{O}{\underset{\|}{C}}NH_2 \xrightarrow[\Delta]{Ar'NHNH_2 \atop 12}$$
19

13

A variation of Scheme 4, shown in Scheme 5, has been described by P. Gold-Aubert, D. Melkonian, and L. Toribio, *Helv. Chim. Acta*, 47, 1188 (1964) and A. L. Langis, U.S. Pat. No. 3,499,000 (1970). The readily prepared acylurea 19 upon heating with an arylhydrazine 12 (at about 150°–200° C.) is converted to the triazolinone intermediate 13.

SCHEME 6

$$R^6\overset{O}{\underset{\|}{C}}CO_2H + Ar'NHNH_2 \longrightarrow$$
20   12

$$R^6\overset{NNHAr'}{\underset{\|}{C}}CO_2H \xrightarrow[Et_3N, \Delta]{(PhO)_2PN_3 \atop 22}$$
21

13

In a quite different approach (Scheme 6), L. Maravetz, U.S. Pat. No. 4,705,557 (1987) and G. Theodoridis, International Patent Application W087/03782 (1987) disclose condensing an α-keto acid 20 with the arylhydrazine 12 to give derivatives such as 21, which can be converted to the triazolinone intermediate 13 by heating with diphenylphosphoryl azide and triethylamine (typically at 75°–115° C.). In the last step, an intermediate acyl azide loses nitrogen and undergoes the Curtius rearrangement to an isocyanate, which undergoes ring closure. As shown in Scheme 3, 13 can then be alkylated on N⁴ to give the trisubstituted triazolinone 15.

SCHEME 7

ArCH₂NCX + R' NHNH₂ ⟶
22   23

$$ArCH_2NH\overset{X}{\underset{\|}{C}}NH_2 \xrightarrow[\text{base}]{(R^6C)_2O \text{ or} \atop R^6COCl} ArCH_2NH\overset{X}{\underset{\|}{C}}N\overset{O}{\underset{\|}{NHCR^6}}$$
24   R'         25   R'

R⁶C(OMe)₃'  ↓ Δ        ↙ NaOH or NaOEt, Δ
27

26 (triazolinone structure with R', N-N, R⁶, N, Ar, =X)

where X = O or S 2,4,5-Trisubstituted-2,4-dihydro-3H-1,2,4-triazole-3-thiones ("triazolinethiones") cannot generally be prepared by routes analogous to those in Schemes 1 to 6 because of the propensity for alkylation to occur on sulfur rather than on the open ring nitrogen. It is thus preferable to have all of the substituents in place at the time of the ring closure to form the heterocycle. As shown in Scheme 7, for certain R' groups (e.g., R'=CH₃), reaction of the hydrazine derivative 23 with the appropriate isocyanate or isothiocyanate 22 yields the 2,4-disubstituted semicarbazide or thiosemicarbazide 24. Acylation of 24 gives 25, which can be cyclized upon heating with hydroxide or alkoxide to give the trisubstituted triazolinone or triazolinethione 26. This approach has been detailed by J. M. Kane and F. P. Miller, U.S. Pat. No. 4,775,688 (1988) and G. F. Duffin, J. D. Kendall, and H. R. J. Waddington, *J. Chem. Soc.*, 3799 (1959). Alternative methods of ring closure, such as heating 24 with the orthoester 27, can also be utilized.

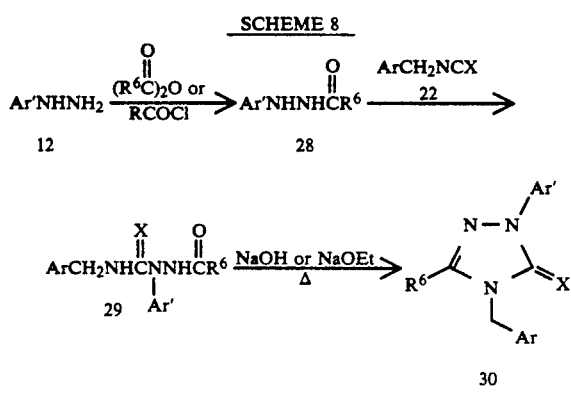

In Scheme 8, acylation of an aryl- or heteroaryl hydrazine gives 28, which can be reacted with the isocyanate or isothiocyanate 22 to yield the 1-acyl-2,4-disubstituted-semicarbazide or thiosemicarbazide 29. Cyclization of 29 upon heating with hydroxide or alkoxide affords the triazolinone or triazolinethione 30. This chemistry has been described by H. Gehlen and W. Schade, *Liebigs Ann. Chem.*, 675, 180 (1964).

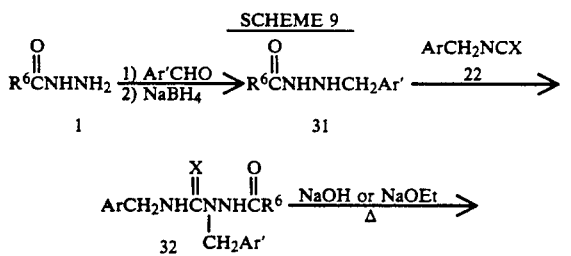

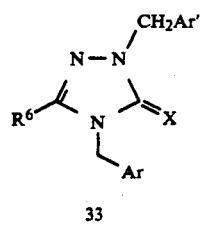

The method of F. Russo, M. Santagati, and G. Pappalardo [*Ann. Chim. (Rome)*, 62, 351 (1972)] (Scheme 9) is useful for the synthesis of trisubstituted triazolinones and triazolinethiones having benzylic substituents at $N^2$. Treatment of a hydrazide 1 with an aromatic or heteroaromatic aldehyde followed by reduction with sodium borohydride gives the substituted hydrazide 31. Reaction of 31 with the isocyanate or isothiocyanate 22 affords the semicarbazide or thiosemicarbazide derivative 32, which is cyclized to the triazolinone or triazolinethione 33 upon heating with hydroxide or alkoxide.

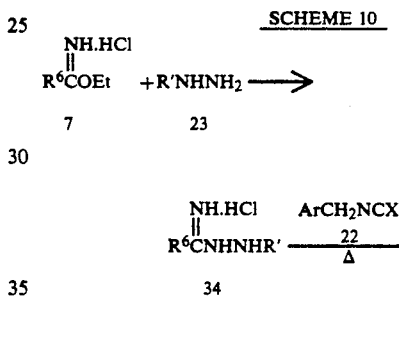

In another approach (Scheme 10), imidate 7 is treated with a substituted hydrazine 23 (especially an aryl or heteroaryl hydrazine) to give the amidrazone 34. Heating 34 with the isocyanate or isothiocyanate 22 gives the triazolinone or triazolinethione 26. Syntheses of this type have been reported by M. Santus, *Acta Pol. Pharm.*, 37, 293 (1980); T. Bany, *Rocz. Chem.*, 42, 247 (1968); and, T. Bany and M. Dobosz, *Ann. Univ. Mariae Curie-Sklodowska, Sect. AA*, 26/27, 23 (1971).

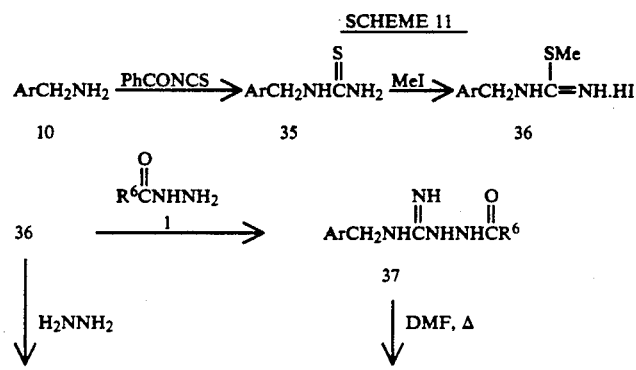

SCHEME 11

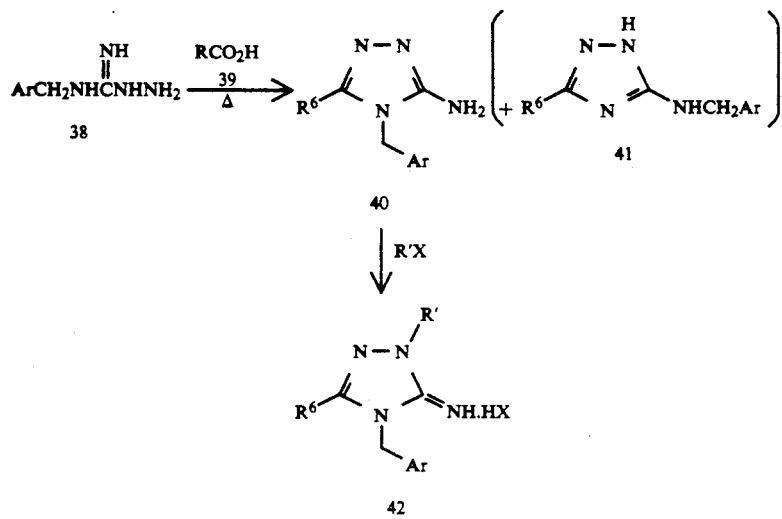

A route to 2,4,5-trisubstituted-2,4-dihydro-3H-1,2,4-triazol-3-imines ("triazolinimines") is outlined in Scheme 11. Reaction of the (arylmethyl)amine 10 with benzoyl isothiocyanate (or by other means) gives the substituted thiourea 35, which is methylated to prepare the isothiourea derivative 36. Compound 36 can be transformed to the acylaminoguanidine 37 by reacting with the hydrazide 1 or to the aminoguanidine 38 by reacting with hydrazine. Ring closure of 37 by heating in DMF or cyclization of 38 with carboxylic acid 39 at elevated temperature affords the aminotriazole 40, which can be separated from the isomer 41. Such pathways have been described by G. J. Durant, G. M. Smith, R. G. W. Spickett, and S. H. B. Wright, *J. Med. Chem.*, 9, 22 (1966) and E. Akerblom, *Acta Chem. Scand.*, 19, 1135 (1965). Finally, alkylation of 40 with the appropriate R'X (where X is a leaving group such as iodo, bromo, chloro, p-toluenesulfonate, or methanesulfonate) leads to the triazolinimine 42, which can be separated from any other isomers or by-products formed during the reaction. This method has been described by E. B. Akerblom and D. E. S. Campbell, *J. Med. Chem.*, 16, 312 (1973).

SCHEME 12

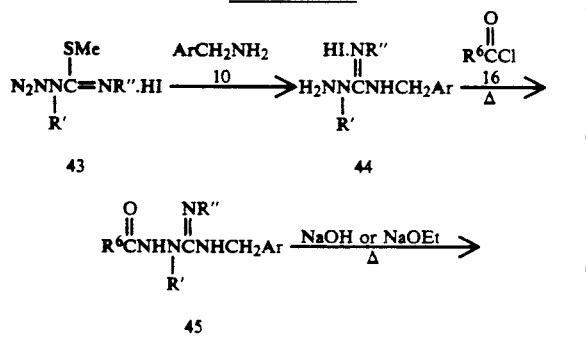

The route shown in Scheme 12 utilizes chemistry reported by E. Akerblom, *Acta Chem. Scand.*, 19, 1135 (1965). The substituted isothiourea 43 is treated with amine 10 to give the aminoguanidine derivative 44. Acylation of 44 with the acid chloride 16 provides the intermediate 45, which can be cyclized by heating with hydroxide or alkoxide. The desired triazolinimine 46 is separated from the isomeric product 47.

SCHEME 13

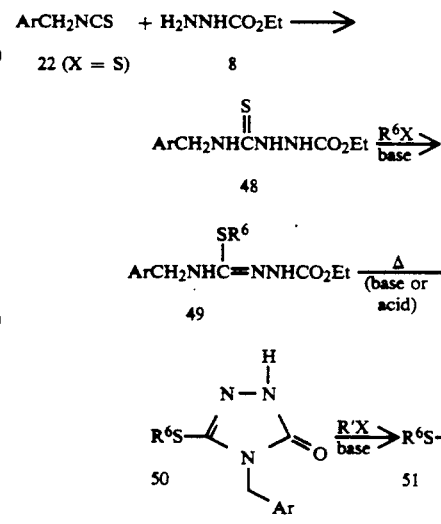

For the synthesis of compounds of formula (I) wherein E=—S—, Schemes 13 and 14 may be utilized. In Scheme 13, the isothiocyanate 22 is reacted with ethyl carbazate (8) to give the 1-(carbethoxy)thiosemicarbazide 48. By standard conditions, 48 is S-alkylated to yield 49, which can be cyclized to the triazolinone 50 by heating, optionally in the presence of base or acid [F. Kurzer and D. R. Hanks, Chem. Ind. (London), 1143 (1966]. Finally, alkylation of the triazolinone as in Scheme 1 provides the fully substituted product 51.

SCHEME 14

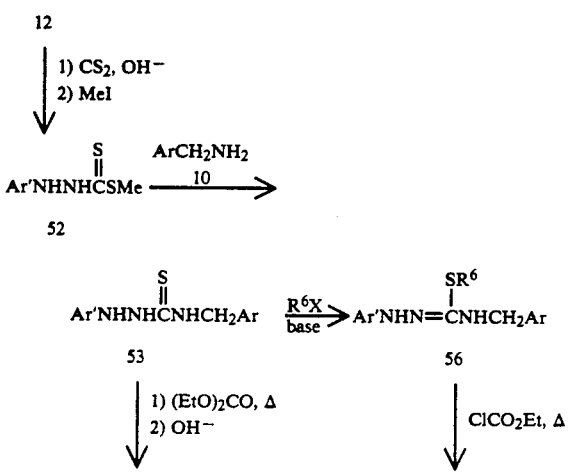

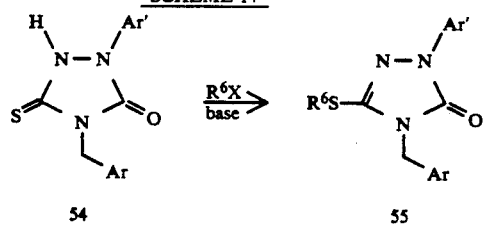

Following the chemistry of K. Sasse [Liebigs Ann. Chem., 735, 158 (1970)](Scheme 14), an arylhydrazine 12 is treated with carbon disulfide in the presence of base followed by treatment with methyl iodide to give the dithiocarbamoyl derivative 52. Reaction of 52 with the (arylmethyl)amine 10 yields the 1,4-disubstituted thiosemicarbazide 53. Cyclization of 53 to 54 is accomplished in two steps by first heating with diethyl carbonate and then treating with hydroxide to induce ring closure. Further treatment of 54 with an alkyl halide gives the desired S-alkyl triazolinone 55. A modification allowing the synthesis of compounds analogous to 55 in which the "Ar" substituent is replaced by an alkyl (or aralkyl) group has also been described by Sasse (see reference above). In a variation [method of A. Dornow and H. Paucksch, Chem. Ber., 99, 85 (1966)], 53 may be first S-alkylated to give 56, which can be cyclized to 55 upon heating with ethyl chloroformate.

SCHEME 15

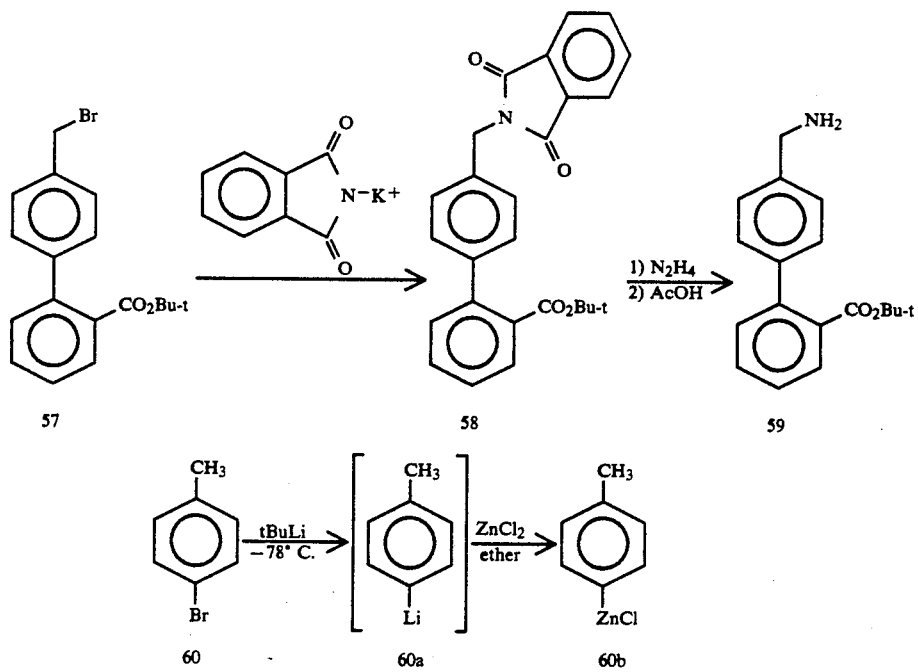

SCHEME 15

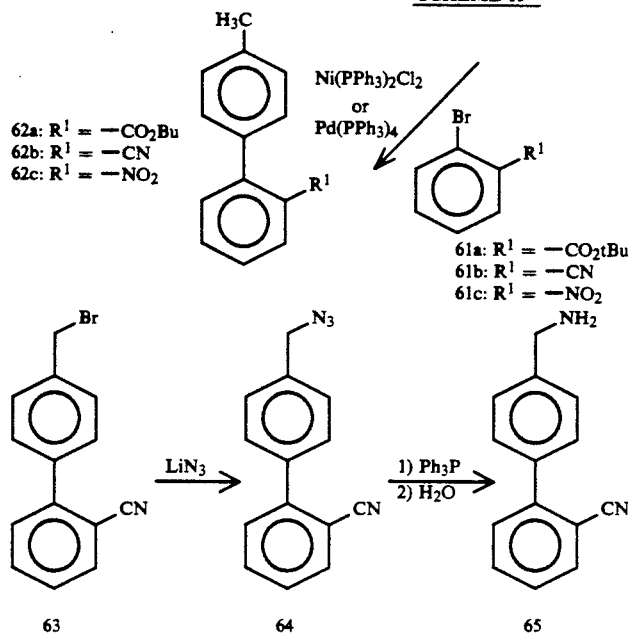

Scheme 15 shows routes to key intermediates used for incorporation of a (2'-(t-butoxycarbonyl)biphenyl-4-yl)methyl or [2'-cyanobiphenyl-4-yl]methyl substituent into a 2,4-dihydro-3H-1,2,4-triazol-3-one or triazole-3-thione at the 4-position. One starting material, 4-bromomethyl-2'-(t-butoxycarbonyl)biphenyl (57), can be prepared as described in European Patent Application 253,310 (or as modified in U.S. application Ser. No. 351,508 filed May 15, 1989. Treatment of 57 with potassium phthalimide at room temperature in a suitable solvent such as N,N-dimethylformamide gives the phthalimido product 58, which is converted to the amine 59 by a standard hydrazinolysis procedure. Alternatively, using the methods described in European Patent Application 253,310, 57 may be treated with sodium azide in dimethylformamide, and the resulting azide intermediate may be reduced to the amine 59 by hydrogenation in the presence of palladium catalyst or by other methods known in the literature. After conversion of 57 or 59 to a triazolinone, triazolinethione, or triazolinimine by methods illustrated in the previous schemes, the t-butyl ester is readily deprotected by treatment with trifluoroacetic acid at room temperature.

A preferred method to prepare the biphenyl precursors 62a, 62b and 62c using Ni(O) or Pd(O) catalyzed cross-coupling reaction [E. Negishi, T. Takahashi, and A. O. King, Org. Synthesis, 66, 67 (1987)] is also outlined in Scheme 15. As shown in Scheme 15, treatment of 4-bromotoluene (60) with t-BuLi, followed by the addition of a solution of $ZnCl_2$, produces the organo-zinc compound (60b). Compound (60b) is then coupled with 61a or 61b in the presence of $Ni(PPh_3)_2Cl_2$ catalyst to produce the desired biphenyl compound 62a or 62b ($PPh_3$=triphenylphosphine). Similarily, 1-iodo-2-nitrobenzene (61c) is coupled with organo-zinc compound 60b in the presence of $Pd(PPh_3)_4$ catalyst [prepared by treating $Cl_2Pd(PPh_3)_2$ with $(i-Bu)_2AlH$ (2 equiv.)] to give the biphenyl compound 62c.

Alternatively, 4-bromomethyl-2'-cyanobiphenyl (63) (described in European Patent Application 253,310) can be reacted with lithium azide, as shown, to form the azide intermediate 64. Reduction of 64 by the method described above for the synthesis of 62 gives the amine 65.

Although specific examples have been shown for the synthesis of compounds of formula (I) wherein X is a single bond, these methods are readily extended to the preparation of compounds of formula (I) having other X linkages allowed by the specifications. Depending on the nature of X, this linkage may be constructed either before or after assembly of the triazole ring. The construction of heterocyclic side chains analogous to the $N^4$ side chain of compounds of formula (I), in which variations of the X group are exemplified, has been disclosed in U.S. patent application Ser. No. 351,508, filed May 15, 1989, U.S. patent application Ser. No. 382,138, filed Jul. 19, 1989 and European Patent Application 253,310.

SCHEME 16

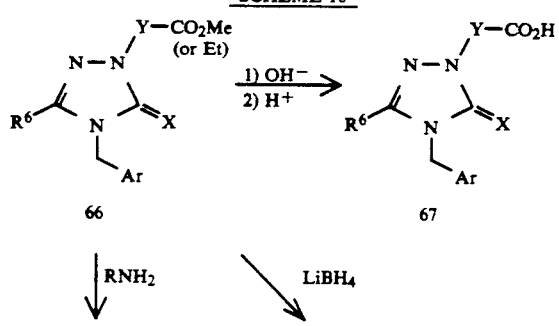

-continued
SCHEME 16

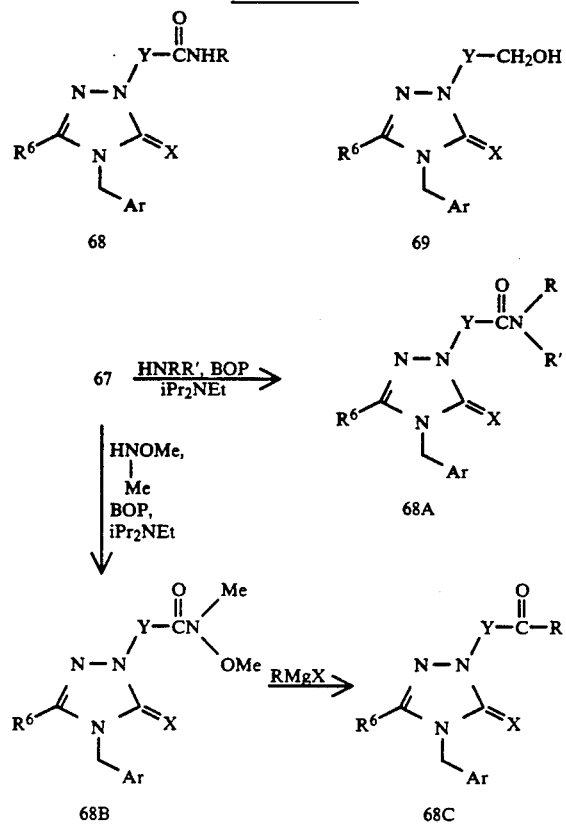

wherein:

Y represents an alkyl, aryl, heteroaryl, or aralkyl group bearing the designated substituent (i.e., carbomethoxy, carboxy, etc.) and which may bear one or more additional compatible substituents as well.

Further transformations of substituent functional groups can be carried out after assembly of the triazole ring and either before or after full elaboration of the arylmethyl substituent at $N^4$. Typical examples are shown in Schemes 16 and 16A. Thus the methyl ester of 66 can be saponified by treatment with aqueous sodium hydroxide (optionally in the presence of a cosolvent such as alcohol, tetrahydrofuran, or dioxane) at room temperature to give, after acidification, the acid 67. The N-alkyl amide 68 is readily obtained, in the case wherein R is methyl, by reaction of 66 with excess aqueous methylamine at room temperature in the presence of a cosolvent such as methanol. For higher molecular weight and/or less reactive amines, the neat amine may be used as reaction solvent. Alternatively, the carboxylic acid 67 may be converted to an amide by reaction with an amine 68A in the presence of a condensing agent, such as BOP reagent, N,N'-dicyclohexylcarbodiimide or 1,1'-carbonyldiimidazole. Reduction of the methyl ester 66 to the alcohol 69 can be accomplished by treatment with lithium borohydride in a solvent such as tetrahydrofuran. By the method of Weinreb [S. Nahm and S. M. Weinreb, *Tetrahedron Lett.*, 22, 3815 (1981)], the acid 67 may be coupled with N,O-dimethylhydroxylamine (for example, in the presence of BOP reagent) to give the N-methoxy-N-methyl amide 68B, which is transformed to the ketone derivative 68C upon reaction with an alkyl- or arylmagnesium halide.

SCHEME 16A

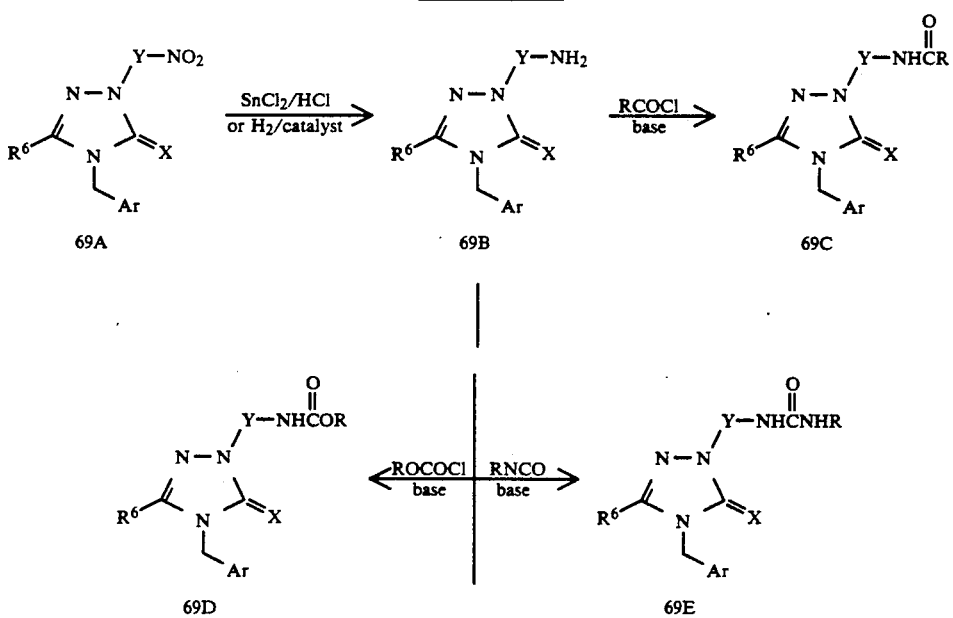

-continued
SCHEME 16A

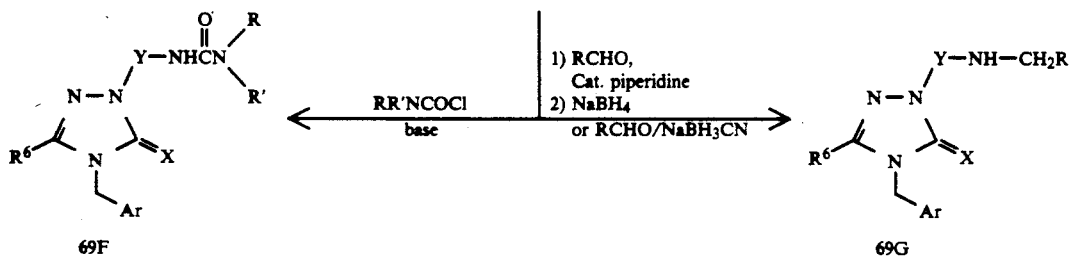

wherein:

Y represents an aryl, heteroaryl, or aralkyl group bearing the designated substituent (i.e., nitro, amino, etc.) and which may bear one or more additional compatible substituents as well.

An additional set of substituent functional group transformations is shown in Scheme 16A. A triazolinone (or triazolinethione or triazolinimine) 69A bearing a nitro-substituted aryl, aralkyl, or heteroaryl group at $N^2$ is reduced, as appropriate, with stannous chloride in the presence of concentrated hydrochloric acid or by catalytic hydrogenation to give the amino derivative 69B. In the presence of a base such as sodium hydride, 69B can be reacted with an acid chloride to give the amide 69C, with a chloroformate to give the carbamate 69D, with an isocyanate to give the urea 69E, or with a carbamoyl chloride to give a trisubstituted urea 69F. Also, 69B can be converted to a substituted-amino derivative 69G. For R=aryl, this may be accomplished conveniently by first heating 69B with the aldehyde in the presence of a catalytic amount of piperidine in a solvent such as isopropanol. The intermediate Schiff base is then reduced (optionally without isolation) by use of sodium borohydride in ethanol to provide 69G. For R=alkyl or aralkyl, the transformation may be accomplished by reacting 69B with the aldehyde in the presence of sodium cyanoborohydride, preferably at about 10°–40° C. These examples are in no way exclusive of other functional group transformations which can be accomplished after formation of the triazolinone, triazolinethione, or triazolinimine system, and which will be apparent to anyone skilled in the art.

SCHEME 17

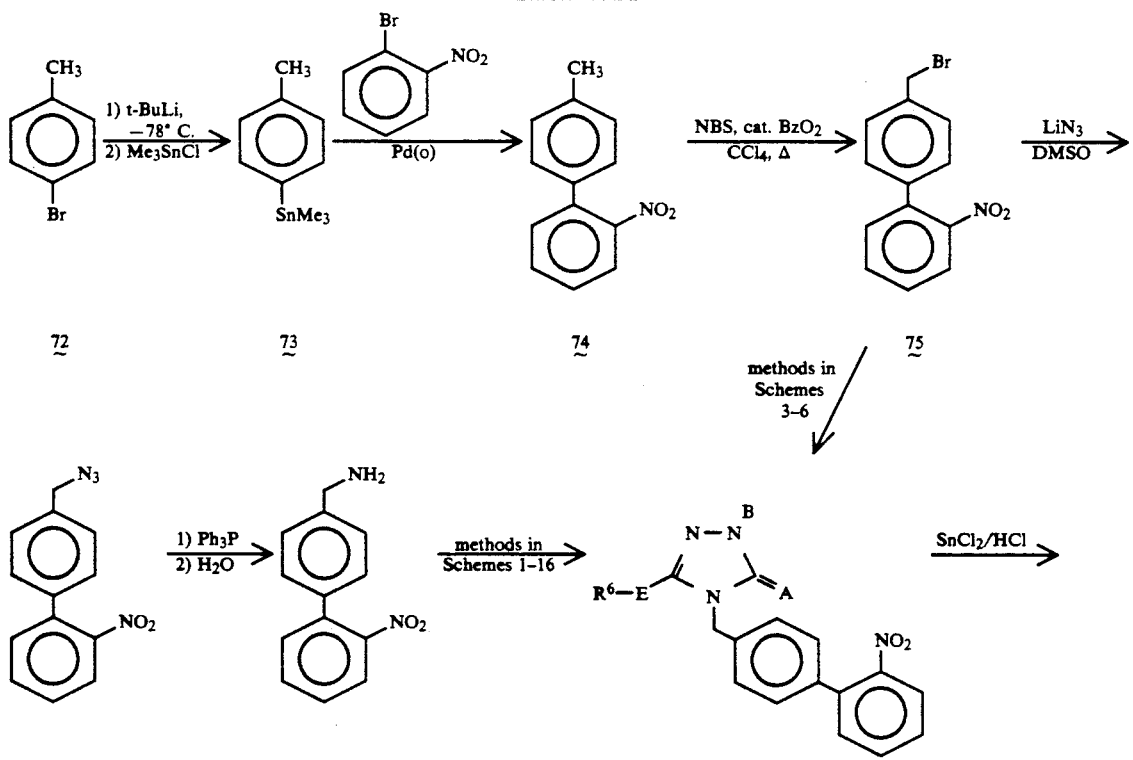

SCHEME 17 -continued

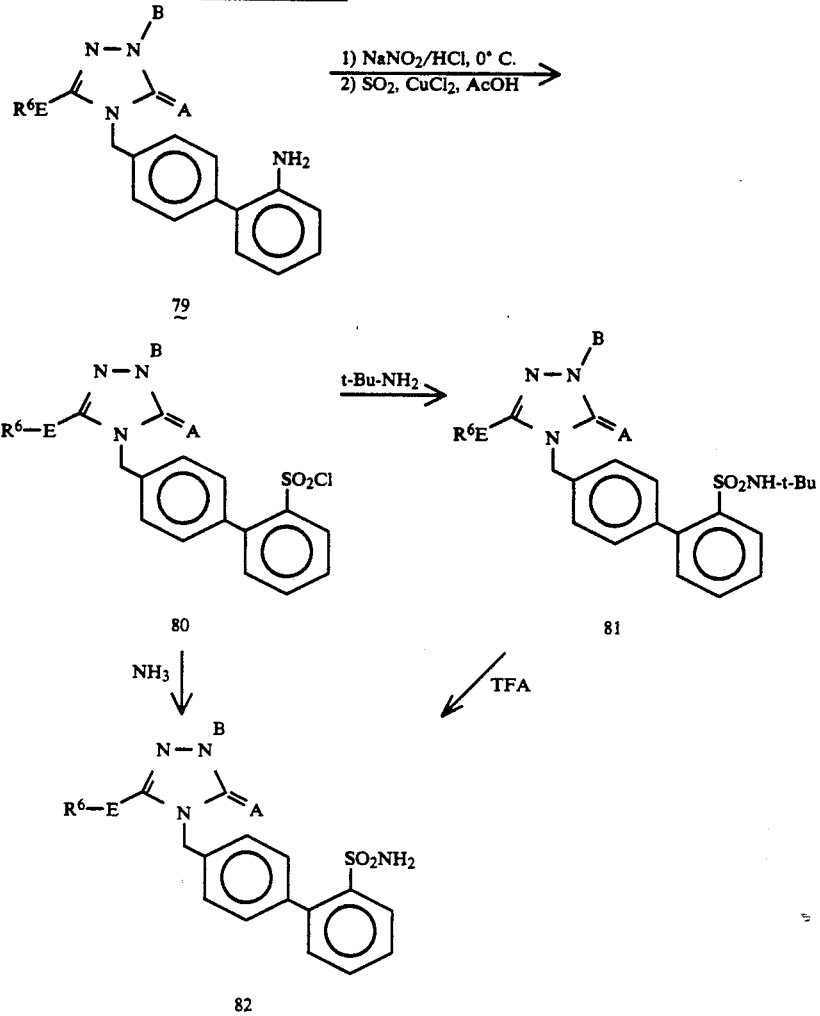

where
NBS = N-bromosuccinimide
Bz = benzoyl

The preparation of compounds of formula (I) wherein $R^1$ is —$SO_2NH_2$ is outlined in Scheme 17. p-Bromotoluene (72) is converted to the trimethylstannane derivative 73 [S. M. Moerlein, *J. Organometal. Chem.*, 319, 29 (1987)], which may be coupled with o-bromonitrobenzene in the presence of $(Ph_3P)_4Pd$ or $(Ph_3P)_2PdCl_2$ catalyst to give the biphenyl derivative 74. Such couplings have been described by J. K. Stille, *Pure Appl. Chem.*, 57, 1771 (1985); T. R. Bailey, *Tetrahedron Lett.*, 27, 4407 (1986); and D. A. Widdowson and Y.-Z. Zhang, *Tetrahedron*, 42, 2111 (1986). Bromination of 74 with N-bromosuccinimide in the presence of catalytic benzoyl peroxide gives 75, which upon treatment with lithium azide in DMSO yields the azido derivative 76. Reduction of 76 to the amine 77 may be accomplished by treatment with triphenylphosphine followed by water. In an alternative route, the bromo group of 75 may be displaced by potassium phthalimide. Hydrazinolysis of the phthalimide derivative yields 77.

By the methods described in the previous schemes, the amine 77 can be converted to a variety of triazolinones, triazolinethiones, and triazolinimines of the general formula 78. Certain triazolinones, especially those in which B is aryl or heteroaryl, may be made directly from 75 by alkylation of a pre-formed triazolinone as in Schemes 3-6. Reduction of the nitro group of 78, preferably with stannous chloride/hydrochloric acid gives the amino derivative 79. Diazotization of the amine 79 and reaction of the diazonium salt with sulfur dioxide in the presence of cupric chloride affords the corresponding arylsulfonyl chloride 80 [see H. Meerwein, et al., *Chem. Ber.*, 90, 841 (1957); A. J. Prinsen and H. Cerfontain, *Rec. Trav. Chim.*, 84, 24 (1965); E. E. Gilbert, *Synthesis*, 3 (1969); and references cited therein]. Treatment of the sulfonyl chloride 80 with an t-butylamine provides the sulfonamide 81. Reaction of the sulfonyl chloride with ammonia yields the sulfonamide 82. Treatment of 81 with trifluoroacetic acid also gives 82.

Compounds of formula I where $R^1$ is

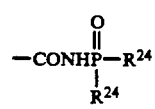

may be prepared from the corresponding carboxylic acid derivatives (83) as outlined in Scheme 18. The carboxylic acid (83), prepared using the chemistry described in preceding schemes, can be converted into the corresponding amide by treatment with carbonyldiimidazole and then with ammonia. The resulting amide then can be treated with sodium hydride or n-butyllithium in THF at −20° C. followed by an appropriately substituted phosphonyl or phosphinyl halide to form the desired compounds (84).

SCHEME 18

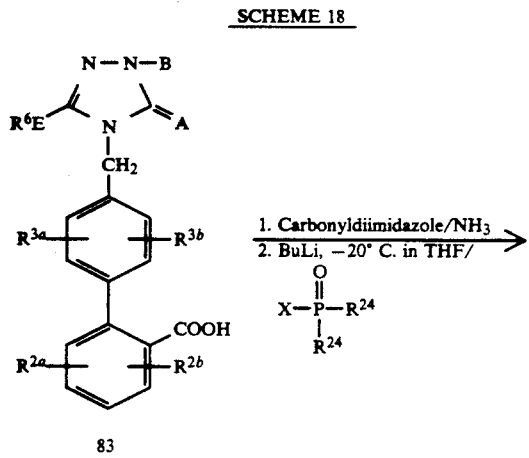

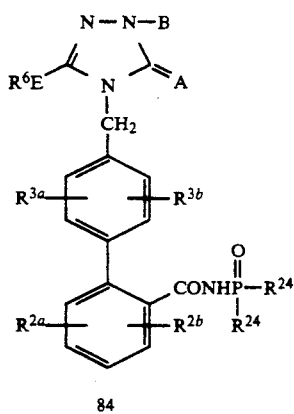

The biaryl sulfonamides (90) and (95), precursors for the alkylating agent 91, can be prepared from appropriate aryl-organotin precursors using palladium(0) catalyzed cross-coupling reactions [J. K. Stille, *Pure Appl. Chem.*, 57, 1771 (1985); T. R. Bailey, *Tetrahedron Lett.*, 27, 4407 (1986); D. A. Widdowson and Y. Z. Zhang, *Tetrahedron*, 42, 2111 (1986)], as outlined in Schemes 19 and 20. The organotin compound (87) [S. M. Moerlein, *J. Organometallic Chem.*, 319, 29 (1987)], obtained from the aromatic precursors (85 or 86), may be coupled with aryl sulfonamide (89) using Pd(PPh3)4 or (PPh3)2PdCl2 as catalysts to give biaryl sulfonamide 90. Similarly, the biphenylmethyl bromide (91) may be alternatively prepared from the appropriate organotin precursor (94) using the Pd(0) catalyzed cross-coupling reaction as outlined in Scheme 20.

SCHEME 19

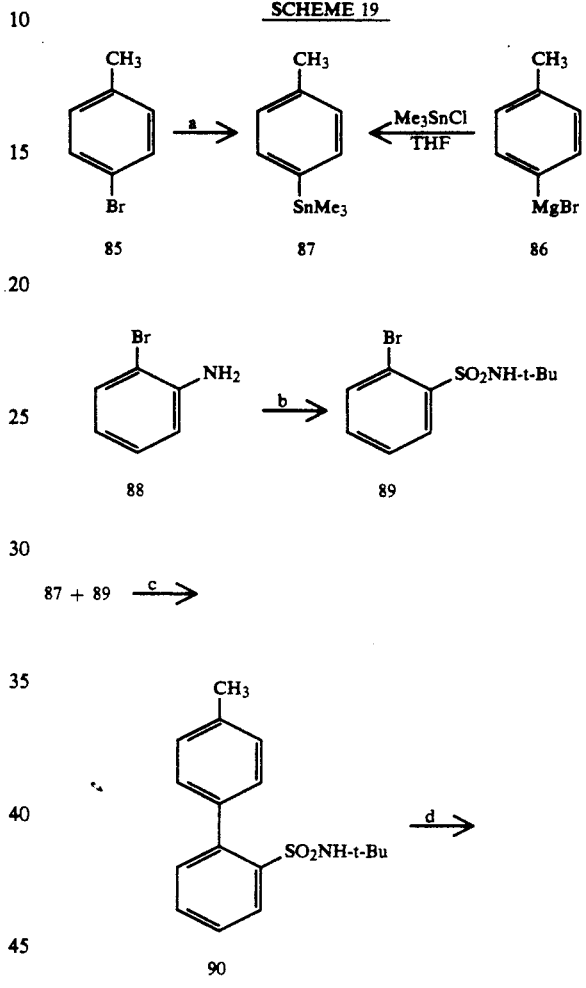

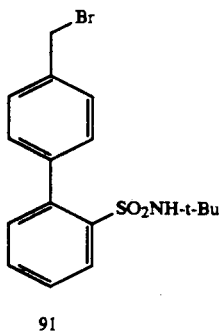

a. i) t-BuLi/ether, −78° C. ii) Me3SnCl b. i) NaNO2/HCl ii) SO2, CuCl2 (iii) t-butylamine c. Pd(PPh3)4, Toluene or (PPh3)2PdCl2, DMF, Heat d. NBS/CCl4, AIBN, Reflux

SCHEME 20

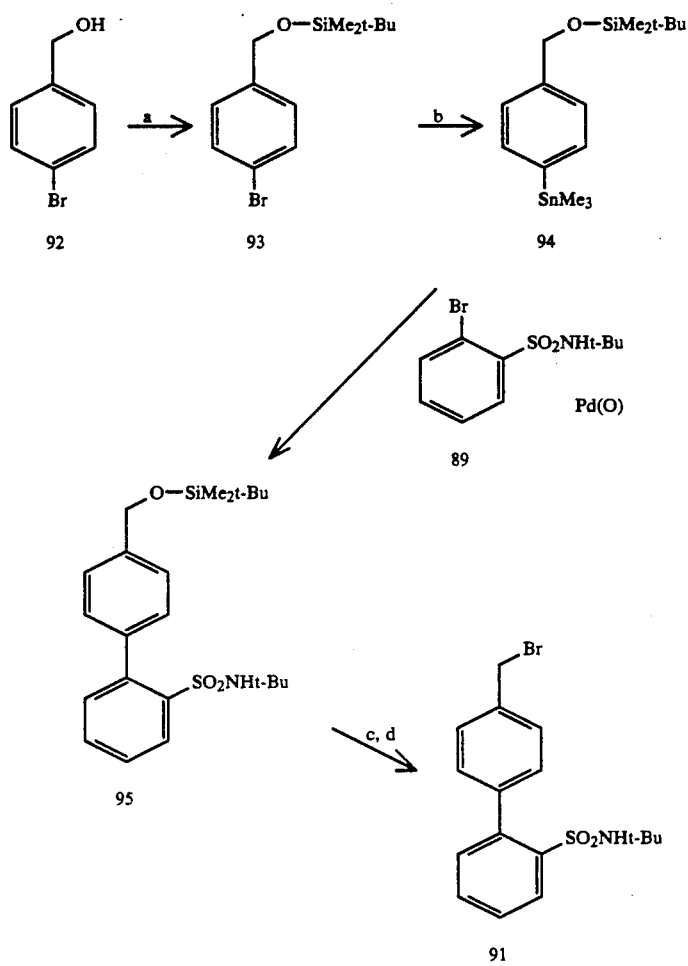

a. t-BuMe₂Si—Cl/Imidazole, DMF
b. t-BuLi, −78° C., Me₃SnCl
c. Tetrabutylammonium fluoride
d. CBr₄Ph₃P.

Compounds of Formula I where $R^1$ is $-SO_2NHSO_2R^{22}$ may be prepared from the key sulfonamide intermediate 81 as outlined in Scheme 21. The intermediate 81 may be prepared by the alkylation of appropriate heterocycles with the alkylating agent 91 as outlined hereinabove. Treatment of 81 with trifluoroacetic acid followed by acylation of the resulting sulfonamide 82 with appropriate sulfonyl chlorides or sulfonic anhydrides may produce the desired compounds (96).

SCHEME 21

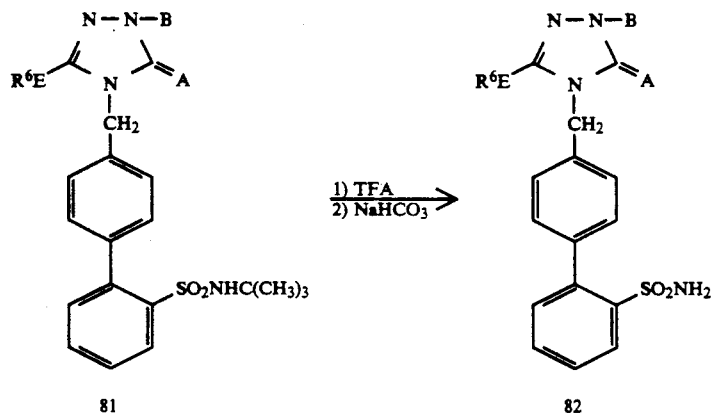

a. i) NaH/THF or DMF (ii) $R^{22}SO_2Cl$
b. $R^{22}SO_2Cl$, DBU, THF
c. $(R^{22}SO_2)_2O$, pyridine Compounds of Formula (I) wherein $R^1$ is $-SO_2NH-CO_2R^{22}$ may be prepared by reacting an appropriate chloroformate or dicarbonate with the sulfonamide (82) in pyridine or in the presence of DBU or NaH in THF to afford the desired compound (97), as outlined in Scheme 22.

SCHEME 22

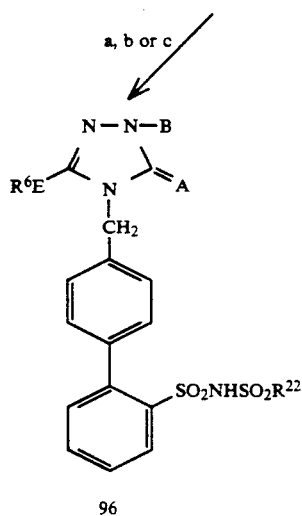

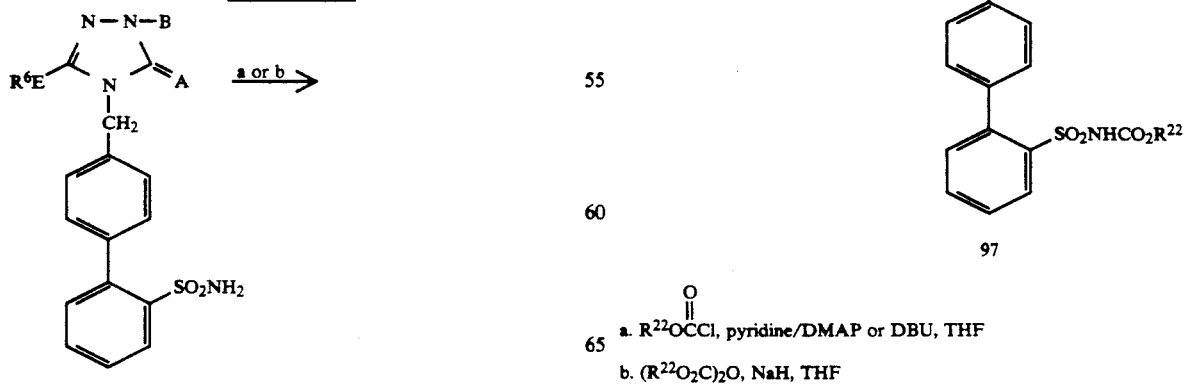

a. $R^{22}O\overset{O}{\underset{\|}{C}}Cl$, pyridine/DMAP or DBU, THF
b. $(R^{22}O_2C)_2O$, NaH, THF Compounds of Formula (I) wherein $R^1$ is

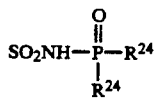

may be prepared by treating sulfonamide (82) with n-butyllithium in THF followed by the treatment of the resulting anion with an appropriately substituted phosphonyl or phosphinyl halide to form the desired compounds (98). (Scheme 23)

SCHEME 23

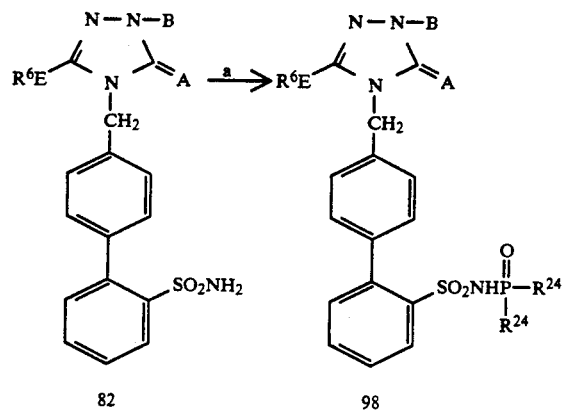

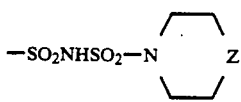

Compounds of Formula (I) wherein $R^1$ is $SO_2N$-$HSO_2N(R^4)(R^9)$ or

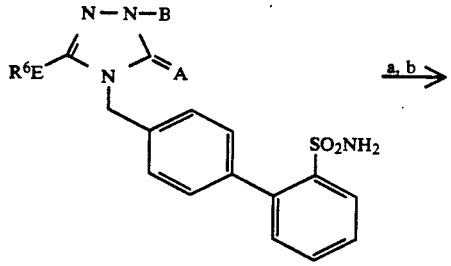

may also be prepared from sulfonamide 82 as outlined in Scheme 24. Treatment of 82 with sodium hydride or n-butyllithium in THF and then with an appropriate sulfamoyl halide may produce the desired product 99 or 100.

SCHEME 24

-continued SCHEME 24

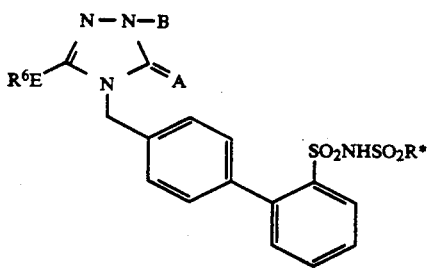

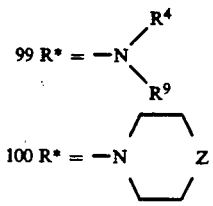

a. nBuLi or NaH in THF
b. R* $SO_2Cl$

The route shown in Scheme 24A is particularly useful for preparing analogs of 96, 97, 98, 99, and 100, in which the distal ring of the biphenylmethyl side chain bears a substituent (for example, alkyl) at the 5'-position in addition to the sulfamoyl moiety at the 2'-position. A 4-substituted benzenesulfonyl chloride 100A is converted to the N-t-butylsulfonamide 100B as in Scheme 19. Based on a literature method [M. J. Sharp, W. Cheng, and V. Snieckus, Tetrahdron Lett., 28, 5093 (1987)], metalation ortho to the sulfonamide is achieved with n-butyllithium in THF at −40° to 0° C. Then treatment with triisopropyl borate followed by acidic work-up affords the boronic acid 100C. This undergoes cross-coupling with 4-bromobenzyl alcohol (92) in the presence of tetrakis(triphenylphosphine)palladium(0) according to literature methods [M. J. Sharp, et al., op. cit.; N. Miyaura, T. Yanagi, and A. Suzuki, Synth. Commun., 11, 513 (1981)] to give the biphenylmethyl alcohol 100D. A triazolinone base 100E, prepared as in the previous schemes, can be directly alkylated with 100D in the presence of diisopropyl azodicarboxylate (DIAD) in THF at −10° C. to room temperature, following the methods of Mitsunobu [O. Mitsunobu, Synthesis, 1 (1981)]. The product 100F can be further converted to compounds of formula I analogous to 96-100 by the methods of Schemes 21 to 24.

SCHEME 24A

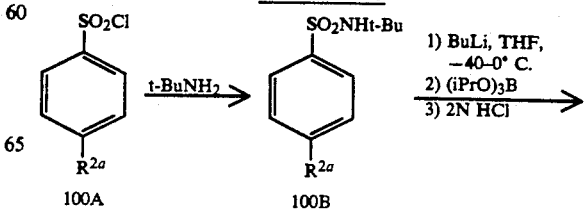

-continued
SCHEME 24A

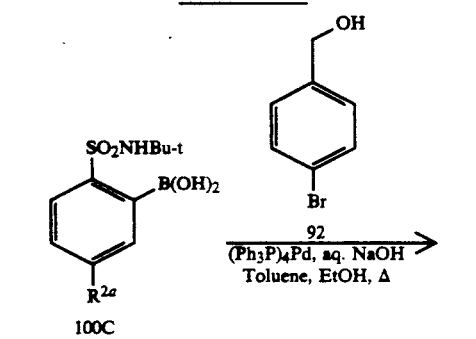

100C

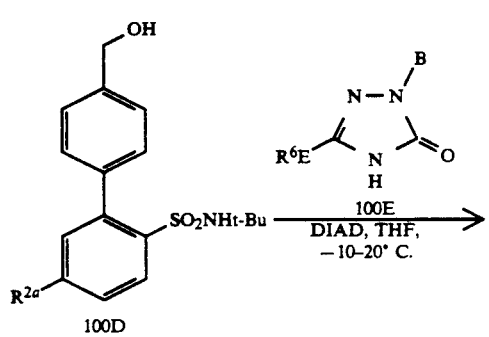

100D

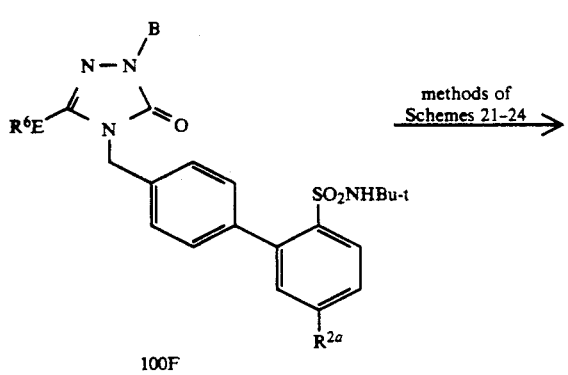

100F compounds of formula I

SCHEME 24B

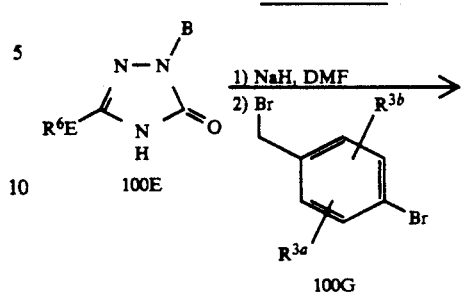

100G

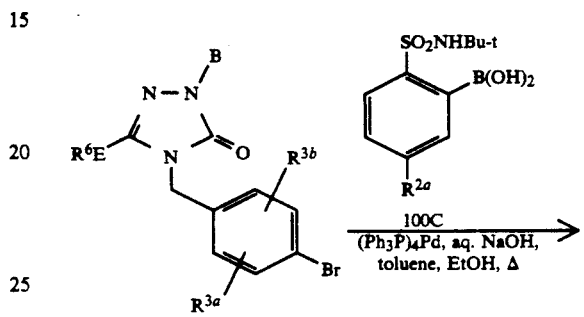

100H

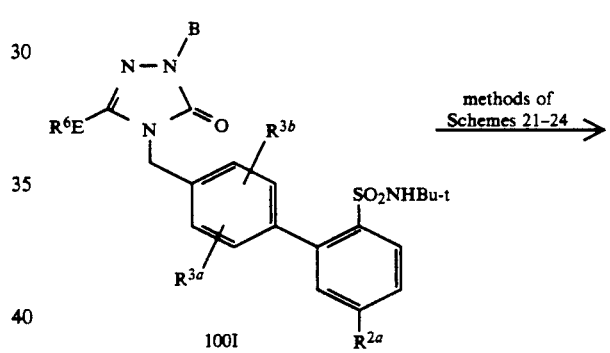

100I compounds of formula I

Scheme 24B illustrates a variation of Scheme 24A in which the coupling reaction to form the biphenyl side chain is carried out after alkylation of the triazolinone ring. This variation is especially useful for the introduction of one or two substituents (R$^{3a}$, R$^{3b}$) on the proximal ring of the biphenyl. The distal ring may be unsubstituted or substituted (for example, as shown in the scheme, R$^{2a}$ may be hydrogen or alkyl). The triazolinone 100E is deprotonated with a base such as sodium hydride in a solvent like DMF and treated with the 4-bromobenzyl bromide derivative 100G to yield the N$^4$-benzylated triazolinone 100H. Useful examples of 100G include 4-bromo-2-fluorobenzyl bromide (commercially available) and 4-bromo-3-fluorobenzyl bromide (readily prepared by photochemical bromination of the commercially available 4-bromo-3-fluorotoluene). Palladium(0)-catalyzed coupling of 100H with the boronic acid 100C as in Scheme 24A gives triazolinone 100I bearing the substituted biphenyl side chain. This is elaborated to the desired compounds of formula I by the methods of Schemes 21-24.

In a variation of Scheme 24B, shown in Scheme 24B', the 4-bromotoluene derivative 100Ia is coupled with 100C to give the 4-methylbiphenyl product 100Ib. This is photochemically brominated, for example, with N-bromosuccinimide in the presence of an initiator such as AIBN or benzoyl peroxide, or with bromine, to give the bromomethyl derivative 100Ic. Alkylation of the sodium salt of triazolinone 100E with 100Ic affords 100I, which is processed further as in Scheme 24B to yield the desired compounds of formula I.

SCHEME 24B'

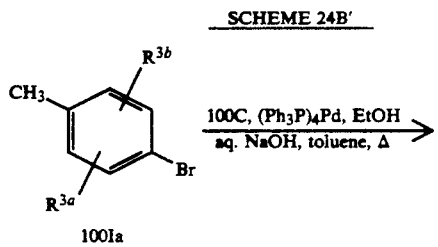

100Ia

-continued
SCHEME 24B'

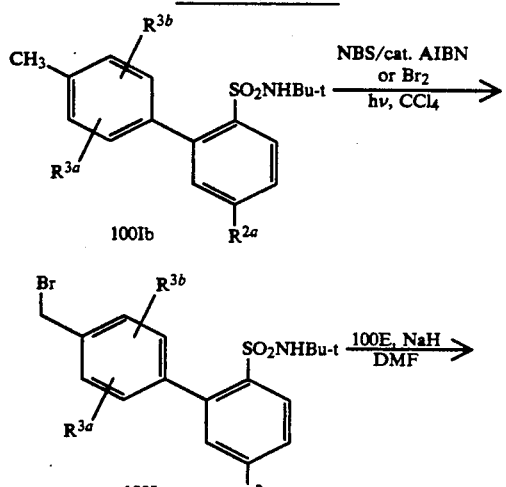

-continued
SCHEME 24C

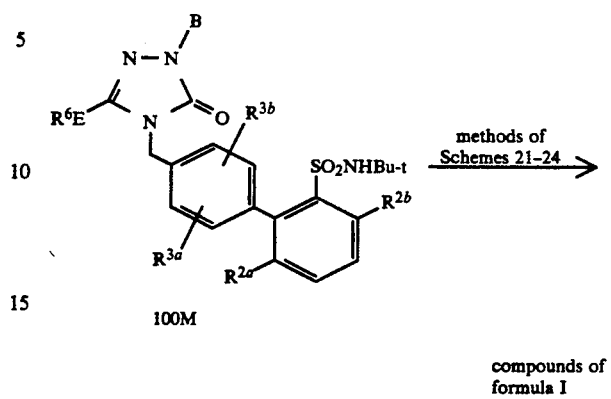

↓ methods of Schemes 21-24 compounds of formula I

A further variation of Schemes 24A, 24B, and 24B', depicted in Scheme 24C, allows the formation of compounds of formula I with a different pattern of substitution on the distal ring of the biphenyl side chain. This method is most effective when a 2,5-disubstituted benzenesulfonyl chloride 100J is available, such that $R^{2a}$ and $R^{2b}$ are not hydrogen and are not strongly activating for the ortho-directed metalation step. Under these circumstances, transformation of 100J as in Scheme 24A via the t-butylsulfonamide 100K leads to a single regioisomer of the boronic acid 100L. (A useful example of 100J is 2,5-difluorobenzenesulfonyl chloride, which may be prepared from 2,5-difluoroaniline via diazotization and treatment with $CuCl_2/SO_2$ as in Scheme 17.) By the methods of Schemes 24A and 24B, 100L is converted to the substituted biphenylmethyl triazolinone 100M. Further transformation to the desired compounds of formula I is accomplished as previously described.

The synthesis of triazolinones having at $N^2$ a phenyl group substituted with trifluoromethyl at the 2-position and acylamino at the 5-position is presented in Scheme 24D. Thus, 2-bromo-5-nitroaniline (100N) is diazotized and reduced to the arylhydrazine 100P. By the methods of Scheme 3, this is converted to the 2-bromo-5-nitrophenyl-substituted triazlinone 100Q. Based on literature conditions [D.-B. Su, J.-X. Duan, and Q.-Y. Chen, *Tetrahedron Lett.*, 32, 7689 (1991)], 100Q is heated at about 120° C. with methyl chlorodifluoroacetate, cuprous iodide, potassium fluoride, and potassium bromide in DMF, resulting in displacement of bromo by trifluoromethyl to give 100R. This transformation may be carried out at the N-t-butyl-biphenylsulfonamide stage corresponding to 100I or 100M. Reduction of the nitro group in 100R with hydrogen in the presence of a catalyst like platinum oxide or with stannous chloride-hydrochloric acid affords the amine 100S, which is acylated as in Scheme 16A to give the desired acylamino product 100T.

SCHEME 24C

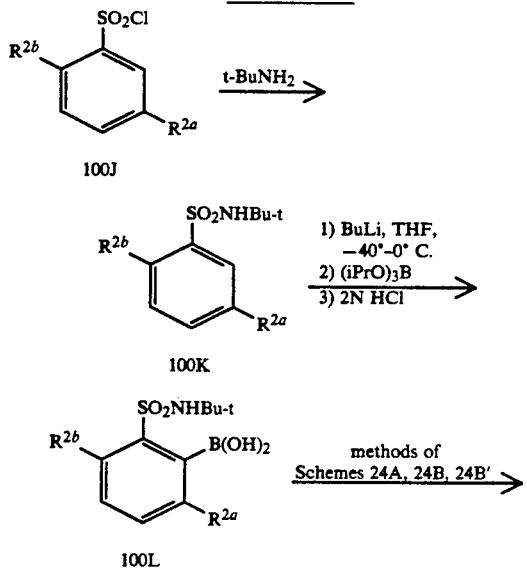

SCHEME 24D

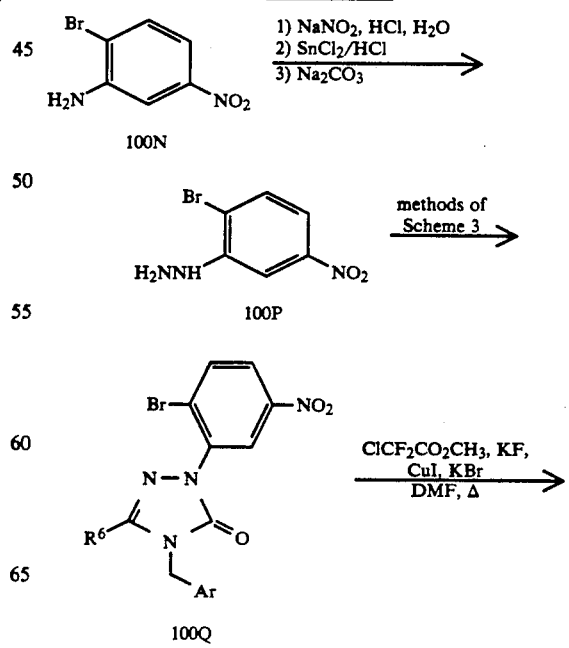

-continued
SCHEME 24D

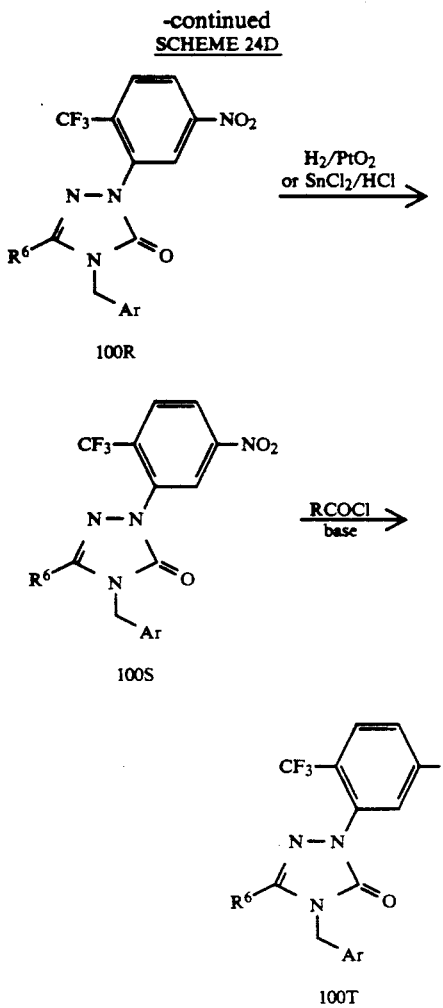

Scheme 24E illustrates the synthesis of triazolinones in which the N²-phenyl moiety is substituted with a trifluoromethyl group at the 2-position and a substituted aminocarbonyl or ketone group at the 5-position. The commercially available compound 4-bromo-3-nitrotoluene (100U) is converted to the trifluoromethyl analog 100V by the chemistry described in Scheme 24D. The methyl group of 100V is oxidized to the carboxylic acid with potassium permanganate [H. T. Clarke and E. R. Taylor, Org. Syn., Coll. Vol., 2, 135 (1943)] and then esterified to the methyl ester 100W under standard conditions by heating with methanol in the presence of concentrated sulfuric acid. Catalytic hydrogenation of 100W provides the amine 100X, which is converted to the substituted triazolinone 100Y by the methods of Scheme 24D. Following the methods of Scheme 16, the methyl ester of 100Y is transformed to the N-substituted aminocarbonyl group (as in 100Z) or the acyl group (as in 100AA).

SCHEME 24E

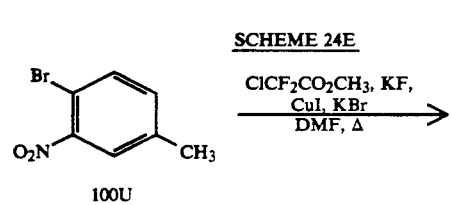

-continued
SCHEME 24E

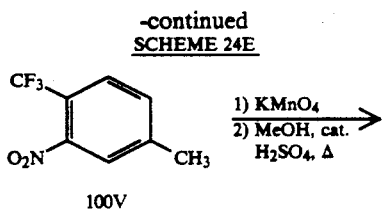

Compounds of Formula (I) wherein $R^1$ is —NHSO$_2$NHSO$_2R^{22}$ or

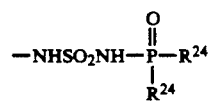

may be prepared from arylamine (102) as outlined in Scheme 25. The arylamine (102) obtained from the corresponding nitro compound 101 can be treated with t-butylsulfamoyl chloride to afford the protected amino sulfonamide (103). The amino sulfonamide (104) obtained after removal of the t-butyl protecting group may then be reacted with an appropriate acylating agent in the presence of a base such as pyridine or DBU in an organic solvent such as THF or DMF to form the desired products 105 or 106.

Compounds of the Formula (I) wherein $R^1$ is —NHSO$_2$R$^{22}$ may be prepared by the reaction of an appropriate sulfonyl halide (R$^{22}$SO$_2$Cl) or sulfonyl imidazole derivative with the aryl amine 102 in the presence of an appropriate base such as pyridine, triethylamine or DBU.

described in U.S. Pat. No. 4,910,019. The cyano derivatives (107), obtained as described in preceding Schemes 1–15, can be converted into the corresponding amidoxime (108) by treatment with hydroxylamine hydrochloride and sodium methoxide in an organic solvent, such as methanol or DMSO. The amidoxime (108) then can be treated with base and thionyl chloride in an aprotic solvent to form the desired 1,2,3,5-oxathiadiazole-2-oxide (109). Similarly, the oxathiadiazole-2,2-dioxide 110 can be prepared by treatment of amidoxime 108 with a base and sulfuryl chloride. As shown in Scheme 27, the cyano precursor (62b) may be converted into the

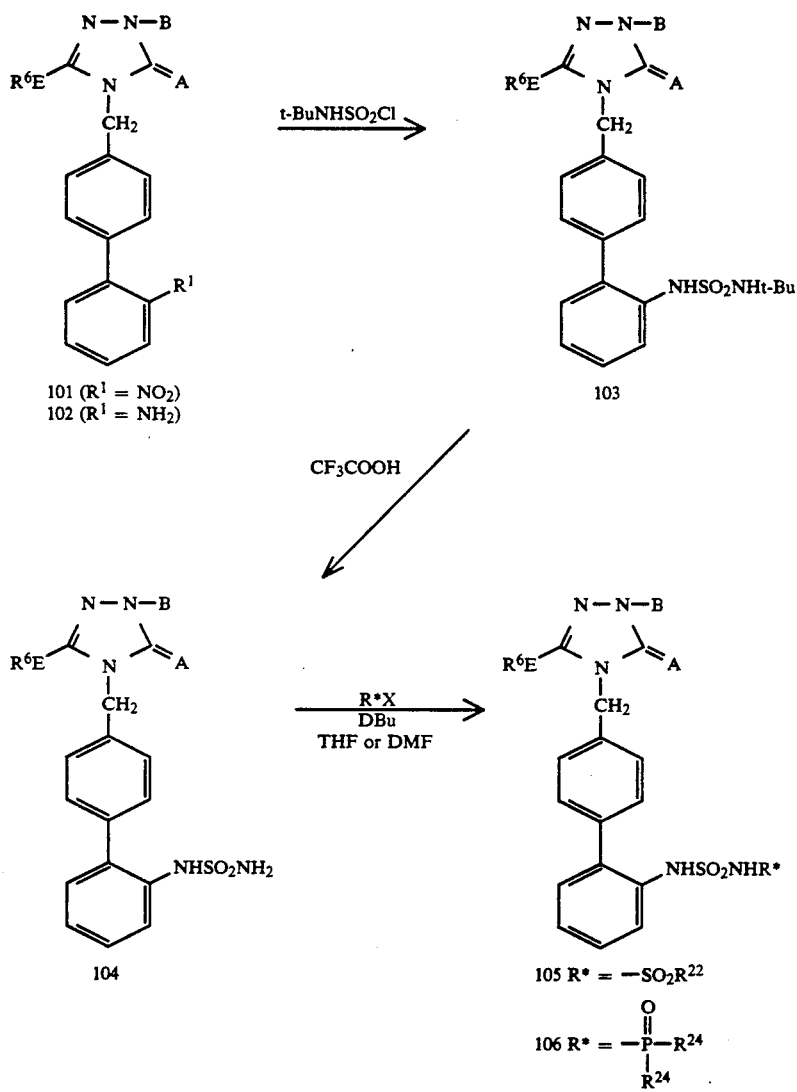

SCHEME 25

Compounds of Formula (I) and the benzyl halides of the formula (113) wherein $R^1$ is 1,2,3,5-oxathiadiazole-2-oxide may be prepared from the corresponding cyano derivative (107) or cyano precursor (62b) as outlined in Schemes 26 and 27, respectively utilizing procedures desired 1,2,3,5-oxathiadiazole (112) which is then protected with the trityl group prior to the formation of the desired benzyl halide (113). The protecting group is removed subsequent to the alkylation of heterocycle 13 to give the desired product (114).

SCHEME 26

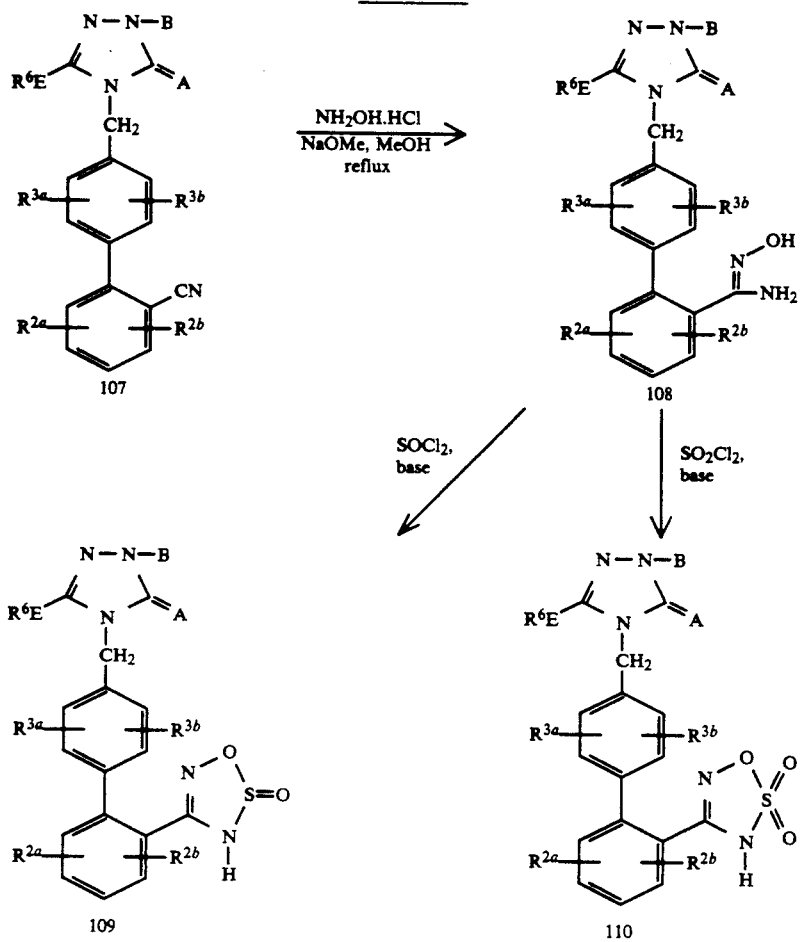

SCHEME 27

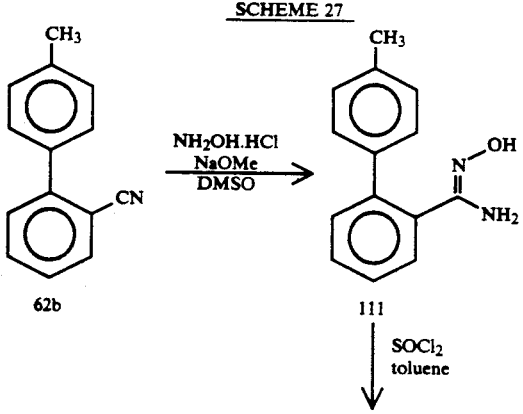

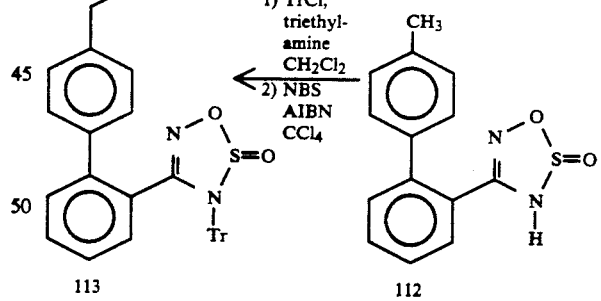

Compounds of Formula (I) and the benzyl halides of the formula (3) wherein $R^1$ is 1,2,3,5-thiatriazole-1-oxide may be prepared from the corresponding precursors 114 or 119 as outlined in Schemes 28 and 29, respectively. Intermediate 119 may be prepared from the biphenyl 62a according to the scheme illustrated (see procedures in U.S. Pat. No. 4,870,186). Intermediates (115) and (119) can be treated with $SOCl_2$ (see procedures in: *Ber. Deutsch. Chem. Ges.* 1971, 104 pp 639) to give intermediates, 116 and 120. Bromination of the N-protected compounds 117 and 121 provides intermediates 118 and 122 respectively. After alkylation with an appropriate heterocycle, the trityl group of the intermediate derived from 118 is removed with protic acid and the cyanoethyl group of the intermediate derived from 122 is removed upon treatment with hydroxide. Alternatively, 118 and 122 may be prepared as shown in Scheme 30 and 31. Treatment of 123 with SOCl$_2$ (see procedures in: *Ber. Deutsch. Chem. Ges.* 1971, 104 pp 639) provides 115, which under mild hydrolytic conditions provides 116. The conversion of 116 to 118 is as described for Scheme 28. Alkylation of the trityl protected analog (125) by treatment with a base such as NaH and an alkyl halide would provide 117, which then may be converted to 122 as previously described.

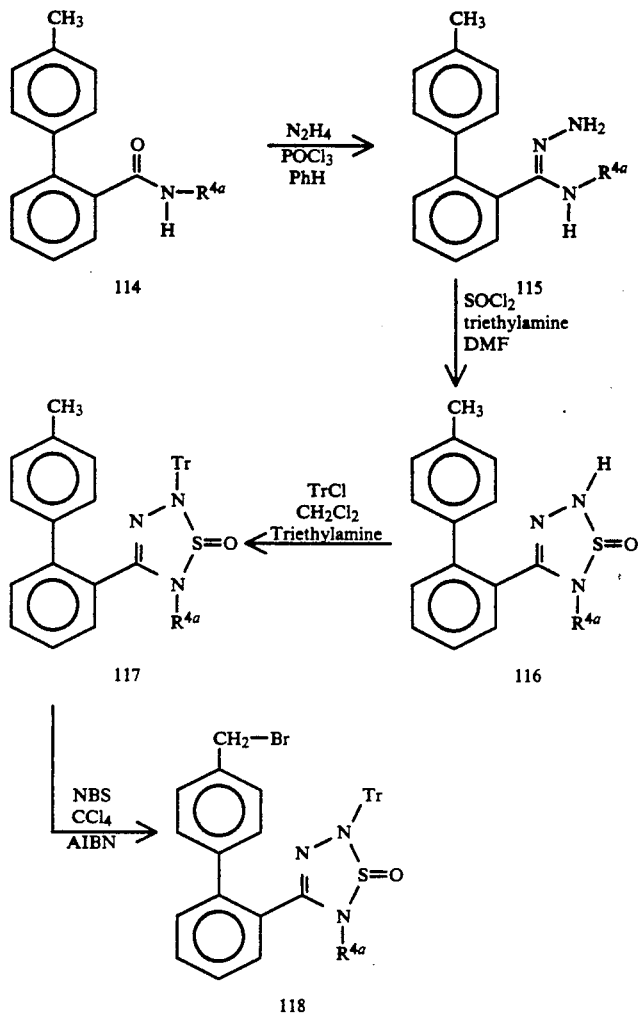

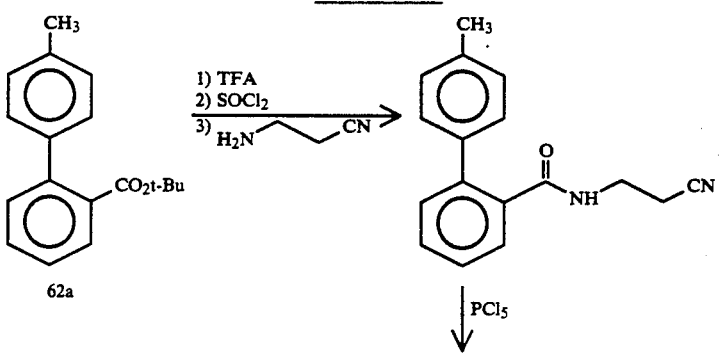

SCHEME 29
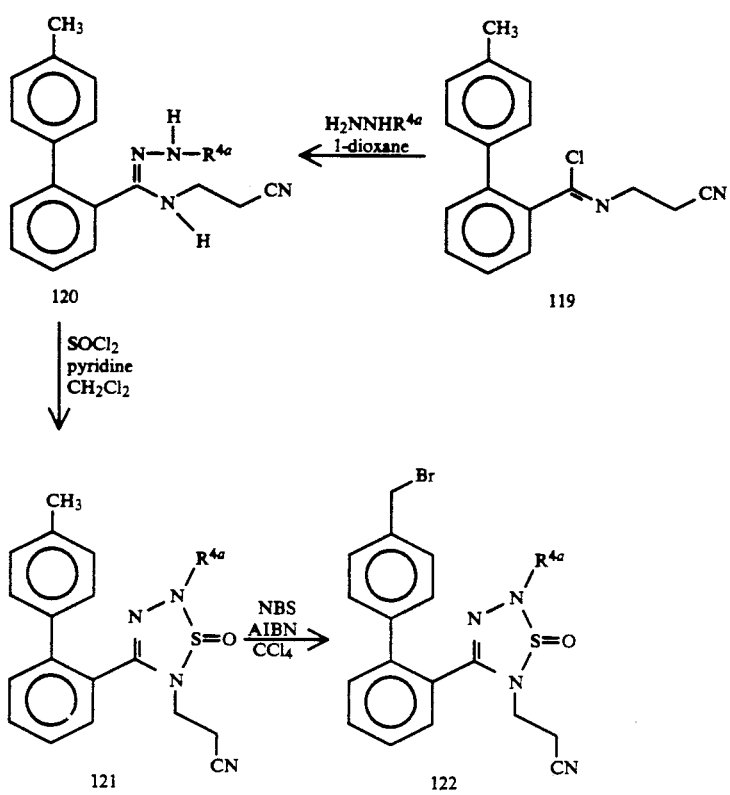
SCHEME 30
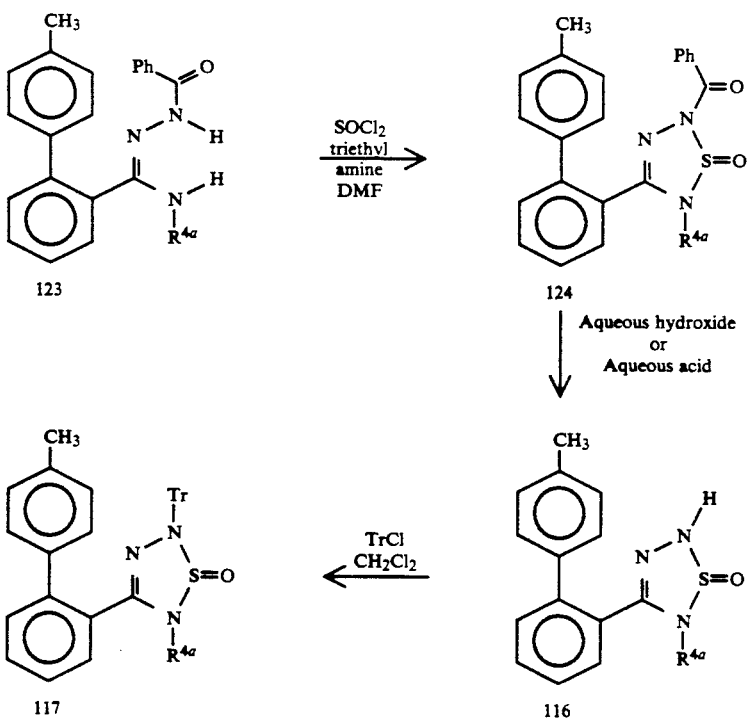

SCHEME 30

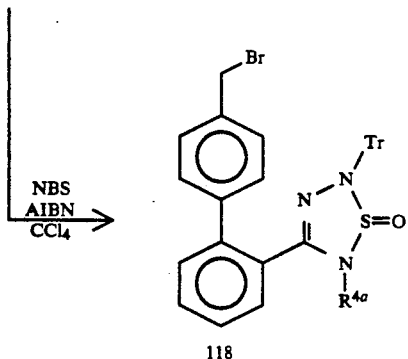

SCHEME 31

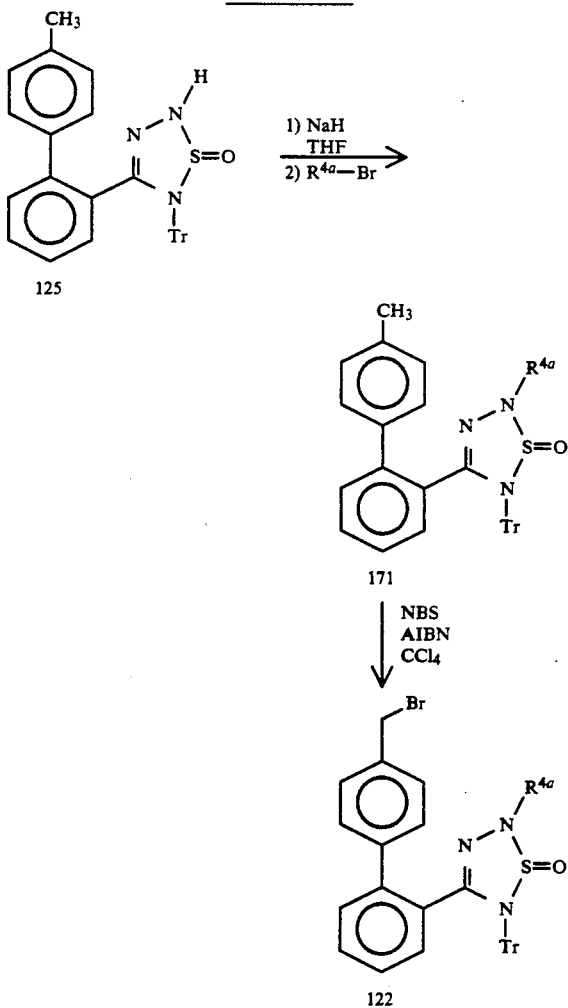

Compounds of Formula (I) and the benzyl halides of formula 14 wherein $R^1$ is 1,2,3,5-thiatriazole-1,1-dioxide-4-yl may be prepared using procedures described in *Monatsh. Chem.*, 1985, 116, pp 1321 and described herein. Sequential treatment of intermediates such as 119 or 115 with n-BuLi and $SO_2F_2$ will provide the 1,2,3,5-thiatriazol-1,1-dioxide analogs of 116 and 120. Further elaboration of the afore mentioned analogs by the methods described for the conversion of 116 to 118 in Scheme 28 and the methods described for the conversion of 120 to 122 in Scheme 29 would give the benzyl halides of formula (2) wherein $R^1$ is 2-triphenylmethyl-1,2,3,5-thiatriazole-1,1-dioxide-4-yl and 5-triphenylmethyl-1,2,3,5-thiatriazole-1,1-dioxide-4-yl, respectively.

Compound of Formula (I) wherein $R^1$ is 3-oxo-1,2,4-thiadiazolidine-1,1-dioxide may be prepared from the nitro derivative (62c) as outlined in Scheme 32. The amino compound 126 obtained from 62c may be reacted with t-butyl sulfamoylchloride to form the intermediate 127 which then can be alkylated with an appropriate bromoacetic acid derivative to give 128. Treatment of 128 with trifluoroacetic acid followed by the treatment with an appropriate base such as sodium or potassium alkoxide may produce the desired compound 129, which can be elaborated further to give the key alkylating agent 131 as outline in the scheme. Alkylation of an appropriate heterocyclic compound with 131 may then furnish the desired antagonist.

SCHEME 32

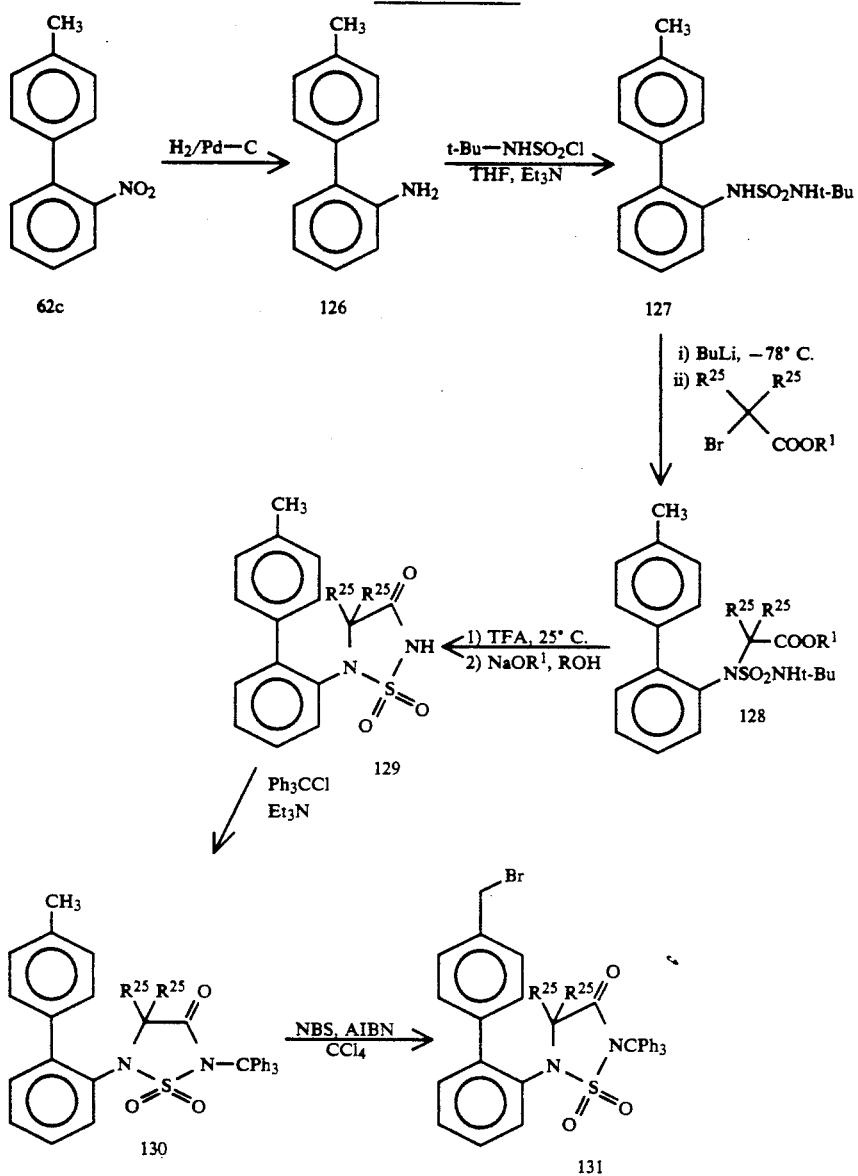

Compound of Formula (I) wherein $R^1$ is 5-aminosulfonyl-1,2,4-oxadiazole may be prepared using the bromomethyl biphenyl derivative 135 and an appropriate heterocyclic compound. The synthesis of 135 can be accomplished as outlined in Scheme 33. The amidoxime 111 may be reacted with S-methylisothiourea to form the 5-amino-1,2,4-oxadiazole 132, which can be then treated with an appropriate sulfonylchloride to give the corresponding 5-aminosulfonyl-1,2,4-oxadiazole 133. The appropriately protected derivative 134 then can be brominated to form the desired alkylating agent 135.

SCHEME 33

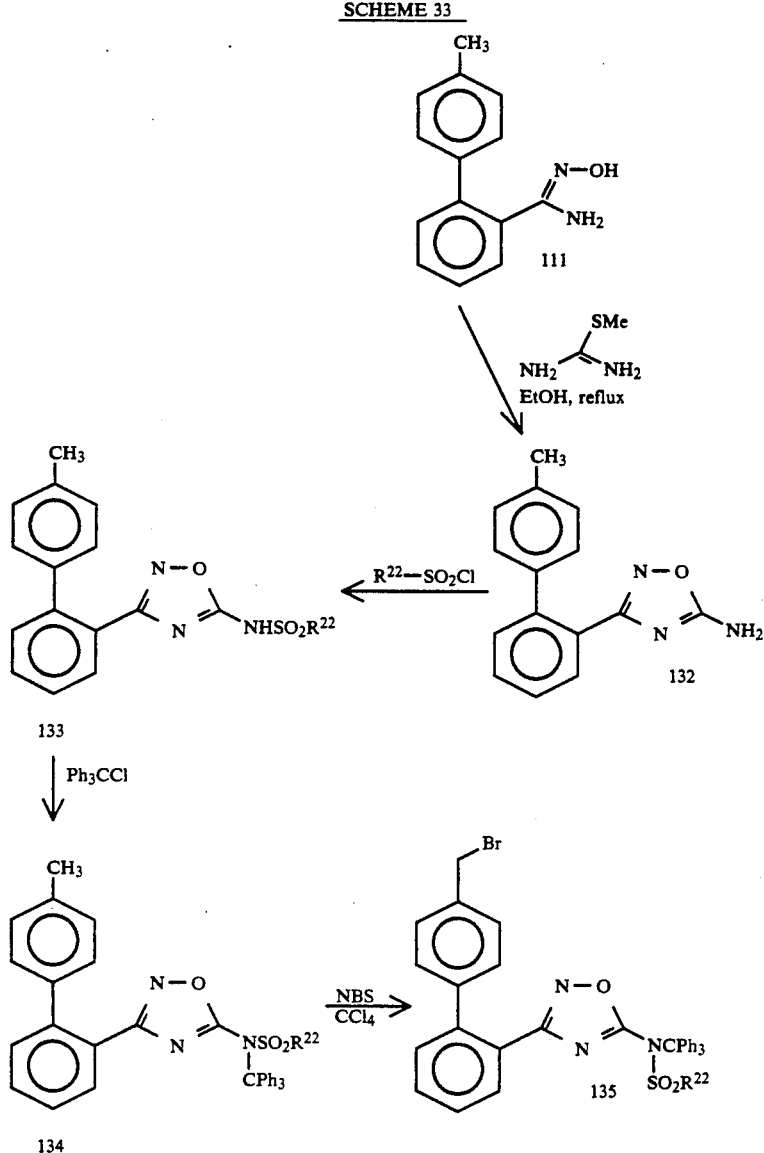

Compounds of Formula (I) wherein $R^1$ is 3-aminosulfonyl-1,2,4-oxadiazole can be prepared starting from the carboxylate derivative (62a) as outlined in Scheme 34. The ester derivative 136 obtained from 62a is treated with N-hydroxy guanidine sulfate in the presence of an alkoxide base to form the 3-amino-1,2,4-oxadiazole derivative 137, which may be reacted with an appropriate sulfonyl chloride to give the 3-aminosulfonyl-1,2,4-oxadiazole compound 138. The compound 139 can be prepared from 138 as outlined in Scheme 35.

SCHEME 34

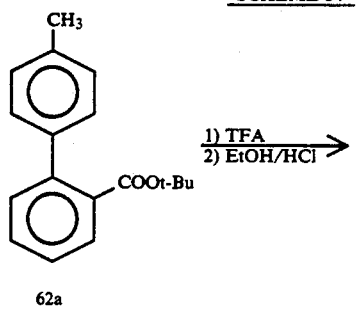

-continued
SCHEME 34

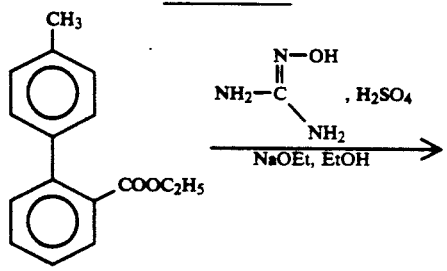

136

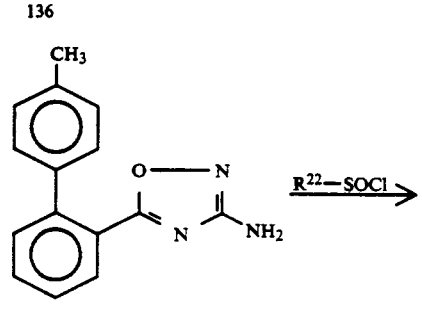

137

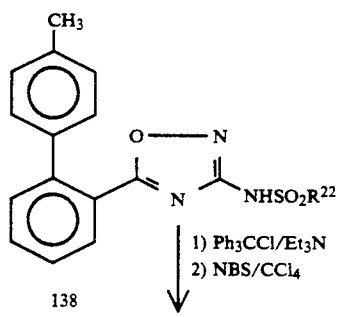

138

1) Ph₃CCl/Et₃N
2) NBS/CCl₄

-continued
SCHEME 34

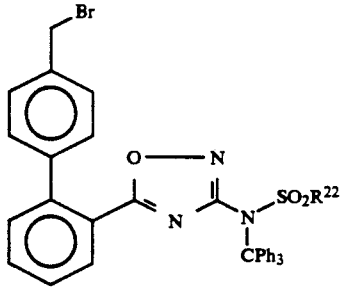

139

Compounds of Formula (I) and the benzyl halides of formula (2) wherein R¹ is 1,2,3-oxathiazin-4(3H)-one-2,2-dioxide-6-yl may be prepared as outlined in Scheme 35. As shown and according to procedures in *Angew. Chem. Int. Edn.*, (1973), 12, pp 869, the betaketoester (140) is treated with fluorosulphonyl isocyante, heated to extrude CO₂ and iso-butene, then treated with base such as KOH to form the oxathiazolinone dioxide intermediate (141). Treatment of (141) with triphenylmethyl chloride and triethylamine in CH₂Cl₂ gives (142) which in turn is converted to benzyl halide (143) by treatment with N-bromosuccinimide, AIBN, in CCl₄ at reflux.

SCHEME 35

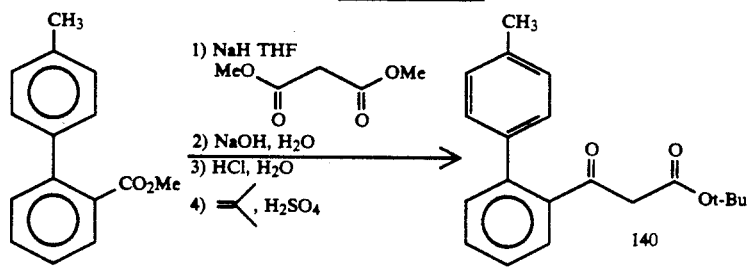

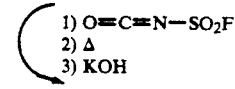

1) O=C=N—SO₂F
2) Δ
3) KOH

SCHEME 35

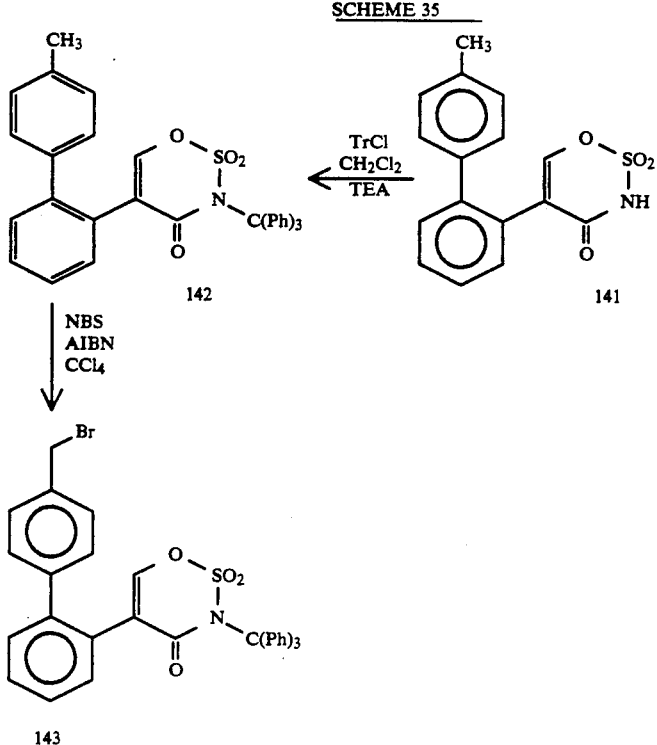

Compounds of Formula (I) wherein R¹ is oxamic acid may be prepared utilizing procedures described in J. Med. Chem., 1981, 24, pp 742-748 and as outlined in Scheme 36. The amine 104 is reacted with ethyl oxalyl chloride in the presence of a base such as pyridine or triethylamine and a solvent such as $CH_2Cl_2$ to form the intermediate oxalyl ester which is subsequently saponified with hydroxide to form oxamic acid 144.

SCHEME 36

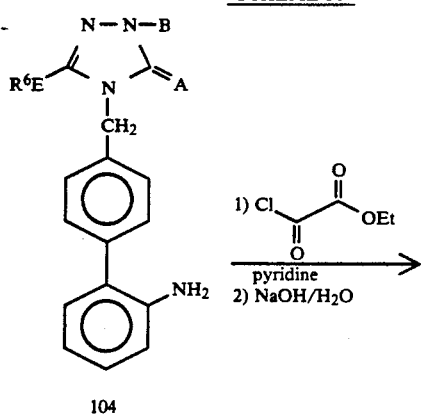

-continued
SCHEME 36

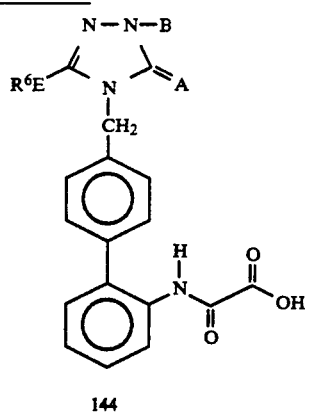

Compounds of Formula (I) wherein R¹ is $-SO_2NR^{23}OR^{23}$ may be prepared as outlined in Scheme 37. The key intermediate 147 is prepared by the reaction of an appropriate heterocyclic compound (1), preferably as an alkali metal salt, with the alkylating agent 145 (prepared from 94). The compound 149, prepared from the sulfonyl chloride 148 and O-t-butylhydroxylamine, is then reacted with 147 in the presence of a Pd(0) catalyst to give 150. Removal of the t-butyl protecting group produces the desired N-hydroxy sulfonamide 151.

SCHEME 37

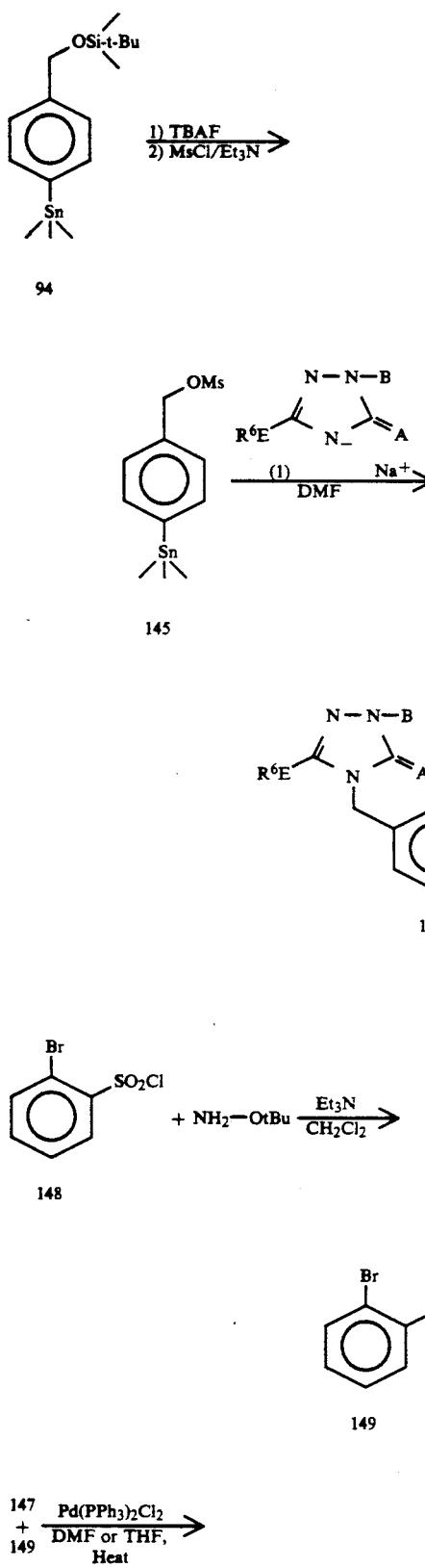

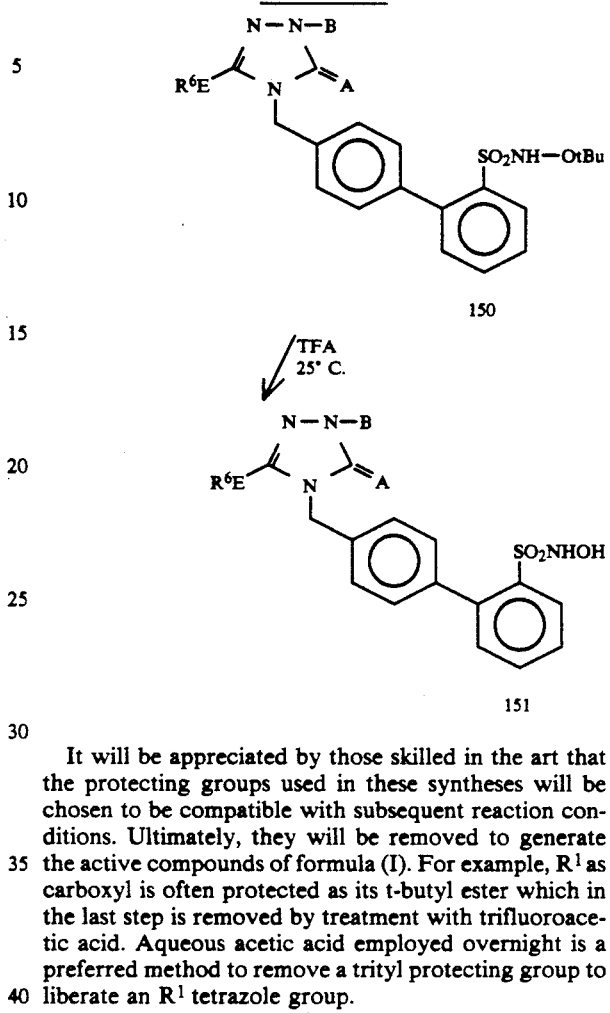

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (A II) is a powerful arterial vasoconstrictor, and it exerts its action by interacting with specific receptors present on cell membranes. In order to identify A II antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM MgCl$_2$ buffer containing 0.2% Bovine Serum Albumin and 0.2 mg/ml Bacitracin and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Receptor assay using Bovine adrenal cortex preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [Na$_2$HPO$_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of a potential AII antagonist which gives 50% displacement of the total specifically bound $^3$H-angiotensin II is presented as a measure of the efficacy of such compounds as AII antagonists.

Receptor assay using rat brain membrane preparation

Membranes from rat brain (thalamus, hypothamus and midbrain) are prepared by homogenization in 50 mM Tris HCl (pH 7.4), and centrifuged at 50,000×g. The resulting pellets are washed twice in 100 mM NaCl, 5 mM Na$_2$•EDTA, 10 mM Na$_2$HPO$_4$ (pH 7.4) and 0.1 mM PMSF by resuspension and centrifugation. For binding assays, the pellets are resuspended in 160 volumes of binding assay buffer (100 mM NaCl, 10 mM Na$_2$HPO$_4$, 5 mM Na$_2$•EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$, Ile$^8$-angiotensin II (23-46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an IC$_{50}$>50 μM determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300-375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down the spinal column. The rats are immediately placed on a Harvard Rodent Ventilator (rate—60 strokes per minute, volume—1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidine sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, verapamil, and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereo-typed motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and buspirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto.

EXAMPLE 1

5-n-Butyl-4-[(2'-carboxybiphenyl-4-yl)methyl]-2,4-dihydro-3H-1,2,4-triazole-3-thione Step A: N-[[2'-(t-Butoxycarbonyl)biphenyl-4-yl]methyl]phthalimide A mixture of 2.99 g (8 mmole, based on 93% purity) of 4-bromomethyl-2'-(t-butoxycarbonyl)biphenyl (EP 253,310), 1.63 g (8.8 mmole) of potassium phthalimide, and 24 ml of dry dimethylformamide (DMF) was stirred at room temperature for 7 hours and then partitioned between 200 ml of ether and 250 ml of H$_2$O. The organic phase was washed with 4×250 ml of H$_2$O, then dried (MgSO$_4$), filtered, and concentrated. The residue was leached twice with hot ether (15-20 ml), which was decanted off after cooling. The remaining solid was collected on a filter, washed with petroleum ether, and dried to yield 2.08 g of colorless crystals, mp 108.5°–109°, homogeneous by TLC in 4:1 hexane-EtOAc. The residue from evaporation of the mother liquor was triturated with two portions of ether to give a second crop of colorless crystals: 0.58 g, mp 122°–123° (preliminary softening). Despite the difference in melting point, the second crop was identical to the first by NMR and TLC. The total yield was thus 2.66 g (82%).

Analysis ($C_{26}H_{23}NO_4$): Calcd: C, 75.53; H, 5.61; N, 3.39; Found: C, 75.25; H, 5.75; N, 3.18.

300 MHz NMR ($CDCl_3$) δ1.17 (s, 9H), 4.90 (s, 2H), 7.2–7.9 (m, 12H).

Step B: 4-Aminomethyl-2'-(t-butoxycarbonyl)biphenyl

A mixture of 2.62 g (6.35 mmole) of N-[[2'-(t-butoxycarbonyl)biphenyl-4-yl]methyl]phthalimide, 1.21 ml (1.25 g, 25 mmole) of 100% hydrazine hydrate, and 35 ml of absolute ethanol was stirred at room temperature for 7.5 hours. During this time all of the solid gradually dissolved, followed by precipitation. Glacial acetic acid (3.7 ml) was added, and stirring was continued overnight. The white solid was then removed by filtration, and the filtrate was concentrated at room temperature. The residual oil was taken up in 100 ml of ether and washed with 2×50 ml of saturated aqueous $Na_2CO_3$ solution. Next, the product was extracted by shaking the ethereal solution with 50 ml of 0.5N HCl. The aqueous layer was separated and basified by addition of excess saturated $Na_2CO_3$. The product, which oiled out, was extracted with 100 ml of ether. The other phase was dried ($Na_2SO_4$), filtered, and concentrated at 30° C. to give 1.58 g (88%)of a very pale yellow, viscous oil, homogeneous by TLC in 95:5:0.5 $CH_2Cl_2$-MeOH-concd. $NH_4OH$.

Analysis ($C_{18}H_{21}NO_2 \cdot 0.25 H_2O$): Calcd: C, 75.10; H, 7.53; N, 4.87; Found: C, 75.14; H, 7.39; N, 4.78.

300 MHz NMR ($CDCl_3$) δ1.27 (s, 9H), 1.50 (br s, 2H), 3.92 (s, 2H), 7.2–7.8 (m, 8H).

Step C: Methyl N-[[2'-(t-Butoxycarbonyl)biphenyl-4-yl]methyl]dithiocarbamate

A solution of 1.415 g (5 mmole) of 4-aminomethyl-2'-(t-butoxycarbonyl)biphenyl and 751 μl (545 mg, 5.4 mmole) of triethylamine in 5 ml of methanol was stirred under $N_2$ at room temperature as a solution of 342 μl (434 mg, 5.7 mmole) of carbon disulfide in 2 ml of methanol was added dropwise over about 10 minutes. After 2.5 hours the solution was cooled in an ice-methanol bath, and a solution of 311 μl (710 mg, 5 mmole) of methyl iodide in 2 ml of methanol was added dropwise over about 10 minutes. The cooling bath was removed, and the solution was allowed to warm to room temperature. After 2 hours the solution was concentrated at 25° C. The residue was partitioned between 50 ml of ether plus 10 ml of $CH_2Cl_2$ and 50 ml of 0.2N HCl. The organic phase was washed with 25 ml of saturated NaCl solution (aqueous), dried over $MgSO_4$, filtered, and concentrated. Crystallization of the residual oil from ether yielded 1.57 g (84%) of nearly colorless crystals, mp 127.5°–128.5° C., satisfactory purity by TLC in 4:1 hexane-EtOAc; mass spectrum (FAB) m/e 374 (M+1)+.

Analysis ($C_{20}H_{23}NO_2S_2$): Calcd: C, 64.31; H, 6.21; N, 3.75. Found: C, 64.54; H, 6.46; N, 3.82.

300 MHz NMR ($CDCl_3$) δ1.28 (s, 9H), 2.66 (s, 3H), 4.97 (d, J=5 Hz, 2H), 7.13 (br, m 1H), 7.2–7.8 (m, 8H).

Step D: 4-[[2'-(t-Butoxycarbonyl)biphenyl-4-yl]methyl]-3-thiosemicarbazide

A mixture of 1.53 g (4.1 mmole) of methyl N-[[2'-(t-butoxycarbonyl)biphenyl-4-yl]methyl]dithiocarbamate, 796 μl (820 mg, 16.4 mmole) of hydrazine hydrate, and 10 ml of absolute ethanol was stirred at reflux under $N_2$. After 2 hours the resulting solution was cooled and concentrated. The residual oil was chromatographed on a column of silica gel (elution with 99:1 and the 98:2 $CH_2Cl_2$) to give (after concentration and vacuum-drying) 1.15 g (79%) of a stiff, white foam, mp>45° C. (gradual); homogeneous by TLC in 19:1 $CH_2Cl_2$-MeOH; mass spectrum (FAB) m/e 358 (M+1)+.

Analysis ($C_{19}H_{23}N_3O_2S \cdot 0.1H_2O$): Calcd: C, 63.51; H, 6.51; N, 11.70. Found: C, 63.41; H, 6.50; N, 11.54.

300 MHz NMR ($CDCl_3$) δ1.28 (s, 9H), 3.76 (br s, 2H), 4.90 (d, J=5 Hz, 2H), 7.2–7.8 (m, 9H).

Step E: 4-[[2'-(t-Butoxycarbonyl)biphenyl-4-yl]-5-n-butyl-2,4-dihydro-3H-1,2,4-triazole-3-thione A solution of 1.11 g (3.1 mmole) of 4-[[2'-(t-butoxycarbonyl)biphenyl-4-yl]methyl]-3-thiosemicarbazide and 792 μl (745 mg, 4.6 mmole) of trimethyl orthovalerate in 10 ml of 2-methoxyethanol was stirred at reflux under $N_2$ for 15 hours. The cooled solution was concentrated, and the residue was purified by column chromatography on silica gel (gradient elution with 0–1% methanol in $CH_2Cl_2$) to give a gum which could be crystallized by trituration with petroleum ether. The total yield was 828 mg (63%), mp 135°–137° C., homogeneous by TLC in 19:1 $CH_2Cl_2$-MeOH; mass spectrum (FAB) m/e 424 (M+1)+.

Analysis ($C_{24}H_{29}N_3O_2S$): Calcd: C, 68.05; H, 6.90; N, 9.92. Found: C, 67.95; H, 6.65; N, 9.84.

300 MHz NMR ($CDCl_3$) δ0.87 (t, J=7 Hz, 3H), 1.22 (s, 9H), 1.32 (m, 2H), 1.62 (m, 2H), 2.48 (t, J=7 Hz, 2H), 5.27 (s, 2H), 7.2–7.5 (m, 7H), 7.74 (d, J=8 Hz, 1H)

Step F: 5-n-Butyl-4-[(2'-carboxybiphenyl-4-yl)-methyl]-2,4-dihydro-3H-1,2,4-triazole-3-thione A solution of 51 mg (0.12 mmole) of 4-[[2'-(t-butoxycarbonyl)biphenyl-4-yl]methyl]-5-n-butyl-2,4-dihydro-3H-1,2,4-triazole-3-thione in 0.5 ml of anhydrous trifluoroacetic acid was stirred under $N_2$ at room temperature for 2 hours and then evaporated to dryness under a stream of $N_2$. The residue was dissolved in a small volume of methanol and evaporated onto 1 g of silica gel. This was layered on top of a column of silica gel (43×2.4 cm) packed in $CH_2Cl_2$. Gradient elution with 1–5% methanol in $CH_2Cl_2$ containing 0.1% acetic acid eluted two major products. Concentration of fractions containing the first (higher $R_f$) product gave a residue which solidified upon trituration with ether: white powder, mp 218°–219° C., homogeneous by TLC in 95:5:0.1 $CH_2Cl_2$-MeOH-AcOH; mass spectrum (FAB) m/e 368 (M+1)+.

Analysis ($C_{20}H_{21}N_3O_2S \cdot 0.5H_2O$): Calcd: C, 63.80; H, 5.89; N, 11.16. Found: C, 63.93; H, 5.86; N, 10.82.

300 MHz NMR (DMSO-$d_6$) δ0.79 (t, J=7.5 Hz, 3H), 1.25 (m, 2H), 1.46 (m, 2H), 2.53 (partially obsured t, J=8 Hz, 2H), 5.29 (s, 2H), 7.25–7.4 (m, 5H), 7.45 (t, J=8 Hz, 1H), 7.57 (t, J=8 Hz, 1H), 7.72 (d, J=8 Hz, 1H), 12.7 (v br s, 1H)

Concentration of fractions containing the second (lower $R_f$) product and work-up as above gave a white powder, mp 166.5°–168° C. dec., identified as 3-n-butyl-5-(t-butylthio)-4-[(2'-carboxybiphenyl-4-yl)methyl]-4H-1,2,4-triazole, a by-product arising from t-butyl migration.

EXAMPLE 2

5-n-Butyl-2,4-dihydro-4-[[2'-cyanobiphenyl-4-yl]methyl]-3H-1,2,4-triazol-3-one Step A: Ethyl Valerate Carbethoxyhydrazone To a solution of 7.0 g (25.3 mmole) of ethyl valerimidate hydrochloride [prepared by method of A. J. Hill and I. Rabinowitz, *J. Am. Chem. Soc.*, 48, 734 (1926)] in 35 ml of dry ethanol stirred under $N_2$ at $-78°$ C. was added dropwise a solution of 24 g (23 mmole) of ethyl carbazate in 35 ml of dry ethanol. Precipitation occurred during the addition, which took 20 minutes and was accompanied by a rise in the internal temperature to $-50°$ C. The mixture was allowed to stand at 5° C. for 60 hours and then filtered. The filtrate was concentrated, and the residue was flash chromatographed on a silica gel column (elution with 98.5:1.5 $CH_2Cl_2$—MeOH), yielding a clear oil, homogeneous by TLC in 97:3 $CH_2Cl_2$—MeOH; mass spectrum (FAB) m/e 217 $(M+1)^+$. NMR suggested a mixture of syn and anti isomers.

200 MHz NMR ($CDCl_3$) δ0.91 (t, J=7 Hz, 3H), 1.2–1.4 (m, 8H), 1.4–1.6 (m, 2H), 2.2–2.4 (m, 2H), 3.95–4.3 (m, 4H), 6.91, 8.11 (br s, 1H total).

Step B: 4-Azidomethyl-2'-cyanobiphenyl

To a stirred suspension of 20 mmole of 4-bromomethyl-2'-cyanobiphenyl [P. E. Aldrich, M. E. Pierce, and J. J. V. Duncia, European Patent Application 291,969 (1988)] in 55 ml of dry DMSO was added 1.23 g (25 mmole) of freshly pulverized lithium azide, and the mixture was stirred at room temperature under $N_2$. Within a few minutes virtually all of the solid had dissolved, accompanied by a mild exotherm, and this was followed immediately by precipitation of product. After 4 hours the solid was collected on a filter and washed with some methanol, then with a relatively large volume of $H_2O$, and finally again with methanol. The solid was air-dried overnight and then dried further in a vacuum oven at 70° C. (<1 mm) to give white crystals, satisfactory purity by TLC (9:1 hexane-ethyl acetate) for use in the next step. From the combined filtrate and washes was recovered a less pure second crop (cream-colored crystals), which was also usable in the next step. Mass spectrum (FAB) m/e 235 $(M^+ +1)$.

Step C: 4-Aminomethyl-2'-cyanobiphenyl

A solution of 4-azidomethyl-2'-cyanobiphenyl (4.68 g, 20 mmole) in 40 ml of dry tetrahydrofuran (THF) was stirred under $N_2$ at room temperature as 5.3 g (20 mmole) of triphenylphosphine was added in small portions over a period of about 10 minutes. After 2 hours, 532 μl (532 mg, 29.6 mmole) of $H_2O$ was added. After an additional 23 hours, the solution was concentrated in vacuo to give a pale golden gum. This material was chromatographed on a column of silica gel (50×8.5 cm) packed in $CH_2Cl_2$. The column was eluted with a gradient of 0–6% methanol in $CH_2Cl_2$. Concentration of the product fractions gave a foam which solidified upon trituration with ether. This material was collected on a filter, washed further with some ether, and dried in vacuo at 50° C. to give white crystals, of satisfactory purity; mass spectrum (FAB) m/e 209 $(M+1)^+$.

Step D: 5-n-Butyl-2,4-dihydro-4-[[2'-cyanobiphenyl-4-yl]methyl]-3H-1,2,4-triazol-3-one A mixture of 0.52 g (2.45 mmole) of 4-aminomethyl-2'-cyanobiphenyl 683 mg (3.16 mmole) of ethyl valerimidate carbethoxyhydrazone, and 5 ml of ethanol was stirred under $N_2$ in an oil bath at 80° C. All of the solid dissolved within 15 minutes, and precipitation began after about 2 hours. After 3.5 hours the mixture was cooled and concentrated. The residue was re-concentrated from $CH_2Cl_2$ and then flash chromatographed on a column containing 400 cc of silica gel. Gradient elution with 1–5% methanol in $CH_2Cl_2$ afforded a white powder, homogeneous by TLC in 9:1 $CH_2Cl_2$-MeOH; mass spectrum (FAB) m/e 332 $(M+1)^+$.

EXAMPLE 3

5-n-Butyl-2,4-dihydro-2-phenyl-3H-1,2,4-triazol-3-one

Step A: Ethyl Valerimidate (Free Base)

A 12.7 g (76.7 mmole) sample of ethyl valerimidate hydrochloride [prepared from valeronitrile, ethanol, and hydrogen chloride gas as described by A. J. Hill and I. Rabinowitz, *J. Am. Chem. Soc.*, 48, 734 (1926)] was dissolved in 33% (w/w) potassium carbonate solution (made by dissolving 15 g of $K_2CO_3$ in 30 ml of $H_2O$) and immediately extracted with ether (3×40 ml). The combined ether layers were dried over $Na_2SO_4$, filtered, and concentrated in vacuo to give 7.09 g (72%) of the product as a clear oil, which was used directly in the next step.

300 MHz NMR ($CDCl_3$) δ0.88 (t, J=7 Hz, 3H), 1.24 (t, J=7 Hz, 3H), 1.31 (m, 2H), 1.50 (m, 2H), 2.19 (t, J=7.5 Hz, 2H), 4.06 (q, J=7 Hz, 2H), 6.84 (br s, 1H).

Step B: Ethyl N-Carbethoxyvalerimidate

A solution of 6.5 g (50.3 mmole) of ethyl valerimidate (free base) in 90 ml of dry $CH_2Cl_2$ was treated with 7.71 ml (5.60 g, 55.3 mmole) of triethylamine. The resulting solution was stirred under $N_2$ at $-10°$ C. in an ice-salt bath as a solution of 4.81 ml (5.46 g, 50.3 mmole) of ethyl chloroformate in 10 ml of $CH_2Cl_2$ was added dropwise over 25 minutes. Upon completion of the addition, the cooling bath was removed, and the mixture was stirred at room temperature for 2 hours. Next, the solvent was removed by evaporation in vacuo. The residue was taken up in hexane and filtered to remove triethylamine hydrochloride. Concentration of the filtrate yielded 7.08 g (70%) of the product as a yellow oil, suitable for use in the next step without further purification. NMR indicated a mixture of syn and anti isomers. TLC (98:2 $CH_2Cl_2$—MeOH) showed a close pair of spots, $R_f$ 0.48, 0.52; mass spectrum (EI) m/e 201 $(M^+)$.

200 MHz NMR ($CDCl_3$) δ0.86 (distorted t, J=7.5 Hz, 3H), 2.15–2.35 (m, 8H), 2.4–2.65 (m, 2H), 2.19, 2.35 (t, J=7.5 Hz, 2H total), 4.0–4.2 (m, 4H).

Step C: 5-n-Butyl-2,4-dihydro-2-phenyl-3H-1,2,4-triazol-3-one

To a solution of 197 μl (216 mg, 2.0 mmole) of phenylhydrazine in 3 ml of toluene was added 442 mg (2.2 mmole) of ethyl N-carbethoxyvalerimidate, and the mixture was heated at 45°–50° C. for 1.5 hours. At this time 307 μl (223 mg, 2.2 mmole) of triethylamine was added, and the bath temperature was raised to 95° C. After being maintained at this temperature overnight, the dark red solution was cooled and concentrated in vacuo. Flash chromatography of the residue on silica gel (elution with 0.5% methanol in $CH_2Cl_2$) gave 252 mg (58%) of the product as an off-white solid, mp 107.5°–109° C., homogeneous by TLC in 19:1 $CH_2Cl_2$—MeOH; mass spectrum (FAB) m/e 218 $(M+1)^+$.

Analysis [$C_{12}H_{15}N_3O \cdot 0.1 H_2O \cdot 0.1 C_7H_8$ (toluene)]: Calcd: C, 66.82; H, 7.06; N, 18.41. Found: C, 66.59; H, 6.89; N, 18.02.

200 MHz NMR (CDCl₃) δ0.96 (t, J=7 Hz, 3H), 1.44 (m, 2H), 1.74 (m, 2H), 2.64 (t, J=7.5 Hz, 2H), 7.24 (d, J=8 Hz, 1H), 7.44 (t, J=8 Hz, 2H), 7.95 (d, J=8 Hz, 2H), 11.8 (br s, 1H).

EXAMPLE 4

5-n-Butyl-2-(2-chlorophenyl)-2,4-dihydro-3H-1,2,4-triazol-3-one

By the procedure of Example 3, Step C, o-chlorophenylhydrazine (generated from the hydrochloride by partitioning between ether and 1N Na₂CO₃) was reacted with N-carbethoxyvalerimidate. After work-up, the residue was purified by flash chromatography on silica gel (gradient elution with 0.6–2% methanol in CH₂Cl₂) to give a 51% yield of the product as an off-white solid, mp 103°–104° C., homogeneous by TLC in 19:1 CH₂Cl₂—MeOH; mass spectrum (FAB) m/e 252 (M+1)⁺.

Analysis (C₁₂H₁₄ClN₃O): Calcd: C, 57.26; H, 5.61; N, 16.69. Found: C, 57.31; H, 5.69; N, 16.58.

200 MHz NMR (CDCl₃) δ0.92 (t, J=7 Hz, 3H), 1.38 (m, 2H), 1.68 (m, 2H), 2.57 (t, J=7.5 Hz, 2H), 7.3–7.55 (m, 4H), 12.04 (br s, 1H).

EXAMPLE 5

5-n-Butyl-2-[2-(carbomethoxy)phenyl]-2,4-dihydro-3H-1,2,4-triazol-3-one

By the procedure of Example 3, Step C, o-(carbomethoxy)phenylhydrazine [generated from the hydrochloride which was prepared according to H. Stroh and G. Westphal, Chem. Ber. 96, 184 (1963), by partitioning between ether and 5% aqueous sodium bicarbonate] was reacted with ethyl N-carbethoxyvalerimidate (Example 4, Step B). After work-up, the residue was purified by flash chromatography on silica gel (gradient elution with 0.6–2% methanol in CH₂Cl₂) to give a 51% yield of the product as a pale yellow oil, homogeneous by TLC (19:1 CH₂Cl₂—MeOH), mass spectrum (FAB) m/e 276 (M+1)⁺.

200 MHz ¹HNMR (CDCl₃) δ0.93 (t, J=7.2 Hz, 3H), 1.35 (m, 2H), 1.68 (m, 2H) 2.56 (t, J=7.8 Hz, 2H), 3.83 (s, 3H), 7.40 (m, 1H), 7.61 (d, J=3.7 Hz, 2H) 7.90 (d, J=7.8 Hz, 1H), 12.03 (s, 1H).

EXAMPLE 6

5-n-Butyl-2,4-dihydro-2-[4-methylbenzyl]-4-[[2'-cyanobiphenyl-4-yl]methyl]-3H-1,2,4,-triazol-3-one Step A: 4-Azidomethyl-2'-cyanobiphenyl A mixture of 1.97 g (725 mmole) of 4-bromomethyl-2'-cyanobiphenyl (EP 253,310), 445 mg (9.1 mmole) of lithium azide and 5 ml of dry DMSO was stirred at room temperature under nitrogen for one hour and then partitioned between 100 ml of ether and 100 ml of H₂O. The organic phase was washed with 3×100 ml of H₂O, then dried (MgSO₄), filtered, and concentrated in vacuo to give a residual oil which solidified on standing. This solid was triturated with petroleum ether, collected on a filter, washed with petroleum ether and dried overnight to yield the title compound as white crystals, mp 69°–70° C.; mass spectrum (EI) m/e 234 (M+). TLC in 4:1 hexane-EtOAc showed only minor impurities and the material was of sufficient purity to use in the next step.

300 MHz NMR (CDCl₃) δ4.41 (s, 2H), 7.4–7.7 (m, 7H), 7.75 (d, J=8 Hz, 1H).

Step B: [(2'-Cyanobiphenyl-4-yl)methyl]amine

A solution of 5.85 g (25 mmole) of 4-azidomethyl-2'-cyanobiphenyl (from Step A) in 50 ml of dry tetrahydrofuran was treated portionwise with 6.55 g (25 mmole) of triphenylphospine over 3–4 minutes. The solution was stirred at ambient temperature under N₂, and gas evolution proceeded at a moderate rate. A mild exotherm occurred, and the solution was cooled in a water bath as necessary. After 2 hours, by which time gas evolution had ceased, 675 μl (37.5 mmole) of H₂O was added, and stirring was continued at room temperature under N₂. After 22 hours, the solution was concentrated in vacuo, and the residual oil was chromatographed on a column of silica gel (gradient elution with 2–10% methanol in CH₂Cl₂). The residue from evaporation of the pooled product fractions was partitioned between ether-CH₂Cl₂ and saturated Na₂CO₃ (aqueous). The organic phase was dried (Na₂SO₄), filtered, and concentrated in vacuo to yield the title compound as air-sensitive, nearly white crystals, mp 54°–55° C., homogeneous by TLC in 9:1 CH₂Cl₂—MeOH; mass spectrum (FAB) m/e 209(M+1)⁺.

Analysis (C₁₄H₁₂N₂) Calcd: C, 80.74; H, 5.81; N, 13.45 Found: C, 80.53; H, 5.89; N, 13.12

300 MHz NMR(CDCl₃) δ1.50 (br s, 2H), 3.92 (s, 2H), 7.35–7.65 (m, 7H), 7.75 (d, J=8 Hz, 1H)

Step C: 5-n-Butyl-4-[(2'-cyanobiphenyl-4-yl)methyl]-2,4-dihydro-3H-1,2,4-triazol-3-one A mixture of 400 mg (1.923 mmole) of [(2'-cyanobiphenyl-4-yl)methyl]amine, 457 mg (2.12 mmole) of ethyl valerimidate carbethoxyhydrazone (from Example 2, Step A), and 7 mL of ethanol was stirred under N₂ in an oil bath at 50° C. for 3 hours and then at 80° C. for 2 days. The mixture was cooled and concentrated. The residue, re-concentrated from toluene, was flash chromatographed over silica gel (gradient elution with 1.5–5% methanol in CH₂Cl₂) to give the desired product, homogeneous in TLC (90:10 CH₂Cl₂—MeOH); mass spectrum (FAB) m/e 333 (M+1)⁺.

300 MHz ¹HNMR(CDCl₃) δ0.85 (t, J=7.2 Hz, 3H), 1.35 (m, 2H), 1.60 (m, 2H), 2.42 (t, J=7.2 Hz, 2H), 4.87 (s, 3H), 7.35 (d, J=7 Hz, 2H), 7.50 (m, 4H), 7.62 (d, J=8.5 Hz, 1H), 7.75 (d, J=8.5 Hz, 1H), 9.13 (br s, 1H).

Step D: 5-n-Butyl-2,4-dihydro-2-(4-methylbenzyl)-4-[(2'-cyanobiphenyl-4-yl)methyl]-3H-1,2,4-triazol-3-one The alkylation of 5-n-butyl-4-[(2'-cyanobiphenyl-4-yl)methyl]-2,4-dihydro-3H-1,2,4-triazol-3-one with 4-methylbenzyl bromide was carried out as described in Example 3, Step A, except that no excess sodium hydride was used. After work-up, flash chromatography of the crude product on silica gel (eluting with 0.6% methanol in CH₂Cl₂) provided the title compound as a clear oil, homogeneous by TLC (98:2 CH₂Cl₂—MeOH), mass spectrum (FAB) m/e 437 (M+1)⁺.

300 MHz ¹HNMR (CDCl3) δ0.84 (t, J=7.3 Hz, 3H), 1.40 (m, 2H), 1.52 (m, 2H), 2.31 (s, 3H), 2.38 (m, 2H), 4.87 (s, 2H), 4.93 (s, 2H), 7.12 (d, J=7.8 Hz, 2H), 7.26 (d, J=8.5 Hz, 2H), 7.33 (d, J=8.2 Hz, 2H), 7.50 (m, 4H), 7.62 (m, 1H), 7.74 (m, 1H).

EXAMPLE 7

4'-Bromomethylbiphenyl-2-tert-butyl-sulfonamide

Step A: 2-Bromobenzene(tert-butyl)sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tert-butyl)sulfonamide as a white solid;

$^1$H NMR (300 MHz, CDCl$_3$) δ8.18 (d, J=8.5 Hz, 1H), 7.73 (d, J=8.5 Hz, 1H), 7.50–7.35 (m, 2H), 5.11 (s, 1H), 1.20 (s, 9H).

Step B: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 h then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°–40° C., 0.1 mm Hg) which was further purified by flash chromatography (silica gel, hexane) to give p-tolyltrimethyltin as a colorless liquid; $^1$H NMR (300 MHz, CDCl$_3$) δ7.40 (d, J=7.7 Hz, 2H), 7.19 (d, J=7.7 Hz, 2H), 2.34 (s, 3H), 0.30 (s, 9H).

Step C: 4′-Methylbiphenyl-2-tert-butylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 h. The black suspension was cooled to room temperature, then filtered through a pad of celite which was washed with tetrahydrofuran. The colorless filtrate was evaporated to dryness then chromatographed (silica gel, 8,10% ethyl acetate-hexane) to give 4′-methylbiphenyl-2-tert-butylsulfonamide as a white solid;

$^1$H NMR (300 MHz, CDCl$_3$) δ8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step D: 4′-Bromomethylbiphenyl-2-tert-butylsulfonamide

N-Bromosuccinimide (0.387 g, 2.17 mmol), 2,2′-azobis(isobutyronitrile) (catalytic), 4′-methylbiphenyl-2-tert-butylsulfonamide (0.55 g, 1.81 mmol) and carbon tetrachloride (50 ml) were heated with stirring at reflux for 3 h. After cooling to room temperature the mixture was filtered and the filtrate evaporated to dryness. Flash chromatography (silica gel, 10,20% ethyl acetate-hexane) afforded 4′-bromomethylbiphenyl-2-tert-butylsulfonamide (77% pure (the remainder of the material was 4′-dibromomethylbiphenyl-2-tert-butylsulfonamide)) as a white solid;

$^1$H NMR (300 MHz, CDCl$_3$) δ8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

EXAMPLE 8

5-n-Butyl-2,4-dihydro-2-phenyl-4-(2′-(aminosulfonylbiphen-4-yl)methyl)-3H-1,2,4-triazol3-one Step A: 5-n-Butyl-2,4-dihydro-2-phenyl-4-(2′-((tert-butylamino)-sulfonylbiphen-4-yl)methyl)-3H-1,2,4-triazol-3-one 5-n-Butyl-2,4-dihydro-2-phenyl-3H-1,2,4-triazol-3-one, from Step C of Example 3, is added to a stirred suspension of sodium hydride (60% dispersion) in dimethylformamide at room temperature under nitrogen. The mixture is heated at 50° C. and then cooled to room temperature. A solution of 4′-(bromomethyl)-biphenyl-2-tert-butylsulfonamide (77% pure) in dimethylformamide is added dropwise and the solution heated at 50° C. for 4 h. After cooling to room temperature the solvent is removed in vacuo. Flash chromatography (silica gel) of the crude product affords the titled compound.

Step B: 5-n-Butyl-2,4-dihydro-2-phenyl-4-(2′-(aminosulfonylbiphen-4-yl)methyl)-3H-1,2,4-triazol-3-one Anisole is added to a stirred solution of the compound from Step A in trifluoroacetic acid under nitrogen at room temperature. The solution is stirred at room temperature for 8 h, and then the solvent is removed in vacuo. The crude product is purified by flash chromatography (silica gel) to afford the titled compound.

EXAMPLE 9

5-n-Butyl-2,4-dihydro-2-phenyl-4-(2′-(isopropylsulfonylamino)sulfonylbiphen-4-yl)methyl)-3H-1,2,4-triazol-3-one To a stirred suspension of NaH in dry DMF under nitrogen at room temperature is added 5-n-butyl-2,4-dihydro-2-phenyl-4-(2′-(aminosulfonylbiphen-4-yl)methyl)-3H-1,2,4-triazol-3-one. After stirring for 30 minutes at room temperature, isopropylsulfonyl-chloride is added, and the resulting mixture is stirred at room temperature overnight. The reaction mixture is poured into ice water, acidified with 5% citric acid solution and extracted with chloroform. The organic phase is washed with water and brine, and then dried over MgSO$_4$. The crude product obtained after removal of the solvent is purified by flash-chromatography to give the desired product.

EXAMPLE 10

5-n-Butyl-2,4-dihydro-2-phenyl-4-(2′-(dibenzylphosphonylamino)sulfonylbiphen-4-yl)methyl)-3H-1,2,4-triazol-3-one To a stirred solution of the compound from Step B of Example 8 in dry THF is added n-BuLi (1.6M solution in hexane) at 0° C. After stirring for 15 minutes at that temperature, a solution of dibenzylphosphorylchloride in THF is added, and the resulting mixture is stirred at room temperature for 18 h. The reaction mixture is concentrated under reduced pressure, and the residue is treated with 5% citric acid solution and extracted with methylene chloride. The organic phase is washed with water and brine, and then dried over MgSO$_4$. The crude product obtained after removal of the solvent is purified on silica-gel by flash-chromatography to give the title product.

EXAMPLE 11

4′-Bromomethylbiphenyl-2-(O-tert-butyl)-N-hydroxysulfonamide

Step A: 2-Bromobenzene(O-tert-butyl)-N-hydroxysulfonamide

To a stirred solution of 2-bromobenzenesulfonyl chloride (Lancaster Synthesis) (1.0 g, 4.0 mmol) in chloroform (10 ml) under nitrogen at 0° C. was added O-tert-butylhydroxylamine hydrochloride (Fluka) (0.6 g, 4.77 mmol) in three portions. The solution was stirred at room temperature for 18 h and then diluted with methylene chloride (20 ml). The organic phase was washed successively with 5% citric acid, water and then dried over MgSO$_4$. Removal of the solvent in vacuo gave the crude product as white solid, which was then purified by flash chromatography (silica gel, 10% ethyl acetate-hexane) to afford 2-bromobenzene(O-tert-butyl)N-hydroxysulfonamide (1.12 g, 89%) as a white solid;

$^1$H NMR (300 MHz, CDCl$_3$) δ8.15 (dd, J=7.5, 2.1 Hz, 1H), 7.75 (d, J=7.6, 1.8 Hz, 1H), 7.55–7.35 (m, 3H), 5.11 (s, 1H), 1.21 (s, 9H). FAB-MS: 309 (M+H).

Step B: 4'-Methylbiphenyl-2-(O-tert-butyl)-N-hydroxy sulfonamide

A solution of 2-bromobenzene(O-tert-butyl)-N-hydroxysulfonamide (0.31 g, 1.0 mmol), p-tolyltrimethyltin (0.3 g, 1.18 mmol) and bis(triphenylphosphine)palladium(II) chloride (Aldrich) (0.036 g) in dry dimethylformamide (6 ml) was stirred under nitrogen at 90° C. for 6 h. The black suspension was cooled to room temperature, then filtered through a pad of celite which was washed with tetrahydrofuran. The colorless filtrate was evaporated to dryness then purified by flash chromatography (silica gel, 8% ethyl acetate-hexane) to give the titled compound as a semi-solid mass.

$^1$H NMR (300 MHz, CDCl$_3$) δ8.15 (d, J=7.8, 1.6 Hz, 1H), 7.67–7.50 (m, 2H), 7.36–7.24 (m, 5H), 5.78 (s, 1H), 2.42 (s, 3H), 1.08 (s, 9H). FAB-MS: 320 (M+H).

Step C: 4'-Bromomethylbiphenyl-2-(O-tert-butyl)-N-hydroxysulfonamide

A mixture of N-Bromosuccinimide (0.14 g, 0.78 mmol), a,a'-azoisobutyronitrile (10 mg) and 4'-methylbiphenyl-2-(O-tert-butyl)-N-hydroxy sulfonamide (0.25 g, 0.78 mmol) in carbon tetrachloride (10 ml) was refluxed for 7 h. After cooling to room temperature the mixture was filtered and the filtrate evaporated to dryness. Flash chromatography (silica gel, 10% ethyl acetate-hexane) afforded 4'-methylbiphenyl-2-(O-tert-butyl)-N-hydroxy sulfonamide as a white solid.

$^1$H NMR (300 MHz, CDCl$_3$) δ8.15 (d, J=7.8 Hz, 1H), 7.70–7.30 (m, 7H), 5.72 (s, 1H), 4.55 (s, 2H), 1.08 (s, 9H). FAB-MS: 398, 400 (M+H).

EXAMPLE 12

5-n-Butyl-2,4-dihydro-2-phenyl-4-(2'-(N-hydroxyamino)sulfonylbiphen-4-yl)methyl)-3H-1,2,4-triazol-3-one Step A: 5-n-Butyl-2,4-dihydro-2-phenyl-4-(2'-((O-tert-butyl-N-hydroxyamino)-sulfonylbiphen-4-yl)-methyl)-3H-1,2,4-triazol-3-one 5-n-Butyl-2,4-dihydro-2-phenyl-3H-1,2,4-triazol-3-one is added to a stirred suspension of sodium hydride (60% dispersion) in dimethylformamide at room temperature under nitrogen. The mixture is stirred at room temperature for 30 min, and then a solution of 4'-bromomethylbiphenyl-2-(O-tert-butyl)-N-hydroxysulfonamide in dimethylformamide is added dropwise. The resulting solution is stirred at room temperature overnight. The solvent is removed in vacuo and the crude product is purified by flash chromatography (silica gel) to afford the titled compound.

Step B: 5-n-Butyl-2,4-dihydro-2-phenyl-4-(2'-((N-hydroxyamino)-sulfonylbiphen-4-yl)methyl)-3H-1,2,4-triazol-3-one Anisole is added to a stirred solution of 5-n-butyl-2,4-dihydro-2-phenyl-4-(2'-((O-tert-butyl-N-hydroxyamino)-sulfonyl-biphen-4-yl)-methyl)-3H-1,2,4-triazol-3-one in trifluoroacetic acid at room temperature under nitrogen and stirring continued at room temperature overnight. The solvent is removed in vacuo, and the residue is triturated with dry ether and filtered. The isolated solid is crystallized to give the desired product.

EXAMPLE 13

5-n-Butyl-2,4-dihydro-4-[(2'-sulfamoylbiphenyl-4-yl)methyl]-2-[2-(trifluoromethyl)phenyl]-3H-1,2,4-triazol-3-one Step A: 5-n-Butyl-2,4-dihydro-2-[2-(trifluoromethyl)-phenyl]-3H-1,2,4-triazol-3-one Ethyl-N-carbethoxyvalerimidate (from Example 3, Step B) was reacted with 2-(trifluoromethyl)phenylhydrazine according to the procedure of Example 3, Step C. Flash chromatography of the crude product on silica gel (gradient elution with 0.5–2% MeOH in CH$_2$Cl$_2$) gave a 66% yield of the title compound as white crystals, mp 124°–126° C.; homogeneous by TLC in 19:1 CH$_2$Cl$_2$—MeOH; mass spectrum (FAB) m/e 286 (M+1)$^+$.

400 MHz NMR (CDCl$_3$) δ0.88 (t, 3H), 1.34 (m, 2H), 1.62 (m, 2H), 2.52 (t, 2H), 7.5–7.6 (m, 2H), 7.66 (dd, 1H), 7.79 (d, 1H), 11.75 (br s, 1H).

Step B: 5-n-Butyl-4-[[2'-(N-t-butylsulfamoyl)biphenyl-4-yl]methyl]-2,4-dihydro-2-[2-(trifluoromethyl)-phenyl]-3H-1,2,4-triazol-3-one By the procedure of Example 8, Step A, 5-n-butyl-2,4-dihydro-2-[2-(trifluoromethyl)phenyl]-3H-1,2,4-triazol-3-one (from Step A) was alkylated with 4'-bromomethylbiphenyl-2-tert-butylsulfonamide (from Example 7). Flash chromatography of the crude product on silica gel (gradient elution with 0.5–5% MeOH in CH$_2$Cl$_2$) gave a 61% yield of the title compound as cream-colored crystals, mp 168°–170° C.; satisfactory purity by TLC in 98:2 CH$_2$Cl$_2$—MeOH; mass spectrum (FAB) m/e 587 (M+1)$^+$.

400 MHz NMR (CDCl$_3$) δ0.89 (t, 3H), 0.97 (s, 9H), 1.37 (m, 2H), 1.64 (m, 2H), 2.48 (t, 2H), 3.48 (s, 1H), 4.95 (s, 2H), 7.2–7.6 (m, 9H), 7.66 (dd, 1H), 7.78 (d, 1H), 8.15 (d, 1H).

Step C: 5-n-Butyl-2,4-dihydro-4-[(2'-sulfamoylbiphenyl-4-yl)methyl]-2-[2-(trifluoromethyl)phenyl]-3H-1,2,4-triazol-3-one The title compound was prepared according to the procedure of Example 8, Step B and was obtained in 92% yield as white crystals, mp 74°–76° C.; satisfactory purity by TLC in 98:2 CH$_2$Cl$_2$—MeOH; mass spectrum (FAB) m/e 531 (M+1)$^+$.

400 MHz NMR (CDCl$_3$) δ0.88 (t, 3H), 1.36 (m, 2H), 1.63 (m, 2H), 2.50 (t, 2H), 4.23 (br s, 2H), 4.95 (s, 2H), 7.3–7.6 (m, 9H), 7.65 (dd, 1H), 7.78 (d, 1H), 8.14 (d, 1H).

EXAMPLE 14

5-n-Butyl-2,4-dihydro-4-[[2'-[N-(N,N-dimethylsulfamoyl)sulfamoyl]biphenyl-4-yl]methyl]-2-[2-(trifluoromethyl)phenyl]-3H-1,2,4-triazol-3-one To a mixture of 50 mg (0.0943 mmole) of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) and 4.53 mg (0.189 mmole) of sodium hydride in 0.2 mL of THF, which had been stirring at room temperature for 3 h, was added 101 μL (135 mg, 0.943 mmole) of N,N-dimethylsulfamoyl chloride. After stirring at 60° C. overnight, the reaction was quenched with water, the organic material was extracted with ethyl acetate, washed with water and brine, and dried over sodium sulfate. The crude product obtained after filtration and evaporation of volatiles was flash chromatographed over silica gel (gradient elution using 0.5-8.0% MeOH/CH$_2$Cl$_2$) to afford the desired material as a glassy white solid, mp 119°-121° C.; homogeneous by TLC (10% MeOH/CH$_2$Cl$_2$); mass spectrum (FAB) m/e 660 (M+Na)$^+$, 676 (M+K)$^+$.

400 MHz NMR (CD$_3$OD) δ0.90 (t, J=7.4 Hz, 3H), 1.40 (m, 2H), 1.65 (m, 2H), 2.59 (t, J=7.7 Hz, 2H), 2.61 (s, 6H), 5.01 (s, 2H), 7.22-7.90 (m, 11H), 8.19 (dd, J=7.9 Hz, 1.3 Hz, 1H).

EXAMPLE 15

5-n-Butyl-2,4-dihydro-4-[[2'-[N-(isopropylsulfonyl)sulfamoyl]biphenyl-4-yl]methyl]-2-[2-(trifluoromethyl)phenyl]-3H-1,2,4-triazol-3-one The title compound was prepared from 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) and isopropylsulfonyl chloride according to the procedure of Example 14, except that the mixture was heated overnight at 65° C. Flash chromatography of the crude product on silica gel gave the title compound as a glass; satisfactory purity by TLC in 9:1 CH$_2$Cl$_2$—MeOH; mass spectrum (FAB) m/e 659 (M+Na)$^+$, 675 (M+K)$^+$.

400 MHz NMR (CDCl$_3$/CD$_3$OD) δ0.85 (t, 3H), 1.27 (d, 6H), 1.34 (m, 2H), 1.61 (m, 2H), 2.51 (t, 2H), 3.52 (m, 1H), 4.91 (s, 2H), 7.15-7.6 (m, 9H), 7.64 (dd, 1H), 7.76 (d, 1H), 8.11 (d, 1H).

EXAMPLE 16

5-n-Butyl-2,4-dihydro-4-[[2'-[N-(trifluoromethanesulfonyl)sulfamoyl]biphenyl-4-yl]methyl]-2-[2-(trifluoromethyl)phenyl]-3H-1,2,4-triazol-3-one To a solution of 75 mg (0.142 mmole) of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) in pyridine (1 mL), was added 400 mg (1.42 mmole) of trifluoromethansulfonic anhydride. The crude product was flash chromatographed twice on silica gel (gradient elution with 0.5-5% MeOH in CH$_2$Cl$_2$ and then 1-5% MeOH in CH$_2$Cl$_2$) to give the title compound as a peach-colored solid, mp 132°-134° C.; satisfactory purity by TLC in 19:1 CH$_2$Cl$_2$—MeOH; mass spectrum (FAB) m/e 685 (M+Na)$^+$.

400 MHz NMR (CDCl$_3$) δ0.91 (t, 3H), 1.40 (m, 2H), 1.68 (m, 2H), 2.59 (t, 2H), 4.85 (s, 2H), 7.13 (d, 2H), 7.2-7.6 (m, 8H), 7.70 (d, 1H), 8.04 (d, 1H).

EXAMPLE 17

4-[[2'-[N-(Benzenesulfonyl)sulfamoyl]biphenyl-4-yl]methyl]-5-n-butyl-2,4-dihydro-2-[2-(trifluoromethyl)phenyl]-3H-1,2,4-triazol-3-one The title compound was prepared from 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) according to the procedure of Example 14, except that a total of 2.4 equivalents of benzenesulfonyl chloride was used, and the mixture was heated at 60° C. for 4 hours. The crude produce was purified by flash chromotography on silica gel (gradient elution with 0.5-5% MeOH in CH$_2$Cl$_2$). The residue from evaporation of the product fractions was partitioned between CH$_2$Cl$_2$ and 1N HCl. The organic phase was dried (Na$_2$SO$_4$), filtered, and concentrated in vacuo to give the title compound as a cream-colored, sticky solid, homogeneous by TLC in 9:1 CH$_2$Cl$_2$—MeOH; mass spectrum (FAB) m/e 671 (M+1)$^+$.

400 MHz NMR (CD$_3$OD) δ0.88 (t, 3H), 1.37 (m, 2H), 1.60 (m, 2H), 2.56 (t, 2H), 5.00 (s, 2H), 7.1-7.75 (m, 14H), 7.81 (dd, 1H), 7.89 (d, 1H), 8.04 (d, 1H).

EXAMPLE 18

5-n-Butyl-4-[[2'-[N-carbethoxysulfamoyl]biphenyl-4-yl]methyl]-2,4-dihydro-2-[2-(trifluoromethyl)phenyl]-3H-1,2,4-triazol-3-one The title compound was prepared from 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) and ethyl chloroformate, according to the procedure of Example 14. The crude product was flash chromatographed over silica gel (gradient elution using 0.3-5.0% MeOH/CH$_2$Cl$_2$) to afford the desired material as a white solid, mp 79°-81° C.; homogeneous by TLC (5% MeOH/CH$_2$Cl$_2$); mass spectrum (FAB) m/e 603 (M+1)$^+$, 625 (M+Na)$^+$.

Analysis C$_{29}$H$_{29}$F$_3$N$_4$O$_5$S: Calcd: C, 57.80; H, 4.85; N, 9.30. Found: C, 57.58; H, 4.78; N, 9.11.

400 MHz NMR (CDCl$_3$) δ0.89 (t, J=7.3 Hz, 3H), 1.12 (t, J=7.3 Hz, 3H) 1.38 (m, 2H), 1.65 (m, 2H), 2.51 (t, J=7.7 Hz, 2H), 4.04 (q, J=7.0 Hz, 2H), 4.96 (s, 2H), 6.89 (s, 1H), 7.29-7.36 (m, 5H), 7.53-7.80 (m, 6H), 8.26 (dd, J=8.0 Hz, 1.2 Hz, 1H).

EXAMPLE 19

4-[[2'-[N-(t-Butoxycarbonyl)sulfamoyl]biphenyl-4-yl]methyl]-5-n-butyl-2,4-dihydro-2-[2-(trifluoromethyl)phenyl]-3H-1,2,4-triazol-3-one The title compound was prepared from 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) and di-t-butyl dicarbonate, according to the procedure of Example 14 except that the reaction mixture was heated at 60° C. overnight. The crude product was flash chromatographed over silica gel (gradient elution using 0.3-5.0% MeOH/CH$_2$Cl$_2$) to afford the desired material as a white solid, mp 140°-142° C.; homogeneous by TLC (5% MeOH/CH$_2$Cl$_2$); mass spectrum (FAB) m/e 631 (M+1)$^+$; mp 140°-142° C.

Analysis: C$_{31}$H$_{33}$F$_3$N$_4$O$_5$S: Calc'd: C, 59.00; H, 5.27; N, 8.88. Found: C, 58.81; H, 4.98, N, 8.68.

400 MHz NMR (CDCl$_3$) δ0.88 (t, J=7.3 Hz, 3H), 1.28 (s, 9H), 1.36 (m, 2H), 1.62 (m, 2H), 2.50 (t, J=7.6 Hz, 2H), 4.96 (s, 2H), 6.54 (s, br, 1H), 7.29-7.79 (m, 11H), 8.23 (dd, J=8.0 Hz, 1.3 Hz, 1H).

EXAMPLE 20

4-[[2'-[N-(t-Butoxycarbonyl)sulfamoyl]-5'-n-propyl-biphenyl-4-yl]methyl]-5-n-butyl-2,4-dihydro-2-[2-(trifluoromethyl)phenyl]-3H-1,2,4-triazol-3-one Step A: N-t-butyl-4-n-propylbenzenesulfonamide To a solution of 4-n-propylbenzenesulfonyl chloride (Lancaster) in anhydrous CH$_2$Cl$_2$ (0.5M solution) cooled to 0° C. under N$_2$ was added t-butylamine (2.2 equiv) slowly through a dropping funnel. After complete addition, the reaction was stirred at room temperature for 12 hours. The CH$_2$Cl$_2$ was removed under reduced pressure, and the residue was extracted into ether and washed with 2N NaOH, H$_2$O and brine. The organic phase was dried over anhydrous MgSO$_4$ and concentrated in vacuo to afford the titled product; R$_f$=0.46 (3:1 hexane-EtOAc).

¹H NMR (200 MHz, CDCl₃) δ0.93 (t, 3H), 1.22 (s, 9H), 1.62 (m, 2H), 2.65 (t, 2H), 4.67 (bs, 1H), 7.27 (d, 2H), 7.79 (d, 2H).

Step B: 2-(N-t-butylsulfamoyl)-5-n-propylphenylboronic acid

To a solution of 2.85 g (11.2 mmol) of N-t-butyl-4-n-propylbenzenesulfonamide (from Step A) in anhydrous THF (20 mL) cooled to −40° C. under N₂ was added 2.5M n-BuLi solution (11.2 mL, 2.5 equiv). The mixture was warmed to room temperature and stirred for 2 hours. To the mixture, containing the bright red dianion at 0° C., was added triisopropyl borate (3.9 mL, 1.5 equiv). The next day, 2N HCl (3 mL) was added and the mixture was stirredfor 1 hour. The solvent was removed under reduced pressure and the residue was extracted with ethyl acetate. The organic solution was washed washed with 2N HCl, H₂O and brine. The organic phase was dried over anhydrous MgSO₄ and concentrated in vacuo to afford the titled compound; $R_f$=0.5 (1:1 EtOAc-hexane). The material was used in the next step without further purification.

Step C: [2'-(N-t-Butylsulfamoyl)-5'-n-propylbiphenyl-4-yl]methanol

To a solution of 2.80 g (9.36 mmol) of 2-(N-t-butylsulfamoyl)-5-n-propylphenylboronic acid (from Step B) and 4-bromobenzyl alcohol (5.25 g, 3 equiv) in toluene (125 mL) was added 1.25N NaOH (32 mL), EtOH (86 mL) and tetrakis(triphenylphosphine)palladium(0) (325 mg, 3 mol %). The mixture was stirred at 100° C. under N₂ for 3 hours. The reaction was concentrated and the residue was extracted with ethyl acetate. The organic solution was washed with 1N NaOH, H₂O and brine. Next, the organic phase was dried over anhydrous MgSO₄ and concentrated in vacuo. The product was purified by flash chromatography, eluting with 2:1 hexane-EtOAc, to provide the titled compound; $R_f$=0.42 (1:1 EtOAc-hexane).

¹H NMR (400 MHz, CDCl₃) δ0.92 (t, 3H), 0.98 (s, 9H), 1.63 (m, 2H), 1.83 (bs, 1H), 2.63 (t, 2H), 3.57 (bs, 1H), 4.74 (s, 2H), 7.07 (d, 1H), 7.23 (dd, 1H), 7.42 (d, 2H), 7.49 (d, 2H), 8.02 (d, 1H).

Step D: 5-n-Butyl-4-[[2'-(N-t-butylsulfamoyl)-5'-n-propylbiphenyl-4-yl]methyl]-2,4-dihydro-2-[2-(trifluoromethyl)phenyl]-3H-1,2,4-triazol-3-one Under nitrogen, to a solution of 110 mg (0.386 mmole) of 5-n-butyl-2,4-dihydro-2-[2-(trifluoromethyl)-phenyl]-3H-1,2,4-triazol-3-one (from Example 13, Step A), 100 mg (0.257 mmole) of [2'-(N-t-butylsulfamoyl)-5'-n-propylbiphenyl-4-yl]methanol (from Step C), and 101 mg (0.386 mmole) of triphenylphosphine in 1.2 mL of THF at −10° C., was added dropwise 78 mg (0.386 mmole) of diisopropyl azodicarboxylate. The reaction mixture was warmed up to room temperature, stirred overnight, and concentrated in vacuo. The crude product thus obtained was flash chromatographed over 40 mL silica gel (gradient elution, 5:1 to 3:1 hexane/ethyl acetate) to afford a foam, homogeneous by TLC (1:1 hexane-EtOAc); mass spectrum (FAB) m/e 629 (M+1)⁺.

400 MHz NMR (CDCl₃) δ0.89 (t, J=7.2 Hz, 3H), 0.93 (t, J=7.2 Hz, 3H), 0.97 (s, 9H), 1.38 (m, 2H), 1.64 (m, 4H), 2.46 (t, J=7.9 Hz, 2H), 2.63 (t, J=7.6 Hz, 2H), 3.46 (s, 1H), 4.94 (s, 2H), 7.06-7.79 (m, 10H), 8.04 (d, J=8.3 Hz, 1H).

Step E: 5-n-Butyl-2,4-dihydro-4-[(2'-sulfamoyl-5'-n-propylbiphenyl-4-yl)methyl]-2-[2-(trifluoromethyl)-phenyl]-3H-1,2,4-triazol-3-one The title compound was prepared from 5-n-butyl-4-[(2'-sulfamoyl-5'-n-propylbiphenyl-4-yl)methyl]-2-[2-(trifluoromethyl)phenyl]-3H-1,2,4-triazol-3-one (from Step D) according to the procedure of Example 8, Step B. The crude product was flash chromatographed over silica gel (gradient elution with 0.5-1.0% MeOH in CH₂Cl₂), to provide the titled compound; homogeneous by TLC in 19:1 CH₂Cl₂—MeOH; mass spectrum (FAB) m/e 573 (M+1)⁺.

400 MHz NMR (CDCl₃) δ0.87 (t, J=7.3 Hz, 3H), 0.93 (t, J=7.3 Hz, 3H), 1.35 (m, 2H), 1.64 (m, 4H), 2.49 (t, J=7.6 Hz, 2H), 2.63 (t, J=7.5 Hz, 2H), 4.31 (s, 2H), 4.94 (s, 2H), 7.09-7.78 (m, 10H), 7.99 (d, J=8.1 Hz, 1H).

Step F: 4-[[2'-[N-(t-Butoxycarbonyl)sulfamoyl]-5'-n-propylbiphenyl-4-yl]methyl]-5-n-butyl-2,4-dihydro-2-[2-(trifluoromethyl)phenyl]-3H-1,2,4-triazol-3-one The title compound was prepared from 5-n-butyl-2,4-dihydro-4-[(2'-sulfamoyl-5'-n-propylbiphenyl-4-yl)methyl]-2-[2-(trifluoromethyl)phenyl]-3H-1,2,4-triazol-3-one (from Step E) according to the procedure of Example 14, except that the reaction mixture was heated at 50° C. for 3.5 days. The crude product was flash chromatographed over 30 mL of silica gel (gradient elution using 0.3-3% MeOH in CH₂Cl₂) to afford the title compound as a white solid, mp 76°-78° C.; homogeneous by TLC in 19:1 CH₂Cl₂—MeOH; mass spectrum (FAB) m/e 673 (M+1)⁺.

Analysis $C_{34}H_{39}F_3N_4O_5S$: Calcd: C, 60.70; H, 5.84; N, 8.33. Found: C, 60.34; H, 5.86; N, 8.20.

400 MHz NMR (CDCl₃) δ0.88 (t, J=7.3 Hz, 3H), 0.93 (t, J=7.3 Hz, 3H), 1.28 (s, 9H), 1.36 (m, 2H), 1.62 (m, 4H), 2.50 (t, J=7.7 Hz, 2H), 2.65 (t, J=7.5 Hz, 2H), 4.96 (s, 2H), 6.51 (s, br, 1H), 7.09-7.79 (m, 10H), 8.12 (d, J=8.1 Hz, 1H).

EXAMPLE 21

4-[[2'-[N-(t-Butoxycarbonyl)sulfamoyl]biphenyl-4-yl]methyl]-5-n-butyl-2,4-dihydro-2-[4-nitro-2-(trifluoromethyl)phenyl]-3H-1,2,4-triazol-3-one Step A: 5-n-Butyl-2,4-dihydro-2-[4-nitro-2-(trifluoromethyl)phenyl]-3H-1,2,4-triazol-3-one By the procedure of Example 3 Step C, 4-nitro-2-(trifluoromethyl)phenylhydrazine [generated from the hydrochloride which was prepared from 4-nitro-2-(trifluoromethyl)aniline according to H. Stroh and G. Westphal, Chem. Ber., 96, 184 (1963), by partitioning between ether and 1N sodium carbonate] was reacted with ethyl N-carbethoxyvalerimidate (Example 3, Step B). After work-up, the residue was purified by flash chromatography on silica gel (gradient elution with 0.5-5.0 methanol in CH₂Cl₂) to give the title compound as an orange solid, mp 126°-128° C.; homogeneous by TLC (19:1 CH₂Cl₂—MeOH); mass spectrum (FAB) m/e 331 (M+1)⁺.

400 MHz ¹H NMR (CDCl₃) δ0.91 (t, J=7.3 Hz, 3H), 1.38 (m, 2H), 1.66 (m, 2H), 2.57 (t, J=7.6 Hz, 2H), 7.83 (d, J=8.8 Hz, 1H), 8.50 (dd, J=8.8, 2.6 Hz, 1H), 8.67 (d, J=2.6 Hz, 1H), 11.25 (br s, 1H).

Step B: 5-n-Butyl-4-[[2'-(N-t-butylsulfamoyl)biphenyl-4-yl]methyl]-2,4-dihydro-2-[4-nitro-2-(trifluoromethyl)phenyl]-3H-1,2,4-triazol-3-one By the procedure of Example 8, Step A, 5-n-butyl-2,4-dihydro-2-[4-nitro-2-(trifluoromethyl)phenyl]-3H-1,2,4-triazol-3-one (from Step A) was alkylated with [2-(N-t-butylsulfamoyl)biphenyl-4-yl]methyl bromide (from Example 7). Flash chromatography of the crude product on silica gel (gradient elution with 0.5-5.0%

MeOH in CH$_2$Cl$_2$) gave the title compound as an orange solid, mp >78° C. (gradual); homogeneous by TLC (98:2 CH$_2$Cl$_2$—MeOH), mass spectrum (FAB) m/e 632 (M+1)$^+$.

400 MHz $^1$H NMR (CDCl$_3$) δ0.90 (t, J=7.4 Hz, 3H), 0.98 (s, 9H), 1.40 (m, 2H), 1.66 (m, 2H), 2.50 (t, J=7.5 Hz, 2H), 3.47 (s, 1H), 4.95 (s, 2H), 7.25-7.60 (m, 7H), 7.92 (d, J=9.1 Hz, 1H), 8.15 (dd, J=7.9, 1.4 Hz, 1H), 8.48 (dd, J=8.9, 2.6 Hz, 1H), 8.66 (d, J=2.5 Hz, 1H).

Step C: 5-n-Butyl-2,4-dihydro-2-[4-nitro-2-(trifluoromethyl)phenyl]-4-[(2'-sulfamoylbiphenyl-4-yl)methyl]-3H-1,2,4-triazol-3-one The title compound was prepared from 5-n-butyl-4-[[2'-(N-t-butylsulfamoyl)biphenyl-4-yl]methyl]-2,4-dihydro-2-[4-nitro-2-(trifluoromethyl)phenyl]-3H-1,2,4-triazol-3-one (from Step B) according to the procedure of Example 8, Step B, as a cream-colored solid, mp 218°-220° C.; homogeneous by TLC (19:1 CH$_2$Cl$_2$—MeOH); mass spectrum (FAB) m/e 576 (M+1)$^+$.

400 MHz $^1$H NMR (CDCl$_3$) δ0.89 (t, J=7.3 Hz, 3H), 1.38 (m, 2H), 1.65 (m, 2H), 2.52 (t, J=7.5 Hz, 2H), 4.20 (s, 2H), 4.96 (s, 2H), 7.25-7.61 (m, 7H), 7.92 (d, J=8.9 Hz, 1H), 8.14 (dd, J=7.6, 1.0 Hz, 1H), 8.48 (dd, J=8.8, 2.5 Hz, 1H), 8.66 (d, J=2.5 Hz, 1H).

Step D: 4-[[2'-[N-(t-Butoxycarbonyl)sulfamoyl]-biphenyl-4-yl]methyl]-5-n-butyl-2,4-dihydro-2-[4-nitro-2-(trifluoromethyl)phenyl}-3H-1,2,4-triazol-3-one This material is prepared from 5-n-butyl-2,4-dihydro-2-[4-nitro-2-(trifluoromethyl)phenyl]-4-[(2'-sulfamoylbiphenyl-4-yl)methyl]-3H-1,2,4-triazol-3-one (from Step C) and di-t-butyl dicarbonate, according to the procedure of Example 14. The crude product is flash chromatographed over silica gel to afford the title compound.

EXAMPLE 22

2-[4-Amino-2-(trifluoromethyl)phenyl]-4-[[2'-[N-(t-butoxycarbonyl)sulfamoyl]biphenyl-4-yl]methyl]-5-n-butyl-2,4-dihydro-3H-1,2,4-triazol-3-one The title compound is prepared from 4-[[2'-[N-(t-butoxycarbonyl)sulfamoyl]biphenyl-4-yl]methyl]-5-n-butyl-2,4-dihydro-2-[4-nitro-2-(trifluoromethyl)-phenyl]-3H-1,2,4-triazol-3-one (from Example 21) by treatment with excess stannous chloride and concentrated hydrochloric acid in THF at 0° C. The reaction is worked up by treatment with excess sodium hydroxide, and the product is extracted with ethyl acetate. After drying over anhydrous sodium sulfate and removal of volatiles, the crude product is flash chromatographed over silica gel to afford the desired material.

EXAMPLE 23

4-[[2'-[N-(t-Butoxycarbonyl)sulfamoyl]biphenyl-4-yl]methyl]-5-n-butyl-2,4-dihydro-2-[4-(propionylamino)-2-(trifluoromethyl)phenyl]-3H-1,2,4-triazol-3-one This material is prepared from 2-[4-amino-2-(trifluoromethyl)phenyl]-4-[[2'-[N-(t-butoxycarbonyl)sulfamoyl]biphenyl-4-yl]methyl]-5-n-butyl-2,4-dihydro-3H-1,2,4-triazol-3-one (from Example 22) and propionyl chloride in the presence of sodium hydride in THF. The crude product is flash chromatographed over silica gel to give the title compound.

EXAMPLE 24

4-[[2'-[N-(t-Butoxycarbonyl)sulfamoyl]biphenyl-4-yl]methyl]-5-n-butyl-2-(2-chloro-5-nitrophenyl)-2,4-dihydro-3H-1,2,4-triazol-3-one Step A: 5-n-Butyl-2-(2-chloro-5-nitrophenyl)-2,4-dihydro-3H-1,2,4-triazol-3-one By the procedure of Example 3, Step C, 2-chloro-5-nitrophenylhydrazine [generated from the hydrochloride, which was prepared from 2-chloro-5-nitroaniline according to H. Stroh and G. Westphal, Chem. Ber. 96, 184 (1963), by partitioning between ether and 1N sodium carbonate] was reacted with ethyl N-carbethoxyvalerimidate (from Example 3, Step B). Enough THF was added to the reaction mixture to ensure dissolution of all starting material. After work-up, the residue was purified by flash chromatography on silica gel (gradient elution with 0.5-5.0 methanol in CH$_2$Cl$_2$) to give the title compound as an orange solid, mp 145°-147° C.; homogeneous by TLC (19:1 CH$_2$Cl$_2$—MeOH), mass spectrum (FAB) m/e 297 (M+1)$^+$.

400 MHz $^1$H NMR (CDCl$_3$) δ0.91 (t, J=7.3 Hz, 3H), 1.39 (m, 2H), 1.67 (m, 2H), 2.58 (t, J=7.7 Hz, 2H), 7.70 (d, J=8.9 Hz, 1H), 8.22 (dd, J=8.8, 2.6 Hz, 1H), 8.38 (d, J=2.6 Hz, 1H), 11.62 (s, 1H).

Step B: 5-n-Butyl-4-[[2'-(N-t-butylsulfamoyl)biphenyl-4-yl]methyl]-2-(2-chloro-5-nitrophenyl)-2,4-dihydro-3H-1,2,4-triazol-3-one By the procedure of Example 8, Step A, 5-n-butyl-2-(2-chloro-5-nitrophenyl)-2,4-dihydro-3H-1,2,4-triazol-3-one (from Step A) was alkylated with [2-(N-t-butylsulfamoyl)biphenyl-4-yl]methyl bromide (from Example 7). Flash chromatography of the crude product on silica gel (gradient elution with 0.5-5.0% MeOH in CH$_2$Cl$_2$) gave the title compound as an orange solid, mp >78° C. (gradual), homogeneous by TLC (98:2 CH$_2$Cl$_2$—MeOH), mass spectrum (FAB) m/e 598 (M+1)$^+$.

400 MHz $^1$H NMR (CDCl$_3$) δ0.91 (t, J=7.4 Hz, 3H), 0.98 (s, 9H), 1.40 (m, 2H), 1.66 (m, 2H), 2.52 (t, J=7.6 Hz, 2H), 3.49 (s, 1H), 4.96 (s, 2H), 7.25-7.60 (m, 7H), 7.69 (d, J=8.8 Hz, 1H), 8.15 (dd, J=7.7, 1.5 Hz, 1H) 8.21 (dd, J=8.8, 2.6 Hz, 1H), 8.39 (d, J=2.6 Hz, 1H)

Step C: 5-n-Butyl-2-(2-chloro-5-nitrophenyl)-2,4-dihydro-4-[(2'-sulfamoylbiphenyl-4-yl)methyl]-3H-1,2,4-triazol-3-one The title compound was prepared from 5-n-butyl-4-[[2'-(N-t-butylsulfamoyl)biphenyl-4-yl]methyl]-2-(2-chloro-5-nitrophenyl)-2,4-dihydro-3H-1,2,4-triazol-3-one (from Step B) according to the procedure of Example 8, Step B, and was obtained as a pale yellow solid, mp >90° C. (gradual), homogeneous by TLC (19:1 CH$_2$Cl$_2$—MeOH); mass spectrum (FAB) m/e 542 (M+1)$^+$.

400 MHz $^1$H NMR (CDCl$_3$) δ0.90 (t, J=7.4 Hz, 3H), 1.39 (m, 2H), 1.67 (m, 2H), 2.53 (t, J=7.6 Hz, 2H), 4.23 (s, 2H), 4.96 (s, 2H), 7.25-7.61 (m, 7H), 7.69 (d, J=8.8 Hz, 1H), 8.14 (dd, J=7.9, 1.2 Hz, 1H), 8.20 (dd, J=8.8, 2.6 Hz, 1H), 8.39 (d, J=2.6 Hz, 1H).

Step D: 4-[[2'-[N-(t-Butoxycarbonyl)sulfamoyl]-biphenyl-4-yl]methyl]-5-n-butyl-2-(2-chloro-5-nitrophenyl)-2,4-dihydro-3H-1,2,4-triazol-3-one The title compound was prepared from 5-n-butyl-2-(2-chloro-5-nitrophenyl)-2,4-dihydro-4-[(2'-sulfamoylbiphenyl-4-yl)methyl]-3H-1,2,4-triazol-3-one (from Step C) and di-t-butyl dicarbonate, according to the procedure of Example 14. The crude product was flash chromatographed over silica gel (gradient elution using 0.5-2.0% MeOH/CH$_2$Cl$_2$) to afford the desired material as a glassy solid, homogeneous by TLC (19:1 CH$_2$Cl$_2$—MeOH); mass spectrum (FAB) m/e 642 (M+1)+.

400 MHz $^1$H NMR (CDCl$_3$) δ0.91 (t, J=7.4 Hz, 3H), 1.28 (s, 9H), 1.39 (m, 2H), 1.67 (m, 2H), 2.53 (t, J=7.5 Hz, 2H), 4.97 (s, 2H), 6.50 (s, 1H), 7.29-7.38 (m, 5H), 7.52-7.70 (m, 3H), 8.19-8.24 (m, 2H), 8.39 (d, J=2.6 Hz, 1H)

EXAMPLE 25

2-(5-Amino-2-chlorophenyl)-4-[[2'-[N-(t-butoxycarbonyl)sulfamoyl]biphenyl-4-yl]methyl]-5-n-butyl-2,4-dihydro-3H-1,2,4-triazol-3-one A mixture of 128 mg (0.2 mmol) of 4-[[2'-[N-(t-butoxycarbonyl)sulfamoyl]-biphenyl-4-yl]methyl]-5-n-butyl-2-(2-chloro-5-nitrophenyl)-2,4-dihydro-3H -1,2,4-triazol-3-one (from Example 24), 10 mg of 10% platinum oxide on carbon, and 2 mL of ethyl acetate was stirred under a hydrogen atmosphere (balloon) for 4 hours. The mixture was then filtered through Celite, and the product was chromatographed on a column of silica gel (gradient elution with 0.5-5% methanol in CH$_2$Cl$_2$) to yield 78 mg of the title compound as a white solid, mp 185°-188° C.; nearly homogeneous by TLC (9:1 CH$_2$Cl$_2$—MeOH).

400 MHz $^1$H NMR (CDCl$_3$) δ0.89 (t, J=7.3 Hz, 3H), 1.27 (s, 9H), 1.37 (m, 2H), 1.65 (m, 2H), 2.51 (t, J=7.6 Hz, 2H), 4.95 (s, 2H), 6.85 (br d, 1H), 7.07 (br s, 1H), 7.25-7.4 (m, 6H), 7.5-7.65 (m, 2H), 8.23 (d, J=8 Hz, 1H).

EXAMPLE 26

4-[[2'-[N-(t-Butoxycarbonyl)sulfamoyl]biphenyl-4-yl]methyl]-5-n-butyl-2-[2-chloro-5-(valerylamino)-phenyl]-2,4-dihydro-3H-1,2,4-triazol-3-one A solution of 78 mg (0.128 mmol) of 2-(5-amino-2-chlorophenyl)-4-[[2'-[N-(t-butoxycarbonyl)sulfamoyl]-biphenyl-4-yl]methyl]-5-n-butyl-2,4-dihydro-3H-1,2,4-triazol-3-one (from Example 25), 76 μL (77 mg, 0.64 mmol) of valeryl chloride, and 15.6 mg (0.128 mmol) of 4-(dimethylamino)pyridine (DMAP) in 1 mL of dry pyridine was stirred overnight at room temperature. The mixture was quenched by addition of water and extracted twice with ethyl acetate. The combined organic fractions were washed twice with water, then with brine, and dried over Na$_2$SO$_4$. The filtered solution was concentrated, and the residue was flash chromatographed twice on silica gel (gradient elution with 0.5-3% methanol in CH$_2$Cl$_2$) to provide 41 mg (46%) of the title compound as a white solid, mp 177°-179° C.; homogeneous by TLC (9:1 CH$_2$Cl$_2$—MeOH).

Analysis: C$_{35}$H$_{42}$ClN$_5$O$_6$S•0.25H$_2$O. Calc'd: C, 59.99; H, 6.11; N, 9.99. Found: C, 59.84; H, 5.88; N, 9.93.

400 MHz $^1$H NMR (CD$_3$OD) δ0.91 (t, J=7.4 Hz, 3H), 0.95 (t, J=7.4 Hz; 3H), 1.29 (s, 9H), 1.40 (m, 4H), 1.66 (m, 4H), 2.38 (t, J=7.5 Hz, 2H), 2.63 (t, J=7.5 Hz, 2H), 5.05 (s, 2H), 7.3-7.7 (m, 9H) 7.95 (d, J=2.5 Hz, 1H), 8.23 (d, J=8.1 Hz, 1H).

EXAMPLE 27

5-n-Butyl-4-[[2'-(N-cyanosulfamoyl)biphenyl-4-yl]methyl]-2-[(2-trifluoromethyl)phenyl]-2,4-dihydro-3H-1,2,4-triazol-3-one To a mixture of 135 mg (0.255 mmole) of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 13, Step C) dissolved in 1.5 mL of THF at 0° C. was added dropwise 0.255 mL of a 1M solution of sodium bis(trimethylsilyl)amide in THF (0.255 mmole). After stirring at room temperature for 1 h, the reaction mixture was cooled to 0° C. and 28 mg (0.260 mmole) of cyanogen bromide, dissolved in 0.2 mL of THF, was added. After stirring at room temperature overnight, the reaction was quenched with water, the organic material was extracted with EtOAc, washed with water and brine, and dried over anhydrous sodium sulfate. The crude product obtained after filtration and evaporation of volatiles was flash chromatographed over silica gel (gradient elution using 1-5% MeOH/CH$_2$Cl$_2$) to afford the desired material as a glassy white solid, homogeneous by TLC (10% MeOH/CH$_2$Cl$_2$), mass spectrum (FAB) m/e 578 (M+Na)+, 594 (M+K)+; mp 187°-190° C.

400 MHz $^1$H NMR (CD$_3$OD) δ0.94 (t, J=7.3 Hz, 3H), 1.42 (m, 2H), 1.63 (m, 2H), 2.63 (t, J=7.3 Hz, 2H), 5.07 (s, 2H), 7.32-7.95 (m, 11H), 8.17 (d, J=7.7 Hz, 1H).

EXAMPLE 28

4-[[2'-[N-(t-Butoxycarbonyl)sulfamoyl]-3-fluorobiphenyl-4-yl]methyl]-5-n-butyl-2-[5-(N-n-butylcarbamoyl)-2-chlorophenyl]-2,4-dihydro-3H-1,2,4-triazol-3-one Step A: Methyl 3-Amino-4-chlorobenzoate To a solution of 2 mL of concentrated sulfuric acid in 50 mL of methanol was added 7.0 g (41 mmol) of 2-amino-3-chlorobenzoic acid, and the mixture was stirred under gentle reflux for 24 hours. The cooled solution was partially evaporated to remove most of the methanol, and the residue was partitioned between ethyl acetate and water. The organic layer was washed successively with 5% NaHCO$_3$ (aqueous), water, and brine. The ethyl acetate phase was then dried over Na$_2$SO$_4$, filtered, and concentrated to yield 7 g (92%) of the title compound as a solid, mp 83°-84° C.; homogeneous by TLC in 98:2 CH$_2$Cl$_2$—MeOH.

200 MHz $^1$H NMR (CDCl$_3$) δ3.89 (s, 3H, superimposed on v br mound, 2H), 7.2-7.5 (m, 3H).

Step B: Methyl 4-Chloro-3-hydrazinobenzoate

A solution of 11.9 g (63.9 mmol) of methyl 3-amino-4-chlorobenzoate (prepared as in Step A) was maintained at −5° to +5° C. and subjected to vigorous mechanical stirring as a solution of 4.41 g (63.9 mmol) of sodium nitrite in 19.3 mL of H$_2$O was added slowly via a dropping funnel. Stirring was continued at this temperature for 1 hour, and the mixture was filtered while cold. The filtrate was immediately added to a rapidly stirred solution of 28.8 g (128 mmol) of stannous chloride dihydrate in 37.3 mL of concentrated HCl, which was also maintained at ≦0° C. Precipitation of a cream-colored solid began at once. After being stirred at 0° C. for 0.5 hour, the mixture was refrigerated overnight. The solid was collected on a filter and triturated with ether to give, after air-drying, approximately 22 g of cream-colored solid (mp 218°-220° C.), which was stored in the freezer. As needed, a portion of this hydrochloride salt was partitioned between 5% NaHCO$_3$ (aqueous) and a mixture of CH$_2$Cl$_2$ and ethyl acetate to liberate the title compound as the free base, which was isolated by concentration of the organic phase to give a cream-colored solid, mp 218°-220° C.; homogeneous by TLC (95:5 CH$_2$Cl$_2$—MeOH); mass spectrum (EI) m/e 200 (M+). This material was used immediately in the next reaction.

200 MHz $^1$H NMR (CDCl$_3$ doped with CD$_3$OD) δ3.85 (s, 3H), 7.2–7.6 (m, 3H).

Step C: 5n-Butyl-2-[2-chloro-5-(methoxycarbonyl)phenyl]-2,4-dihydro-3H-1,2,4-triazol-3-one By the procedure of Example 3, Step C, the title compound was prepared from methyl 4-chloro-3-hydrazinobenzoate (from Step B) in 37% yield as an orange gum (TLC in 95:5 CH$_2$Cl$_2$—MeOH), mass spectrum (FAB) m/e 310 (M+1)$^+$.

400 MHz $^1$H NMR (CDCl$_3$) δ0.87 (t, J=7.3 Hz, 3H), 1.34 (m, 2H), 1.61 (m, 2H), 2.53 (t, J=7.7 Hz, 2H), 3.90 (s, 3H), 7.58 (d, J=8.4 Hz, 1H), 8.01 (dd, J=8.4, 2 Hz, 1H), 8.13 (d, J=2 Hz, 1H), 11.96 (s, 1H).

Step D: 4-(4-Bromo-2-fluorobenzyl)-5-n-butyl-2-[2-chloro-5-(methoxycarbonyl)phenyl]-2,4-dihydro-3H-1,2,4-triazol-3-one A mixture of 789 mg (2.55 mmol) of 5-n-butyl-2-[2-chloro-5-(methoxycarbonyl)phenyl]-2,4-dihydro-3H-1,2,4-triazol-3-one (from Step C), 122.4 mg (3.06 mmol) of sodium hydride (60% in oil), and 2 mL of dry DMF was stirred at 50° C. for 2.5 hours, during which time hydrogen was evolved. A solution of 820 mg (3.06 mmol) of 4-bromo-2-fluorobenzyl bromide in DMF was added, and the mixture was stirred at 50° C. overnight. The cooled reaction mixture was diluted with H$_2$O and extracted twice with ethyl acetate. The combined organic phase was washed with H$_2$O and brine and then dried over Na$_2$SO$_4$. The filtered solution was concentrated, and the residue was flash chromatographed on 250 cc of silica gel packed in hexane (gradient elution with 6:1 to 5:1 hexane-EtOAc; some unreacted starting material was recovered by further elution with 95:5 CH$_2$Cl$_2$—MeOH), yielding 503 mg (40%) of the title compound as an orange gum (TLC in 4:1 hexane-EtOAc), mass spectrum (FAB) m/e 496, 498 (M+1)$^+$.

400 MHz $^1$H NMR (CDCl$_3$) δ0.87 (t, J=7.4 Hz, 3H), 1.36 (m, 2H), 1.62 (m, 2H), 2.48 (t, J=7.7 Hz, 2H), 3.88 (s, 3H), 4.87 (s, 2H), 7.2–7.3 (m, 3H), 7.55 (d, J=8.4 Hz, 1H), 7.98 (dd, J=8.4, 1.0 Hz, 1H), 8.11 (d, J=1.0 Hz, 1H).

Step E: 4-(4-Bromo-2-fluorobenzyl)-5-n-butyl-2-[5-(N-n-butylcarbamoyl)-2-chlorophenyl]-2,4-dihydro-3H-1,2,4-triazol-3-one A solution of 50 mg (0.10 mmol) of 4-(4-bromo-2-fluorobenzyl)-5-n-butyl-2-[2-chloro-5-(methoxycarbonyl)phenyl]-2,4-dihydro-3H-1,2,4-triazol-3-one (from Step D) in 1 mL of n-butylamine was stirred overnight at 65° C. and then evaporated in vacuo. The residue was flash chromatographed on 15 cc of silica gel (gradient elution with 1–5% MeOH in CH$_2$Cl$_2$) to yield 41 mg (76%) of colorless, glassy solid, mp 114°–116° C.; homogeneous by TLC (95:5 CH$_2$Cl$_2$—MeOH); mass spectrum (FAB) M/e 537, 539 (M+1)$^+$.

400 MHz $^1$H NMR (CDCl$_3$) δ0.88 (t, J=7.4 Hz, 3H), 0.94 (t, J=7.3 Hz, 3H), 1.38 (m, 4H), 1.58 (m, 4H), 2.58 (t, J=7.5 Hz, 2H), 3.35 (t, J=7.2 Hz, 2H), 4.98 (s, 2H), 7.25 (dd, J=8, 8 Hz, 1H), 7.35–7.45 (m, 2H), 7.67 (d, J=8.4 Hz, 1H), 7.89 (dd, J=8.4, 2.2 Hz, 1H), 7.96 (d, J=2.2 Hz, 1H).

Step F: 5-n-Butyl-2-[5-(N-n-butylcarbamoyl)-2-chlorophenyl]-4-[[2'-(N-t-butylsulfamoyl)-3-fluorobiphenyl-4-yl]methyl]-2,4-dihydro-3H-1,2,4-triazol-3-one A solution of 41 mg (0.076 mmol) of 4-(4-bromo-2-fluorobenzyl)-5-n-butyl-2-[5-(N-n-butylcarbamoyl)-2-chlorophenyl]-2,4-dihydro-3H-1,2,4-triazol-3-one (from Step E) in 1 mL of toluene was treated with 39.2 mg (0.153 mmol) of 2-(N-t-butylsulfamoyl)phenylboronic acid (prepared from benzenesulfonyl chloride according to the procedures of Example 20, Steps A and B) in 157 mL of ethanol, followed by an additional 0.5 mL of ethanol, 0.24 mL (0.305 mmol) of 1.25N sodium hydroxide (aqueous), and 4.4 mg 0.0038 mmol) of tetrakis(triphenylphosphine)palladium(0). The mixture was stirred at 90° C. for 6 hours and then concentrated. The residue was taken up in ethyl acetate and washed with H$_2$O and then brine. The organic phase was dried over Na$_2$SO$_4$, filtered, and concentrated. The crude product was purified by flash chromatography on 15 cc of silica gel (gradient elution with 0.5–2% MeOH in CH$_2$Cl$_2$), yielding 36 mg (71%) of white solid, mp 84°–86° C.; TLC in 95:5 CH$_2$Cl$_2$—MeOH; mass spectrum (FAB) m/e 676 (M+Li)$^+$.

400 MHz $^1$H NMR (CD$_3$OD) δ0.9–1.0 (m, 6H), 1.04 (s, 9H), 1.35–1.46 (m, 4H), 1.59 (m, 2H), 1.61 (m, 2H), 2.66 (t, J=7.6 Hz, 2H), 3.37 (t, J=7.2 Hz, 2H), 5.10 (s, 2H), 7.25–7.66 (m, 6H), 7.67 (d, J=8.4 Hz, 1H), 7.92 (dd, J=8.4, 2.2 Hz, 1H), 7.98 (d, J=2.2 Hz, 1H), 8.11 (d, J=8 Hz, 1H).

Step G: 5-n-Butyl-2-[5-(N-n-butylcarbamoyl)-2-chlorophenyl]-4-[(3-fluoro-2'-sulfamoylbiphenyl-4-yl)methyl]-2,4-dihydro-3H-1,2,4-triazol-3-one A solution of 32 mg (0.048 mmol) of 5-n-butyl-2-[5-(N-n-butylcarbamoyl)-2-chlorophenyl]-4-[[2'-(N-t-butylsulfamoyl)-3-fluorobiphenyl-4-yl]methyl]-2,4-dihydro-3H-1,2,4-triazol-3-one (from Step F) in 0.5 mL of trifluoroacetic acid (TFA) containing 2 drops of anisole was stirred overnight at room temperature. The excess TFA was removed by evaporation under a gentle stream of N$_2$. The residue was reconcentrated from toluene twice in vacuo and flash chromatographed over 15 cc of silica gel (gradient elution with 0.5–2% MeOH in CH$_2$Cl$_2$) to give 20 mg (69%) of the title compound as a white solid, mp 108°–110° C.; homogeneous by TLC (95:5 CH$_2$Cl$_2$—MeOH); mass spectrum (FAB) m/e 614 (M+1)$^+$.

400 MHz $^1$H NMR (CD$_3$OD) δ0.92, 0.96 (overlapping t, J=7.4 Hz, 6H total), 1.41 (m, 4H), 1.59 (m, 2H), 1.59, 1.65 (overlapping m, 4H total), 2.65 (t, J=7.6 Hz, 2H), 3.37 (t, J=7.1 Hz, 2H), 5.10 (s, 2H), 7.23–7.36 (m, 4H), 7.53–7.64 (m, 2H), 7.71 (d, J=8.4 Hz, 1H), 7.92 (dd, J=8.4, 2.2 Hz, 1H), 7.98 (d, J=2.2 Hz, 1H), 8.11 (d, J=8 Hz, 1H).

Step H: 4-[[2'-[N-(t-Butoxycarbonyl)sulfamoyl]-3-fluorobiphenyl-4-yl]methyl]-5-n-butyl-2-[5-(N-n-butylcarbamoyl)-2-chlorophenyl]-2,4-dihydro-3H-1,2,4-triazol-3-one A solution of 18 mg (0.029 mmol) of 5-n-butyl-2-[5-(N-n-butylcarbamoyl)-2-chlorophenyl]-4-[(3-fluoro-2'-sulfamoylbiphenyl-4-yl)methyl]-2,4-dihydro-3H-1,2,4-triazol-3-one (from Step G) in 0.5 mL of dry THF was treated with 1.4 mg (0.035 mmol) of sodium hydride (60% in oil), and the mixture was stirred at 60° C. for 4 hours, during which time hydrogen was evolved. Then 13.5 μL (12.8 mg, 0.058 mmol) of di-t-butyl dicarbonate was added, and stirring was continued at 60° C. overnight. The cooled mixture was partitioned between water and ethyl acetate. The organic phase was washed with water (2×) and brine, then dried over Na$_2$SO$_4$. The filtered solution was concentrated, and the residue was flash chromatographed over 15 cc of silica gel (gradient elution with 1–4% MeOH in CH$_2$Cl$_2$) to give 18 mg (86%) of the title compound as a glassy solid, mp 98°–100° C.; homogeneous by TLC (95:5 CH$_2$Cl$_2$—MeOH); mass spectrum (FAB) m/e 714 (M+1)$^+$.

400 MHz $^1$H NMR (CD$_3$OD) δ0.94, 0.96 (overlapping t, J~7.4 Hz, 6H total), 1.30 (s, 9H), 1.42 (m, 4H), 1.59 (m, 2H), 1.60 (m, 2H), 1.69 (m, 2H), 2.68 (t, J=7.6 Hz, 2H), 3.37 (m, 2H), 5.11 (s, 2H), 7.15–7.2 (m, 2H), 7.3–7.4 (m, 2H), 7.61 (m, 1H), 7.68–7.73 (m, 2H), 7.92 (dd, J=8.4, 2.2 Hz, 1H), 7.98 (d, J=2.2 Hz, 1H), 8.16 (dd, J=7.9, 1.3 Hz, 1H), 8.62 (br t, 1H).

EXAMPLE 29

4-[[2'-[N-(t-Butoxycarbonyl)sulfamoyl]-3-fluorobiphenyl-4-yl]methyl]-5-n-butyl-2-[2-(trifluoromethyl)-phenyl]-2,4-dihydro-3H-1,2,4-triazol-3-one By a sequence analogous to Example 28 (Steps C, D, F, G, H) beginning with 2-(trifluoromethyl)phenylhydrazine, the title compound was obtained as a solid, mp 83°–85° C.; homogeneous by TLC in 95:5 CH$_2$Cl$_2$—MeOH; mass spectrum (FAB) m/e 655 (M+Li)$^+$.

400 MHz $^1$H NMR (CDCl$_3$) δ0.90 (t, J=7.4 Hz, 3H), 1.29 (s, 9H), 1.40 (m, 2H), 1.67 (m, 2H), 2.56 (t, J=7.6 Hz, 2H), 5.01 (s, 2H), 6.87 (br d, J=6.6 Hz, 1H), 7.1–7.3 (m, 4H), 7.5–7.7 (m, 5H), 7.78 (d, J=7.0 Hz, 1H), 8.24 (dd, J=8.0, 1.3 Hz, 1H).

EXAMPLE 30

4-[[2'-[N-(t-Butoxycarbonyl)sulfamoyl]biphenyl-4-yl]methyl]-5-n-butyl-2-[2-(trifluoromethyl)-5-(propionylamino)phenyl]-2,4-dihydro-3H-1,2,4-triazol-3-one Step A: 2-(2-Bromo-5-nitrophenyl)-5-n-butyl-2,4-dihydro-3H-1,2,4-triazol-3-one By the procedure of Example 3, Step C, the title compound was prepared from 2-bromo-5-nitrophenylhydrazine [generated from the hydrochloride, which was prepared from 2-bromo-5-nitroaniline according to H. Stroh and G. Westphal, Chem. Ber., 96, 184 (1963), by partitioning between ether and 1N sodium carbonate] in 58% yield as a brown solid, mp 125°–127° C.; homogeneous by TLC in 98:2 CH$_2$Cl$_2$—MeOH; mass spectrum (FAB) m/e 341, 343 (M+1)$^+$.

200 MHz $^1$H NMR (CDCl$_3$) δ0.90 (t, J=7.3 Hz, 3H), 1.37 (m, 2H), 1.66 (m, 2H), 2.57 (t, J=7.6 Hz, 2H), 7.89 (d, J=8.8 Hz, 1H), 8.14 (dd, J=8.8, 2.6 Hz, 1H), 8.34 (d, J=2.6 Hz, 1H), 11.93 (br s, 1H).

Step B: 2-(2-Bromo-5-nitrophenyl)-4-[[2'-(N-t-butylsulfamoyl)biphenyl-4-yl]methyl]-5-n-butyl-2,4-dihydro-3H-1,2,4-triazol-3-one The alkylation of 2-(2-bromo-5-nitrophenyl)-5-n-butyl-2,4-dihydro-3H-1,2,4-triazol-3-one (from Step A) with [2'-(N-t-butylsulfamoyl)biphenyl-4-yl]methyl bromide (from Example 7) was carried out according to the procedure of Example 8, Step A, to give a 92% yield of the title compound as a yellow solid, mp 126°–128° C.; homogeneous by TLC in 98:2 CH$_2$Cl$_2$—MeOH; mass spectrum (FAB) m/e 642, 644 (M+1)$^+$.

400 MHz $^1$H NMR (CDCl$_3$) δ0.91 (t, J=7.3 Hz, 3H), 0.98 (s, 9H), 1.40 (m, 2H), 1.68 (m, 2H), 2.52 (t, J=7.7 Hz, 2H), 3.47 (s, 1H), 4.96 (s, 2H), 7.2–7.6 (m, 7H), 7.89 (d, J=8.8 Hz, 1H), 8.11–8.17 (m, 2H), 8.35 (d, J=2.6 Hz, 1H).

Step C: 5-n-Butyl-4-[[2'-(N-t-butylsulfamoyl)biphenyl-4-yl]methyl]-2,4-dihydro-2-[5-nitro-2-(trifluoromethyl)phenyl]-3H-1,2,4-triazol-3-one To a solution of 600 mg (0.935 mmol) of 2-(2-bromo-5-nitrophenyl)-4-[[2'-(N-t-butylsulfamoyl)biphenyl-4-yl]methyl]-5-n-butyl-2,4-dihydro-3H-1,2,4-triazol-3-one (from Step B) in 1.87 mL of DMF were added 65 mg (1.12 mmol) of potassium fluoride, 179 mg (0.935 mmol) of cuprous iodide, and 197 μL (270 mg, 1.87 mmol) of methyl chlorodifluoroacetate. The mixture was stirred in a sealed tube at 120° C. for 12 hours. The cooled mixture was diluted with H$_2$O and extracted 3× with ethyl acetate. The combined organic extracts were washed with H$_2$O, then brine, and dried over Na$_2$SO$_4$. The residue obtained upon evaporation of the filtered solution was flash chromatographed on silica gel (gradient elution with 8.5:1 to 5:1 hexane-EtOAc) to give 216 mg (37%) of the title compound as a solid, mp 135°–137° C. [Subsequently eluted was 187 mg (32%) of the corresponding 2-chloro-5-nitrophenyl analog, obtained as a byproduct.] The desired product was homogeneous by TLC (98:2 CH$_2$Cl$_2$—MeOH); mass spectrum (FAB) m/e 638 (M+Li)$^+$.

400 MHz $^1$H NMR (CDCl$_3$) δ0.90 (t, J=7.3 Hz, 3H), 0.98 (s, 9H), 1.39 (m, 2H), 1.66 (m, 2H), 2.51 (t, J=7.6 Hz, 2H), 4.96 (s, 2H), 7.25–7.6 (m, 7H), 7.99 (d, J=8.7 Hz, 1H), 8.16 (dd, J=7.8, 1.3 Hz, 1H), 8.36 (dd, J=8.6, 1.5 Hz, 1H), 8.47 (d, J=2.2 Hz, 1H).

Step D: 5-n-Butyl-2,4-dihydro-2-[5-nitro-2-(trifluoromethyl)phenyl]-4-[(2'-sulfamoylbiphenyl-4-yl)methyl]-3H-1,2,4-triazol-3-one The title compound was prepared from 5-n-butyl-4-[[2'-(N-t-butylsulfamoyl)-biphenyl-4-yl]methyl]-2,4-dihydro-2-[5-nitro-2-(trifluoromethyl)phenyl]-3H-1,2,4-triazol-3-one (from Step C) by reaction with trifluoroacetic acid in the presence of anisole according to the method of Example 28, Step G. Flash chromatography on silica gel (elution with 0.3% MeOH in CH$_2$Cl$_2$) yielded 60 mg (79%) of the product, homogeneous by TLC in 95:5 CH$_2$Cl$_2$—MeOH; mass spectrum (FAB) m/e 576 (M+1)$^+$.

400 MHz $^1$H NMR (CDCl$_3$) δ0.89 (t, J=7.3 Hz, 3H), 1.38 (m, 2H), 1.64 (m, 2H), 2.52 (t, J=7.6 Hz, 2H), 4.34 (br s, 2H), 4.96 (s, 2H), 7.25–7.6 (m, 7H), 7.99 (d, J=8.8 Hz, 1H), 8.11 (m, 1H), 8.35 (d, J=8.7 Hz, 1H), 8.46 (s, 1H).

Step E: 4-[[2'-[N-(t-Butoxycarbonyl)sulfamoyl]biphenyl-4-yl]methyl]-5-n-butyl-2,4-dihydro-2-[5-nitro-2-(trifluoromethyl)phenyl]-3H-1,2,4-triazol-3-one The title compound was prepared in 57% yield from 5-n-butyl-2,4-dihydro-2-[5-nitro-2-(trifluoromethyl)-phenyl]-4-[(2'-sulfamoylbiphenyl-4-yl)methyl]3H-1,2,4-triazol-3-one (from Step D) and di-t-butyl dicarbonate by the procedure of Example 28, Step H. The material showed minor impurities by TLC in 95:5 CH$_2$Cl$_2$—MeOH; mass spectrum (FAB) m/e 688 (M+2Li)$^+$.

400 MHz $^1$H NMR (CDCl$_3$) δ0.90 (t, J=7.3 Hz, 3H), 1.28 (s, 9H), 1.39 (m, 2H), 1.66 (m, 2H), 2.53 (t, J=7.6 Hz, 2H), 4.97 (s, 2H), 7.25–7.7 (m, 7H), 7.99 (d, J=8.8 Hz, 1H), 8.23 (dd, J=8.0, 1.3 Hz, 1H), 8.35 (d, J~9 Hz, 1H), 8.47 (d, J=2.1 Hz, 1H).

Step F: 2-[5-Amino-2-(trifluoromethyl)phenyl]-4-[[2'-[N-(t-butoxycarbonyl)sulfamoyl]biphenyl-4-yl]methyl]-5-n-butyl-2,4-dihydro-3H-1,2,4-triazol-3-one Hydrogenation of 4-[[2'-[N-(t-butoxycarbonyl)sulfamoyl]biphenyl-4-yl]-methyl]-5-n-butyl-2,4-dihydro-2-[5-nitro-2-(trifluoromethyl)phenyl]-3H-1,2,4-triazol-3-one (from Step E) according to the procedure of Example 25 provided a 69% yield of the title compound as a solid, mp 154°–156° C.; homogeneous by TLC in 95:5 CH$_2$Cl$_2$—MeOH; mass spectrum (FAB) m/e 646 (M+1)$^+$.

400 MHz $^1$H NMR (CD$_3$OD) δ0.89 (t, J=7.4 Hz, 3H), 1.30 (s, 9H), 1.38 (m, 2H), 1.63 (m, 2H), 2.59 (t,

J=7.5 Hz, 2H), 5.04 (s, 2H), 6.71 (d, J=2 Hz, 1H), 6.80 (dd, J=8.8, 2 Hz, 1H), 7.25–7.7 (m, 8H), 8.16 (d, J=8.0 Hz, 1H).

Step G: 4-[[2'-[N-(t-Butoxycarbonyl)sulfamoyl]-biphenyl-4-yl]methyl]-5-n-butyl-2,4-dihydro-2-[5-(propionylamino)-2-(trifluoromethyl)phenyl]-3H-1,2,4-triazol-3-one Propionyl bromide was reacted with 2-[5-amino-2-(trifluoromethyl)phenyl]-4-[[2'-[N-(t-butoxycarbonyl)-sulfamoyl]biphenyl-4-yl]methyl]-5-n-butyl-2,4-dihydro-3H-1,2,4-triazol-3-one (from Step F) according to the method of Example 26. Purification by silica gel flash chromatography (gradient elution with 0.5–5% MeOH in CH$_2$Cl$_2$) followed by semi-preparative HPLC (Zorbax C8 reverse phase column, elution with 60:40 and then 65:35 MeCN—H$_2$O) gave 13 mg (52%) of the title compound as a solid, mp 158°–161° C.; homogeneous by TLC in 95:5 CH$_2$Cl$_2$—MeOH; mass spectrum (FAB) m/e 714 (M+2Li)$^+$.

400 MHz $^1$H NMR (CD$_3$OD) δ0.90 (t, J=7.4 Hz, 3H), 1.19 (t, J=7.6 Hz, 3H), 1.30 (s, 9H), 1.39 (m, 2H), 1.63 (m, 2H), 2.43 (q, J=7.6 Hz, 2H), 2.61 (t, J=7.4 Hz, 2H), 5.05 (s, 2H), 7.3–7.4 (m, 5H), 7.59 (dd, J=7.5, 7.5 Hz, 1H), 7.69 (dd, J=7.5, 7.5 Hz, 1H), 7.80 (m, 2H), 7.96 (s, 1H), 8.16 (d, J=8.0 Hz, 1H).

EXAMPLE 31

2-[2-Bromo-5-(propionylamino)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one Step A: 3-Fluoro-4-methyl-2'-(N-t-butylsulfamoyl)-biphenyl The palladium (0)-catalyzed coupling of 4-bromo-2-fluorotoluene with 2-(N-t-butylsulfamoyl)phenylboronic acid was carried out according to the procedure of Example 28 Step F. Purification of the crude product by flash chromatography (elution with hexane-EtOAc) gave a 92% yield of the title compound as an off-white foam (TLC in 4:1 hexane-EtOAc); mass spectrum (FAB) m/e 322 (M+1)$^+$.

400 MHz $^1$H NMR (CDCl$_3$) δ1.01 (s, 9H), 2.32 (s, 3H), 3.59 (br s, 1H), 7.13–7.28 (m, 4H), 7.44–7.56 (m, 2H), 8.14 (dd, J=7.8, 1.4 Hz, 1H).

Step B: [3-Fluoro-2'-(N-t-butylsulfamoyl)biphenyl-4-yl]methyl Bromide

A solution of 1.08 g (3.36 mmol) of 3-fluoro-4-methyl-2'-(N-t-butyl-sulfamoyl)biphenyl (from Step A) in 20 mL of CCl$_4$ was stirred at reflux under irradiation from a 100-watt tungsten lamp as a solution of 3.5 mmol of bromine in approximately 13 mL of CCl$_4$ was added dropwise over 1.5 hour. After being stirred at reflux overnight, the solution was cooled and concentrated. The residue was crystallized from EtOAc-hexane to give 1.10 g of the title compound as an off-white solid, mp 138°–140° C. (estimated purity 87%; contains minor unbrominated and dibrominated contaminants by TLC); mass spectrum (FAB) m/e 400, 402 (M+1)$^+$.

400 MHz $^1$H NMR (CDCl$_3$) δ1.01 (s, 9H), 3.56 (br s, 1H), 4.54 (s, 2H), 7.2–7.6 (m, 6H), 8.15 (dd, J=8, 1.3 Hz, 1H).

Step C: 2-(2-Bromo-5-nitrophenyl)-4-[[2'-(N-t-butyl-sulfamoyl)-3-fluorobiphenyl-4-yl]methyl]-5-n-butyl-2,4-dihydro-3H-1,2,4-triazol-3-one The alkylation of 2-(2-bromo-5-nitrophenyl)-5-n-butyl-2,4-dihydro-3H-1,2,4-triazol-3-one (from Example 30, Step A) with [3-fluoro-2'-(N-t-butylsulfamoyl)-biphenyl-4-yl]methyl bromide (from Step B) was carried out according to the procedure of Example 8, Step A, to give a 93% yield of the title compound as a stiff, brownish foam, mp 137°–139° C., homogeneous by TLC in 98:2 CH$_2$Cl$_2$—MeOH; mass spectrum (FAB) m/e 666, 668 (M+Li)$^+$.

400 MHz $^1$H NMR (CDCl$_3$) δ0.93 (t, J=7.4 Hz, 3H), 1.03 (s, 9H), 1.43 (m, 2H), 1.70 (m, 2H), 2.58 (t, J=7.7 Hz, 2H), 3.62 (s, 1H), 5.00 (s, 2H), 7.23–7.33 (m, 3H), 7.42–7.58 (m, 3H), 7.88 (d, J=8.8 Hz, 1H), 8.10–8.16 (m, 2H), 8.33 (d, J=2.6 Hz, 1H).

Step D: 2-(5-Amino-2-bromophenyl)-4-[[2'-(N-t-butylsulfamoyl)-3-fluorobiphenyl-4-yl]methyl]-5-n-butyl-2,4-dihydro-3H-1,2,4-triazol-3-one A stirred solution of 200 mg (0.303 mmol) of 2-(2-bromo-5-nitrophenyl)-4-[[2'-(N-t-butylsulfamoyl)-3-fluorobiphenyl-4-yl]methyl]-5-n-butyl-2,4-dihydro-3H-1,2,4-triazol-3-one (from Step C) in 3.5 mL of THF was cooled to 0° C. and treated dropwise with a solution of 542 mg (2.4 mmol) of stannous chloride dihydrate in 1.5 mL of concentrated hydrochloric acid. After 45 minutes, the mixture was added to a vigorously stirred mixture of 50% NaOH and ice. Ethyl acetate (15 mL) was added, and the mixture was stirred at 0° C. for 1.5 hours. The phases were separated, and the aqueous fraction was re-extracted twice with ethyl acetate. The combined organic fractions were washed with water and brine and dried over anhydrous Na$_2$SO$_4$. The filtered solution was concentrated, and the residue was flash chromatographed on silica gel to give 131 mg (68%) of the title compound as a stiff, off-white foam, mp 103°–105° C.; homogeneous by TLC (95:5 CH$_2$Cl$_2$—MeOH); mass spectrum (FAB) m/e 629, 631 (M+1)$^+$.

400 MHz $^1$H NMR (CDCl$_3$) δ0.88 (t, J=7.4 Hz, 3H), 1.00 (s, 9H), 1.38 (m, 2H), 1.63 (m, 2H), 2.51 (t, J=7.8 Hz, 2H), 3.96 (br s, 1H), 4.97 (s, 2H), 7.0–7.6 (m, 9H), 8.13 (d, J=7.8 Hz, 1H).

Step E: 2-[2-Bromo-5-(propionylamino)phenyl]-4-[[2'-(N-t-butylsulfamoyl)-3-fluorobiphenyl-4-yl]methyl]-5-n-butyl-2,4-dihydro-3H-1,2,4-triazol-3-one Propionyl bromide was reacted with 2-(5-amino-2-bromophenyl)-4-[[2'-(N-t-butylsulfamoyl)-3-fluorobiphenyl-4-yl]methyl]-5-n-butyl-2,4-dihydro-3H-1,2,4-triazol-3-one (from Step D) according to the procedure of Example 26 to give a 77% yield of the title compound as a stiff, off-white foam, mp 119°–121° C.; homogeneous by TLC in 95:5 CH$_2$Cl$_2$—MeOH; mass spectrum (FAB) m/e 686,688 (M+1)$^+$.

400 MHz $^1$H NMR (CDCl$_3$) δ0.88 (t, J=7.3 Hz, 3H), 1.02 (s, 9H), 1.13 (t, J=7.5 Hz, 3H), 1.38 (m, 2H), 1.64 (m, 2H), 2.30 (q, J=7.5 Hz, 2H), 2.52 (t, J=7.7 Hz, 2H), 3.77 (s, 1H), 5.01 (s, 2H), 7.2–7.6 (m, 8H), 7.74 (d, J=2.5 Hz, 1H), 8.14 (dd, J=7.9, 1.4 Hz, 1H), 8.49 (br s, 1H).

Step F: 2-[2-Bromo-5-(propionylamino)phenyl]-5-n-butyl-2,4-dihydro-4-[(3-fluoro-2'-sulfamoylbiphenyl-4-yl)methyl]-3H-1,2,4-triazol-3-one The title compound was prepared from 2-[2-bromo-5-(propionylamino)-phenyl]-4-[[2'-(N-t-butylsulfamoyl)-3-fluorobiphenyl-4-yl]methyl]-5-n-butyl-2,4-dihydro-3H-1,2,4-triazol-3-one (from Step E) by reaction with trifluoroacetic acid in the presence of anisole according to the procedure of Example 28, Step G, giving an 88% yield of the title compound as an off-white foam; homogeneous by TLC in 95:5 CH$_2$Cl$_2$—MeOH; mass spectrum (FAB) m/e 630,632 (M+1)$^+$.

400 MHz $^1$H NMR (CD$_3$OD) δ0.92 (m, 3H), 1.18 (m, 3H), 1.42 (m, 2H), 1.64 (m, 2H), 2.39 (m, 2H), 2.64 (m,

2H), 3.77 (s, 1H), 5.09 (s, 2H), 7.2–7.4 (m, 4H), 7.5–7.7 (m, 4H), 7.89 (d, J=2.4 Hz, 1H), 8.10 (d, J=8 Hz, 1H).

Step G: 2-[2-Bromo-5-(propionylamino)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one By the procedure of Example 28, Step H, 2-[2-bromo-5-(propionylamino)-phenyl]-5-n-butyl-2,4-dihydro-4-[(3-fluoro-2'-sulfamoylbiphenyl-4-yl)methyl]-3H-1,2,4-triazol-3-one (from Step F, above) was reacted with di-t-butyl dicarbonate. Purification of the crude product by flash chromatography on silica gel (elution with 0.8% MeOH in $CH_2Cl_2$) afforded a 58% yield of the title compound as a solid, mp 123°–126° C.; homogeneous by TLC in 95:5 $CH_2Cl_2$—MeOH; mass spectrum (FAB) m/e 736, 738 (M+Li)+.

400 MHz $^1$H NMR (CDCl$_3$) δ0.92 (t, J=7.3 Hz, 3H), 1.18 (t, J=7.3 Hz, 3H), 1.28 (s, 9H), 1.42 (m, 2H), 1.69 (m, 2H), 2.34 (q, J=7.3 Hz, 2H), 2.58 (t, J=7.7 Hz, 2H), 4.99 (s, 2H), 7.1–7.4 (m, 5H), 7.5–7.7 (m, 4H), 8.24 (d, J=8 Hz, 1H).

EXAMPLE 32

2-[5-(Benzoylamino)-2-bromophenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one The title compound was prepared by the sequence described in Example 31, except that benzoyl chloride was substituted for propionyl bromide in the step corresponding to Example 31, Step E: stiff, off-white foam, mp 130°–133° C.; homogeneous by TLC in 95:5 $CH_2Cl_2$—MeOH; mass spectrum (FAB) m/e 785, 787 (M+Li)+.

400 MHz $^1$H NMR (CDCl$_3$) δ0.92 (t, J=7.3 Hz, 3H), 1.25 (s, 9H), 1.42 (m, 2H), 1.70 (m, 2H), 2.59 (t, J=7.7 Hz, 2H), 4.99 (s, 2H), 7.11 (d, J=10.5 Hz, 1H), 7.16 (d, J=7.9 Hz, 1H), 7.30 (d, J=7.6 Hz, 1H), 7.36 (dd, J=7.7, 7.7 Hz, 1H), 7.46 (dd, J=7.5, 7.5 Hz, 2H), 7.5–7.8 (m, 6H), 7.85 (d, J=7.1 Hz, 2H), 8.24 (m, 2H).

EXAMPLE 33

4-[[2'-[N-(t-Butoxycarbonyl)sulfamoyl]-3-fluorobiphenyl-4-yl]methyl]-5-n-butyl-2,4-dihydro-2-[5-(propionylamino)-2-(trifluoromethyl)phenyl]-3H-1,2,4-triazol-3-one Step A: 5-n-Butyl-4-[[2'-(N-t-butylsulfamoyl)-3-fluorobiphenyl-4-yl]methyl]-2,4-dihydro-2-[5-nitro-2-(trifluoromethyl)phenyl]-3H-1,2,4-triazol-3-one A mixture of 400 mg (0.606 mmol) of 2-(2-bromo-5-nitrophenyl)-4-[[2'-(N-t-butylsulfamoyl)-3-fluorobiphenyl-4-yl]methyl]-5-n-butyl-2,4-dihydro-3H-1,2,4-triazol-3-one (from Example 31, Step C), 128 μL (175 mg, 1.21 mmol) of methyl chlorodifluoroacetate, 42 mg (0.73 mmol) of potassium fluoride, 116 mg (0.606 mmol) of cuprous iodide, 72 mg (0.606 mmol) of potassium bromide, and 1.2 mL of DMF was stirred under N$_2$ at 120° C. in a sealed tube for 15 hours. The cooled mixture was diluted with water and extracted 3× with ethyl acetate. The combined organic fractions were washed with brine, dried (Na$_2$SO$_4$), and filtered. The filtrate was concentrated, and the residue was flash chromatographed on silica gel (elution with 6:1 hexane-EtOAc) to give 243 mg (62%) of the title compound as a stiff, pale yellow foam, mp 145°–146° C. [Subsequently eluted was 28 mg of the 2-chloro-5-nitrophenyl analog.] The desired product was homogeneous by TLC in 5:1 hexane-EtOAc; mass spectrum (FAB) m/e 656 (M+Li)+.

400 MHz $^1$H NMR (CDCl$_3$) δ0.92 (t, J=7.3 Hz, 3H), 1.02 (s, 9H), 1.41 (m, 2H), 1.68 (m, 2H), 2.57 (t, J=7.6 Hz, 2H), 3.60 (s, 1H), 5.00 (s, 2H), 7.2–7.6 (m, 6H), 7.99 (d, J=8.8 Hz, 1H), 8.15 (dd, J=8, 1.3 Hz, 1H), 8.35 (dd, J~9, 2 Hz, 1H), 8.45 (d, J=2.2 Hz, 1H).

Step B: 5-n-Butyl-2,4-dihydro-4-[(3-fluoro-2'-sulfamoylbiphenyl-4-yl)methyl]-2-[5-nitro-2-(trifluoromethyl)phenyl]-3H-1,2,4-triazol-3-one Reaction of 5-n-butyl-4-[[2'-(N-t-butylsulfamoyl)-3-fluorobiphenyl-4-yl]methyl]-2,4-dihydro-2-[5-nitro-2-(trifluoromethyl)phenyl]-3H-1,2,4-triazol-3-one (from Step A) with trifluoroacetic acid in the presence of anisole according to the procedure of Example 28, Step G, gave a 94% yield of the title compound as a pale yellow foam, homogeneous by TLC (95:5 $CH_2Cl_2$—MeOH); mass spectrum (FAB) m/e 594 (M+1)+.

400 MHz $^1$H NMR (CDCl$_3$) δ0.91 (t, J=7.3 Hz, 3H), 1.41 (m, 2H), 1.68 (m, 2H), 2.58 (t, J=7.6 Hz, 2H), 4.38 (s, 1H), 5.00 (s, 2H), 7.25–7.62 (m, 6H), 7.99 (d, J=8.8 Hz, 1H), 8.14 (dd, J=8.0, 1.4 Hz, 1H), 8.35 (dd, J=8.7, 1.5 Hz, 1H), 8.46 (d, J=2.1 Hz, 1H).

Step C: 4-[[2'-[N-(t-Butoxycarbonyl)sulfamoyl]-3-fluorobiphenyl-4-yl]methyl]-5-n-butyl-2,4-dihydro-2-[5-nitro-2-(trifluoromethyl)phenyl]-3H-1,2,4-triazol-3-one By the procedure of Example 28, Step H, 5-n-butyl-2,4-dihydro-4-[(3-fluoro-2'-sulfamoylbiphenyl-4-yl)methyl]-2-[5-nitro-2-(trifluoromethyl)phenyl]-3H-1,2,4-triazol-3-one (from Step B) was reacted with di-t-butyl dicarbonate. The crude product was flash chromatographed on silica gel to give a 90% yield of the title compound as a pale yellow foam, homogeneous by TLC (95:5 $CH_2Cl_2$—MeOH); mass spectrum (FAB) m/e 700 (M+Li)$^{30}$.

400 MHz $^1$H NMR (CDCl$_3$) δ0.92 (t, J=7.4 Hz, 3H), 1.30 (s, 9H), 1.42 (m, 2H), 1.69 (m, 2H), 2.59 (t, J=7.6 Hz, 2H), 5.01 (s, 2H), 6.66 (br s, 1H), 7.12–7.35 (m, 4H), 7.55–7.67 (m, 2H), 7.99 (d, J=8.8 Hz, 1H), 8.24 (dd, J=8.0, 1.3 Hz, 1H), 8.35 (dd, J=8.7, 1.5 Hz, 1H), 8.45 (d, J=2.5 Hz, 1H).

Step D: 2-[5-Amino-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one A mixture of 185 mg (0.267 mmol) of 4-[[2'-[N-(t-butoxycarbonyl)sulfamoyl]-3-fluorobiphenyl-4-yl]methyl]-5-n-butyl-2,4-dihydro-2-[5-nitro-2-(trifluoromethyl)phenyl]-3H-1,2,4-triazol-3-one (from Step C), 25 mg of platinum oxide, 2 mL of ethyl acetate, and 10 mL of ethanol was shaken with hydrogen at approximately 3 atm for 2 hours. The mixture was centrifuged, and the supernatant was concentrated. Flash chromatography of the residue on silica gel (gradient elution with 1–5% MeOH in $CH_2Cl_2$) yielded 118 mg (67%) of the title compound as a white foam, homogeneous by TLC (95:5 $CH_2Cl_2$—MeOH); mass spectrum (FAB) m/e 664 (M+1)+.

400 MHz $^1$H NMR (CD$_3$OD) δ0.92 (t, J=7.4 Hz, 3H), 1.30 (s, 9H), 1.41 (m, 2H), 1.64 (m, 2H), 2.63 (t, J=7.5 Hz, 2H), 5.08 (s, 2H), 6.69 (d, J=2.3 Hz, 1H), 6.79 (dd, J=8.6, 1.8 Hz, 1H), 7.12–7.19 (m, 2H), 7.24 (dd, J=7.8, 7.8 Hz, 1H), 7.35 (dd, J=7.6, 1.3 Hz, 1H), 7.47 (d, J=8.7 Hz, 1H), 7.61 (m, 1H), 7.70 (m, 1H), 8.16 (dd, J=8.0, 1.3 Hz, 1H).

Step E: 4-[[2'-[N-(t-Butoxycarbonyl)sulfamoyl]-3-fluorobiphenyl-4-yl]methyl]-5-n-butyl-2,4-dihydro-2-[5-

(propionylamino)-2-(trifluoromethyl)phenyl]-3H-1,2,4-triazol-3-one

Propionyl bromide was reacted with 2-[5-amino-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one (from Step D) according to the procedure of Example 26 to give a 95% yield of the title compound as a white solid, mp 167°-169° C.; homogeneous by TLC in 95:5 $CH_2Cl_2$—MeOH; mass spectrum (FAB) m/e 726 (M+Li)+.

400 MHz $^1$H NMR (CDCl$_3$) δ0.90 (t, J=7.3 Hz, 3H), 1.17 (t, J=7.4 Hz, 3H), 1.27 (s, 9H), 1.40 (m, 2H), 1.66 (m, 2H, partially obscured by H$_2$O peak), 2.35 (q, J=7.4 Hz, 2H), 2.57 (t, J=7.6 Hz, 2H), 4.98 (s, 2H), 7.09-7.31 (m, 4H), 7.54-7.67 (m, 4H), 7.74 (d, J=8.4 Hz, 1H), 8.17 (br s, 1H), 8.24 (dd, J=8.0, 1.3 Hz, 1H).

EXAMPLE 34

4-[[2'-[N-(t-Butoxycarbonyl)sulfamoyl]-3-fluorobiphenyl-4-yl]methyl]-5-n-butyl-2,4-dihydro-2-[2-(trifluoromethyl)-5-(valerylamino)phenyl]-3H-1,2,4-triazol-3-one Valeryl chloride was reacted with 2-[5-amino-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one (from Example 33, Step D) according to the procedure of Example 26 to give a 91% yield of the title compound as a white solid, mp 179°-182° C.; homogeneous by TLC in 95:5 $CH_2Cl_2$—MeOH; mass spectrum (FAB) m/e 754 (M+Li)+.

400 MHz $^1$H NMR (CDCl$_3$) δ0.90 (t, J=7.3 Hz, 6H), 1.27 (s, 9H), 1.39 (m, 4H), ~1.65 (m, 4H, obscured by H$_2$O peak), 2.33 (t, J=7.5 Hz, 2H), 2.57 (t, J=7.6 Hz, 2H), 4.97 (s, 2H), 7.08-7.16 (m, 2H), 7.23-7.31 (m, 2H), 7.54-7.67 (m, 4H), 7.84 (d, J=8.4 Hz, 1H), 8.07 (br s, 1H), 8.24 (dd, J=8.0, 1.3 Hz, 1H).

EXAMPLE 35

2-[5-(Benzoylamino)-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one Benzoyl chloride was reacted with 2-[5-amino-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one (from Example 33, Step D) according to the procedure of Example 26 to give a 95% yield of the title compound as a white solid, mp 117°-120° C.; homogeneous by TLC in 95:5 $CH_2Cl_2$—MeOH; mass spectrum (FAB) m/e 774 (M+Li)+.

400 MHz $^1$H NMR (CDCl$_3$) δ0.91 (t, J=7.3 Hz, 3H), 1.21 (s, 9H), 1.40 (m, 2H), 1.67 (m, 2H), 2.33 (t, J=7.5 Hz, 2H), 2.58 (t, J=7.6 Hz, 2H), 4.96 (s, 2H), 7.11 (dd, J=10.5, 1.6 Hz, 1H), 7.16 (dd, J=7.9, 1.6 Hz, 1H), 7.25-7.31 (m, 2H), 7.4-7.9 (m, 10H), 8.07 (m, 2H), 8.24 (dd, J=8.0, 1.3 Hz, 1H), 8.58 (s, 1H).

EXAMPLE 36

4-[[2'-[N-(t-Butoxycarbonyl)sulfamoyl]-3-fluorobiphenyl-4-yl]methyl]-5-n-butyl-2-[2-chloro-5-(propionylamino)phenyl]-2,4-dihydro-3H-1,2,4-triazol-3-one Step A: 4-(4-Bromo-2-fluorobenzyl)-5-n-butyl-2-(2-chloro-5-nitrophenyl)-2,4-dihydro-3H-1,2,4-triazol-3-one By the procedure of Example 28, Step D, 5-n-butyl-2-(2-chloro-5-nitrophenyl)-2,4-dihydro-3H-1,2,4-triazol-3-one (from Example 24, Step A) was alkylated with 4-bromo-2-fluorobenzyl bromide to give a 79% yield of the title compound as an off-white foam, homogeneous by TLC in 4:1 hexane-EtOAc; mass spectrum (FAB) m/e 483, 485 (M+1)+.

400 MHz $^1$H NMR (CDCl$_3$) δ0.91 (t, J=7.3 Hz, 3H), 1.40 (m, 2H), 1.65 (m, 2H), 2.52 (t, J=7.7 Hz, 2H), 4.89 (s, 2H), 7.24-7.32 (m, 3H), 7.68 (d, J=8.8 Hz, 1H), 8.19 (dd, J=8.8, 2.6 Hz, 1H), 8.36 (d, J=2.6 Hz, 1H).

Step B: 5-n-Butyl-4-[[2'-(N-t-butylsulfamoyl)-3-fluorobiphenyl-4-yl]methyl]-2-(2-chloro-5-nitrophenyl)-2,4-dihydro-3H-1,2,4-triazol-3-one The palladium(0)-catalyzed coupling of 4-(4-bromo-2-fluorobenzyl)-5-n-butyl-2-(2-chloro-5-nitrophenyl)-2,4-dihydro-3H-1,2,4-triazol-3-one (from Step A) with 2-(N-t-butylsulfamoyl)phenylboronic acid was carried out according to the procedure of Example 28, Step F. Purification of the crude product by flash chromatography on silica gel (gradient elution with 6:1 to 4:1 hexane-EtOAc) provided a 52% yield of the title compound as a stiff, pale yellow foam, mp 124°-126° C.; homogeneous by TLC in 4:1 hexane-EtOAc); mass spectrum (FAB) m/e 616 (M+1)+.

400 MHz $^1$H NMR (CDCl$_3$) δ0.93 (t, J=7.3 Hz, 3H), 1.03 (s, 9H), 1.43 (m, 2H), 1.70 (m, 2H), 2.59 (t, J=7.7 Hz, 2H), 3.62 (s, 1H), 5.00 (s, 2H), 7.2-7.6 (m, 6H), 7.69 (d, J=8.8 Hz, 1H), 8.15 (dd, J=7.8, 1.3 Hz, 1H), 8.20 (dd, J=8.8, 2.6 Hz, 1H), 8.38 (d, J=2.6 Hz, 1H).

Step C: 2-(5-Amino-2-chlorophenyl)-5-n-butyl-4-[[2'-(N-t-butylsulfamoyl)-3-fluorobiphenyl-4-yl]-methyl]-2,4-dihydro-3H-1,2,4-triazol-3-one By the method of Example 25, 5-n-butyl-4-[[2'-(N-t-butylsulfamoyl)-3-fluorobiphenyl-4-yl]-methyl]-2-(2-chloro-5-nitrophenyl)-2,4-dihydro-3H-1,2,4-triazol-3-one (from Step B) was hydrogenated to give a 78% yield of the title compound as a stiff, off-white foam, mp 167°-170° C.; homogeneous by TLC in 1:1 hexane-EtOAc; mass spectrum (FAB) m/e 586 (M+1)+.

400 MHz $^1$H NMR (CDCl$_3$) δ0.90 (t, J=7.3 Hz, 3H), 1.00 (s, 9H), 1.39 (m, 2H), 1.66 (m, 2H), 2.53 (t, J=7.7 Hz, 2H), 3.74 (s, 1H), 4.98 (s, 2H), 6.68 (br m, 1H), 6.85 (br m, 1H), 7.19-7.30 (m, 4H), 7.38-7.56 (m, 3H), 8.14 (dd, J=7.9, 1.4 Hz, 1H).

Step D: 5-n-Butyl-4-[[2'-(N-t-butylsulfamoyl)-3-fluorobiphenyl-4-yl]methyl]-2-[2-chloro-5-(propionylamino)phenyl]-2,4-dihydro-3H-1,2,4-triazol-3-one Propionyl bromide was reacted with 2-(5-amino-2-chlorophenyl)-5-n-butyl-4-[[2'-(N-t-butylsulfamoyl)-3-fluorobiphenyl-4-yl]methyl]-2,4-dihydro-3H-1,2,4-triazol-3-one (from Step C) according to the procedure of Example 26. Flash chromatography of the crude product on silica gel (gradient elution with 3:1 to 1:1 hexane-EtOAc) gave an 84% yield of the title compound as a white solid, mp 103°-105° C.; homogeneous by TLC (1:1 hexane-EtOAc); mass spectrum (FAB) m/e 648 (M+Li)+.

400 MHz $^1$H NMR (CDCl$_3$) δ0.91 (t, J=7.3 Hz, 3H), 1.02 (s, 9H), 1.19 (t, J=7.5 Hz, 3H), 1.40 (m, 2H), 1.65 (m, 2H), 2.35 (q, J=7.5 Hz, 2H), 2.55 (t, J=7.7 Hz, 2H), 3.67 (s, 1H), 5.00 (s, 2H), 7.23-7.58 (m, 8H), 7.71 (d, J=2.9 Hz, 1H), 8.15 (dd, J=7.9, 1.3 Hz, 1H).

Step E: 5-n-Butyl-2-[2-chloro-5-(propionylamino)-phenyl]-2,4-dihydro-4-[(3-fluoro-2'-sulfamoylbiphenyl-4-yl)methyl]-3H-1,2,4-triazol-3-one The title compound was prepared in 90% yield by deprotection of 5-n-butyl-4-[[2'-(N-t-butylsulfamoyl)-3-fluorobiphenyl-4-yl]methyl]-2-[2-chloro-5-(propionylamino)-phenyl]-2,4-dihydro-3H-1,2,4-triazol-3-one (from Step D) with trifluoroacetic acid in the presence of anisole according to the procedure of Example 28, Step G. The material was obtained as a white solid, mp 135°-137° C.; satisfactory purity by TLC (95:5 $CH_2Cl_2$—MeOH); mass spectrum (FAB) m/e 586 (M+1)+.

400 MHz $^1$H NMR ($CDCl_3$) δ0.91 (t, J=7.4 Hz, 3H), 1.17 (t, J=7.5 Hz, 3H), 1.40 (m, 2H), 1.67 (m, 2H), 2.33 (q, J=7.5 Hz, 2H), 2.57 (t, J=7.7 Hz, 2H), 4.48 (br s, 2H), 4.99 (s, 2H), 7.2-7.6 (m, 8H), 7.71 (d, J=2.3 Hz, 1H), 7.75 (br s, 1H), 8.14 (dd, J=7.9, 1.3 Hz, 1H).

Step F: 4-[[2'-[N-(t-Butoxycarbonyl)sulfamoyl]-3-fluorobiphenyl-4-yl]methyl]-5-n-butyl-2-[2-chloro-5-(propionylamino)phenyl]-2,4-dihydro-3H-1,2,4-triazol-3-one Reaction of 5-n-butyl-2-[2-chloro-5-(propionylamino)phenyl]-2,4-dihydro-4-[(3-fluoro-2'-sulfamoylbiphenyl-4-yl)methyl]-3H-1,2,4-triazol-3-one (from Step E) with di-t-butyl dicarbonate according to the procedure of Example 28, Step H, gave a 91% yield of the title compound as a white solid, mp 137°-140° C.; homogeneous by TLC (95:5 $CH_2Cl_2$—MeOH).

400 MHz $^1$H NMR ($CDCl_3$) δ0.93 (t, J=7.4 Hz, 3H), 1.19 (t, J=7.6 Hz, 3H), 1.30 (s, 9H), 1.44 (m, 2H), 1.68 (m, 2H), 2.39 (q, J=7.6 Hz, 2H), 2.66 (t, J=7.5 Hz, 2H), 5.10 (s, 2H), 7.16 (m, 2H), 7.33 (m, 2H), 7.51 (d, J=8.8 Hz, 1H), 7.61 (m, 2H), 7.70 (m, 1H), 7.93 (d, J=2.5 Hz, 1H), 8.16 (d, J=8.0, Hz, 1H).

EXAMPLE 37

4-[[2'-[N-(t-Butoxycarbonyl)sulfamoyl]biphenyl-4-yl]methyl]-5-n-butyl-2-[2-chloro-5-(propionylamino)-phenyl]-2,4-dihydro-3H-1,2,4-triazol-3-one This material was prepared from 5-n-butyl-4-[[2'(N-t-butylsulfamoyl)biphenyl-4-yl]methyl]-2-(2-chloro-5-nitrophenyl)-2,4-dihydro-3H-1,2,4-triazol-3-one (from Example 24, Step B) by a sequence analogous to that described in Example 36, Steps C-F. The title compound was obtained as a white solid, mp 133°-135° C.; homogeneous by TLC (95:5 $CH_2Cl_2$—MeOH).

Analysis: $C_{33}H_{38}ClN_5O_6S$•0.5$H_2O$: Calc'd: C, 58.53; H, 5.80; N, 10.30. Found: C, 58.40; H, 5.70; N, 10.18.

400 MHz $^1$H NMR ($CDCl_3$) δ0.88 (t, J=7.3 Hz, 3H), 1.16 (t, J=7.5 Hz, 3H), 1.27 (s, 9H), 1.36 (m, 2H), 1.63 (m, 2H), 2.32 (q, J=7.5 Hz, 2H), 2.50 (t, J=7.7 Hz, 2H), 4.94 (s, 2H), 6.94 (br s, 1H), 7.23-7.37 (m, 5H), 7.46 (dd, J=8.8, 2.5 Hz, 1H), 7.54 (m, 1H), 7.63 (m, 1H), 7.71 (d, J=2.2 Hz, 1H), 8.23 (m, 2H).

EXAMPLE 38

2-[5-(Acetylamino)-2-chlorophenyl]-4-[[2'-[N-(t-butoxycarbonyl)sulfamoyl]-3-fluoro-5'-n-propylbiphenyl-4-yl]methyl]-5-n-butyl-2,4-dihydro-3H-1,2,4-triazol-3-one Step A: 5-n-Butyl-4-[[2'-(N-t-butylsulfamoyl)-3-fluoro-5'-n-propylbiphenyl-4-yl]methyl]-2-(2-chloro-5-nitrophenyl)-2,4-dihydro-3H-1,2,4-triazol-3-one Using the method of Example 28, Step F, 4-(4-bromo-2-fluorobenzyl)-5-n-butyl-2-(2-chloro-5-nitrophenyl)-2,4-dihydro-3H-1,2,4-triazol-3-one (from Example 36, Step A) was coupled with 2-(N-t-butylsulfamoyl)-5-n-propylphenylboronic acid (from Example 20, Step B). Flash chromatography of the crude product on silica gel (gradient elution with 6:1 to 2:1 hexane-EtOAc) gave a 43% yield of the title compound as a cream-colored solid, mp 84°-86° C.; homogeneous by TLC (4:1 hexane-EtOAc).

400 MHz $^1$H NMR ($CDCl_3$) δ0.91 (m, 6H), 1.01 (s, 9H), 1.41 (m, 2H), 1.58-1.72 (m, 4H), 2.54-2.64 (m, 4H), 3.62 (s, 1H), 4.98 (s, 2H), 7.04 (d, J=1.7 Hz, 1H), 7.23-7.31 (m, 3H), 7.42 (dd, J=7.8, 7.8 Hz, 1H), 7.67 (d, J=8.9 Hz, 1H), 8.01 (d, J=8.2 Hz, 1H), 8.17 (dd, J=8.9, 2.7 Hz, 1H), 8.37 (d, J=2.7 Hz, 1H).

Step B: 2-(5-Amino-2-chlorophenyl)-5-n-butyl-4-[[2'-(N-t-butylsulfamoyl)-3-fluoro-5'-n-propylbiphenyl-4-yl]methyl]-2,4-dihydro-3H-1,2,4-triazol-3-one By the procedure of Example 25, 5-n-butyl-4-[[2'-(N-t-butylsulfamoyl)-3-fluoro-5'-n-propylbiphenyl-4-yl]methyl]-2-(2-chloro-5-nitrophenyl)-2,4-dihydro-3H-1,2,4-triazol-3-one (from Step A) was hydrogenated to give the title compound as a cream-colored solid, mp 85°-87° C.; satisfactory purity by TLC in 95:5 $CH_2Cl_2$—MeOH.

400 MHz $^1$H NMR ($CD_3OD$) δ0.92, 0.95 (overlapping t, 6H total), 1.02 (s, 9H), 1.41 (m, 2H), 1.61-1.72 (m, 4H), 2.61-2.70 (m, 4H), 5.08 (s, 2H), 6.73-6.78 (m, 2H), 7.13 (d, J=1.8 Hz, 1H), 7.20-7.38 (m, 5H), 8.37 (dd, J=8.3, 2.5 Hz, 1H).

Step C: 2-[5-(Acetylamino)-2-chlorophenyl]-5-n-butyl-4-[[2'-(N-t-butylsulfamoyl)-3-fluoro-5'-n-propylbiphenyl-4-yl]methyl]-2,4-dihydro-3H-1,2,4-triazol-3-one The reaction of 2-(5-amino-2-chlorophenyl)-5-n-butyl-4-[[2'-(N-t-butylsulfamoyl)-3-fluoro-5'-n-propylbiphenyl-4-yl]methyl]-2,4-dihydro-3H-1,2,4-triazol-3-one (from Step B) was carried out according to the procedure of Example 26, affording an 88% yield of the title compound as a cream-colored solid, mp 125°-128° C.; satisfactory purity by TLC in 95:5 $CH_2Cl_2$—MeOH; mass spectrum (FAB) m/e 676 (M+Li)+.

400 MHz $^1$H NMR ($CD_3OD$) δ0.93, 0.95 (overlapping t, 6H total), 1.03 (s, 9H), 1.43 (m, 2H), 1.67 (m, 4H), 2.13 (s, 3H), 2.63-2.70 (m, 4H), 5.09 (s, 2H), 7.14 (d, J=1.8 Hz, 1H), 7.24-7.38 (m, 4H), 7.51 (d, J=8.8 Hz, 1H), 7.61 (dd, J=8.8, 2.6 Hz, 1H), 7.90 (d, J=2.5 Hz, 1H), 8.01 (d, J=8.2 Hz, 1H).

Step D: 2-[5-(Acetylamino)-2-chlorophenyl]-5-n-butyl-2,4-dihydro-4-[(3-fluoro-5'-n-propyl-2'-sulfamoylbiphenyl-4-yl)methyl]-3H-1,2,4-triazol-3-one Deprotection of 2-[5-(acetylamino)-2-chlorophenyl]-5-n-butyl-4-[[2'-(N-t-butylsulfamoyl)-3-fluoro-5'-n-propylbiphenyl-4-yl]methyl]-2,4-dihydro-3H-1,2,4-triazol-3-one (from Step C) with trifluoroacetic acid according to the procedure of Example 28, Step G, gave an 88% yield of the title compound as a white powder, mp 149°-152° C.; homogeneous by TLC (95:5 $CH_2Cl_2$—MeOH); mass spectrum (FAB) m/e 614 (M+1) +.

400 MHz $^1$H NMR ($CD_3OD$) δ0.92, 0.95 (overlapping t, J=7.3 Hz, 3H each), 1.41 (m, 2H), 1.6-1.7 (m, 4H), 2.13 (s, 3H), 2.64, 2.68 (overlapping t, J=7.6 Hz, 2H each), 5.09 (s, 2H), 7.14 (d, J=1.8 Hz, 1H), 7.22-7.39 (m, 4H), 7.51 (d, J=8.8 Hz, 1H), 7.63 (dd, J=8.8, 2.5 Hz, 1H), 7.88 (d, J=2.5 Hz, 1H), 8.00 (d, J=8.2 Hz, 1H).

Step E: 2-[5-(Acetylamino)-2-chlorophenyl]-4-[[2'-[N-(t-butoxycarbonyl)sulfamoyl]-3-fluoro-5'-n-propylbiphenyl-4-yl]methyl]-5-n-butyl-2,4-dihydro-3H-1,2,4-triazol-3-one Di-t-butyl dicarbonate was reacted with 2-[5-(acetylamino)-2-chlorophenyl]-5-n-butyl-2,4-dihydro-4-[(3-fluoro-5'-n-propyl-2'-sulfamoylbiphenyl-4-yl)methyl]-3H-1,2,4-triazol-3-one (from Step D) according to the procedure of Example 28, Step H. Purification of the crude product by flash chromatography on silica gel (gradient elution with 0.5-5% MeOH in $CH_2Cl_2$) gave a 69% yield of the title compound as a white, glassy solid, mp ≦130° C. (gradual); homogeneous by TLC (95:5 $CH_2Cl_2$—MeOH); mass spectrum (FAB) m/e 720 (M+Li)+, 736 (M+Na)+.

Analysis: $C_{35}H_{41}ClFN_5O_6S \cdot 0.33CH_2Cl_2$: Calc'd: C, 57.15; H, 5.66; N, 9.43. Found: C, 57.01; H, 5.42; N, 9.42.

400 MHz $^1$H NMR (CD$_3$OD) δ0.93, 0.96 (overlapping t, J=7.3 Hz, 3H each), 1.30 (s, 9H), 1.43 (m, 2H), 1.68 (m, 4H), 2.13 (s, 3H), 2.68 (m, 4H), 5.09 (s, 2H), 7.16 (m, 3H), 7.32 (dd, J=7.9, 7.9 Hz, 1H), 7.43 (dd, J=8.2, 1.8 Hz, 1H), 7.51 (d, J=8.8 Hz, 1H), 7.60 (dd, J=8.8, 2.5 Hz, 1H), 7.91 (d, J=2.5 Hz, 1H), 8.05 (d, J=8.2 Hz, 1H).

EXAMPLE 39

4-[[2'-[N-(t-Butoxycarbonyl)sulfamoyl]-3-fluorobiphenyl-4-yl]methyl]-5-n-butyl-2-[2-chloro-5-(2-ethoxyacetylamino)phenyl]-2,4-dihydro-3H-1,2,4-triazol-3-one Step A: 5-n-Butyl-2-(2-chloro-5-nitrophenyl)-2,4-dihydro-4-[(3-fluoro-2'-sulfamoylbiphenyl-4-yl)methyl]-3H-1,2,4-triazol-3-one By the procedure of Example 28, Step G, 5-n-butyl-4-[[2'-(N-t-butylsulfamoyl)-3-fluorobiphenyl-4-yl]methyl]-2-(2-chloro-5-nitrophenyl)-2,4-dihydro-3H-1,2,4-triazol-3-one (from Example 36, Step B) was deprotected with trifluoroacetic acid. Flash chromatography of the crude product on silica gel (gradient elution with 0.5-5% MeOH in $CH_2Cl_2$) gave a 94% yield of the title compound as a cream-colored solid; homogeneous by TLC in 95:5 $CH_2Cl_2$—MeOH; mass spectrum (FAB) m/e 560 (M+1)+.

400 MHz $^1$H NMR (CDCl$_3$) δ0.93 (t, J=7.3 Hz, 3H), 1.43 (m, 2H), 1.70 (m, 2H), 2.60 (t, J=7.7 Hz, 2H), 4.36 (s, 2H), 5.00 (s, 2H), 7.24-7.31 (m, 3H), 7.43 (dd, J=7.7, 7.7 Hz, 1H), 7.52 (m, 1H), 7.59 (m, 1H), 7.68 (d, J=8.8 Hz, 1H), 8.15 (dd, J=7.9, 1.4 Hz, 1H), 8.20 (dd, J=8.8, 2.7 Hz, 1H), 8.39 (d, J=2.6 Hz, 1H).

Step B: 4-[[2'-[N-(t-Butoxycarbonyl)sulfamoyl]-3-fluorobiphenyl-4-yl]methyl]-5-n-butyl-2-(2-chloro-5-nitrophenyl)-2,4-dihydro-3H-1,2,4-triazol-3-one The reaction of 5-n-butyl-2-(2-chloro-5-nitrophenyl)-2,4-dihydro-4-[(3-fluoro-2'-sulfamoylbiphenyl-4-yl)methyl]-3H-1,2,4-triazol-3-one (from Step A) was carried out according to the procedure of Example 28, Step H. Flash chromatography of the crude product on silica gel (gradient elution with 0.5-5% MeOH in $CH_2Cl_2$) gave an 80% yield of the title compound as a cream-colored solid; satisfactory purity by TLC in 95:5 $CH_2Cl_2$—MeOH; mass spectrum (FAB) m/e 666 (M+Li)+.

400 MHz $^1$H NMR (CDCl$_3$) δ0.94 (t, J=7.3 Hz, 3H), 1.30 (s, 9H), 1.43 (m, 2H), 1.71 (m, 2H), 2.61 (t, J=7.7 Hz, 2H), 5.01 (s, 2H), 7.12-7.18 (m, 2H), 7.30 (dd, J=7.5, 1.4 Hz, 1H), 7.39 (dd, J=7.8, 7.8 Hz, 1H), 7.57 (m, 1H), 7.65 (m, 1H), 7.69 (d, J=8.9 Hz, 1H), 8.18-8.25 (m, 2H), 8.38 (d, J=2.6 Hz, 1H).

Step C: 2-(5-Amino-2-chlorophenyl)-4-[[2'-[N-(t-butoxycarbonyl)sulfamoyl]-3-fluorobiphenyl-4-yl]methyl]-5-n-butyl-2,4-dihydro-3H-1,2,4-triazol-3-one A mixture of 313 mg (0.475 mmol) of 4-[[2'-[N-(t-butoxycarbonyl)sulfamoyl]-3-fluorobiphenyl-4-yl]methyl]-5-n-butyl-2-(2-chloro-5-nitrophenyl)-2,4-dihydro-3H-1,2,4-triazol-3-one (from Step B), 10 mg of platinum oxide, and 4 mL of ethanol was shaken with hydrogen at approximately 3 atm for 2.5 hours. The mixture was filtered through Celite, and the filtrate was concentrated to dryness. The residue was flash chromatographed on about 60 cc of silica gel (gradient elution with 0.5-2% MeOH in $CH_2Cl_2$) to give a 57% yield of the title compound as a cream-colored solid, mp 208°-210° C.; homogeneous by TLC in 95:5 $CH_2Cl_2$—MeOH.

400 MHz $^1$H NMR (CDCl$_3$) δ0.90 (t, J=7.3 Hz, 3H), 1.29 (s, 9H), 1.40 (m, 2H), 1.67 (m, 2H), 2.57 (t, J=7.7 Hz, 2H), 4.98 (s, 2H), 6.91 (br d, 1H), 7.05-7.36 (m, 6H), 7.55 (m, 1H), 7.62 (m, 1H), 8.22 (dd, J=8.0, 1.4 Hz, 1H).

Step D: 4-[[2'-[N-(t-Butoxycarbonyl)sulfamoyl]-3-fluorobiphenyl-4-yl]methyl]-5-n-butyl-2-[2-chloro-5-[(ethoxyacetyl)amino]phenyl]-2,4-dihydro-3H-1,2,4-triazol-3-one A mixture of 12 μL (13.2 mg, 0.127 mmol) of ethoxyacetic acid, 20.6 mg (0.127 mmol) of 1,1'-carbonyldiimidazole (CDI), and 1 mL of dry THF was stirred at 60° C. for 4 hours. To this solution was then added 40 mg (0.0635 mmol) of 2-(5-amino2-chlorophenyl)-4-[[2'-[N-(t-butoxycarbonyl)sulfamoyl]-3-fluorobiphenyl-4-yl]methyl]-5-n-butyl-2,4-dihydro-3H-1,2,4-triazol-3-one (from Step C) dissolved in THF, followed by 19 μL (19.3 mg, 0.127 mmol) of 1,8-diazabicyclo[5.4.0]undec-7-ene (DBU). After being stirred overnight at 60° C., the reaction mixture was diluted with 5% citric acid (aqueous) and extracted 2X with ethyl acetate. The combined organic fractions were washed twice with water, then with brine, and dried over Na$_2$SO$_4$. The filtered solution was concentrated, and the residue was flash chromatographed on silica gel (gradient elution with 0.5-2% MeOH in $CH_2Cl_2$), yielding 9 mg (20%) of the title compound as a white, glassy solid, mp 100°-102° C.; satisfactory purity by TLC in 95:5 $CH_2Cl_2$—MeOH; mass spectrum (FAB) m/e 622 (M+Li)+.

400 MHz $^1$H NMR (CD$_3$OD) δ0.93 (t, J=7.4 Hz, 3H), 1.27 (t, J=7.0 Hz, 3H), 1.30 (s, 9H), 1.44 (m, 2H), 1.68 (m, 2H), 2.67 (t, J=7.6 Hz, 2H), 3.64 (q, J=7.0 Hz, 2H), 4.08 (s, 2H), 5.10 (s, 2H), 7.14-7.36 (m, 4H), 7.53 (d, J=8.8 Hz, 1H), 7.61 (m, 2H), 7.70 (m, 1H), 7.94 (d, J=2.5 Hz, 1H), 8.16 (dd, J=8.0, 1.3 Hz, 1H).

EXAMPLE 40

4-[[2'-[N-(t-Butoxycarbonyl)sulfamoyl]-3-fluorobiphenyl-4-yl]methyl]-5-n-butyl-2-[2-chloro-5-[(ethylthioacetyl)amino]phenyl]-2,4-dihydro-3H-1,2,4-triazol-3-one The title compound was prepared according to the procedure of Example 39, Step D, except that ethylthioacetic acid was substituted for ethoxyacetic acid. Purification of the crude product by flash chromatography on silica gel (gradient elution with 0.5-5% MeOH in $CH_2Cl_2$) furnished a 30% yield of yellow, glassy solid, mp 115°-117° C.; satisfactory purity by TLC in 95:5 $CH_2Cl_2$—MeOH; mass spectrum (FAB) m/e 732 (M+1)+.

400 MHz $^1$H NMR (CD$_3$OD) δ0.93 (t, J=7.4 Hz, 3H), 1.27 (t, J=7.4 Hz, 3H), 1.30 (s, 9H), 1.44 (m, 2H), 1.68 (m, 2H), 2.63-2.69 (m, 4H), 3.2 (s, 2H, partially obscured by CD$_2$HOD peak), 5.10 (s, 2H), 7.14-7.36 (m, 4H), 7.54 (d, J=8.9 Hz, 1H), 7.61 (m, 1H), 7.68-7.74 (m, 2H), 7.97 (d, J=2.5 Hz, 1H), 8.16 (dd, J=8.0, 1.3 Hz, 1H).

EXAMPLES 41 TO 42

The compounds of the Formula (IV) exemplified in Table C were prepared from the appropriate substituted starting materials utilizing the general procedures outlined in the examples hereinabove and the noted schemes.

TABLE C

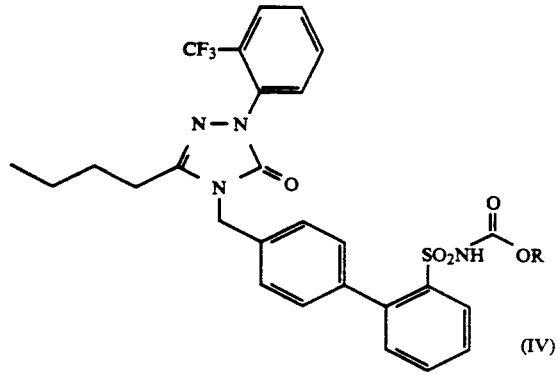

(IV)

| Ex | R | mp | formula | Analysis C | H | N |
|---|---|---|---|---|---|---|
| 41 | iBu | 171–173° C. | $C_{31}H_{33}F_3N_4O_5S$ | calc'd 59.00 | 5.27 | 8.88 |
|    |     |             |                           | found 58.77 | 5.01 | 8.67 |
| 42 | nBu | 67–69° C. | $C_{31}H_{33}F_3N_4O_5S$ | calc'd 59.00 | 5.27 | 8.88 |
|    |     |           |                           | found 58.86 | 4.98 | 8.74 |

EXAMPLES 43 TO 52

The compounds of the Formula (V) exemplified in Table D are prepared from the appropriate substituted starting materials utilizing the general procedures outlined in the examples hereinabove and the noted schemes.

TABLE D

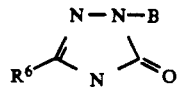

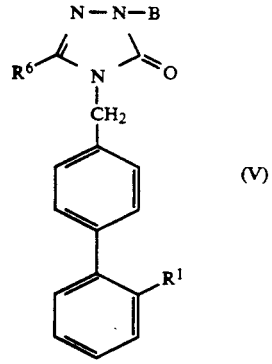

(V)

| Example # | $R^1$ | $R^6$ | B | Scheme |
|---|---|---|---|---|
| 43 | —SO₂NHSO₂Me | Pr | iPr | 21 |
| 44 | —SO₂NHSO₂iPr | Bu | 2-Cl-Ph | 21 |
| 45 | [N-O-S(=O)-N-H heterocycle] | Bu | Ph | 26 |

TABLE D-continued (V)

| Example # | $R^1$ | $R^6$ | B | Scheme |
|---|---|---|---|---|
| 46 | [N-N(Ph)-S(=O)-NH heterocycle] | Bu | Ph | 29 |
| 47 | —NH—C(=O)—COH (with =O) | Bu | Ph | 36 |
| 48 | —SO₂NHSO₂iPr | Pr | 2-CF₃-Ph | 21 |
| 49 | —SO₂NHPOCH₂Ph, OCH₂Ph | Pr | Ph | 18 |
| 50 | [—N-S(O₂)-N-H cyclic with ketone] | Bu | 2-CF₃-Ph | 32 |
| 51 | [N—O / N heterocycle —NHSO₂Ph] | Pr | Ph | 33 |
| 52 | [N—O / N-S(O₂) heterocycle] | Bu | 2-Cl-Ph | 26 |

EXAMPLE 53

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 4-[[2'-[N-(t-butoxy-carbonyl)sulfamoyl]-biphenyl-4-yl]methyl]-5-n-butyl-2,4-dihydro-2-[2-(trifluoromethyl)-phenyl]-3H-1,2,4-triazol-3-one | 50 |
| Lactose | 149 |
| Magnesium stearate | 1 |

-continued

| Ingredient | Amount per capsule (mg) |
|---|---|
| Capsule (size No. 1) | 200 |

4-[[2'-[N-(t-Butoxycarbonyl)sulfamoyl]biphenyl-4-yl]methyl]-5-n-butyl-2,4-dihydro-2-[2(trifluoromethyl)-phenyl]-3H-1,2,4-triazol-3-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 4-[[2'-[N-(t-butoxycarbonyl)sulfamoyl]biphenyl-4-yl]methyl]-5-n-butyl-2,4-dihydro-2-[2(trifluoromethyl)phenyl]-3H-1,2,4-triazol-3-one (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 4-[[2'-[N-(t-butoxycarbonyl)sulfamoyl]biphenyl-4-yl]methyl]-5-n-butyl-2,4-dihydro-2-[2-(trifluoromethyl)phenyl]-3H-1,2,4triazol-3-one (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 4-[[2'-[N-(t-butoxycarbonyl)sulfamoyl]biphenyl-4-yl]methyl]-5-n-butyl-2,4-dihydro-2-[2-(trifluoromethyl)phenyl]-3H-1,2,4-triazol-3-one (1–25 mg), butylated hydroxyanizsole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 4-[[2'-[N-(t-butoxycarbonyl)sulfamoyl]biphenyl-4-yl]methyl]-5-n-butyl-2,4-dihydro-2-[2-(trifluoromethyl)phenyl]-3H-1,2,4-triazol-3-one (5.42 mg), sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound having the formula (I):

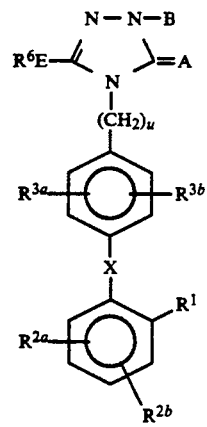

or a pharmaceutically acceptable salt thereof, wherein:

$R^1$ is (a) $-SO_2NHSO_2R^{22}$, (b) $-SO_2NH-\overset{O}{\underset{\|}{P}}(R^{24})_2$, (c) $-CONH-\overset{O}{\underset{\|}{P}}(R^{24})_2$, (d) $-SO_2NHCN$, (e) $-SO_2NHCO_2R^{22}$, (f) $-SO_2NHSO_2-N\underset{\diagdown}{\diagup}Z$, (g) $-NHSO_2NHSO_2R^{22}$, (h) $-NHSO_2NH\overset{O}{\underset{\|}{P}}(R^{24})_2$, (i) structure with $R^{25}$, $R^{25}$, N, S(=O)(=O), NH, O, (j) structure with $R^{25}$, $R^{25}$, N, S(=O)(=O), NH, O, (k) cyclopentenone structure with HO, $R^{23}$, $R^{23}$, =O, (l) structure with N, Y, N, $NHSO_2R^{22}$,

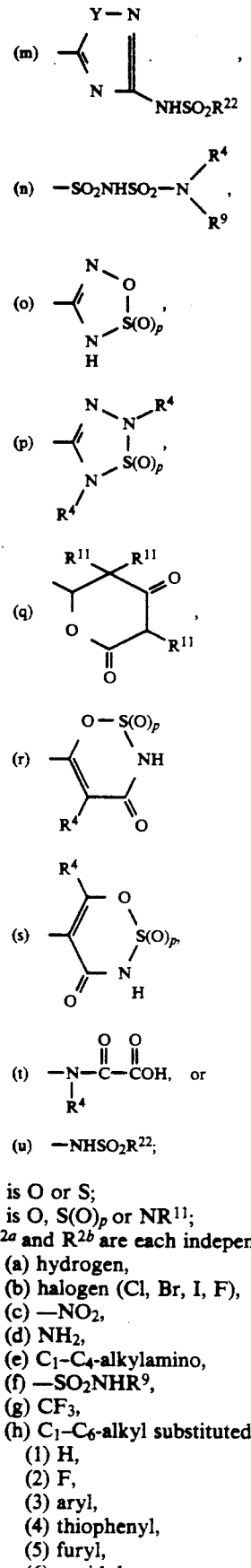

(m), (n) —SO₂NHSO₂—NR⁴R⁹, (o), (p), (q), (r), (s), (t) —N(R⁴)—C(O)—C(O)—COH, or (u) —NHSO₂R²²;

Y is O or S;
Z is O, S(O)$_p$ or NR¹¹;
R²ᵃ and R²ᵇ are each independently:
(a) hydrogen,
(b) halogen (Cl, Br, I, F),
(c) —NO₂,
(d) NH₂,
(e) C₁-C₄-alkylamino,
(f) —SO₂NHR⁹,
(g) CF₃,
(h) C₁-C₆-alkyl substituted with:
 (1) H,
 (2) F,
 (3) aryl,
 (4) thiophenyl,
 (5) furyl,
 (6) pyridyl,
 (7) imidazoyl,
 (8) pyrimidinyl,
 (9) C₁-C₆-alkoxy,
 (10) —O(CH₂)$_m$—O—C₁-C₄-alkyl, wherein m is 2 to 4, or
 (11) C₃-C₇-cycloalkyl, or
 when R²ᵃ and R²ᵇ are on adjacent carbons, they can be bonded together to form a phenyl ring;
R³ᵃ is
(a) H,
(b) halo (Cl, Br, I, F)
(c) C₁-C₆-alkyl,
(d) C₁-C₆-alkoxy,
(e) C₁-C₆-alkoxy-C₁-C₄-alkyl;
R³ᵇ is
(a) H,
(b) halo (Cl, Br, I, F),
(c) NO₂,
(d) C₁-C₆-alkyl,
(e) C₁-C₅-alkylcarbonyloxy,
(f) C₃-C₆-cycloalkyl;
(g) C₁-C₆-alkoxy,
(h) —NHSO₂R⁴,
(i) hydroxy-C₁-C₄-alkyl,
(j) aryl-C₁-C₄-alkyl,
(k) C₁-C₄-alkylthio,
(l) C₁-C₄-alkylsulfinyl,
(m) C₁-C₄-alkylsulfonyl,
(n) NH₂,
(o) C₁-C₄-alkylamino,
(p) di(C₁-C₄-alkyl)amino,
(q) CF₃,
(r) —SO₂—NHR⁹,
(s) aryl,
(t) furyl, or
when R³ᵃ and R³ᵇ are on adjacent carbons, they can be bonded together to form a phenyl ring;
wherein aryl is phenyl, biphenyl or naphthyl unsubstituted or substituted with one, two or three substituents selected from the group consisting of halo (Cl, Br, I, F), C₁-C₄-alkyl, C₁-C₄-alkoxy, NO₂, CF₃, C₁-C₄-alkyl-S(O)$_p$—, CF₃SO₂—, —OH, —NR⁹R¹⁰, —SO₂NR⁹R¹⁰, C₃-C₇-cycloalkyl, —CO₂H, —CO₂—C₁-C₄-alkyl, —CONR²¹R²², —CN, C₃-C₁₀-alkenyl, —NHCOR⁹, —OCF₃, phenyl-C₁-C₂-alkyl, phenyl-S(O)$_p$ and phenyl-C₁-C₂-alkyl-S(O)$_p$;
R⁴ is H, straight chain or branched C₁-C₆ alkyl, —CH₂-aryl or aryl;
R⁵ is H or —CH(R⁴)—O—CO—R⁴ᵃ; wherein R⁴ᵃ is C₁-C₆-alkyl, aryl or —CH₂-aryl;
E is a single bond, —NR¹³(CH₂)$_s$—, —S(O)$_x$(CH₂)$_s$— where x is 0 to 2 and s is 0 to 5, —CH(OH)—, —O(CH₂)$_s$—, or —CO—;
R⁶ is
(a) phenyl unsubstituted or substituted with 1 or 2 substituents selected from the group consisting of Cl, Br, I or F, —O—C₁-C₄-alkyl, C₁-C₄-alkyl, —NO₂, —CF₃, —SO₂NR⁹R¹⁰, —S—C₁-C₄-alkyl, —OH, —NH₂, C₃-C₇-cycloalkyl and C₃-C₁₀-alkenyl;
(b) straight chain or branched C₁-C₆-alkyl, C₂-C₆-alkenyl or C₂-C₆-alkynyl each of which is unsubstituted or substituted with one or more substituents selected from the group consisting of aryl as defined above, C₃-C₇-cycloalkyl, halo (Cl, Br, I, F), —OH, —O—C₁-C₄-alkyl, —NH₂, —NH(C₁-C₄-alkyl), —N(C₁-C₄-alkyl)₂, —N-

H—SO$_2$R$^4$, —COOR$^4$, —SO$_2$NHR$^9$, —S—C$_1$-C$_4$-alkyl;

(c) heteroaryl, wherein heteroaryl is an unsubstituted, monosubstituted or disubstituted five- or six-membered aromatic ring which contains 1 to 2 heteroatoms selected from the group consisting of O, N and S and wherein the substituents are members selected from the group consisting of —OH, —SH, —C$_1$-C$_4$-alkyl, —C$_1$-C$_4$-alkoxy, —CF$_3$, Cl, Br, F, I, —NO$_2$, —CO$_2$H, —CO$_2$—C$_1$-C$_4$-alkyl, —NH$_2$, —NH(C$_1$-C$_4$-alkyl) and —N(C$_1$-C$_4$-alkyl)$_2$;

(d) mono-, di-, tri- or polyfluoro-C$_1$-C$_5$-alkyl;

(e) C$_3$-C$_7$-cycloalkyl optionally substituted with one or more substituents selected from the group consisting of C$_1$-C$_4$-alkyl, O—C$_1$-C$_4$-alkyl, S—C$_1$-C$_4$-alkyl, OH, perfluoro-C$_1$-C$_4$-alkyl, or halo (Cl, Br, F, I); or (f) C$_3$-C$_7$-cycloalkyl-C$_1$-C$_3$-alkyl wherein the cycloalkyl is substituted as in (e) above;

A is O, S or NR$^{21}$;

B is (a) H provided A is not NR$^{21}$, (b) C$_1$-C$_{10}$-alkyl, (c) substituted C$_1$-C$_{10}$-alkyl in which one or more substituent(s) is selected from (1) halogen (I, Br, Cl, F),
(2) hydroxy,
(3) C$_1$-C$_{10}$-alkoxy,
(4) C$_1$-C$_5$-alkoxycarbonyl,
(5) C$_1$-C$_4$-alkylcarbonyloxy,
(6) C$_3$-C$_8$-cycloalkyl,
(7) phenyl, biphenyl or naphthyl,
(8) substituted phenyl, biphenyl or naphthyl in which the substituents are V$_1$, V$_2$, V$_3$, V$_4$ and V$_5$,
(9) C$_1$-C$_{10}$-alkyl-S(O)$_p$,
(10) C$_3$-C$_8$-cycloalkyl-S(O)$_p$,
(11) phenyl-S(O)$_p$,
(12) substituted phenyl-S(O)$_p$ in which the substituents are V$_1$-V$_5$,
(13) oxo,
(14) carboxy,
(15) NR$^9$R$^9$,
(16) C$_1$-C$_5$-alkylaminocarbonyl,
(17) di(C$_1$-C$_5$-alkyl)aminocarbonyl,
(18) cyano,
(19) —OCONR$^{21}$R$^{22}$,
(20) —NR$^{21}$COR$^{22}$,
(21) —NR$^{21}$CO$_2$R$^{22}$,
(22) —NR$^{21}$CONR$^{21}$R$^{22}$,
(23) —NR$^{21}$CON(CH$_2$CH$_2$)$_2$L,
(24) —OCON(CH$_2$CH$_2$)$_2$L, wherein L is a single bond, CH$_2$, O, S(O)$_p$ or NR$^9$, (d) C$_2$-C$_{10}$-alkenyl,
(e) C$_2$-C$_{10}$-alkynyl,
(f) C$_3$-C$_8$-cycloalkyl,
(g) substituted C$_3$-C$_8$-cycloalkyl or substituted C$_3$-C$_8$-cycloalkyl-C$_1$-C$_4$-alkyl having one or more substituents selected from the group:
(1) halo (Cl, Br, F, I),
(2) hydroxy,
(3) C$_1$-C$_6$-alkyl,
(4) C$_1$-C$_6$-alkoxy,
(5) C$_1$-C$_4$-alkylcarbonyloxy,
(6) C$_1$-C$_5$-alkoxycarbonyl,
(7) carboxy,
(8) oxo,
(9) C$_1$-C$_5$-alkylaminocarbonyl,
(10) di(C$_1$-C$_5$-alkyl)aminocarbonyl,
(11) C$_1$-C$_4$-alkylcarbonyl,
(12) aryl,
(13) substituted phenyl or naphthyl in which the substituents are V$_1$, V$_2$, V$_3$, V$_4$ and V$_5$,
(14) —NR$^{21}$COR$^{22}$,
(15) —NR$^{21}$CO$_2$R$^{22}$,
(16) —OCONR$^{21}$R$^{22}$, and
(17) —CN, (h) phenyl, biphenyl or naphthyl, .
(i) substituted phenyl, biphenyl or naphthyl in which the substituents are V$_1$, V$_2$, V$_3$, V$_4$ and V$_5$,
(j) phenyl-(CH$_2$)$_r$—(Q)$_c$—(CH$_2$)$_r$—,
(k) substituted phenyl-(CH$_2$)$_r$—(Q)$_c$—(CH$_2$)$_r$— in which the phenyl group is substituted with V$_1$, V$_2$, V$_3$, V$_4$ and V$_5$,
(l) heterocycle-(CH$_2$)$_r$—(Q)$_c$—(CH$_2$)$_r$—, wherein the heterocycle is 5- or 6-membered containing one or two heteroatoms such as pyridine, furan, pyrrole, imidazole or thiazole and unsubstituted or substituted with V$_1$ and V$_2$;

R$^9$ is H, C$_1$-C$_5$-alkyl, aryl or —CH$_2$-aryl;
R$^{10}$ is H, C$_1$-C$_4$-alkyl, or
R$^9$ and R$^{10}$ together can be —(CH$_2$)$_m$— where m is 3-6;
R$^{11}$ is H, C$_1$-C$_6$-alkyl, C$_2$-C$_4$-alkenyl, C$_1$-C$_4$-alkoxy-C$_1$-C$_4$-alkyl, or —CH$_2$—C$_6$H$_4$R$^{20}$;
R$^{12}$ is —CN, —NO$_2$ or —CO$_2$R$^4$;
R$^{13}$ is H, C$_2$-C$_4$-alkanoyl, C$_1$-C$_6$-alkyl, allyl, C$_3$-C$_6$-cycloalkyl, phenyl or benzyl;
R$^{14}$ is H, C$_1$-C$_8$-alkyl, C$_1$-C$_8$-perfluoroalkyl, C$_3$-C$_6$-cycloalkyl, phenyl or benzyl;
R$^{15}$ is H, C$_1$-C$_6$-alkyl, or hydroxy;
R$^{16}$ is H, C$_1$-C$_6$-alkyl, C$_3$-C$_6$-cycloalkyl, phenyl or benzyl;
R$^{17}$ is —NR$^9$R$^{10}$, —OR$^{10}$, —NHCONH$_2$, —NHCSNH$_2$, —NHSO$_2$CF$_3$,

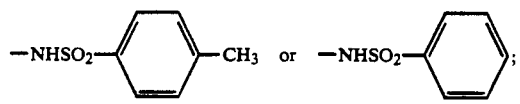

R$^{18}$ and R$^{19}$ are independently C$_1$-C$_4$-alkyl or taken together are —(CH$_2$)$_q$— where q is 2 or 3;
R$^{20}$ is H, —NO$_2$, —NH$_2$, —OH or —OCH$_3$;
R$^{21}$ is (a) H,
(b) phenyl unsubstituted or substituted with 1 or 2 substituents selected from the group consisting of Cl, Br, I or F, —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, —COOR$^4$, C$_3$-C$_7$-cycloalkyl and C$_3$-C$_{10}$-alkenyl,
(c) straight chain or branched C$_1$-C$_6$-alkyl, C$_2$-C$_6$-alkenyl or C$_2$-C$_6$-alkynyl each of which is unsubstituted or substituted with one or more substituents selected from the group consisting of aryl as defined above, C$_3$-C$_7$-cycloalkyl, halo (Cl, Br, I, F), —OH, —O—C$_1$-C$_4$-alkyl, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, and —S—C$_1$-C$_4$-alkyl,
(d) heteroaryl as defined hereinabove, or
(e) C$_3$-C$_7$-cycloalkyl unsubstituted or substituted with one or more selected from the group consisting of $C_1$-$C_4$-alkyl, —O—$C_1$-$C_4$-alkyl, —S—$C_1$-$C_4$-alkyl, —OH, —COOR$^4$, perfluoro-$C_1$-$C_4$-alkyl or halo (Cl, Br, F, I);

$R^{22}$ is $R^{21}$, excluding H;

$R^{23}$ is
 (a) H,
 (b) aryl as defined above, or
 (c) $C_1$-$C_6$-alkyl unsubstituted or substituted with aryl, F, Cl, Br, —OH, —NH$_2$, —NH($C_1$-$C_4$-alkyl), —N($C_1$-$C_4$-alkyl)$_2$, or CF$_3$;

$R^{24}$ is
 (a) aryl as defined above,
 (b) $C_1$-$C_6$-alkyl unsubstituted or substituted with aryl, F, Cl, Br, —OH, —NH$_2$, —NH($C_1$-$C_4$-alkyl), —N($C_1$-$C_4$-alkyl)$_2$, CF$_3$, —COOR$^4$, or CN,
 (c) —OCH(R$^4$)—O—CO—R$^{4a}$, or
 (d) —OH, —O—$C_1$-$C_6$-alkyl wherein alkyl is as defined in (b);

$R^{25}$ is
 (a) H,
 (b) $C_1$-$C_6$-alkyl unsubstituted or substituted with aryl, F, Cl, Br, —OH, —NH$_2$, —NH($C_1$-$C_4$-alkyl), —N($C_1$-$C_4$-alkyl)$_2$, CF$_3$, —COOR$^4$, or CN, or
 (c) F, Cl, Br;

X is
 (a) a single bond,
 (b) —CO—,
 (c) —O—,
 (d) —S—, (e) 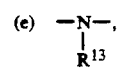

(f) 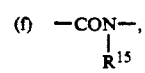

(g) 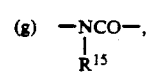

(h) —OCH$_2$—,
(i) —CH$_2$O—,
(j) —SCH$_2$—,
(k) —CH$_2$S—,
(l) —NHC(R$^9$)(R$^{10}$)—,
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—, (v) 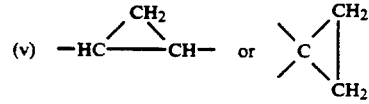

(w) 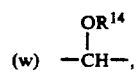

(x) 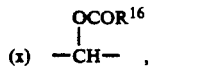

(y) 

(z) 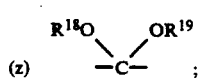

Q is —C(O)—, —S—, —O— or —NR$^4$;
c is 0 or 1;
p, r and t are 0 to 2;
$V_1$, $V_2$, $V_3$, $V_4$ and $V_5$ are each independently selected from:
 (a) H,
 (b) $C_1$-$C_5$-alkoxy,
 (c) $C_1$-$C_5$-alkyl,
 (d) hydroxy,
 (e) $C_1$-$C_5$-alkyl-S(O)$_p$,
 (f) —CN,
 (g) —NO$_2$,
 (h) —NR$^9$R$^{10}$,
 (i) $C_1$-$C_5$-alkyl-CONR$^{21}$R$^{22}$,
 (j) —CONR$^{21}$R$^{22}$,
 (k) —CO$_2$R$^9$,
 (l) —(CH$_2$)$_r$COR$^{22}$,
 (m) CF$_3$,
 (n) halogen (I, Br, Cl, F),
 (o) hydroxy-$C_1$-$C_4$-alkyl-,
 (p) carboxy-$C_1$-$C_4$-alkyl-,
 (q) -1H-tetrazol-5-yl,
 (r) —NH—SO$_2$CF$_3$,
 (s) aryl,
 (t) $C_1$-$C_5$-alkyl-CO$_2$R$^9$,
 (u) aryloxy,
 (v) aryl-$C_1$-$C_3$-alkoxy,
 (w) aryl-$C_1$-$C_3$-alkyl,
 (x) carboxyphenyl,
 (y) heteroaryl,
 (z) 2-oxazolin-2-yl optionally bearing one or more $C_1$-$C_4$-alkyl substituents,
 (aa) —(CH$_2$)$_r$OCOR$^{22}$,
 (bb) —(CH$_2$)$_r$OCONR$^{21}$R$^{22}$,
 (cc) —(CH$_2$)$_t$NR$^{21}$COR$^{22}$,
 (dd) —(CH$_2$)$_t$NR$^{21}$CO$_2$R$^{22}$,
 (ee) —(CH$_2$)$_t$NR$^{21}$CONR$^{21}$R$^{22}$,
 (ff) —(CH$_2$)$_t$NR$^{21}$CON(CH$_2$CH$_2$)$_2$L,
 (gg) —(CH$_2$)$_r$OCON(CH$_2$CH$_2$)$_2$L,
 (hh) —N(CH$_2$CH$_2$)$_2$L,
 (ii) —$C_1$-$C_5$-alkyl-CON(CH$_2$CH$_2$)$_2$L, or
 (jj) —CON(CH$_2$CH$_2$)$_2$L,
wherein L is a single bond, O, CH$_2$, S(O)$_p$ or NR$^9$;
u is 1 or 2; and
Z is O, NR$^{13}$ or S.

2. The compound according to claim 1, wherein:
$R^1$ is:

(a) —SO$_2$NHSO$_2$R$^{22}$, (b) 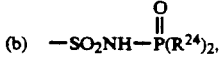

(c) —SO$_2$NHCN, (d) —SO$_2$NHCO$_2$R$^{22}$, (e) —SO$_2$NHSO$_2$—N⟨ ⟩Z, (f) —SO$_2$NHSO$_2$—N(R$^4$)(R$^9$), (g) —NHSO$_2$NHSO$_2$R$^{22}$, or (h) —NHSO$_2$NHP(R$^{24}$)$_2$;
      ‖
      O (i) 
$$\begin{array}{c} R^{25} \quad R^{25} \\ -N-\underset{|}{\overset{|}{C}}-\overset{O}{\underset{\|}{C}} \\ \phantom{-N-}S\!-\!NH \\ \phantom{-N-}\overset{\|}{\underset{\|}{O}} \\ \phantom{-N-}O \end{array}$$

(j) 
$$\begin{array}{c} Y-N \\ \diagdown \\ \phantom{x}N \\ \phantom{xxx}NHSO_2R^{22} \end{array}$$

(k) 
$$\begin{array}{c} N\!-\!O \\ \diagdown\phantom{x}| \\ \phantom{xx}N\!-\!S(O)_p \\ \phantom{xx}H \end{array}$$

(l) 
$$\begin{array}{c} N\!-\!N\!-\!R^4 \\ \diagdown\phantom{xx}| \\ \phantom{xxx}N\!-\!S(O)_p \\ \phantom{xxx}R^4 \end{array}$$

(m) 
$$\begin{array}{c} O \quad O \\ \| \quad \| \\ -N\!-\!C\!-\!COH, \text{ or} \\ | \\ R^4 \end{array}$$

(n) —NHSO$_2$R$^{22}$;

R$^{2a}$ and R$^{2b}$ are independently: H, F, Cl, CF$_3$ or C$_1$-C$_4$-alkyl;

R$^{3a}$ is H or F;

R$^{3b}$ is H, F, Cl, CF$_3$, C$_1$-C$_4$-alkyl, C$_5$-C$_6$-cycloalkyl, —COOCH$_3$, —COOC$_2$H$_5$, —SO$_2$—CH$_3$, NH$_2$, —N(C$_1$-C$_4$- alkyl)$_2$ or —NH—SO$_2$CH$_3$;

E is a single bond, —O— or —S—;

R$^6$ is (a) C$_1$-C$_6$-alkyl optionally substituted with a substituent selected from the group consisting of Cl, F, CF$_3$, —OH, —O—CH$_3$, —OC$_2$H$_5$, —S—CH$_3$, —S—C$_2$H$_5$, phenyl, C$_1$-C$_2$-alkylcyclopropyl or cyclopropyl, (b) C$_2$-C$_6$-alkenyl or C$_2$-C$_6$-alkynyl, (c) aryl as defined above, (d) a heteroaryl selected from the group consisting of 2-pyridyl, 4-pyridyl, 2-pyrimidyl, 4-pyrimidyl, imidazoyl, thiazolyl, thienyl, or furyl, (e) perfluoro-C$_1$-C$_4$-alkyl which is a member selected from the group consisting of CF$_3$—, CF$_3$CF$_2$—, CF$_3$CF$_2$CF$_2$—, or CF$_3$CF$_2$CF$_2$CF$_2$—, or (f) C$_3$-C$_7$-cycloalkyl optionally substituted with a substituent selected from the group consisting of methyl, ethyl, CF$_3$ or CF$_3$CF$_2$;

A is O, S or NR$^{21}$;

B is (a) H provided A is not NR$^{21}$, (b) C$_1$-C$_{10}$-alkyl, (c) substituted C$_1$-C$_{10}$-alkyl in which one or two substituents are selected from:
  (1) hydroxy,
  (2) C$_1$-C$_5$-alkoxy,
  (3) C$_1$-C$_5$-alkoxycarbonyl,
  (4) C$_1$-C$_4$-alkylcarbonyloxy,
  (5) C$_3$-C$_8$-cycloalkyl,
  (6) phenyl,
  (7) substituted phenyl in which the substituents are V$_1$, V$_2$, V$_3$, V$_4$ and V$_5$,
  (8) C$_1$-C$_5$-alkyl-S(O)$_p$,
  (9) phenyl-S(O)$_p$,
  (10) substituted phenyl-S(O)$_p$ in which the substituent is V,
  (11) oxo,
  (12) carboxy,
  (13) C$_1$-C$_5$-alkylaminocarbonyl, (d) C$_2$-C$_{10}$-alkenyl, (e) C$_2$-C$_{10}$-alkynyl, (f) C$_3$-C$_8$-cycloalkyl, (g) substituted C$_3$-C$_8$-cycloalkyl or substituted C$_3$-C$_8$-cycloalkyl-C$_1$-C$_4$-alkyl in which one or more substituent(s) is selected from:
  (1) hydroxy,
  (2) C$_1$-C$_5$-alkoxy,
  (3) C$_1$-C$_5$-alkoxycarbonyl,
  (4) C$_1$-C$_4$-alkylcarbonyloxy,
  (5) C$_1$-C$_6$-alkyl,
  (6) phenyl,
  (7) substituted phenyl in which the substituents are V$_1$, V$_2$, V$_3$, V$_4$, and V$_5$,
  (8) oxo,
  (9) carboxy,
  (10) C$_1$-C$_5$-alkylaminocarbonyl;

(h) mono-, di-, tri-, or polyfluoro-C$_1$-C$_{10}$-alkyl, (i) phenyl, biphenyl or naphthyl, (j) substituted phenyl, biphenyl or naphthyl in which the substituents are V$_1$, V$_2$, V$_3$, V$_4$ and V$_5$, (k) phenyl—(CH$_2$)$_r$—(Q)$_c$—(CH$_2$)$_r$—, (l) substituted phenyl—(CH$_2$)$_r$—(Q)$_c$—(CH$_2$)$_r$—, (m) heterocycle—(CH$_2$)$_r$—(Q)$_c$—(CH$_2$)$_r$—, wherein the heterocycle is 5- or 6-membered containing one or two heteroatoms such as pyridine, furan, pyrrole, imidazole or thiazole and unsubstituted or substituted with V$_1$ and V$_2$;

V$_1$, V$_2$, V$_3$, V$_4$ and V$_5$ are independently selected from:
(a) hydrogen,
(b) C$_1$-C$_5$-alkoxy,
(c) C$_1$-C$_5$-alkyl,
(d) hydroxy,
(e) NR$^9$R$^{10}$,
(f) CO$_2$R$^9$,
(g) trifluoromethyl,
(h) halogen,
(i) hydroxy-C$_1$-C$_4$-alkyl,
(j) -1H-tetrazol-5-yl,
(k) —NH—SO$_2$CF$_3$,
(l) CN,
(m) NO$_2$,
(n) C$_1$-C$_5$-alkyl-CO$_2$R$^9$, (o) aryl,
(p) aryl-$C_1$-$C_3$-alkyl,
(q) heteroaryl,
(r) $C_1$-$C_5$-alkyl-$CONR^{21}R^{22}$,
(s) —$CONR^{21}R^{22}$,
(t) 2-oxazolin-2-yl optionally bearing one or more $C_1$-$C_4$-alkyl substituents,
(u) $C_1$-$C_5$-alkyl-$S(O)_p$,
(v) $(CH_2)_tOCOR^{22}$,
(w) $(CH_2)_tNR^{21}COR^{22}$,
(x) $(CH_2)_tNR^{21}CONR^{21}R^{22}$,
(y) —$(CH_2)_tOCONR^{21}R^{22}$,
(z) —$(CH_2)_tNR^{21}CO_2R^{22}$,
(aa) —$(CH_2)_tNR^{21}CON(CH_2CH_2)_2L$,
(bb) —$(CH_2)_tOCON(CH_2CH_2)_2L$,
(cc) —$N(CH_2CH_2)_2L$,
(dd) —$C_1$-$C_5$-alkyl-$CON(CH_2CH_2)_2L$,
(ee) —$CON(CH_2CH_2)_2L$,
(ff) aryl-$C_1$-$C_3$-alkoxy, or
(gg) —$(CH_2)_tCOR^{22}$;
u is 1; and
X is:
(a) a single bond,
(b) —C(O)—, or
(c) —$NR^{15}C(O)$—.

3. The compound according to claim 2 wherein:
$R^1$ is (a) —$SO_2NHSO_2R^{22}$,

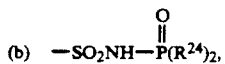
(b) —$SO_2NH$—$P(R^{24})_2$, (c) —$SO_2NHCN$, (d) —$SO_2NHCO_2R^{22}$,

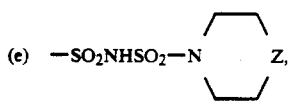
(e) —$SO_2NHSO_2$—N  Z,

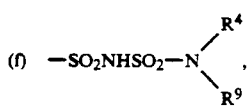
(f) —$SO_2NHSO_2$—N$\begin{smallmatrix}R^4\\R^9\end{smallmatrix}$, (g) —$NHSO_2NHSO_2R^{22}$, or

(h) —$NHSO_2NHP(R^{24})_2$;

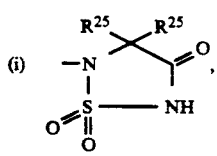
(i)

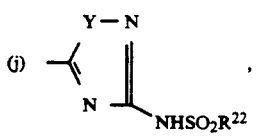
(j)

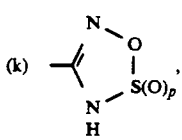
(k)

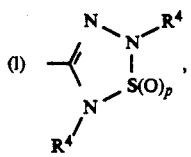
(l)

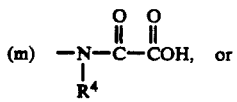
(m) —N(R$^4$)—C(O)—COH, or (n) —$NHSO_2R^{22}$;

E is a single bond or —S—;
$R^6$ is
(a) $C_1$-$C_6$ alkyl unsubstituted or substituted with —F, —$CF_3$, cyclopropyl, or $C_1$-$C_2$-alkyl-cyclopropyl or
(b) cyclopropyl, unsubstituted or substituted with —$CH_3$, —$C_2H_5$, —$CF_3$ or —$CF_2CF_3$;
A is O, S or $NR^{21}$;
B is
(a) H provided A is not $NR^{21}$,
(b) $C_1$-$C_{10}$-alkyl,
(c) substituted $C_1$-$C_{10}$-alkyl in which one or two substituents are selected from:
(1) hydroxy,
(2) $C_1$-$C_5$-alkoxy,
(3) $C_1$-$C_5$-alkoxycarbonyl,
(4) $C_1$-$C_4$-alkylcarbonyloxy,
(5) $C_3$-$C_8$-cycloalkyl,
(6) phenyl,
(7) substituted phenyl in which the substituents are $V_1$, $V_2$, $V_3$, $V_4$ and $V_5$,
(8) $C_1$-$C_5$-alkyl-$S(O)_p$
(9) phenyl-$S(O)_p$
(10) substituted phenyl-$S(O)_p$ in which the substituent is V,
(11) oxo,
(12) carboxy,
(13) $C_1$-$C_5$-alkylaminocarbonyl;
(d) $C_2$-$C_{10}$-alkenyl,
(e) $C_2$-$C_{10}$-alkynyl,
(f) $C_3$-$C_8$-cycloalkyl,
(g) substituted $C_3$-$C_8$-cycloalkyl or substituted $C_3$-$C_8$-cycloalkyl-$C_1$-$C_4$-alkyl in which one or more substituent(s) is selected from:
(1) hydroxy,
(2) $C_1$-$C_5$-alkoxy,
(3) $C_1$-$C_5$-alkoxycarbonyl,
(4) $C_1$-$C_4$-alkylcarbonyloxy,
(5) $C_1$-$C_6$-alkyl,
(6) phenyl,
(7) substituted phenyl in which the substituents are $V_1$, $V_2$, $V_3$, $V_4$, and $V_5$,
(8) oxo,
(9) carboxy,
(10) $C_1$-$C_5$-alkylaminocarbonyl;
(h) mono-, di-, tri-, or polyfluoro-$C_1$-$C_{10}$-alkyl,
(i) phenyl, biphenyl or naphthyl,
(j) substituted phenyl, biphenyl or naphthyl in which the substituents are $V_1$, $V_2$, $V_3$, $V_4$ and $V_5$,
(k) phenyl—$(CH_2)_r$—$(Q)_c$—$(CH_2)_r$—,
(l) substituted phenyl—$(CH_2)_r$—$(Q)_c$—$(CH_2)_r$—,

135

(m) heterocycle—$(CH_2)_r$—$(Q)_c$—$(CH_2)_r$—,
wherein the heterocycle is 5- or 6-membered containing one or two heteroatoms such as pyridine, furan, pyrrole, imidazole or thiazole and unsubstituted or substituted with $V_1$ and $V_2$;

$V_1$, $V_2$, $V_3$, $V_4$ and $V_5$ are independently selected from:
(a) hydrogen,
(b) $C_1$-$C_5$-alkoxy,
(c) $C_1$-$C_5$-alkyl,
(d) hydroxy,
(e) $NR^9R^{10}$,
(f) $CO_2R^9$,
(g) trifluoromethyl,
(h) halogen,
(i) hydroxy-$C_1$-$C_4$-alkyl,
(j) -1H-tetrazol-5-yl,
(k) —NH—$SO_2CF_3$,
(l) CN,
(m) $NO_2$,
(n) $C_1$-$C_5$-alkyl-$CO_2R^9$,
(o) aryl,
(p) aryl-$C_1$-$C_3$-alkyl,
(q) heteroaryl,
(r) $C_1$-$C_5$-alkyl-$CONR^{21}R^{22}$,
(s) —$CONR^{21}R^{22}$,
(t) 2-oxazolin-2-yl optionally bearing one or more $C_1$-$C_4$-alkyl substituents,
(u) $C_1$-$C_5$-alkyl-$S(O)_p$,
(v) $(CH_2)_t OCOR^{22}$,
(w) $(CH_2)_t NR^{21}COR^{22}$,
(x) $(CH_2)_t NR^{21}CONR^{21}R^{22}$,
(y) —$(CH_2)_t OCONR^{21}R^{22}$,
(z) —$(CH_2)_t NR^{21}CO_2R^{22}$,
(aa) —$(CH_2)_t NR^{21}CON(CH_2CH_2)_2L$,
(bb) —$(CH_2)_t OCON(CH_2CH_2)_2L$,
(cc) —$N(CH_2CH_2)_2L$,
(dd) —$C_1$-$C_5$-alkyl-$CON(CH_2CH_2)_2L$,
(ee) —$CON(CH_2CH_2)_2L$,
(ff) aryl-$C_1$-$C_3$-alkoxy, or
(gg) —$(CH_2)_t COR^{22}$,
u is 1; and
X is:
(a) a single bond,
(b) —C(O)—, or
(c) —$NR^{15}C(O)$—.

4. The compound according to claim 3 wherein:
A is O, S or $NR^{21}$;
B is
(a) H provided A is not $NR^{21}$,
(b) $C_1$-$C_{10}$-alkyl,
(c) $C_3$-$C_8$-cycloalkyl,
(d) $C_3$-$C_8$-cycloalkyl-$C_1$-$C_4$-alkyl,
(e) substituted $C_1$-$C_{10}$-alkyl, $C_3$-$C_8$-cycloalkyl, or $C_3$-$C_8$-cycloalkyl-$C_1$-$C_4$-alkyl each of which can have one or two substituents selected from the group;
(1) hydroxy,
(2) $C_1$-$C_5$-alkoxy,
(3) $C_1$-$C_5$-alkoxycarbonyl,
(4) phenyl, naphthyl or biphenyl,
(5) substituted phenyl, naphthyl or biphenyl wherein the substitutents are $V_1$, $V_2$, $V_3$, $V_4$ and $V_5$,
(6) carboxy,
(7) $C_1$-$C_5$-alkylaminocarbonyl,
(8) oxo,
(9) —$NR^{21}COR^{22}$,

136

(10) —$NR^{21}CO_2R^{22}$,
(11) —$OCONR^{21}R^{22}$, or
(12) —CN,
(f) mono-, di-, tri-, or polyfluoro-$C_1$-$C_{10}$-alkyl,
(g) phenyl, biphenyl or naphthyl,
(h) substituted phenyl in which the substituents are $V_1$, $V_2$, $V_3$, $V_4$ and $V_5$,
(i) phenyl-$(CH_2)_r$—$(Q)_c$—$(CH_2)_r$—,
(j) substituted phenyl-$(CH_2)_r$—$(Q)_c$—$(CH_2)_r$— in which the substituents are $V_1$, $V_2$, $V_3$, $V_4$ and $V_5$, or
(k) a heterocyclic moiety selected from:

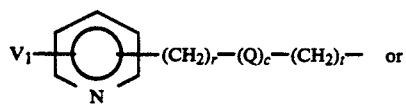

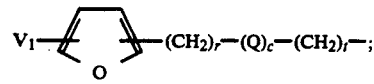

$V_1$, $V_2$, $V_3$, $V_4$ and $V_5$ are selected from:
(a) hydrogen,
(b) $C_1$-$C_5$-alkyl,
(c) $C_1$-$C_5$-alkoxy,
(d) $CO_2R^9$,
(e) halogen,
(f) hydroxy-$C_1$-$C_4$-alkyl-,
(g) $C_1$-$C_5$-alkyl-$CO_2R^9$,
(h) $C_1$-$C_5$-alkyl-$CONR^{21}R^{22}$,
(i) $CONR^{21}R^{22}$,
(j) CN,
(k) $NO_2$,
(l) $CF_3$,
(m) aryl,
(n) heteroaryl,
(o) 2-oxazolin-2-yl optionally bearing one or more $C_1$-$C_4$-alkyl substituents,
(p) $C_1$-$C_5$-alkyl-$S(O)_p$,
(q) $(CH_2)_t OCOR^{22}$,
(r) $(CH_2)_t NR^{21}COR^{22}$,
(s) $(CH_2)_t NR^{21}CO_2R^{22}$,
(t) $(CH_2)_t NR^{21}CONR^{21}R^{22}$,
(u) —$(CH_2)_t OCONR^{21}R^{22}$,
(v) —$(CH_2)_t NR^{21}CON(CH_2CH_2)_2L$,
(w) —$(CH_2)_t OCON(CH_2CH_2)_2L$,
(x) —$N(CH_2CH_2)_2L$,
(y) —$C_1$-$C_5$-alkyl-$CON(CH_2CH_2)_2L$,
(z) —$CON(CH_2CH_2)_2L$,
(aa) hydroxy,
(bb) $NR^9R^{10}$,
(cc) aryl-$C_1$-$C_3$-alkyl,
(dd) aryl-$C_1$-$C_3$-alkoxy, or
(ee) —$(CH_2)_t COR^{22}$,
X is —$NR^{15}C(O)$— or a carbon—carbon single bond.

5. The compound according to claim 4 wherein:
$R^1$ is —$SO_2NHCO_2R^{22}$;
$R^6$ is $C_1$-$C_6$-alkyl;
$R^{21}$ is H, substituted or unsubstituted aryl, substituted or unsubstituted $C_1$-$C_6$-alkyl, or heteroaryl;
$R^{22}$ is
(a) substituted or unsubstituted aryl,
(b) substituted or unsubstituted $C_1$-$C_6$-alkyl, or
(c) heteroaryl;
A is O;

B is substituted phenyl in which the substituents are $V_1$, $V_2$, $V_3$, $V_4$ and $V_5$;

$V_1$, $V_2$, $V_3$, $V_4$ and $V_5$ are selected from:
(a) hydrogen,
(b) $C_1$–$C_5$-alkyl,
(c) $C_1$–$C_5$-alkoxy,
(d) $C_1$–$C_5$-alkyl-S(O)$_p$—,
(e) halogen,
(f) $CONR^{21}R^{22}$,
(g) CN,
(h) $NO_2$,
(i) $CF_3$,
(j) aryl,
(k) heteroaryl,
(l) —$NR^{21}COR^{22}$,
(m) —$NR^{21}CO_2R^{22}$,
(n) —$NR^{21}CONR^{21}R^{22}$,
(o) —$NR^{21}CON(CH_2CH_2)_2L$,
(p) —$CON(CH_2CH_2)_2L$,
(q) $NR^9R^{10}$, or
(r) —$(CH_2)_rCOR^{22}$;

X is a carbon—carbon single bond;
E is a single bond; and
u is 1.

6. The compound according to claim 5 having the formula III:

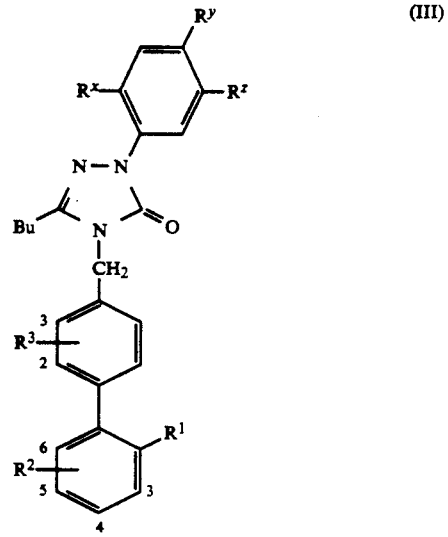

(III)

wherein:

| $R^1$ | $R^2$ | $R^3$ | $R^x$ | $R^y$ | $R^z$ |
|---|---|---|---|---|---|
| —$SO_2NHCO_2Et$ | H | H | $CF_3$ | H | H |
| —$SO_2NHCO_2i$-Pr | H | H | $CF_3$ | H | H |
| —$SO_2NHCO_2n$-Pr | H | H | $CF_3$ | H | H |
| —$SO_2NHCO_2i$-Bu | H | H | $CF_3$ | H | H |
| —$SO_2NHCO_2n$-Bu | H | H | $CF_3$ | H | H |
| —$SO_2NHCO_2t$-Bu | H | H | $CF_3$ | H | H |
| —$SO_2NHCO_2t$-Bu | H | H | Cl | H | H |
| —$SO_2NHCO_2t$-Bu | H | H | Br | H | H |
| —$SO_2NHCO_2t$-Bu | 5'-n-Pr | H | $CF_3$ | H | H |
| —$SO_2NHCO_2t$-Bu | 5'-n-Pr | 3-F | $CF_3$ | H | H |
| —$SO_2NHCO_2t$-Bu | H | 3-F | $CF_3$ | H | H |
| —$SO_2NHCO_2t$-Bu | H | H | $CF_3$ | $NO_2$ | H |
| —$SO_2NHCO_2t$-Bu | H | H | $CF_3$ | $NH_2$ | H |
| —$SO_2NHCO_2t$-Bu | H | H | $CF_3$ | $NHCOCH_2CH_3$ | H |
| —$SO_2NHCO_2t$-Bu | H | H | Cl | H | $NO_2$ |
| —$SO_2NHCO_2t$-Bu | H | H | Cl | H | $NH_2$ |
| —$SO_2NHCO_2t$-Bu | H | H | Cl | H | $NH(CH_2)_3CH_3$ |
| —$SO_2NHCO_2t$-Bu | H | H | Cl | H | $NHCH_2$-phenyl |
| —$SO_2NHCO_2t$-Bu | H | H | Cl | H | $NHCOCH_3$ |
| —$SO_2NHCO_2t$-Bu | H | H | Cl | H | $NHCOCH_2CH_3$ |
| —$SO_2NHCO_2t$-Bu | H | H | Cl | H | $NHCO(CH_2)_2CH_3$ |
| —$SO_2NHCO_2t$-Bu | H | H | Cl | H | $NHCO(CH_2)_3CH_3$ |
| —$SO_2NHCO_2t$-Bu | H | H | Cl | H | $NHCOCH(CH_3)_2$ |
| —$SO_2NHCO_2t$-Bu | H | H | Cl | H | $NHCOCH_2CH(CH_3)_2$ |
| —$SO_2NHCO_2t$-Bu | H | H | Cl | H | NHCO-cyclopropyl |
| —$SO_2NHCO_2t$-Bu | H | H | Cl | H | NHCO-phenyl |
| —$SO_2NHCO_2t$-Bu | H | H | Cl | H | $NHCOCH_2$-phenyl |
| —$SO_2NHCO_2t$-Bu | H | H | Cl | H | $NHCO(CH_2)_2$-phenyl |
| —$SO_2NHCO_2t$-Bu | H | 3-F | Cl | H | NHCO-(4-pyridyl) |
| —$SO_2NHCO_2t$-Bu | H | 3-F | Cl | H | NHCO-(3-pyridyl) |
| —$SO_2NHCO_2t$-Bu | H | H | Cl | H | $NHCOO(CH_2)_2CH_3$ |
| —$SO_2NHCO_2t$-Bu | H | H | Cl | H | $NHCONH(CH_2)_2CH_3$ |
| —$SO_2NHCO_2t$-Bu | H | 3-F | Cl | H | NHCO-(4-morpholinyl) |
| —$SO_2NHCO_2t$-Bu | H | 3-F | Cl | H | $NHCOCH_2OCH_2CH_3$ |
| —$SO_2NHCO_2t$-Bu | H | 3-F | Cl | H | $NHCOCH_2SCH_2CH_3$ |
| —$SO_2NHCO_2t$-Bu | H | 3-F | Cl | H | $CONHCH_2CH_3$ |
| —$SO_2NHCO_2t$-Bu | H | H | Cl | H | $CONH(CH_2)_2CH_3$ |
| —$SO_2NHCO_2t$-Bu | H | H | Cl | H | $CONH(CH_2)_3CH_3$ |
| —$SO_2NHCO_2t$-Bu | H | H | Cl | H | $CON(CH_3)(CH_2)_3CH_3$ |
| —$SO_2NHCO_2t$-Bu | H | 3-F | Cl | H | $COCH_2CH_3$ |
| —$SO_2NHCO_2t$-Bu | H | H | Cl | H | $CO(CH_2)_2CH_3$ |
| —$SO_2NHCO_2t$-Bu | H | H | Cl | H | $CO(CH_2)_3CH_3$ |
| —$SO_2NHCO_2t$-Bu | H | 3-F | Cl | H | $CO(CH_2)_4CH_3$ |
| —$SO_2NHCO_2t$-Bu | H | 3-F | Cl | H | $SO(CH_2)_3CH_3$ |
| —$SO_2NHCO_2t$-Bu | H | 3-F | Cl | H | $NHCOCH_3$ |
| —$SO_2NHCO_2t$-Bu | 5'-n-Pr | 3-F | Cl | H | $NHCOCH_3$ |
| —$SO_2NHCO_2t$-Bu | H | 3-F | Cl | H | $NHCOCH_2CH_3$ |
| —$SO_2NHCO_2t$-Bu | H | 3-F | Cl | H | $NHCO(CH_2)_2CH_3$ |
| —$SO_2NHCO_2t$-Bu | H | 3-F | Cl | H | $NHCO(CH_2)_3CH_3$ |

-continued

| R¹ | R² | R³ | Rˣ | Rʸ | R^z |
|---|---|---|---|---|---|
| —SO₂NHCO₂t-Bu | H | 3-F | Cl | H | NHCO-phenyl |
| —SO₂NHCO₂t-Bu | H | 3-F | Cl | H | CONH(CH₂)₂CH₃ |
| —SO₂NHCO₂t-Bu | H | 3-F | Cl | H | CONH(CH₂)₃CH₃ |
| —SO₂NHCO₂t-Bu | H | 3-F | Cl | H | CO(CH₂)₂CH₃ |
| —SO₂NHCO₂t-Bu | H | 3-F | Cl | H | CO(CH₂)₃CH₃ |
| —SO₂NHCO₂t-Bu | 5'-Et | 3-F | Cl | H | NHCOCH₂CH₃ |
| —SO₂NHCO₂t-Bu | 5'-F | 3-F | Cl | H | NHCOCH₂CH₃ |
| —SO₂NHCO₂t-Bu | 3',6'-diF | H | Cl | H | NHCOCH₂CH₃ |
| —SO₂NHCO₂t-Bu | H | 2-F | Cl | H | NHCOCH₂CH₃ |
| —SO₂NHCO₂t-Bu | H | H | CF₃ | H | NHCOCH₂CH₃ |
| —SO₂NHCO₂t-Bu | H | H | CF₃ | H | NHCO(CH₂)₂CH₃ |
| —SO₂NHCO₂t-Bu | H | H | CF₃ | H | NHCO(CH₂)₃CH₃ |
| —SO₂NHCO₂t-Bu | H | H | CF₃ | H | NHCO-phenyl |
| —SO₂NHCO₂t-Bu | H | H | CF₃ | H | CONH(CH₂)₂CH₃ |
| —SO₂NHCO₂t-Bu | H | H | CF₃ | H | CONH(CH₂)₃CH₃ |
| —SO₂NHCO₂t-Bu | H | H | CF₃ | H | CO(CH₂)₂CH₃ |
| —SO₂NHCO₂t-Bu | H | H | CF₃ | H | CO(CH₂)₃CH₃ |
| —SO₂NHCO₂t-Bu | H | 3-F | CF₃ | H | NHCOCH₂CH₃ |
| —SO₂NHCO₂t-Bu | H | 3-F | CF₃ | H | NHCO(CH₂)₂CH₃ |
| —SO₂NHCO₂t-Bu | H | 3-F | CF₃ | H | NHCO(CH₂)₃CH₃ |
| —SO₂NHCO₂t-Bu | H | 3-F | CF₃ | H | NHCO-phenyl |
| —SO₂NHCO₂t-Bu | H | 3-F | CF₃ | H | CONH(CH₂)₂CH₃ |
| —SO₂NHCO₂t-Bu | H | 3-F | CF₃ | H | CONH(CH₂)₃CH₃ |
| —SO₂NHCO₂t-Bu | H | 3-F | CF₃ | H | CO(CH₂)₂CH₃ |
| —SO₂NHCO₂t-Bu | H | 3-F | CF₃ | H | CO(CH₂)₃CH₃ |
| —SO₂NHCO₂t-Bu | H | H | Br | H | NHCOCH₂CH₃ |
| —SO₂NHCO₂t-Bu | H | H | Br | H | NHCO(CH₂)₂CH₃ |
| —SO₂NHCO₂t-Bu | H | H | Br | H | NHCO(CH₂)₃CH₃ |
| —SO₂NHCO₂t-Bu | H | H | Br | H | NHCO-phenyl |
| —SO₂NHCO₂t-Bu | H | H | Br | H | CONH(CH₂)₂CH₃ |
| —SO₂NHCO₂t-Bu | H | H | Br | H | CONH(CH₂)₃CH₃ |
| —SO₂NHCO₂t-Bu | H | H | Br | H | CO(CH₂)₂CH₃ |
| —SO₂NHCO₂t-Bu | H | H | Br | H | CO(CH₂)₃CH₃ |
| —SO₂NHCO₂t-Bu | H | 3-F | Br | H | NHCOCH₂CH₃ |
| —SO₂NHCO₂t-Bu | H | 3-F | Br | H | NHCO(CH₂)₂CH₃ |
| —SO₂NHCO₂t-Bu | H | 3-F | Br | H | NHCO(CH₂)₃CH₃ |
| —SO₂NHCO₂t-Bu | H | 3-F | Br | H | NHCO-phenyl |
| —SO₂NHCO₂t-Bu | H | 3-F | Br | H | CONH(CH₂)₂CH₃ |
| —SO₂NHCO₂t-Bu | H | 3-F | Br | H | CONH(CH₂)₃CH₃ |
| —SO₂NHCO₂t-Bu | H | 3-F | Br | H | CO(CH₂)₂CH₃ |
| —SO₂NHCO₂t-Bu | H | 3-F | Br | H | CO(CH₂)₃CH₃ |
| —SO₂NHCO₂t-Bu | H | H | H | H | NHCO(CH₂)₃CH₃ |
| —SO₂NHCO₂t-Bu | H | H | H | H | CONH(CH₂)₃CH₃ |
| —SO₂NHCO₂t-Bu | H | 3-F | H | H | NHCO(CH₂)₃CH₃ |
| —SO₂NHCO₂t-Bu | H | 3-F | H | H | CONH(CH₂)₃CH₃ |
| —SO₂NHCO₂t-Bu | 5'-n-Pr | 3-F | H | H | NHCOCH₂CH₃ |
| —SO₂NHCO₂t-Bu | 5'-n-Pr | 3-F | H | H | CONHCH₂CH₃ |
| —SO₂NHCO₂n-Bu | H | 3-F | Cl | H | NHCOCH₂CH₃ |
| —SO₂NHCO₂i-Bu | H | 3-F | Cl | H | NHCOCH₂CH₃ |
| —SO₂NHCO₂n-Pr | H | 3-F | Cl | H | NHCOCH₂CH₃ |
| —SO₂NHCO₂Et | H | 3-F | Cl | H | NHCOCH₂CH₃ |
| —SO₂NHCO₂Et | 5'-n-Pr | 3-F | Cl | H | NHCOCH₃ |
| —SO₂NHCO₂Et | 5'-n-Pr | 3-F | Cl | H | NHCOCH₂CH₃ |
| —SO₂NHCO₂t-Bu | H | 3-F | Cl | H | COCH₂-phenyl |
| —SO₂NHCO₂t-Bu | H | 3-F | Cl | H | Co-phenyl |
| —SO₂NHCO₂t-Bu | H | 3-F | Cl | H | NHCO(CH₂)₄CH₃ |
| —SO₂NHCO₂t-Bu | H | 3-F | Cl | H | NHCO(CH₂)₅CH₃ |
| —SO₂NHCO₂t-Bu | H | 3-F | Cl | H | CONH-phenyl |
| —SO₂NHCO₂t-Bu | 5'-Et | 3-F | Cl | H | NHCO(CH₂)₃CH₃ |
| —SO₂NHCO₂t-Bu | 5'-F | 3-F | CF₃ | H | NHCOCH₂CH₃ |
| —SO₂NHCO₂t-Bu | 3',6'-diF | H | CF₃ | H | NHCOCH₂CH₃ |
| —SO₂NHCO₂t-Bu | H | 2-F | CF₃ | H | NHCOCH₂CH₃ |
| —SO₂NHCO₂t-Bu | H | 3-F | CF₃ | H | NHCO(CH₂)₄CH₃ |
| —SO₂NHCO₂t-Bu | H | 3-F | CF₃ | H | NHCOCH₂OCH₂CH₃ |
| —SO₂NHCO₂t-Bu | H | 3-F | CF₃ | H | NHCOCH₂SCH₂CH₃ |
| —SO₂NHCO₂t-Bu | H | 3-F | CF₃ | H | NHCOCH₂SCH₃ |
| —SO₂NHCO₂t-Bu | H | 3-F | CF₃ | H | NHCOCH₂OCH₃ |
| —SO₂NHCO₂t-Bu | H | 3-F | CF₃ | H | NHCO(CH₂)₂OCH₂CH₃ |
| —SO₂NHCO₂t-Bu | H | 3-F | CF₃ | H | NHCO(CH₂)₂SCH₂CH₃ |
| —SO₂NHCO₂t-Bu | H | 3-F | CF₃ | H | NHCO(CH₂)₂OCH₃ |
| —SO₂NHCO₂t-Bu | H | 3-F | CF₃ | H | NHCO(CH₂)₂SCH₃ |
| —SO₂NHCO₂t-Bu | H | 3-F | Br | H | NHCOCH₂OCH₂CH₃ |
| —SO₂NHCO₂t-Bu | H | 3-F | Br | H | NHCOCH₂SCH₂CH₃ |
| —SO₂NHCO₂t-Bu | H | 3-F | Br | H | NHCOCH₂SCH₃ |
| —SO₂NHCO₂t-Bu | H | 3-F | Br | H | NHCOCH₂OCH₃ |
| —SO₂NHCO₂t-Bu | H | 3-F | Br | H | NHCO(CH₂)₂OCH₂CH₃ |
| —SO₂NHCO₂t-Bu | H | 3-F | Br | H | NHCO(CH₂)₂SCH₂CH₃ |
| —SO₂NHCO₂t-Bu | H | 3-F | Br | H | NHCO(CH₂)₂OCH₃ |
| —SO₂NHCO₂t-Bu | H | 3-F | Br | H | NHCO(CH₂)₂SCH₃ |
| —SO₂NHCO₂t-Bu | H | 3-F | Cl | H | NHCOCH₂SCH₃ |
| —SO₂NHCO₂t-Bu | H | 3-F | Cl | H | NHCOCH₂OCH₃ |

-continued

| R¹ | R² | R³ | Rˣ | Rʸ | Rᶻ |
|---|---|---|---|---|---|
| —SO₂NHCO₂t-Bu | H | 3-F | Cl | H | NHCO(CH₂)₂OCH₂CH₃ |
| —SO₂NHCO₂t-Bu | H | 3-F | Cl | H | NHCO(CH₂)₂SCH₂CH₃ |
| —SO₂NHCO₂t-Bu | H | 3-F | Cl | H | NHCO(CH₂)₂OCH₃ |
| —SO₂NHCO₂t-Bu | H | 3-F | Cl | H | NHCO(CH₂)₂SCH₃ |
| —SO₂NHCO₂t-Bu | H | 3-F | CF₃ | H | CONH(CH₂)₄CH₃ |
| —SO₂NHCO₂t-Bu | H | 3-F | CF₃ | H | CONH(CH₂)₅CH₃ |
| —SO₂NHCO₂t-Bu | H | 3-F | CF₃ | H | CONHCH₂CH₃ |
| —SO₂NHCO₂t-Bu | H | 3-F | CF₃ | H | CONH-phenyl |
| —SO₂NHCO₂t-Bu | H | 3-F | CF₃ | H | CO(CH₂)₄CH₃ |
| —SO₂NHCO₂t-Bu | H | 3-F | CF₃ | H | CO-phenyl |
| —SO₂NHCO₂t-Bu | H | 3-F | CF₃ | H | COCH₂-phenyl |
| —SO₂NHCO₂t-Bu | H | 3-F | Br | H | CONH(CH₂)₄CH₃ |
| —SO₂NHCO₂t-Bu | H | 3-F | Br | H | CONHCH₂CH₃ |
| —SO₂NHCO₂t-Bu | H | 3-F | Br | H | NHCO(CH₂)₄CH₃ |
| —SO₂NHCO₂t-Bu | H | 3-F | Br | H | CO(CH₂)₄CH₃ |
| —SO₂NHCO₂t-Bu | H | 3-F | Br | H | CO-phenyl |
| —SO₂NHCO₂t-Bu | H | 3-F | Br | H | COCH₂-phenyl |
| —SO₂NHCO₂t-Bu | H | 3-F | Cl | H | CONH(CH₂)₂OCH₃ |
| —SO₂NHCO₂t-Bu | H | 3-F | Cl | H | CONH(CH₂)₂SCH₃ |
| —SO₂NHCO₂t-Bu | H | 3-F | Cl | H | CONH(CH₂)₂OCH₂CH₃ |
| —SO₂NHCO₂t-Bu | H | 3-F | Cl | H | CONH(CH₂)₂SCH₂CH₃ |
| —SO₂NHCO₂t-Bu | H | 3-F | Br | H | CONH(CH₂)₂OCH₃ |
| —SO₂NHCO₂t-Bu | H | 3-F | Br | H | CONH(CH₂)₂SCH₃ |
| —SO₂NHCO₂t-Bu | H | 3-F | Br | H | CONH(CH₂)₂OCH₂CH₃ |
| —SO₂NHCO₂t-Bu | H | 3-F | Br | H | CONH(CH₂)₂SCH₂CH₃ |
| —SO₂NHCO₂t-Bu | H | 3-F | CF₃ | H | CONH(CH₂)₂OCH₃ |
| —SO₂NHCO₂t-Bu | H | 3-F | CF₃ | H | CONH(CH₂)₂SCH₃ |
| —SO₂NHCO₂t-Bu | H | 3-F | CF₃ | H | CONH(CH₂)₂OCH₂CH₃ |
| —SO₂NHCO₂t-Bu | H | 3-F | CF₃ | H | CONH(CH₂)₂SCH₂CH₃ |
| —SO₂NHCO₂t-Bu | H | 3-F | CF₃ | H | NHCO-(4-pyridyl) |
| —SO₂NHCO₂t-Bu | H | 3-F | CF₃ | H | NHCO-(3-pyridyl) |
| —SO₂NHCO₂t-Bu | H | 3-F | Br | H | NHCO-(4-pyridyl) |
| —SO₂NHCO₂t-Bu | H | 3-F | Br | H | NHCO-(3-pyridyl) |
| —SO₂NHCO₂n-Pr | H | 3-F | CF₃ | H | NHCOCH₂CH₃ |
| —SO₂NHCO₂t-Bu | 5'-n-Pr | 3-F | Cl | H | NHCO-cyclopropyl |
| —SO₂NHCO₂Et | 5'-n-Pr | 3-F | Cl | H | NHCO-cyclopropyl |
| —SO₂NHCO₂Et | H | 3-F | Cl | H | NHCOCH₃ |
| —SO₂NHCO₂Et | H | 3-F | Cl | H | NHCO-cyclopropyl |
| —SO₂NHCO₂Et | H | 3-F | Cl | H | NHCO(CH₂)₂CH₃ |
| —SO₂NHCO₂Et | H | 3-F | Cl | H | NHCO(CH₂)₃CH₃ |
| —SO₂NHCO₂Et | H | 3-F | Cl | H | NHCO(CH₂)₄CH₃ |
| —SO₂NHCO₂Et | H | 3-F | Cl | H | NHCO-phenyl |
| —SO₂NHCO₂Et | H | 3-F | Cl | H | CONHCH₂CH₃ |
| —SO₂NHCO₂Et | H | 3-F | Cl | H | CONH(CH₂)₂CH₃ |
| —SO₂NHCO₂Et | H | 3-F | Cl | H | CONH(CH₂)₃CH₃ |
| —SO₂NHCO₂Et | H | 3-F | Cl | H | CONH(CH₂)₂OCH₂CH₃ |
| —SO₂NHCO₂Et | H | 3-F | Cl | H | CONH(CH₂)₂SCH₂CH₃ |
| —SO₂NHCO₂Et | H | 3-F | Cl | H | CONH(CH₂)₂OCH₃ |
| —SO₂NHCO₂Et | H | 3-F | Cl | H | CONH(CH₂)₂SCH₃ |
| —SO₂NHCO₂Et | H | 3-F | Cl | H | CO(CH₂)₂CH₃ |
| —SO₂NHCO₂Et | H | 3-F | Cl | H | CO(CH₂)₃CH₃ |
| —SO₂NHCO₂Et | H | 3-F | Cl | H | CO-phenyl |
| —SO₂NHCO₂Et | H | 3-F | Cl | H | COCH₂-phenyl |
| —SO₂NHCO₂Et | H | 3-F | Cl | H | NHCOCH₂OCH₂CH₃ |
| —SO₂NHCO₂Et | H | 3-F | Cl | H | NHCOCH₂SCH₂CH₃ |
| —SO₂NHCO₂Et | H | 3-F | Cl | H | NHCOCH₂SCH₃ |
| —SO₂NHCO₂Et | H | 3-F | Cl | H | NHCOCH₂OCH₃ |
| —SO₂NHCO₂Et | H | 3-F | Cl | H | NHCO(CH₂)₂OCH₂CH₃ |
| —SO₂NHCO₂Et | H | 3-F | Cl | H | NHCO(CH₂)₂SCH₂CH₃ |
| —SO₂NHCO₂Et | H | 3-F | Cl | H | NHCO(CH₂)₂OCH₃ |
| —SO₂NHCO₂Et | H | 3-F | Cl | H | NHCO(CH₂)₂SCH₃ |
| —SO₂NHCO₂Et | H | 3-F | Cl | H | NHCO-(4-pyridyl) |
| —SO₂NHCO₂Et | H | 3-F | Cl | H | NHCO-(3-pyridyl) |
| —SO₂NHCO₂Et | H | 3-F | Cl | H | SO(CH₂)₃CH₃ |
| —SO₂NHCO₂Et | H | 3-F | CF₃ | H | NHCOCH₃ |
| —SO₂NHCO₂Et | H | 3-F | CF₃ | H | NHCO-cyclopropyl |
| —SO₂NHCO₂Et | H | 3-F | CF₃ | H | NHCOCH₂CH₃ |
| —SO₂NHCO₂Et | H | 3-F | CF₃ | H | NHCO(CH₂)₂CH₃ |
| —SO₂NHCO₂Et | H | 3-F | CF₃ | H | NHCO(CH₂)₃CH₃ |
| —SO₂NHCO₂Et | H | 3-F | CF₃ | H | NHCO(CH₂)₄CH₃ |
| —SO₂NHCO₂Et | H | 3-F | CF₃ | H | NHCO-phenyl |
| —SO₂NHCO₂Et | H | 3-F | CF₃ | H | CONHCH₂CH₃ |
| —SO₂NHCO₂Et | H | 3-F | CF₃ | H | CONH(CH₂)₂CH₃ |
| —SO₂NHCO₂Et | H | 3-F | CF₃ | H | CONH(CH₂)₃CH₃ |
| —SO₂NHCO₂Et | H | 3-F | CF₃ | H | CONH(CH₂)₂OCH₂CH₃ |
| —SO₂NHCO₂Et | H | 3-F | CF₃ | H | CONH(CH₂)₂SCH₂CH₃ |
| —SO₂NHCO₂Et | H | 3-F | CF₃ | H | CONH(CH₂)₂OCH₃ |
| —SO₂NHCO₂Et | H | 3-F | CF₃ | H | CONH(CH₂)₂SCH₃ |
| —SO₂NHCO₂Et | H | 3-F | CF₃ | H | CO(CH₂)₂CH₃ |
| —SO₂NHCO₂Et | H | 3-F | CF₃ | H | CO(CH₂)₃CH₃ |
| —SO₂NHCO₂Et | H | 3-F | CF₃ | H | CO-phenyl |

-continued

| R¹ | R² | R³ | Rˣ | Rʸ | Rᶻ |
|---|---|---|---|---|---|
| —SO₂NHCO₂Et | H | 3-F | CF₃ | H | COCH₂-phenyl |
| —SO₂NHCO₂Et | H | 3-F | CF₃ | H | NHCOCH₂OCH₂CH₃ |
| —SO₂NHCO₂Et | H | 3-F | CF₃ | H | NHCOCH₂SCH₂CH₃ |
| —SO₂NHCO₂Et | H | 3-F | CF₃ | H | NHCOCH₂SCH₃ |
| —SO₂NHCO₂Et | H | 3-F | CF₃ | H | NHCOCH₂OCH₃ |
| —SO₂NHCO₂Et | H | 3-F | CF₃ | H | NHCO(CH₂)₂OCH₂CH₃ |
| —SO₂NHCO₂Et | H | 3-F | CF₃ | H | NHCO(CH₂)₂SCH₂CH₃ |
| —SO₂NHCO₂Et | H | 3-F | CF₃ | H | NHCO(CH₂)₂OCH₃ |
| —SO₂NHCO₂Et | H | 3-F | CF₃ | H | NHCO(CH₂)₂SCH₃ |
| —SO₂NHCO₂Et | H | 3-F | CF₃ | H | NHCO-(4-pyridyl) |
| —SO₂NHCO₂Et | H | 3-F | CF₃ | H | NHCO-(3-pyridyl) |
| —SO₂NHCO₂Et | H | 3-F | CF₃ | H | SO(CH₂)₃CH₃ |
| —SO₂NHCO₂Et | H | 3-F | Br | H | NHCOCH₃ |
| —SO₂NHCO₂Et | H | 3-F | Br | H | NHCO-cyclopropyl |
| —SO₂NHCO₂Et | H | 3-F | Br | H | NHCOCH₂CH₃ |
| —SO₂NHCO₂Et | H | 3-F | Br | H | NHCO(CH₂)₂CH₃ |
| —SO₂NHCO₂Et | H | 3-F | Br | H | NHCO(CH₂)₃CH₃ |
| —SO₂NHCO₂Et | H | 3-F | Br | H | NHCO(CH₂)₄CH₃ |
| —SO₂NHCO₂Et | H | 3-F | Br | H | NHCO-phenyl |
| —SO₂NHCO₂Et | H | 3-F | Br | H | CONHCH₂CH₃ |
| —SO₂NHCO₂Et | H | 3-F | Br | H | CONH(CH₂)₂CH₃ |
| —SO₂NHCO₂Et | H | 3-F | Br | H | CONH(CH₂)₃CH₃ |
| —SO₂NHCO₂Et | H | 3-F | Br | H | CONH(CH₂)₂OCH₂CH₃ |
| —SO₂NHCO₂Et | H | 3-F | Br | H | CONH(CH₂)₂SCH₂CH₃ |
| —SO₂NHCO₂Et | H | 3-F | Br | H | CONH(CH₂)₂OCH₃ |
| —SO₂NHCO₂Et | H | 3-F | Br | H | CONH(CH₂)₂SCH₃ |
| —SO₂NHCO₂Et | H | 3-F | Br | H | CO(CH₂)₂CH₃ |
| —SO₂NHCO₂Et | H | 3-F | Br | H | CO(CH₂)₃CH₃ |
| —SO₂NHCO₂Et | H | 3-F | Br | H | CO-phenyl |
| —SO₂NHCO₂Et | H | 3-F | Br | H | COCH₂-phenyl |
| —SO₂NHCO₂Et | H | 3-F | Br | H | NHCOCH₂OCH₂CH₃ |
| —SO₂NHCO₂Et | H | 3-F | Br | H | NHCOCH₂SCH₂CH₃ |
| —SO₂NHCO₂Et | H | 3-F | Br | H | NHCOCH₂SCH₃ |
| —SO₂NHCO₂Et | H | 3-F | Br | H | NHCOCH₂OCH₃ |
| —SO₂NHCO₂Et | H | 3-F | Br | H | NHCO(CH₂)₂OCH₂CH₃ |
| —SO₂NHCO₂Et | H | 3-F | Br | H | NHCO(CH₂)₂SCH₂CH₃ |
| —SO₂NHCO₂Et | H | 3-F | Br | H | NHCO(CH₂)₂OCH₃ |
| —SO₂NHCO₂Et | H | 3-F | Br | H | NHCO(CH₂)₂SCH₃ |
| —SO₂NHCO₂Et | H | 3-F | Br | H | NHCO-(4-pyridyl) |
| —SO₂NHCO₂Et | H | 3-F | Br | H | NHCO-(4-pyridyl) |
| —SO₂NHCO₂Et | H | 3-F | Br | H | SO(CH₂)₃CH₃ |

7. The compound according to claim 5 which is:
4-[[2'-[N-(t-Butoxycarbonyl)sulfamoyl]biphenyl-4-yl]methyl]-5-n-butyl-2,4-dihydro-2-[2-(trifluoromethyl)phenyl]-3H-1,2,4-triazol-3-one, 4-[[2'-[N-(t-Butoxycarbonyl)sulfamoyl]biphenyl-4-yl]methyl]-5-n-butyl-2-[2-chloro-5-(valerylamino)-phenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[5-(N-n-butylcarbamoyl)-2-chlorophenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-(trifluoromethyl)phenyl]-2,4-dihydro-3H-1,2,4-triazol-3-one, 4-[[2'-[N-(t-Butoxycarbonyl)sulfamoyl]biphenyl-4-yl]methyl]-5-n-butyl-2-[2-(trifluoromethyl)-5-(propionylamino)phenyl]-2,4-dihydro-3H-1,2,4-triazol-3-one, 2-[2-Bromo-5-(propionylamino)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[5-(Benzoylamino)-2-bromophenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-(propionylamino)-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[2-(trifluoromethyl)-5-(valerylamino)phenyl]-3H-1,2,4-triazol-3-one, 2-[5-(Benzoylamino)-2-(trifluoromethyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-chloro-5-(propionylamino)phenyl]-2,4-dihydro-3H-1,2,4-triazol-3-one, 4-[[2'-[N-(t-Butoxycarbonyl)sulfamoyl]biphenyl-4-yl]methyl]-5-n-butyl-2-[2-chloro-5-(propionylamino)phenyl]-2,4-dihydro-3H-1,2,4-triazol-3-one, 2-[5-(Acetylamino)-2-chlorophenyl]-4-[[2'-[N-(t-butoxycarbonyl)sulfamoyl]-3-fluoro-5'-n-propyl-biphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-chloro-5-(2-ethoxyacetylamino)phenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[2-chloro-5-[(ethylthioacetyl)amino]phenyl]-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2-[5-(N-n-butylcarbamoyl)-2-(trifluoromethyl)phenyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-(N-n-propylcarbamoyl)-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-(N-ethylcarbamoyl)-2-(trifluoromethyl)phenyl]-3H-1,2,4-triazol-3-one, 4-[[2'-[N-t-Butoxycarbonyl)sulfamoyl]-3-fluorobiphenyl-4-yl]methyl]-5-n-butyl-2,4-dihydro-2-[5-(N-phenylcarbamoyl)-2-(trifluoromethyl)phenyl]-3H-1,2,4-triazol-3-one, 2-[2-Bromo-5-(N-n-butylcarbamoyl)phenyl]-4-[[2'-N-(t-butoxycarbonyl)sulfamoyl]-3-fluorobiphenyl-4-yl]-methyl]-5-n-butyl-2,4-dihydro-3H-1,2,4-triazol-3-one, 2-[2-Bromo-5-(N-n-propylcarbamoyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-(N-ethylcarbamoyl)phenyl]-4-[[2'-[N-(t-butoxycarbonyl)sulfamoyl]-3-fluorobiphenyl-4-]methyl]-5-n-butyl-2,4-dihydro-3H-1,2,4-triazol-3-one, 2-[2-Bromo-5-(N-phenylcarbamoyl)phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(ethylthioacetyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(methylthioacetyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[[3-(methylthio)propionyl]amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(ethoxyacetyl)amino]-2-(trifluoromethyl)phenyl]3H-1,2,4-triazol-3-one, 4-[[2'-[N-t-Butoxycarbonyl)sulfamoyl]-3-fluorobiphenyl-4-yl]methyl]-5-n-butyl-2,4-dihydro-2-[5-[(methoxyacetyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(3-methoxypropionyl)amino]-2-(trifluoromethyl)phenyl]-3H-1,2,4-triazol-3-one, 4-[[2'-[N-(t-Butoxycarbonyl)sulfamoyl]-3-fluorobiphenyl-4-yl]methyl]-5-n-butyl-2,4-dihydro-2-[5-[(3-ethoxypropionyl)amino]-2-(trifluoromethyl)phenyl]-3H-1,2,4-triazol-3-one, 2-[2-Bromo-5-[(ethylthioacetyl)amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(methylthioacetyl)amino]phenyl]-4-[[2'-[N-t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[[3-(methylthio)propionyl]amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(ethoxyacetyl)amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(methoxyacetyl)amino]phenyl]-4-[[2'-[N-(t-butoxycarbonyl)sulfamoyl]-3-fluorobiphenyl-4-yl]methyl]-5-n-butyl-2,4-dihydro-3H-1,2,4-triazol-3-one, 2-[2-Bromo-5-[(3-methoxypropionyl)amino]phenyl]-4-[[2'-[N-(t-butoxycarbonyl)sulfamoyl]-3-fluorobiphenyl-4-yl]methyl]methyl]5-n-butyl-2,4-dihydro-3H-1,2,4-triazol-3-one, 2-[2-Bromo-5-[(3-ethoxypropionyl)amino]phenyl-4-[[2'-[N-t-butoxycarbonyl)sulfamoyl]-3-fluorobiphenyl-4-]methyl-5-n-butyl-2,4-dihydro-3H-1,2,4-triazol-3-one, 2-[5-(Acetylamino)-2-chlorophenyl]-5-n-butyl-2,4-dihydro-4-[[2'-[N-(ethoxycarbonyl)sulfamoyl]-3-fluoro-5'-n-propylbiphenyl-4-yl]methyl]-3H-1,2,4-triazol-3-one, 2-[5-(Acetylamino)-2-chlorophenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[2-chloro-5-[(cyclopropanecarbonyl)amino]phenyl]-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[2-chloro-5-(propionylamino)phenyl]-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[5-(N-n-butylcarbamoyl)-2-chlorophenyl]-2,4-dihydro-4-[[2'-[N-(ethoxycarbonyl)sulfamoyl]-3-fluorobiphenyl-4-yl]methyl]-3H-1,2,4-triazol-3-one, 2-[5-(Acetylamino)-2-(trifluoromethyl)phenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2-[5-[(cyclopropanecarbonyl)amino]-2-(trifluoromethyl)phenyl]-2,4-dihydro-4-[[2'-[N-(ethoxycarbonyl)sulfamoyl]-3-fluorobiphenyl-4-yl]methyl]-3H-1,2,4-triazol-3-one, 5-n-Butyl-2,4-dihydro-4-[[2'-[N-(ethoxycarbonyl)sulfamoyl]-3-fluorobiphenyl-4-yl]methyl]-2-[5-(propionylamino)-2-(trifluoromethyl)phenyl]-3H-1,2,4-triazol-3-one, 5-n-Butyl-2-[5-(N-n-butylcarbamoyl)-2-(trifluoromethyl)phenyl]-2,4-dihydro-4-[[2'-[N-(ethoxycarbonyl)sulfamoyl]-3-fluorobiphenyl-4-yl]methyl]-3H-1,2,4-triazol-3-one, 2-[2-Bromo-5-(propionylamino)phenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 2-[2-Bromo-5-(N-n-butylcarbamoyl)phenyl]-5-n-butyl-2,4-dihydro-4-[[2'-[N-(ethoxycarbonyl)sulfamoyl]-3-fluorobiphenyl-4-yl]methyl]-3H-1,2,4-triazol-3-one, 2-[5-(Acetylamino)-2-chlorophenyl]-4-[[2'-[N-(t-butoxycarbonyl)sulfamoyl]-3-fluorobiphenyl-4-yl]methyl]-2,4-dihydro-5-n-propyl-3H-1,2,4-triazol-3-one, 4-[[2'-[N-(t-Butoxycarbonyl)sulfamoyl]-3-fluorobiphenyl-4-yl]methyl]-2-[2-chloro-5-[(cyclopropanecarbonyl)amino]phenyl]-2,4-dihydro-5-n-propyl-3H-1,2,4-triazol-3-one, 4-[[2'-[N-(t-Butoxycarbonyl)sulfamoyl]-3-fluorobiphenyl-4-yl]methyl]-2-[2-chloro-5-(propionylamino)phenyl]-2,4-dihydro-5-n-propyl-3H-1,2,4-triazol-3-one, 2-[5-(N-n-Butylcarbamoyl)-2-chlorophenyl]-4-[[2'-[N-(t-butoxycarbonyl)sulfamoyl]-3-fluorobiphenyl-4-yl]methyl]-2,4-dihydro-5-n-propyl-3H-1,2,4-triazol-3-one, 2-[5-(Acetylamino)-2-(trifluoromethyl)phenyl]-4-[[2'-[N-(t-butoxycarbonyl)sulfamoyl]-3-fluorobiphenyl-4-yl]methyl]-2,4-dihydro-5-n-propyl-3H-1,2,4-triazol-3-one, 4-[[2'-[N-(t-Butoxycarbonyl)sulfamoyl]-3-fluorobiphenyl-4-yl]methyl]-2,4-dihydro-2-[5-[(cyclopropanecarbonyl)amino]-2-(trifluoromethyl)phenyl]-5-n-propyl-3-1,2,4-triazol-3-one, 4-[[2'-[N-(t-Butoxycarbonyl)sulfamoyl]-3-fluorobiphenyl-4-yl]methyl]-2,4-dihydro-2-[5-(propionylamino)-2-(trifluoromethyl)phenyl]-5-n-propyl-3H-1,2,4-triazol-3-one, 4-[[2'-[N-(t-Butoxycarbonyl)sulfamoyl]-3-fluorobiphenyl-4-yl]methyl]-2-[5-(N-n-butylcarbamoyl)-2-(trifluoromethyl)phenyl]-2,4-dihydro-5-n-propyl-3H-1,2,4-triazol-3-one, 2-[5-(Acetylamino)-2-chlorophenyl]-2,4-dihydro-4-[[2'-[N-(ethoxycarbonyl)sulfamoyl]-3-fluorobiphenyl-4-yl]methyl]-5-n-propyl-3H-1,2,4-triazol-3-one, 2-[2-Chloro-5-[(cyclopropanecarbonyl)amino]phenyl]-2,4-dihydro-4-[[2'-[N-(ethoxycarbonyl)sulfamoyl]-3-fluorobiphenyl-4-yl]methyl]-5-n-propyl-3H-1,2,4-triazol-3-one, 2-[2-Chloro-5-(propionylamino)phenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[5-(N-n-Butylcarbamoyl)-2-chlorophenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[5-(Acetylamino)-2-(trifluoromethyl)phenyl]-2,4-dihydro-4-[[2'-[N-(ethoxycarbonyl)-sulfamoyl]-3-fluorobiphenyl-4-yl]methyl]-5-n-propyl-3H-1,2,4-triazol-3-one, 2-[5-[(Cyclopropanecarbonyl)amino]-2-(trifluoromethyl)phenyl]-2,4-dihydro-4-[[2'-[N-(ethoxycarbonyl)sulfamoyl]-3-fluorobiphenyl-4-yl]methyl]-5-n-propyl-3H-1,2,4-triazol-3-one, 2,4-Dihydro-4-[[2'-[N-(ethoxycarbonyl)sulfamoyl]-3-fluorobiphenyl-4-yl]methyl]-2-[5-(propionylamino)-2-(trifluoromethyl)phenyl]-5-n-propyl-3H-1,2,4-triazol-3-one, or 2-[5-(N-n-Butylcarbamoyl)-2-(trifluoromethyl)phenyl]2,4-dihydro-4-[[2'-[N-(ethoxycarbonyl)sulfamoyl]-3-fluorobiphenyl-4-yl]methyl]-5-n-propyl-3H-1,2,4-triazol-3-one.

8. A pharmaceutical composition useful in the treatment of hypertension which comprises a pharmaceutically acceptable carrier and a pharmaceutically effective amount of a compound of claim 1.

9. A method of treating hypertension which comprises administering to a patient in need of such treatment a pharmaceutically effective amount of a compound of claim 1.

10. An ophthalmological formulation for the treatment of ocular hypertension comprising an ophthalmologically acceptable carrier and an effective ocular antihypertensive amount of a compound of claim 1.

11. A method of treating ocular hypertension comprising administering to a patient in need of such treatment an effective ocular antihypertensive amount of a compound of claim 1.

* * * * *